US012692235B2

(12) United States Patent
Lou et al.

(10) Patent No.: US 12,692,235 B2
(45) Date of Patent: Jul. 28, 2026

(54) FUSED RING COMPOUND AND APPLICATION THEREOF

(71) Applicant: WUHAN LL SCIENCE AND TECHNOLOGY DEVELOPMENT CO., LTD., Wuhan (CN)

(72) Inventors: Jun Lou, Wuhan (CN); Yongkai Chen, Wuhan (CN); Yihan Zhang, Wuhan (CN); Xiaodan Guo, Wuhan (CN); Lina Qian, Wuhan (CN); Li Liu, Wuhan (CN); Wei Peng, Wuhan (CN); Fei Rong, Wuhan (CN); Chaodong Wang, Wuhan (CN)

(73) Assignee: WUHAN LL SCIENCE AND TECHNOLOGY DEVELOPMENT CO., LTD., Wuhan (CN)

( * ) Notice: Subject to any disclaimer, the term of this patent is extended or adjusted under 35 U.S.C. 154(b) by 1064 days.

(21) Appl. No.: 17/790,500

(22) PCT Filed: Dec. 29, 2020

(86) PCT No.: PCT/CN2020/140689

§ 371 (c)(1),
(2) Date: Jun. 30, 2022

(87) PCT Pub. No.: WO2021/136238

PCT Pub. Date: Jul. 8, 2021

(65) Prior Publication Data

US 2023/0118751 A1 Apr. 20, 2023

(30) Foreign Application Priority Data

Dec. 30, 2019 (CN) ......................... 201911396567.4

(51) Int. Cl.
*C07D 217/26* (2006.01)
*C07D 237/28* (2006.01)
*C07D 239/72* (2006.01)
*C07D 401/04* (2006.01)
*C07D 401/12* (2006.01)

(52) U.S. Cl.
CPC ......... *C07D 217/26* (2013.01); *C07D 237/28* (2013.01); *C07D 239/72* (2013.01); *C07D 401/04* (2013.01); *C07D 401/12* (2013.01)

(58) Field of Classification Search
CPC .. C07D 217/26; C07D 237/28; C07D 239/72; C07D 401/04; C07D 401/12
See application file for complete search history.

(56) References Cited

U.S. PATENT DOCUMENTS

| | | | |
|---|---|---|---|
| 7,855,220 | B2 | 12/2010 | Neubert et al. |
| 2018/0338980 | A1 | 11/2018 | Werner et al. |
| 2019/0119210 | A1 | 4/2019 | Werner et al. |

FOREIGN PATENT DOCUMENTS

| | | | |
|---|---|---|---|
| CN | 101300235 | A | 11/2008 |
| CN | 101300253 | A | 11/2008 |
| CN | 107848974 | A | 3/2018 |
| CN | 109415321 | A | 3/2019 |
| CN | 114845996 | A | 8/2022 |
| EP | 4053108 | A1 | 9/2022 |
| WO | 2007025901 | A1 | 3/2007 |
| WO | 2018104305 | A1 | 6/2018 |
| WO | 2018104307 | A1 | 6/2018 |

OTHER PUBLICATIONS

Kanellopoulos, Frontiers in Immunology, Mar. 2021, vol. 12, article 645834, 1-21. (Year: 2021).*
Montilla, Int J Mol Sci, 2020, 21, 5562, 1-16. (Year: 2020).*
Shen, Nature Communications, 2023, 1:6437, 1-16. (Year: 2023).*
Sophocleous, Int J Mol Sci, 2022, 23, 5739, 1-16. (Year: 2022).*
Suurvali, Biomedical Journal 40, 2017, 245-256. (Year: 2017).*
Aug. 12, 2023 First Office Action issued in Chinese Patent Application No. 202080091546.6.
Aug. 10, 2023 Chinese Search Report issued in Chinese Patent Application No. 202080091546.6.
Oct. 24, 2023 Extended European Search Report issued in European Patent Application No. 20908535.6.
Mar. 29, 2021 International Search Report issued in International Patent Application No. PCT/CN2020/140689.
Mar. 29, 2021 Written Opinion of the International Searching Authority issued in International Patent Application No. PCT/CN2020/140689.
Stefan Werner et al., "Discovery and Characterization of the Potent and Selective P2X4 Inhibitor N-[4-(3-Chlorophenoxy)-3-sulfamoylphenyl]-2-phenylacetamide (BAY-1797) and Structure-Guided Amelioration of Its CYP3A4 Induction Profile", Journal of Medicinal Chemistry, 2019, 62(24), pp. 11194-11217.
American Chemical Society ACS. "STNext Registry Database" http://next.stn.org, Nov. 11, 2016, compounds having the CAS RN of 1540928-50-4 and 2029333-28-4.

(Continued)

*Primary Examiner* — D Margaret M Seaman

(57) ABSTRACT

Disclosed is a fused ring compound and an application thereof. Disclosed is a fused ring compound represented by formula I, a pharmaceutically acceptable salt, a stereoisomer, a tautomer, an isotope compound, a crystal form, a nitrogen oxide, a solvate, or a solvate of the pharmaceutically acceptable salt thereof. The fused ring compound of the present invention has high P2X4 antagonistic activity, excellent selectivity, low toxicity and excellent metabolic stability.

I

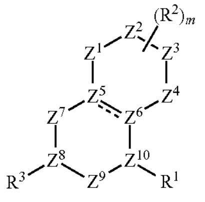

19 Claims, No Drawings

(56) References Cited

OTHER PUBLICATIONS

"March's Advanced Organic Chemistry" by Michael B. Smith and Jerry March, John Wiley and Sons, Inc., New Jersey, 2007.
Berge et al., "Pharmaceutical Salts", Journal of Pharmaceutical Sciences 66: 1-19 (1977).
Handbook of Pharmaceutical Salts: Properties, Selection, and Use (P. Heinrich Stahl and Camille G. Wermuth, eds., Wiley-VCH, 2002).
IUPAC-IUB Commission on Biochemical Nomenclature, Abbreviated Nomenclature of Synthetic Polypeptides (Polymerized Amino Acids)*, Biochem. 1972, 11 : 942-944.
Leslie W. Deady (1977): Ring Nitrogen Oxidation of Amino Substituted Nitrogen Heterocycles with m-Chloroperbenzoic Acid, Synthetic Communications: An International Journal for Rapid Communication of Synthetic Organic Chemistry, 7:8, 509-514.
Handbook of Pharmaceutical Excipients (Raymond C Rowe et al., 2009 Sixth Edition).

* cited by examiner

FUSED RING COMPOUND AND APPLICATION THEREOF

This application claims the priority of Chinese patent application CN2019113965674 filed on Dec. 30, 2019. The present disclosure refers to the full text of the above Chinese patent application.

TECHNICAL FIELD

The present disclosure related to a fused ring compound and use thereof.

BACKGROUND

ATP receptors are classified into two main families, the P2Y-purinoceptors and P2X-purinoceptors, based on their molecular structure, transduction mechanism, and pharmacological properties. The P2X-purinoceptors are a family of ATP-gated cation channels, and several subtypes have been cloned, including: six homopolymer receptors, P2X1; P2X2; P2X3; P2X4; P2X5; and P2X7; and three heteropolymer receptors P2X2/3, P2X4/6, P2X1/5. The P2X4 receptor is the only subtype of the P2X family that the crystal structure has been solved, and the resolution is as high as 2.8 Å, and the study found that P2X4 is the P2X subtype with the strongest permeability to $Ca^{2+}$.

Cough is the main symptom of respiratory diseases, and 70% to 80% of patients in respiratory clinics have cough symptoms. With the increasing prevalence of COPD and IPF and the like, cough, as the main symptom of most respiratory diseases, is in great demand. As the body's defensive nerve reflex, cough is beneficial to clearing respiratory secretions and harmful factors, but frequent and severe cough will seriously affect patients' work, life and social activities.

At present, the indications of drugs under development related to P2X4 targets are mostly neuropathic pain or inflammation, and there is no information in the development of drugs related to cough indications. And there is no drug marketed for P2X4 inhibitory pathway to treat many diseases including chronic cough. Therefore, the development of new compounds that can inhibit the activity of P2X4 has positive significance for the treatment of diseases.

CONTENT OF THE PRESENT INVENTION

The technical problem to be solved by the present disclosure is to provide a new fused ring compound as a P2X4 antagonist in view of the deficiency of insufficient P2X4 antagonists in the prior art. The fused ring compound of the present disclosure has high P2X4 antagonistic activity, good selectivity, low toxicity and good metabolic stability.

The present disclosure solves the above technical problems by the following technical scheme.

The present disclosure provides a fused ring compound represented by formula I, a pharmaceutically acceptable salt thereof, a stereoisomer thereof, a tautomer thereof, an isotopic compound thereof, a crystal form thereof, a nitrogen oxide thereof, a solvate thereof, or a solvate of the pharmaceutically acceptable salt thereof;

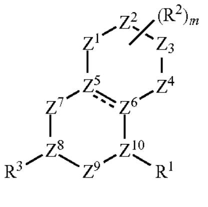

I wherein, 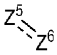 is a single bond or a double bond;

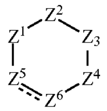

is benzene ring, "6-membered heteroaromatic ring with 1, 2 or 3 heteroatoms selected from one or more of N, O and S" or "6-membered heterocycloalkene with 1, 2 or 3 heteroatoms selected from one or more of N, O and S";

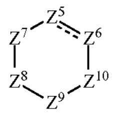

is benzene ring, "6-membered heterocycloalkane with 1, 2 or 3 heteroatoms selected from one or more of N, O and S", "6-membered heterocycloalkene with 1, 2 or 3 heteroatoms selected from one or more of N, O and S" or "6-membered heteroaromatic ring with 1, 2 or 3 heteroatoms selected from one or more of N, O and S";

$R^1$ is

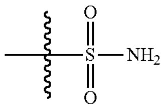 or 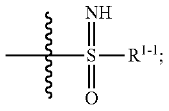

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$ alkyl substituted by one or more $R^{1-1-1}$, $C_3$-$C_6$ cycloalkyl substituted by one or more $R^{1-1-2}$, or, "4- to 7-membered heterocycloalkyl with 1, 2 or 3 heteroatoms selected from one or more of N, O and S" substituted by one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4- to 7-membered heterocycloalkyl with 1, 2 or 3 heteroatoms selected from one or more of N, O and S";

$R^3$ is

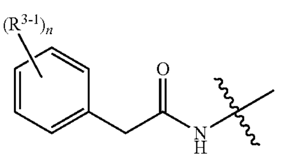 or 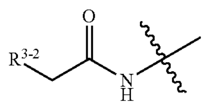 ;

n is 0, 1, 2 or 3;

$R^{3-1}$ is independently halogen, cyano, hydroxyl, $C_1$-$C_6$ alkyl, $C_1$-$C_6$ alkoxy, $C_3$-$C_6$ cycloalkyl, $C_1$-$C_6$ alkyl substituted by one or more $R^{3-1-1}$, $C_1$-$C_6$ alkoxy substituted by one or more $R^{3-1-2}$, or $C_1$-$C_6$ alkoxy substituted by $C_1$-$C_6$ alkoxy; $R^{3-1-1}$ and $R^{3-1-2}$ are independently halogen;

$R^{3-2}$ is $C_3$-$C_6$ cycloalkyl substituted by one or more $R^{3-2-1}$, "5- to 6-membered heterocycloalkyl with 1, 2 or 3 heteroatoms selected from one or more of N, O and S" substituted by one or more $R^{3-2-2}$, "7- to 8-membered heterocycloalkyl with 1, 2 or 3 heteroatoms selected from one or more of N, O and S" substituted by one or more $R^{3-2-2}$ or "5- to 6-membered heteroaryl with 1, 2 or 3 heteroatoms selected from one or more of N, O and S" substituted by one or more $R^{3-2-3}$.

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or, $C_1$-$C_6$ alkoxy substituted by $C_1$-$C_6$ alkoxy;

m is 0, 1, 2, 3 or 4;

$R^2$ is oxo, halogen, cyano, isocyano, amino, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted by one or more $R^{2-26}$, $C_2$-$C_{10}$ alkynyl, $C_2$-$C_{10}$ alkynyl substituted by one or more $R^{2-27}$, $C_3$-$C_6$ cycloalkyl, $C_3$-$C_6$ cycloalkyl substituted by one or more $R^{2-3}$, "5- to 6-membered heterocycloalkyl with 1, 2 or 3 heteroatoms selected from one or more of N, O and S", "3- to 4-membered heterocycloalkyl with 1 or 2 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)—$R^{2-2}$, —$OR^{2-6}$, —C(═O)$OR^{2-7}$, —$NR^{2-8}R^{2-9}$, "5- to 6-membered heterocycloalkyl with 1, 2 or 3 heteroatoms selected from one or more of N, O and S" substituted by one or more $R^{2-10}$, "3- to 4-membered heterocycloalkyl with 1 or 2 heteroatoms selected from one or more of N, O and S" substituted by one or more $R^{2-10}$, —C(═O)$NHR^{2-11}$, —C(═O)$NR^{2-12}R^{2-13}$, —$NR^{2-14}$C(═O)$R^{2-15}$, —$NR^{2-16}$S(═O)$_2R^{2-17}$, —$NR^{2-18}$S(═O)$R^{2-19}$, —S(═O)$_2NHR^{2-20}$, —S(═O)$NHR^{2-21}$, —S(═O)$_2NR^{2-22}R^{2-23}$, —S(═O)$_2R^{2-24}$ or —S(═O)$R^{2-25}$;

$R^{2-1}$ is independently halogen, hydroxyl, $C_3$-$C_6$ cycloalkyl, $C_3$-$C_6$ cycloalkyl substituted by one or more $R^{2-1-8}$, "4- to 6-membered heterocycloalkyl with 1, 2 or 3 heteroatoms selected from one or more of N, O and S", "4- to 6-membered heterocycloalkyl with 1, 2 or 3 heteroatoms selected from one or more of N, O and S" substituted by one or more $R^{2-1-7}$, phenyl, phenyl substituted by one or more $R^{2-1-1}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-1-6}$, —$OR^{2-1-2}$, —N($R^{2-1-3}$)($R^{2-1-4}$), or, —S(═O)$_2$—$R^{2-1-5}$.

$R^{2-1}$, $R^{2-6}$, $R^{2-7}$ and $R^{2-8}$ are independently oxo, hydroxyl, amino, carboxyl, halogen, —CN, $C_1$-$C_6$ alkyl, $C_1$-$C_6$ alkyl substituted by one or more halogen, —$OR^{2-1-1-1}$, or, —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, $C_1$-$C_6$ alkyl, $C_1$-$C_6$ alkyl substituted by one or more $R^{2-4-3}$, —N($R^{2-4-1}$)($R^{2-4-2}$) or $C_1$-$C_6$ alkoxy; $R^{2-4-1}$ and $R^{2-4-2}$ are independently hydrogen, $C_1$-$C_6$ alkyl or $C_3$-$C_6$ cycloalkyl; $R^{2-4-3}$ is halogen;

$R^{2-2}$ is $C_1$-$C_6$ alkyl, $C_3$-$C_6$ cycloalkyl, phenyl, $C_1$-$C_6$ alkyl substituted by one or more $R^{2-2-2}$, or, phenyl substituted by one or more $R^{2-2-1}$; $R^{2-2-1}$ is independently halogen; $R^{2-2-2}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently oxo, halogen, hydroxyl, amino, carboxyl, —CN, $C_1$-$C_6$ alkyl, $C_1$-$C_6$ alkyl substituted by one or more halogen, $C_1$-$C_6$ alkoxy, $C_3$-$C_6$ cycloalkyl, $C_6$-$C_{10}$ aryl, $C_6$-$C_{10}$ aryl substituted by one or more $R^{2-6-1-1}$, —$OR^{2-6-1-2}$ or —N($R^{2-6-1-3}$)($R^{2-6-1-4}$);

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-1-2}$, $R^{2-6-1-3}$ and $R^{2-6-1-4}$ are independently $C_1$-$C_6$ alkyl;

$R^{2-7}$ is $C_1$-$C_6$ alkyl, $C_3$-$C_6$ cycloalkyl or phenyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$.

$R^{2-8-1}$ is halogen or $C_1$-$C_6$ alkoxy;

$R^{2-10}$ is independently $C_1$-$C_6$ alkyl or oxo;

$R^{2-26}$ and $R^{2-27}$ are independently halogen or $C_1$-$C_6$ alkyl;

$R^{2-11}$, $R^{2-12}$, $R^{2-13}$, $R^{2-14}$, $R^{2-15}$, $R^{2-16}$, $R^{2-17}$, $R^{2-18}$, $R^{2-19}$, $R^{2-20}$, $R^{2-21}$, $R^{2-22}$, $R^{2-23}$, $R^{2-24}$ and $R^{2-25}$ are independently $C_1$-$C_6$ alkyl, $C_1$-$C_6$ alkoxy, $C_3$-$C_6$ cycloalkyl, "5- to 6-membered heterocycloalkyl with 1, 2 or 3 heteroatoms selected from one or more of N, O and S", phenyl, phenyl substituted by one or more $R^{2-11-1}$, "5- to 6-membered heteroaryl with 1, 2 or 3 heteroatoms selected from one or more of N, O and S", or "5- to 6-membered heteroaryl with 1, 2 or 3 heteroatoms selected from one or more of N, O and S" substituted by one or more $R^{2-11-2}$.

$R^{2-11-1}$ and $R^{2-11-2}$ are independently halogen, cyano, hydroxyl, $C_1$-$C_6$ alkyl, $C_1$-$C_6$ alkoxy or $C_3$-$C_6$ cycloalkyl;

$R^2$ is located on

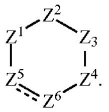

In some embodiments, in the fused ring compound represented by formula I, wherein, 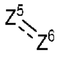 is a single bond or a double bond;

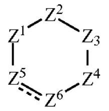

is benzene ring, "6-membered heteroaromatic ring with 1, 2 or 3 heteroatoms selected from one or more of N, O and S" or "6-membered heterocycloalkene with 1, 2 or 3 heteroatoms selected from one or more of N, O and S";

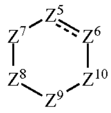

is benzene ring, "6-membered heterocycloalkane with 1, 2 or 3 heteroatoms selected from one or more of N, O and S", "6-membered heterocycloalkene with 1, 2 or 3 heteroatoms selected from one or more of N, O and S" or "6-membered heteroaromatic ring with 1, 2 or 3 heteroatoms selected from one or more of N, O and S";

$R^1$ is

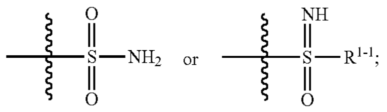

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$ alkyl substituted by one or more $R^{1-1-1}$, $C_3$-$C_6$ cycloalkyl substituted by one or more $R^{1-1-2}$, or, "4- to 7-membered heterocycloalkyl with 1, 2 or 3 heteroatoms selected from one or more of N, O and S" substituted by one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4- to 7-membered heterocycloalkyl with 1, 2 or 3 heteroatoms selected from one or more of N, O and S";

$R^3$ is

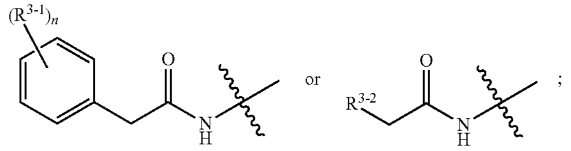

n is 0, 1, 2 or 3;

$R^{3-1}$ is independently halogen, cyano, hydroxyl, $C_1$-$C_6$ alkyl, $C_1$-$C_6$ alkoxy, $C_3$-$C_6$ cycloalkyl, or, $C_1$-$C_6$ alkoxy substituted by $C_1$-$C_6$ alkoxy;

$R^{3-2}$ is $C_3$-$C_6$ cycloalkyl substituted by one or more $R^{3-2-1}$, "5- to 6-membered heterocycloalkyl with 1, 2 or 3 heteroatoms selected from one or more of N, O and S" substituted by one or more $R^{3-2-2}$, "7- to 8-membered heterocycloalkyl with 1, 2 or 3 heteroatoms selected from one or more of N, O and S" substituted by one or more $R^{3-2-2}$ or "5- to 6-membered heteroaryl with 1, 2 or 3 heteroatoms selected from one or more of N, O and S" substituted by one or more $R^{3-2-3}$.

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or, $C_1$-$C_6$ alkoxy substituted by $C_1$-$C_6$ alkoxy;

m is 0, 1, 2, 3 or 4;

$R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, $C_3$-$C_6$ cycloalkyl substituted by one or more $R^{2-3}$, "5- to 6-membered heterocycloalkyl with 1, 2 or 3 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)—$R^{2-2}$, —$OR^{2-6}$, —C(═O)$OR^{2-7}$, —$NR^{2-8}R^{2-9}$, "5- to 6-membered heterocycloalkyl with 1, 2 or 3 heteroatoms selected from one or more of N, O and S" substituted by one or more $R^{2-10}$, —C(═O)$NHR^{2-11}$, —C(═O)$NR^{2-12}R^{2-13}$, —$NR^{2-14}$C(═O)$R^{2-15}$, —$NR^{2-16}S(═O)_2R^{2-17}$, —$NR^{2-18}$S(═O)$R^{2-19}$, —$S(═O)_2NHR^{2-20}$, —S(═O)$NHR^{2-21}$, —$S(═O)_2NR^{2-22}R^{2-23}$, —$S(═O)_2R^{2-24}$ or —S(═O)$R^{2-25}$;

$R^{2-1}$ is independently halogen, hydroxyl, $C_3$-$C_6$ cycloalkyl, $C_3$-$C_6$ cycloalkyl substituted by one or more $R^{2-1-8}$, "4- to 6-membered heterocycloalkyl with 1, 2 or 3 heteroatoms selected from one or more of N, O and S", "4- to 6-membered heterocycloalkyl with 1, 2 or 3 heteroatoms selected from one or more of N, O and S" substituted by one or more $R^{2-17}$, phenyl, phenyl substituted by one or more $R^{2-1-1}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-1-6}$, —$OR^{2-1-2}$, —$N(R^{2-1-3})(R^{2-1-4})$, or, —$S(═O)_2R^{2-1-5}$.

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted by one or more halogen, —$OR^{2-1-1}$, or, —$N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, —$N(R^{2-4-1})(R^{2-4-2})$ or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-2}$ is $C_1$-$C_6$ alkyl, $C_3$-$C_6$ cycloalkyl, phenyl, or, phenyl substituted by one or more $R^{2-2-1}$; $R^{2-2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently oxo, halogen, hydroxyl, amino, carboxyl, —CN, $C_1$-$C_6$ alkyl, $C_1$-$C_6$ alkyl substituted by one or more halogen, $C_1$-$C_6$ alkoxy, $C_3$-$C_6$ cycloalkyl, $C_6$-$C_{10}$ aryl, $C_6$-$C_{10}$ aryl substituted by one or more $R^{2-6-1-1}$, —$OR^{2-6-1-2}$ or —$N(R^{2-6-1-3})(R^{2-6-1-4})$;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-1-2}$, $R^{2-6-1-3}$ and $R^{2-6-1-4}$ are independently $C_1$-$C_6$ alkyl;

$R^{2-7}$ is $C_1$-$C_6$ alkyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$.

$R^{2-8-1}$ is halogen or $C_1$-$C_6$ alkoxy;

$R^{2-10}$ is independently $C_1$-$C_6$ alkyl or oxo;

$R^{2-11}$, $R^{2-12}$, $R^{2-13}$, $R^{2-14}$, $R^{2-15}$, $R^{2-16}$, $R^{2-17}$, $R^{2-18}$, $R^{2-19}$, $R^{2-20}$, $R^{2-21}$, $R^{2-22}$, $R^{2-23}$, $R^{2-24}$ and $R^{2-25}$ are independently $C_1$-$C_6$ alkyl, $C_1$-$C_6$ alkoxy, $C_3$-$C_6$ cycloalkyl, "5- to 6-membered heterocycloalkyl with 1, 2 or 3 heteroatoms selected from one or more of N, O and S", phenyl, phenyl substituted by one or more $R^{2-11-1}$, "5- to 6-membered heteroaryl with 1, 2 or 3 heteroatoms selected from one or more of N, O and S", or "5- to 6-membered heteroaryl with 1, 2 or 3 heteroatoms selected from one or more of N, O and S" substituted by one or more $R^{2-11-2}$.

$R^{2-11-1}$ and $R^{2-11-2}$ are independently halogen, cyano, hydroxyl, $C_1$-$C_6$ alkyl, $C_1$-$C_6$ alkoxy or $C_3$-$C_6$ cycloalkyl.

$R^2$ is located on

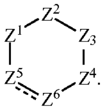

In some embodiments, in the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof; some groups have the following definitions, and unmentioned groups are defined as described in any of the above schemes (this paragraph is hereinafter referred to as "in some embodiments"):

When

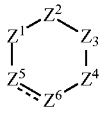

is "6-membered heteroaromatic ring with 1, 2 or 3 heteroatoms selected from one or more of N, O and S", in the 6-membered heteroaromatic ring, the heteroatom is N, and the heteroatom number is preferably 1 or 2.

In some embodiments, when

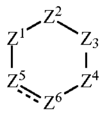

is "6-membered heterocycloalkene with 1, 2 or 3 heteroatoms selected from one or more of N, O and S", in the 6-membered heterocycloalkene, the heteroatom is selected from N, the heteroatom number is 1; and the number of double bonds in the 6-membered heterocycloalkene is preferably 1 or 2; 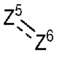 is preferably a double bond. The

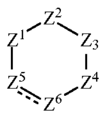

is preferably

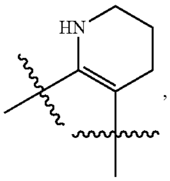
,
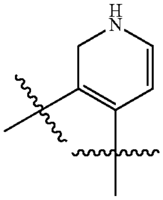
or
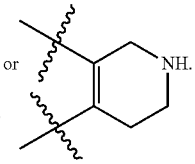

In some embodiments, when

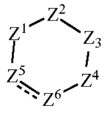

is "6-membered heterocycloalkene with 1, 2 or 3 heteroatoms selected from one or more of N, O and S", in the 6-membered heterocycloalkene, the heteroatom is selected from N, the heteroatom number is 1; and the number of double bonds in the 6-membered heterocycloalkene is preferably 1 or 2; 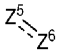 is preferably a double bond.

The

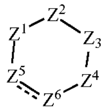

is preferably or

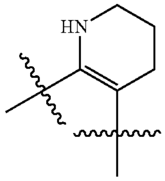
or
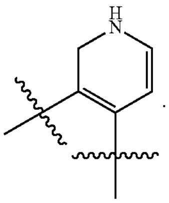
.

In some embodiments, when $R^{1-1}$ is $C_1$-$C_6$ alkyl, the $C_1$-$C_6$ alkyl is $C_1$-$C_4$ alkyl, preferably methyl, ethyl, n-propyl, isopropyl, n-butyl, isobutyl, sec-butyl or tert-butyl, more preferably methyl.

In some embodiments, when $R^{1-1}$ is $C_3$-$C_6$ cycloalkyl, the $C_3$-$C_6$ cycloalkyl is cyclopropyl, cyclobutyl or cyclopentyl.

In some embodiments, when $R^{1-1}$ is $C_1$-$C_6$ alky substituted by one or more $R^{1-1-1}$, in the $C_1$-$C_6$ alky substituted by one or more $R^{1-1-1}$, the $C_1$-$C_6$ alkyl is $C_1$-$C_4$ alkyl, preferably methyl, ethyl, n-propyl, isopropyl, n-butyl, isobutyl, sec-butyl or tert-butyl.

In some embodiments, when $R^{1-1}$ is $C_3$-$C_6$ cycloalkyl substituted by one or more $R^{1-1-2}$, in the $C_3$-$C_6$ cycloalkyl substituted by one or more $R^{1-1-2}$, the $C_3$-$C_6$ cycloalkyl is cyclopropyl, cyclobutyl or cyclopentyl.

In some embodiments, when $R^{1-1-1}$ and $R^{1-1-2}$ are independently halogen, the halogen is fluorine, chlorine, bromine or iodine.

In some embodiments, when $R^{3-1}$ is independently halogen, the halogen is fluorine, chlorine, bromine or iodine, preferably fluorine or chlorine.

In some embodiments, when $R^{3-1}$ is independently $C_1$-$C_6$ alkoxy or $C_1$-$C_6$ alkoxy substituted by one or more $R^{3-1-2}$, in the $C_1$-$C_6$ alkoxy or $C_1$-$C_6$ alkoxy substituted by one or more $R^{3-1-2}$, the $C_1$-$C_6$ alkoxy is $C_1$-$C_4$ alkoxy, preferably methoxy, ethoxy, n-propoxy, isopropoxy, n-butoxy, isobutoxy, sec-butoxy or tert-butoxy, more preferably methoxy.

In some embodiments, when $R^{3-1-1}$ and $R^{3-1-2}$ are independently halogen, the halogen is fluorine, chlorine, bromine or iodine, preferably fluorine or chlorine.

In some embodiments, when $R^2$ is halogen, the halogen is fluorine, chlorine, bromine or iodine, preferably fluorine or chlorine.

In some embodiments, when $R^2$ is $C_1$-$C_{10}$ alkyl, the $C_1$-$C_{10}$ alkyl is $C_1$-$C_4$ alkyl, preferably methyl, ethyl, n-propyl, isopropyl, n-butyl, isobutyl, sec-butyl or tert-butyl, more preferably methyl or isopropyl.

In some embodiments, when $R^2$ is $C_1$-$C_{10}$ alkyl substituted by one or more $R^{2-1}$, the $C_1$-$C_{10}$ alkyl is $C_1$-$C_4$ alkyl, preferably methyl, ethyl, n-propyl, isopropyl, n-butyl, isobutyl, sec-butyl or tert-butyl, more preferably methyl.

In some embodiments, when $R^2$ is $C_2$-$C_{10}$ alkenyl or $C_2$-$C_{10}$ alkenyl substituted by one or more $R^{2-26}$, in the $C_2$-$C_{10}$ alkenyl and $C_2$-$C_{10}$ alkenyl substituted by one or more $R^{2-26}$, the $C_2$-$C_{10}$ alkenyl is $C_2$-$C_4$ alkenyl, for example vinyl and allyl.

In some embodiments, when $R^2$ is $C_2$-$C_{10}$ alkynyl or $C_2$-$C_{10}$ alkynyl substituted by one or more $R^{2-27}$, in the $C_2$-$C_{10}$ alkynyl and $C_2$-$C_{10}$ alkynyl substituted by one or more $R^{2-27}$, the $C_2$-$C_{10}$ alkynyl is $C_2$-$C_4$ alkynyl, for example ethynyl and propynyl.

In some embodiments, when $R^{2-26}$ and $R^{2-27}$ are independently halogen, the halogen is fluorine, chlorine, bromine or iodine, preferably fluorine or chlorine.

In some embodiments, when $R^2$ is $C_3$-$C_6$ cycloalkyl, the $C_3$-$C_6$ cycloalkyl is cyclopropyl, cyclobutyl, cyclopentyl or cyclohexyl, preferably cyclopropyl or cyclobutyl.

In some embodiments, when $R^2$ is "3- to 4-membered heterocycloalkyl with 1 or 2 heteroatoms selected from one or more of N, O and S" or "3- to 4-membered heterocycloalkyl with 1 or 2 heteroatoms selected from one or more of N, O and S" substituted by one or more $R^{2-10}$ in the 3- to 4-membered heterocycloalkyl, the heteroatom is selected from one or more of N and O and the heteroatom number is preferably 1 or 2; the 3- to 4-membered heterocycloalkyl is preferably

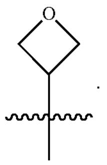 [SMILES: *C1COC1]

In some embodiments, when $R^2$ is "5- to 6-membered heterocycloalkyl with 1, 2 or 3 heteroatoms selected from one or more of N, O and S", in the 5- to 6-membered heterocycloalkyl, the heteroatom is selected from one or more of N and O, the heteroatom number is preferably 1 or 2; the 5- to 6-membered heterocycloalkyl is preferably

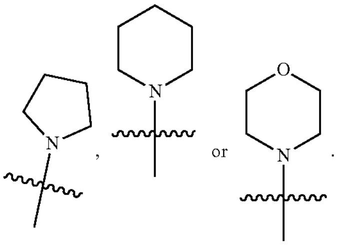

In some embodiments, when $R^2$ is "5- to 6-membered heterocycloalkyl with 1, 2 or 3 heteroatoms selected from one or more of N, O and S", in the 5- to 6-membered heterocycloalkyl, the heteroatom is selected from one or more of N and O, the heteroatom number is preferably 1 or 2; the 5- to 6-membered heterocycloalkyl is preferably

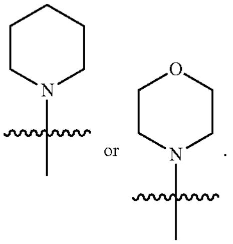

In some embodiments, when $R^2$ is "5- to 6-membered heteroaryl with 1, 2 or 3 heteroatoms selected from one or more of N, O and S", in the 5- to 6-membered heteroaryl, the heteroatom is preferably N, the heteroatom number is preferably 2. The 5- to 6-membered heteroaryl is preferably

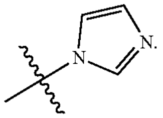 [SMILES: *n1ccnc1]

The 5- to 6-membered heteroaryl is preferably

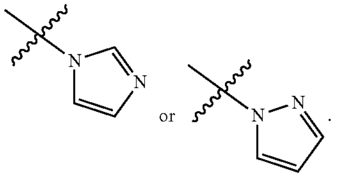 [SMILES: *n1ccnc1 ; *n1cccn1]

In some embodiments, when $R^2$ is "5- to 6-membered heteroaryl with 1, 2 or 3 heteroatoms selected from one or more of N, O and S" substituted by one or more $R^{2-5}$, in the 5- to 6-membered heteroaryl, the heteroatoms are preferably N, the heteroatom number is preferably 1. The 5- to 6-membered heteroaryl is preferably

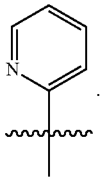

In some embodiments, when $R^2$ is "5- to 6-membered heterocycloalkyl with 1, 2 or 3 heteroatoms selected from one or more of N, O and S" substituted by one or more $R^{2-10}$, in the 5- to 6-membered heterocycloalkyl, the heteroatoms are N, the heteroatom number is preferably 2; the 5- to 6-membered heterocycloalkyl is preferably

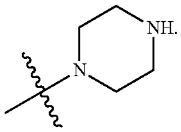 [SMILES: *N1CCNCC1]

In some embodiments, when $R^{2-1}$ is independently halogen, the halogen is fluorine, chlorine, bromine or iodine, preferably fluorine.

In some embodiments, when $R^{2-1}$ is independently $C_3$-$C_6$ cycloalkyl, the $C_3$-$C_6$ cycloalkyl is cyclopropyl, cyclobutyl, cyclopentyl or cyclohexyl, preferably cyclopropyl or cyclobutyl.

In some embodiments, when $R^{2-2}$ is $C_1$-$C_6$ alkyl or $C_1$-$C_6$ alkyl substituted by one or more $R^{2-2-2}$, the $C_1$-$C_6$ alkyl is preferably methyl, ethyl, n-propyl, isopropyl, n-butyl, isobutyl, sec-butyl tert-butyl, n-pentyl, isopentyl or n-butyl, more preferably methyl.

In some embodiments, when $R^{2-2}$ is $C_3$-$C_6$ cycloalkyl, the $C_3$-$C_6$ cycloalkyl is cyclopropyl, cyclobutyl, cyclopentyl or cyclohexyl, preferably cyclopropyl or cyclobutyl.

In some embodiments, when $R^{2-2-2}$ is independently halogen, the halogen is fluorine, chlorine, bromine or iodine, preferably fluorine or chlorine.

In some embodiments, when $R^{2-4}$ and $R^{2-5}$ are independently halogen, the halogen is fluorine, chlorine, bromine or iodine, preferably fluorine or chlorine.

In some embodiments, when $R^{2-4}$ and $R^{2-5}$ are independently $C_1$-$C_6$ alkyl or $C_1$-$C_6$ alkyl substituted by one or more $R^{2-4-3}$, in the $C_1$-$C_6$ alkyl and $C_1$-$C_6$ alkyl substituted by one or more $R^{2-4-3}$, the $C_1$-$C_6$ alkyl is preferably methyl, ethyl, n-propyl, isopropyl, n-butyl, isobutyl, sec-butyl, tert-butyl, n-pentyl or isopentyl, more preferably methyl.

In some embodiments, when $R^{2-4-3}$ is halogen, the halogen is fluorine, chlorine, bromine or iodine, preferably fluorine or chlorine.

In some embodiments, when $R^{2-6}$ is $C_1$-$C_{10}$ alkyl, the $C_1$-$C_{10}$ alkyl is $C_1$-$C_6$ alkyl, preferably methyl, ethyl, n-propyl, isopropyl, n-butyl, isobutyl, sec-butyl tert-butyl, n-pentyl, isopentyl or n-butyl, more preferably methyl, ethyl, isobutyl or isopentyl.

In some embodiments, when $R^{2-6}$ is $C_1$-$C_{10}$ alkyl substituted by one or more $R^{2-6-1}$, the $C_1$-$C_{10}$ alkyl is $C_1$-$C_4$ alkyl, preferably methyl, ethyl, n-propyl, isopropyl, n-butyl, isobutyl, sec-butyl or tert-butyl, more preferably methyl or ethyl.

In some embodiments, when $R^{2-6}$ is $C_3$-$C_6$ cycloalkyl, the $C_3$-$C_6$ cycloalkyl is cyclopropyl, cyclobutyl, cyclopentyl or cyclohexyl, preferably cyclopropyl, cyclobutyl or cyclopentyl.

In some embodiments, when $R^{2-6}$ is $C_6$-$C_{10}$ aryl, the $C_6$-$C_{10}$ aryl is phenyl or naphthyl.

In some embodiments, when $R^{2-6}$ is $C_6$-$C_{10}$ aryl substituted by one or more $R^{2-6-2}$, the $C_6$-$C_{10}$ aryl is phenyl or naphthyl, preferably phenyl.

In some embodiments, when $R^{2-6}$ is "3- to 6-membered heterocycloalkyl with 1, 2 or 3 heteroatoms selected from one or more of N, O and S", the 3- to 6-membered heterocycloalkyl is 3- to 4-membered heterocycloalkyl; in the 3- to 4-membered heterocycloalkyl, the heteroatom is preferably N, the heteroatom number is preferably 1. The 3- to 4-membered heterocycloalkyl is preferably

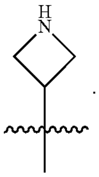

In some embodiments, when $R^{2-6}$ is "3- to 6-membered heterocycloalkyl with 1, 2 or 3 heteroatoms selected from one or more of N, O and S" substituted by one or more $R^{2-6-3}$, the 3- to 6-membered heterocycloalkyl is 3- to 4-membered heterocycloalkyl; in the 3- to 4-membered heterocycloalkyl, the heteroatom is preferably N, the heteroatom number is preferably 1. The 3- to 4-membered heterocycloalkyl is preferably

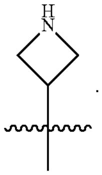 [SMILES: *C1CNC1]

In some embodiments, when $R^{2-6-1}$ is independently halogen, the halogen is fluorine, chlorine, bromine or iodine, preferably fluorine.

In some embodiments, when $R^{2-6-1}$ is independently $C_1$-$C_6$ alkoxy, the $C_1$-$C_6$ alkoxy is $C_1$-$C_4$ alkoxy, preferably methoxy, ethoxy, n-propoxy, isopropoxy, n-butoxy, isobutoxy, sec-butoxy or tert-butoxy, more preferably methoxy. In some embodiments, the $C_1$-$C_6$ alkoxy is preferably ethoxy.

In some embodiments, when $R^{2-6-1}$ is independently $C_3$-$C_6$ cycloalkyl, the $C_3$-$C_6$ cycloalkyl is cyclopropyl, cyclobutyl, cyclopentyl or cyclohexyl, preferably cyclopropyl. In some embodiments, the $C_3$-$C_6$ cycloalkyl is preferably cyclobutyl.

In some embodiments, when $R^{2-6-1}$ is independently $C_6$-$C_{10}$ aryl, the $C_6$-$C_{10}$ aryl is phenyl or naphthyl.

In some embodiments, when $R^{2-6-1}$ is independently $C_6$-$C_{10}$ aryl substituted by one or more $R^{2-6-1-1}$, the $C_6$-$C_{10}$ aryl is phenyl or naphthyl, preferably phenyl.

In some embodiments, when $R^{2-6-2}$ is independently halogen, the halogen is fluorine, chlorine, bromine or iodine, preferably fluorine.

In some embodiments, when $R^{2-6-2}$ is independently $C_1$-$C_6$ alkyl, the $C_1$-$C_6$ alkyl is $C_1$-$C_4$ alkyl, preferably methyl, ethyl, n-propyl, isopropyl, n-butyl, isobutyl, sec-butyl or tert-butyl, more preferably methyl.

In some embodiments, when $R^{2-6-2}$ is independently $C_1$-$C_6$ alkoxy, the $C_1$-$C_6$ alkoxy is $C_1$-$C_4$ alkoxy, preferably methoxy, ethoxy, n-propoxy, isopropoxy, n-butoxy, isobutoxy, sec-butoxy or tert-butoxy, more preferably methoxy.

In some embodiments, when $R^{2-6-3}$ is independently —C(═O)—$C_1$-$C_4$ alkyl, in the —C(═O)—$C_1$-$C_4$ alkyl, the $C_1$-$C_4$ alkyl is preferably methyl, ethyl, n-propyl, isopropyl, n-butyl, isobutyl, sec-butyl or tert-butyl, more preferably methyl.

In some embodiments, $R^{2-6-1-1}$ is independently fluorine, chlorine, bromine or iodine, preferably fluorine.

In some embodiments, $R^{2-7}$ is $C_1$-$C_4$ alkyl, preferably methyl, ethyl, n-propyl, isopropyl, n-butyl, isobutyl, sec-butyl or tert-butyl, more preferably methyl. In some embodiments, $R^{2-7}$ is preferably isopropyl.

In some embodiments, $R^{2-7}$ is $C_3$-$C_6$ cycloalkyl, the $C_3$-$C_6$ cycloalkyl is cyclopropyl, cyclobutyl, cyclopentyl or cyclohexyl, preferably cyclopropyl.

In some embodiments, when $R^{2-8}$ and $R^{2-9}$ are independently $C_1$-$C_6$ alkyl, the $C_1$-$C_6$ alkyl is $C_1$-$C_4$ alkyl, preferably methyl, ethyl, n-propyl, isopropyl, n-butyl, isobutyl, sec-butyl or tert-butyl, more preferably isopropyl. In some embodiments, the $C_1$-$C_6$ alkyl is preferably methyl.

In some embodiments, when $R^{2-8}$ and $R^{2-9}$ are independently $C_6$-$C_{10}$ aryl, the $C_6$-$C_{10}$ aryl is phenyl or naphthyl.

In some embodiments, when $R^{2-8}$ and $R^{2-9}$ are independently $C_6$-$C_{10}$ aryl substituted by one or more $R^{2-8-1}$, in the $C_6$-$C_{10}$ aryl substituted by one or more $R^{2-8-1}$, the $C_6$-$C_{10}$ aryl is phenyl or naphthyl, preferably phenyl.

In some embodiments, when $R^{2-8-1}$ is halogen, the halogen is fluorine, chlorine, bromine or iodine, preferably fluorine.

In some embodiments, when $R^{2-8-1}$ is independently $C_1$-$C_6$ alkoxy, the $C_1$-$C_6$ alkoxy is $C_1$-$C_4$ alkoxy, preferably methoxy, ethoxy, n-propoxy, isopropoxy, n-butoxy, isobutoxy, sec-butoxy or tert-butoxy, more preferably methoxy.

In some embodiments, when $R^{2-10}$ is independently $C_1$-$C_6$ alkyl, the $C_1$-$C_6$ alkyl is $C_1$-$C_4$ alkyl, preferably methyl, ethyl, n-propyl, isopropyl, n-butyl, isobutyl, sec-butyl or tert-butyl, more preferably methyl.

In some embodiments, 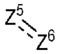 is a double bond.

In some embodiments,

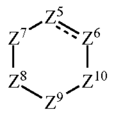

is benzene ring or "6-membered heteroaromatic ring with 1, 2 or 3 heteroatoms selected from N".

In some embodiments,

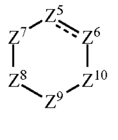

is benzene ring.

In some embodiments, $R^1$ is

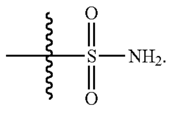 [SMILES: *S(N)(=O)=O]

In some embodiments, $R^{1-1}$ is $C_1$-$C_6$ alkyl, $C_3$-$C_6$ cycloalkyl, $C_1$-$C_6$ alkyl substituted by one or more $R^{1-1-1}$, $C_3$-$C_6$ cycloalkyl substituted by one or more $R^{1-1-2}$.

In some embodiments, $R^{1-1}$ is $C_1$-$C_6$ alkyl.

In some embodiments, $R^{1-1-1}$ and $R^{1-1-2}$ are independently halogen.

In some embodiments, $R^3$ is

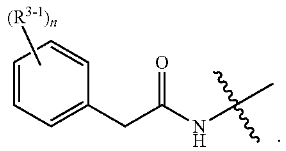

In some embodiments, n is 1, 2 or 3.

In some embodiments, $R^{3-1}$ is independently halogen, cyano, hydroxyl, $C_1$-$C_6$ alkoxy substituted by one or more $R^{3-1-2}$.

In some embodiments, $R^{3-1}$ is independently halogen, cyano or hydroxyl.

In some embodiments, m is 0 or 1.

In some embodiments, $R^2$ is oxo, halogen, cyano, isocyano, amino, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted by one or more $R^{2-26}$, $C_2$-$C_{10}$ alkynyl, $C_2$-$C_{10}$ alkynyl substituted by one or more $R^{2-27}$, $C_3$-$C_6$ cycloalkyl, "5- to 6-membered heterocycloalkyl with 1, 2 or 3 heteroatoms selected from one or more of N, O and S", "3- to 4-membered heterocycloalkyl with 1 or 2 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)—$R^{2-2}$, —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$.

In some embodiments, when

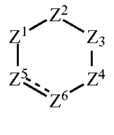

is "6-membered heteroaromatic ring with 1, 2 or 3 heteroatoms selected from one or more of N, O and S", $R^2$ is cyano, isocyano, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted by one or more $R^{2-26}$, phenyl, phenyl substituted by one or more $R^{2-4}$, "5- to 6-membered heteroaryl with 1, 2 or 3 heteroatoms selected from one or more of N, O and S" substituted by one or more $R^{2-5}$, —(C═O)—$R^{2-2}$ or —C(═O)$OR^{2-7}$.

In some embodiments, when

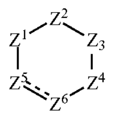

is "6-membered heterocycloalkene with 1, 2 or 3 heteroatoms selected from one or more of N, O and S", $R^2$ is oxo, halogen, cyano, isocyano, amino, $C_3$-$C_6$ cycloalkyl, phenyl, phenyl substituted by one or more $R^{2-4}$, "3- to 4-membered heterocycloalkyl with 1 or 2 heteroatoms selected from one or more of N, O and S", "5- to 6-membered heteroaryl with 1, 2 or 3 heteroatoms selected from one or more of N, O and S", —(C═O)—$R^{2-2}$, or, "5- to 6-membered heterocycloalkyl with 1, 2 or 3 heteroatoms selected from one or more of N, O and S" substituted by one or more $R^{2-10}$.

for example, $C_3$-$C_6$ cycloalkyl, phenyl, phenyl substituted by one or more $R^{2-4}$, "3- to 4-membered heterocycloalkyl with 1 or 2 heteroatoms selected from one or more of N, O and S" or —(C═O)—$R^{2-2}$.

In some embodiments,

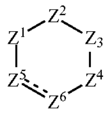

is benzene ring, for example, $R_2$ is cyano.

In some embodiments, $R^2$ is isocyano, phenyl, phenyl substituted by one or more $R^{2-4}$, "3- to 4-membered heterocycloalkyl with 1 or 2 heteroatoms selected from one or more of N, O and S" or —(C═O)—$R^{2-2}$.

In some embodiments, $R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heterocycloalkyl with 1, 2 or 3 heteroatoms selected from one or more of N, O and S", "5- to 6-membered heteroaryl with 1, 2 or 3 heteroatoms selected from one or more of N, O and S", —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$.

In some embodiments, $R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heteroaryl with 1, 2 or 3 heteroatoms selected from one or more of N, O and S", or, —$OR^{2-6}$.

In some embodiments, $R^{2-1}$ is independently halogen, $C_3$-$C_6$ cycloalkyl, phenyl.

In some embodiments, $R^{2-1}$ is independently halogen.

In some embodiments, $R^{2-2}$ is $C_1$-$C_6$ alkyl, $C_3$-$C_6$ cycloalkyl, phenyl, $C_1$-$C_6$ alkyl substituted by one or more $R^{2-2-2}$.

In some embodiments, $R^{2-4}$ and $R^{2-5}$ are independently halogen, $C_1$-$C_6$ alkyl, $C_1$-$C_6$ alkyl substituted by one or more $R^{2-4-3}$.

In some embodiments, $R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

In some embodiments, $R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

In some embodiments, $R^{2-6-1}$ is independently halogen, hydroxyl, $C_1$-$C_6$ alkoxy, $C_3$-$C_6$ cycloalkyl, or, $C_6$-$C_{10}$ aryl substituted by one or more $R^{2-6-1-1}$.

In some embodiments, $R^{2-6-1}$ is independently halogen, $C_3$-$C_6$ cycloalkyl, or, $C_6$-$C_{10}$ aryl substituted by one or more $R^{2-6-1-1}$.

In some embodiments, $R^{2-7}$ is $C_3$-$C_6$ cycloalkyl or phenyl.

In some embodiments, when $R^3$ is

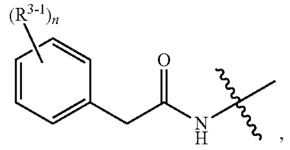

the $R^3$ is

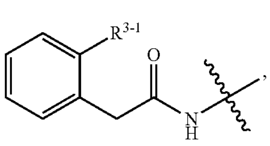
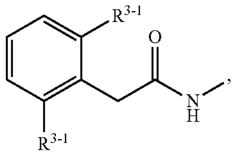
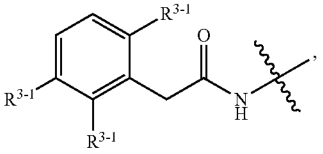
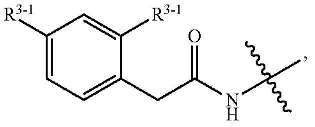
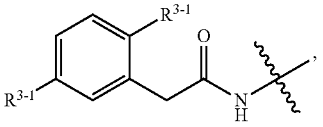
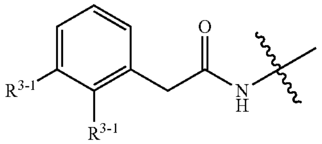

or

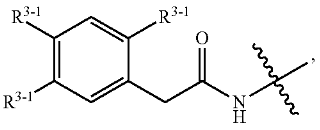

, preferably

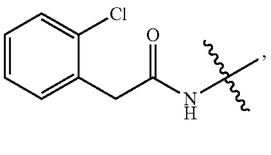
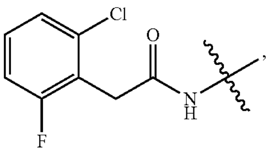
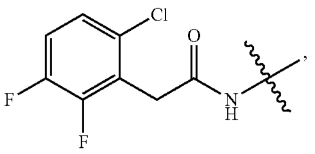

-continued
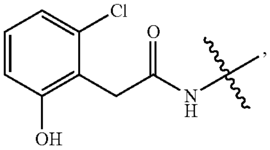,
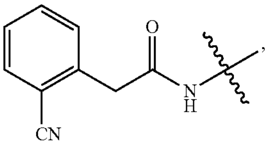,
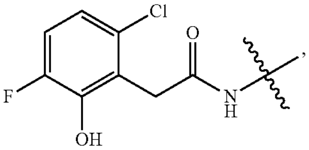,
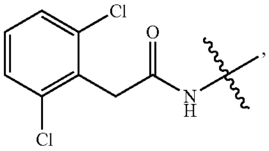,
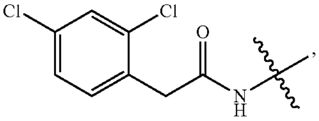,
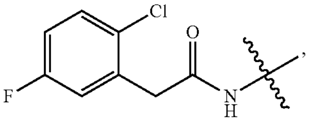,
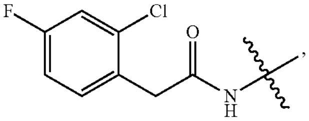,
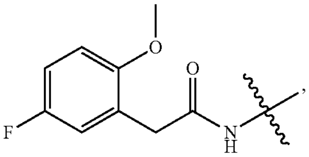,
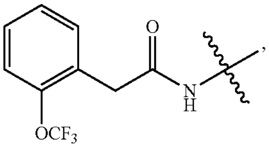,
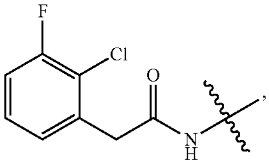, or
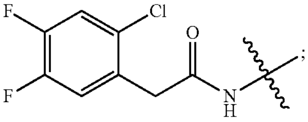; more preferably
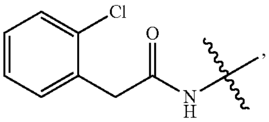,
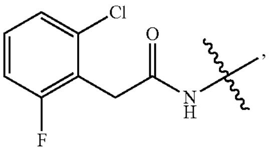,
-continued
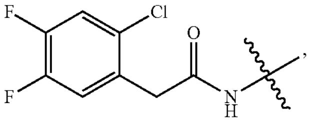,
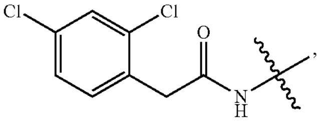,
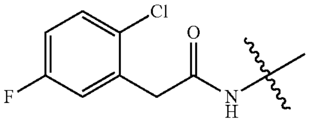 or
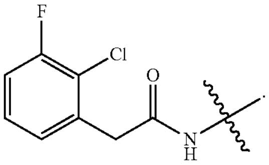.
In some embodiments, when $R^3$ is
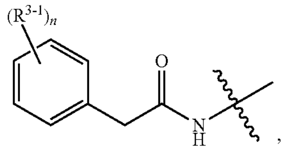,
the $R^3$ is
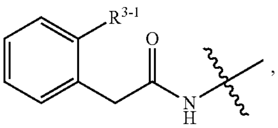,
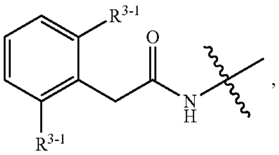,
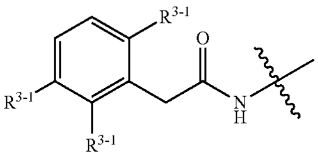 or
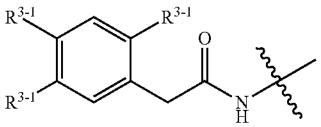, preferably
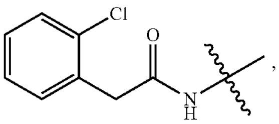,
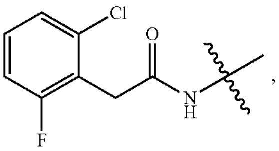,
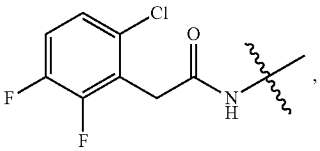, -continued
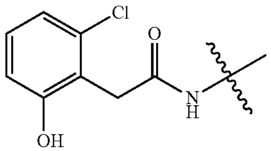, 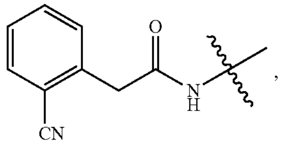,
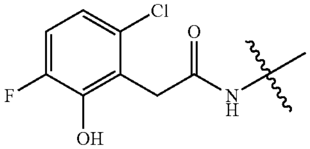 or
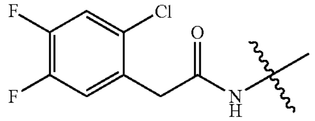.
In some embodiments, when $R^3$ is
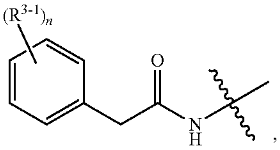,
the $R^3$ is
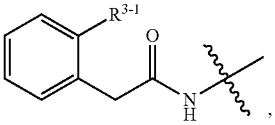, 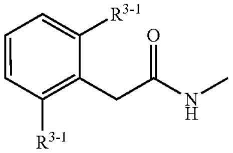 or
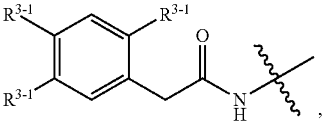, preferably
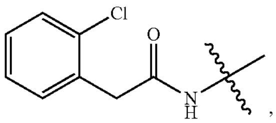, 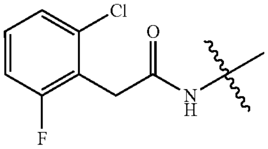 or
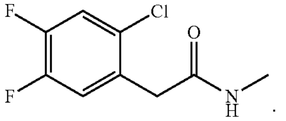.
In some embodiments,
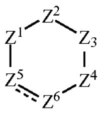 is 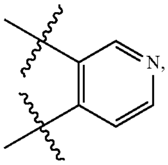, 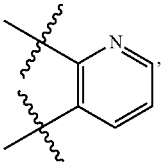,
-continued
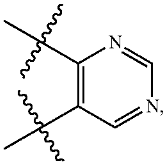, 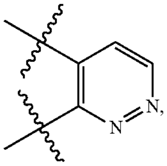, 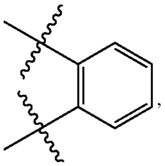,
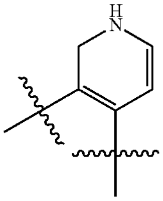 or 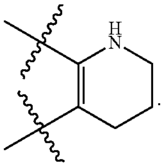.
In some embodiments,
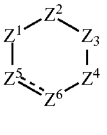 is 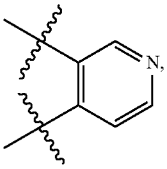, 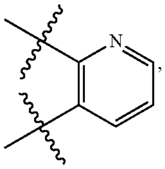,
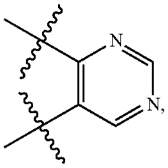, 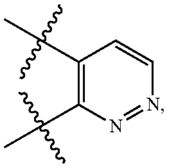,
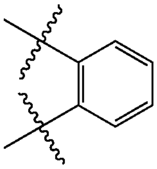 or 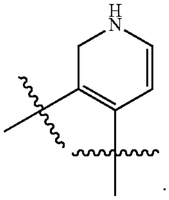.
In some embodiments,
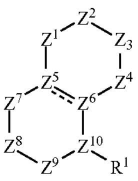 is 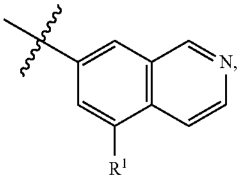,
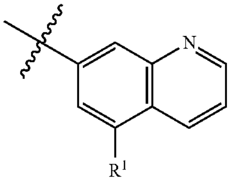, 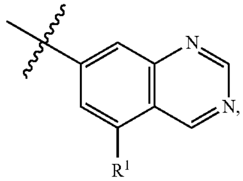

-continued
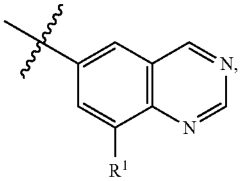
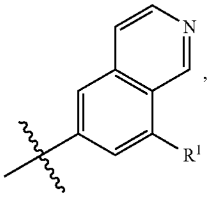
,
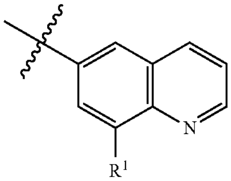
,
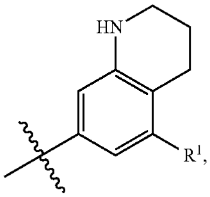
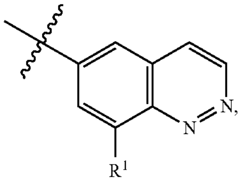
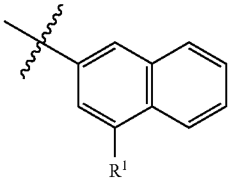
,
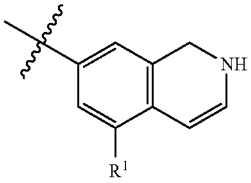
or
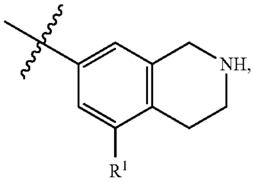
preferably
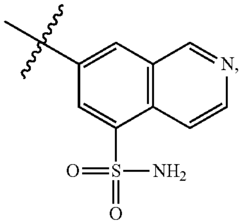
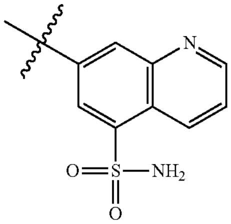
,
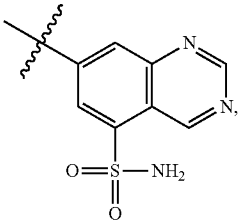
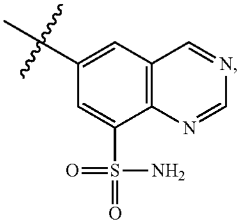
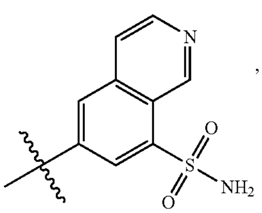
,
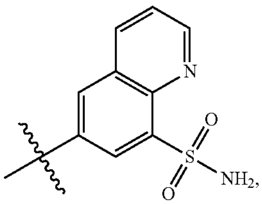
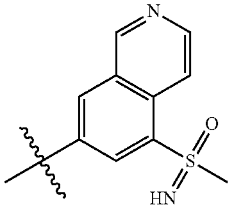
,
-continued
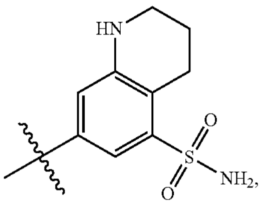
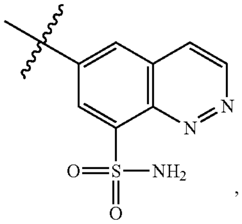
,
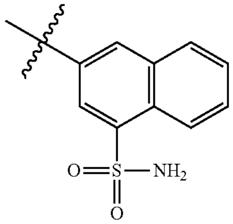
,
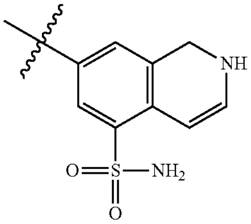
or
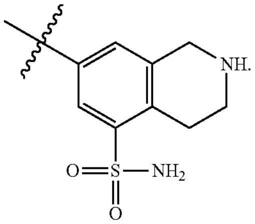
In some embodiments,
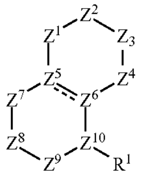
is
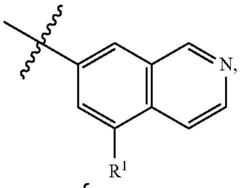
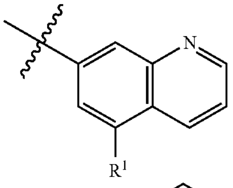
,
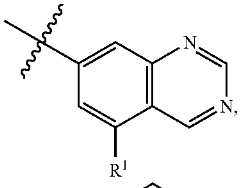
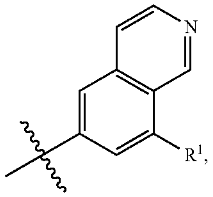
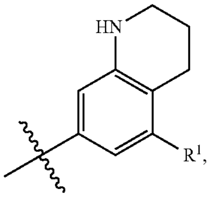
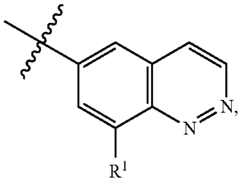
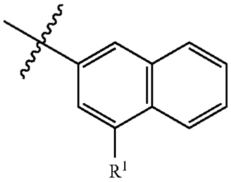
or
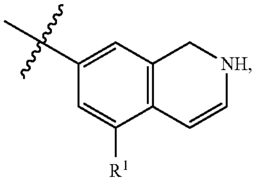
preferably -continued
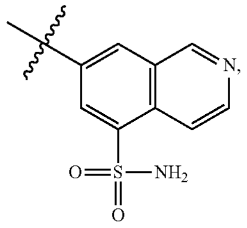
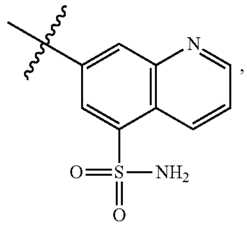
,
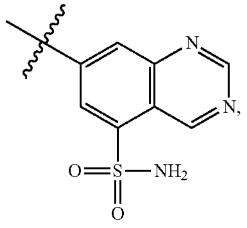
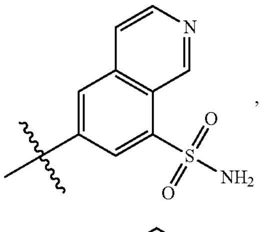
,
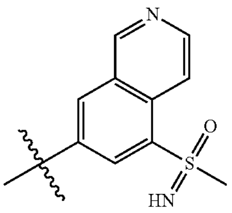
,
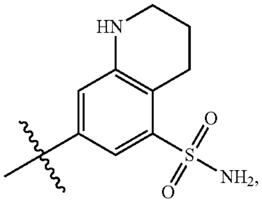
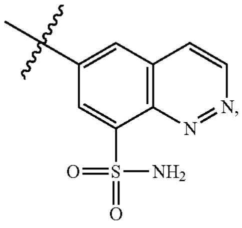
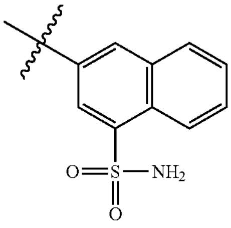
or
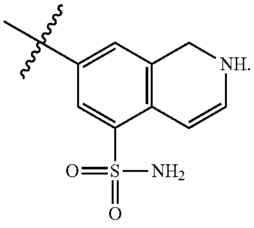
In some embodiments,
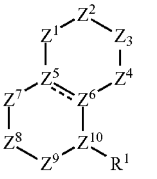
is
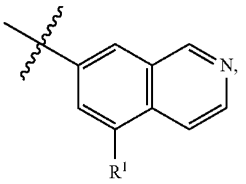
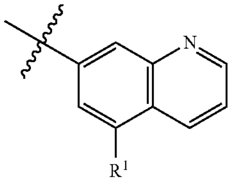
,
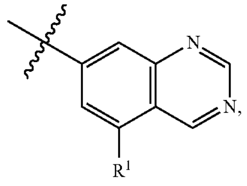
-continued
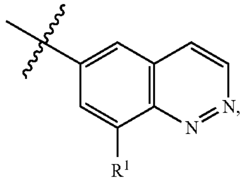
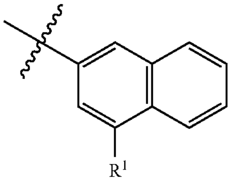
or
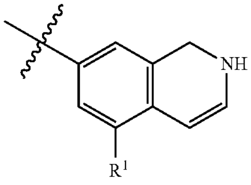
or, preferably
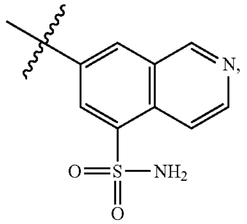
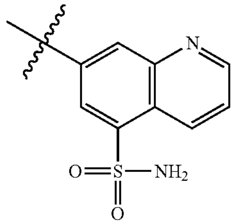
,
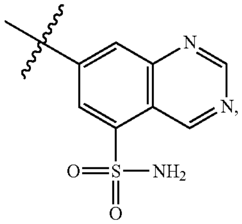
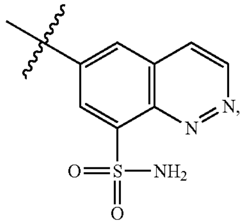
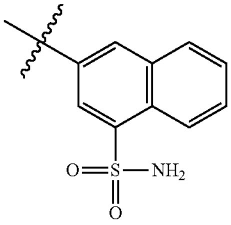
or
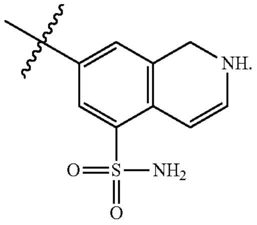
In some embodiments, $R^2$ is oxo, methoxy, fluoro, chloro, hydroxyl, amino, —$CH_2F$, difluoromethyl, trifluoromethyl, methyl, isopropyl, cyclopropyl, cyano, ethoxy, isopropoxy, monofluoromethoxy, difluoromethoxy, trifluoromethoxy,
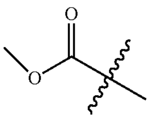
,
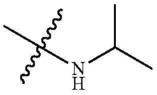
,
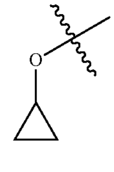
,
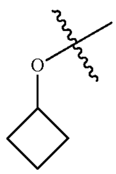
,
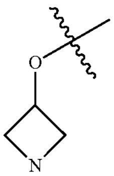
,
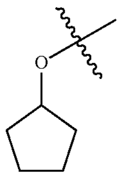
,
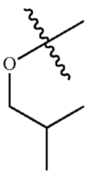
, -continued
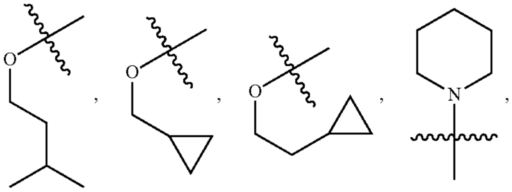
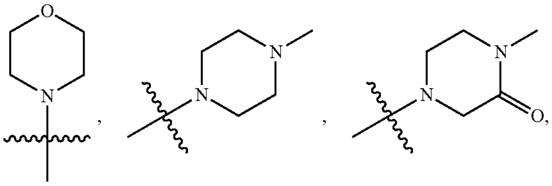
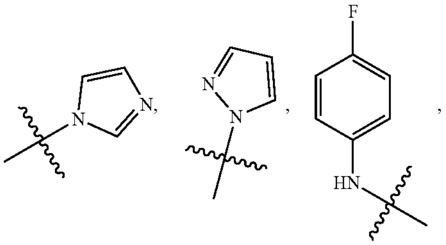
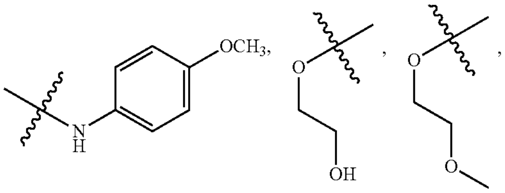
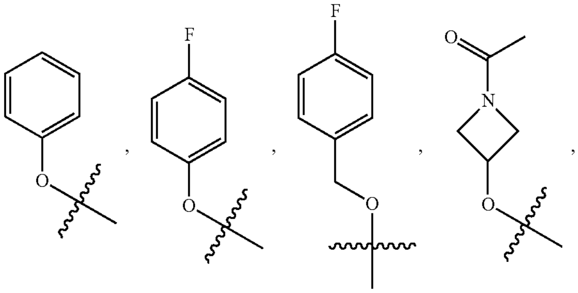
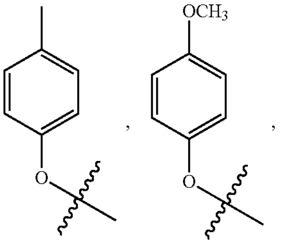
ethyl, dichloromethyl,
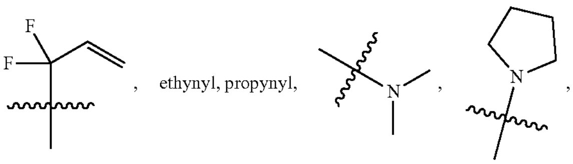
ethynyl, propynyl,
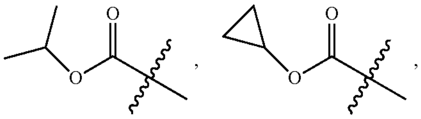
-continued
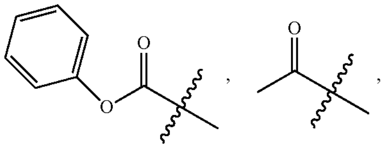
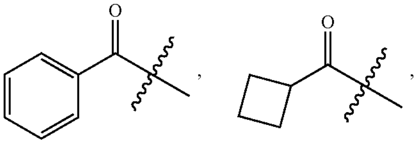
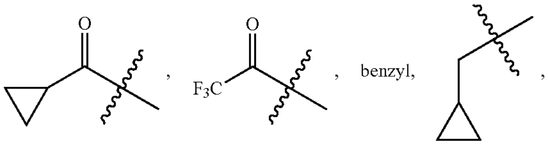
benzyl,
phenyl,
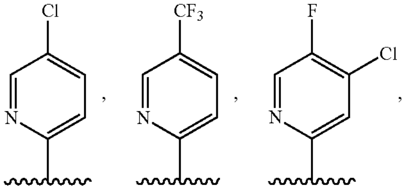
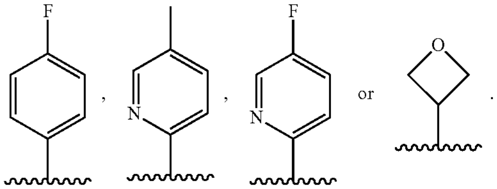
In some embodiments, $R^2$ is oxo, methoxy, fluoro, chloro, hydroxyl, amino, —$CH_2F$, difluoromethyl, trifluoromethyl, methyl, isopropyl, cyclopropyl, cyano, ethoxy, isopropoxy, monofluoromethoxy, difluoromethoxy, trifluoromethoxy,
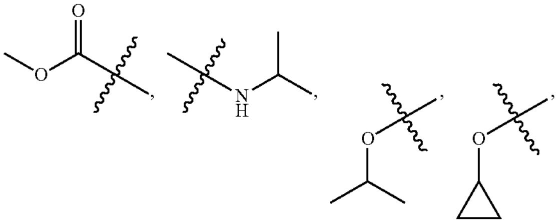
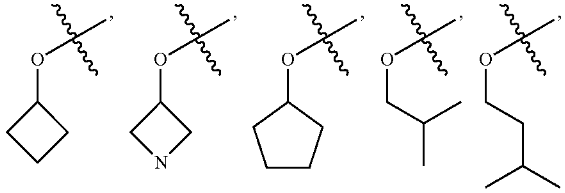
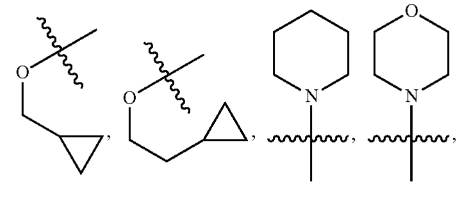

-continued

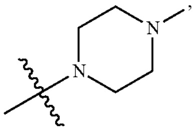, 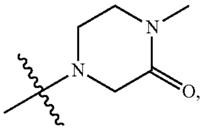, 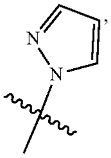,

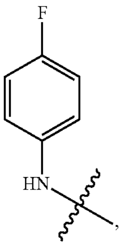,

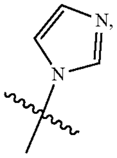, 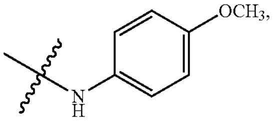,

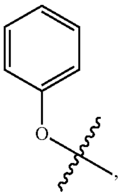, 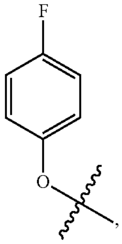,

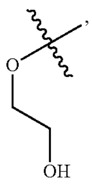, 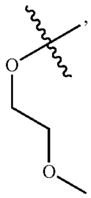,

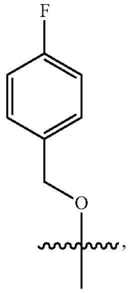, 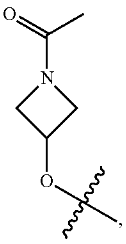, 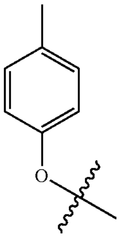 or 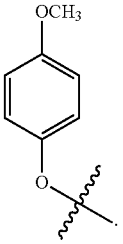.

In some embodiments, $R^2$ is oxo, methoxy, fluoro, chloro, hydroxyl, amino, difluoromethyl, trifluoromethyl, isopropyl, cyclopropyl, cyano, ethoxy, isopropoxy, difluoromethoxy,

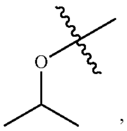, 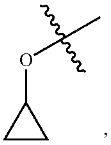, 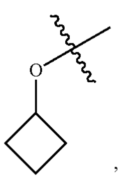, 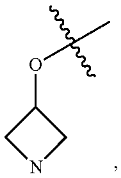,

-continued

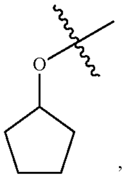, 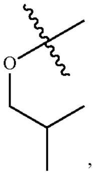, 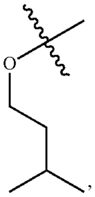, 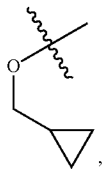, 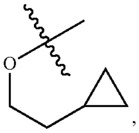,

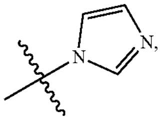, 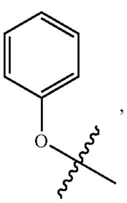, 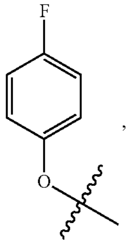, 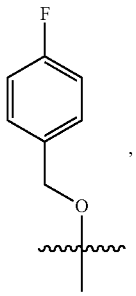,

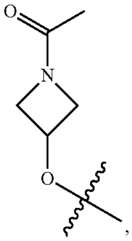, 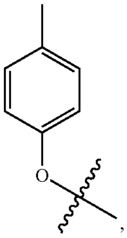, or 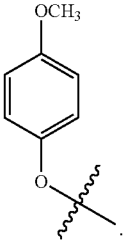.

In some embodiments, in the fused ring compound represented by formula I, wherein, 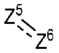 is a single bond;

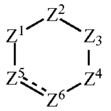

is benzene ring, "6-membered heteroaromatic ring with 1, 2 or 3 heteroatoms selected from one or more of N, O and S" or "6-membered heterocycloalkene with 1, 2 or 3 heteroatoms selected from one or more of N, O and S";

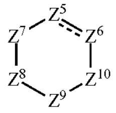

is benzene ring;

$R^1$ is

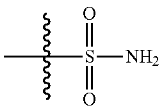 or 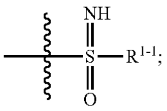;

$R^{1-1}$ is $C_1$-$C_6$ alkyl;

$R^3$ is

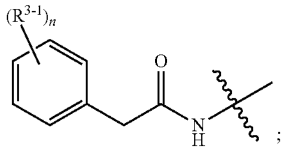

n is 1, 2 or 3;

$R^{3-1}$ is independently halogen, cyano, hydroxyl, $C_1$-$C_6$ alkoxy substituted by one or more $R^{3-1-2}$.

m is 0 or 1;

$R^2$ is oxo, halogen, cyano, amino, isocyano, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted by one or more $R^{2-26}$, $C_2$-$C_{10}$ alkynyl, $C_2$-$C_{10}$ alkynyl substituted by one or more $R^{2-27}$, $C_3$-$C_6$ cycloalkyl, "5- to 6-membered heterocycloalkyl with 1, 2 or 3 heteroatoms selected from one or more of N, O and S", "3- to 4-membered heterocycloalkyl with 1 or 2 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)—$R^{2-2}$, —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$.

$R^{2-1}$ is independently halogen, $C_3$-$C_6$ cycloalkyl or phenyl;

$R^{2-2}$ is $C_1$-$C_6$ alkyl, $C_3$-$C_6$ cycloalkyl, phenyl, or, $C_1$-$C_6$ alkyl substituted by one or more $R^{2-2-2}$; $R^{2-2-2}$ is independently halogen;

$R^{2-4}$ and $R^{2-5}$ are independently halogen, $C_1$-$C_6$ alkyl, $C_1$-$C_6$ alkyl substituted by one or more $R^{2-4-3}$; $R^{2-4-3}$ is halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently halogen, hydroxyl, $C_1$-$C_6$ alkoxy, $C_3$-$C_6$ cycloalkyl, or, $C_6$-$C_{10}$ aryl substituted by one or more $R^{2-6-1-1}$.

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-2-1}$ is independently $C_1$-$C_6$ alkyl;

$R^{2-7}$ is $C_1$-$C_6$ alkyl, $C_3$-$C_6$ cycloalkyl or phenyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$.

$R^{2-8-1}$ is halogen or $C_1$-$C_6$ alkoxy;

$R^{2-10}$ is independently $C_1$-$C_6$ alkyl or oxo;

$R^{2-26}$ and $R^{2-27}$ are independently halogen or $C_1$-$C_6$ alkyl.

In some embodiments, in the fused ring compound represented by formula I, wherein, 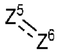 is a double bond;

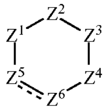

is benzene ring, "6-membered heteroaromatic ring with 1, 2 or 3 heteroatoms selected from one or more of N, O and S" or "6-membered heterocycloalkene with 1, 2 or 3 heteroatoms selected from one or more of N, O and S";

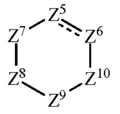

is benzene ring or "6-membered heteroaromatic ring with 1, 2 or 3 heteroatoms selected from N".

$R^1$ is

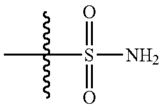

or

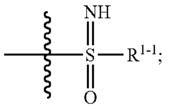

$R^{1-1}$ is $C_1$-$C_6$ alkyl, $C_3$-$C_6$ cycloalkyl, $C_1$-$C_6$ alkyl substituted by one or more $R^{1-1-1}$ or $C_3$-$C_6$ cycloalkyl substituted by one or more $R^{1-1-2}$.

$R^{1-1-1}$ and $R^{1-1-2}$ are independently halogen;

$R^3$ is

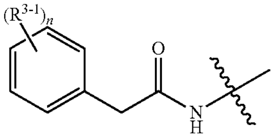

n is 1, 2 or 3;

$R^{3-1}$ is independently halogen, cyano or hydroxyl;

m is 0 or 1;

$R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heterocycloalkyl with 1, 2 or 3 heteroatoms selected from one or more of N, O and S", "5- to 6-membered heteroaryl with 1, 2 or 3 heteroatoms selected from one or more of N, O and S", —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$.

$R^{2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently halogen, hydroxyl, $C_3$-$C_6$ cycloalkyl, or, $C_6$-$C_{10}$ aryl substituted by one or more $R^{2-6-1-1}$.

$R^{2-6-2}$ is independently halogen, $C_1$-$C_6$ alkyl or $C_1$-$C_6$ alkoxy;

$R^{2-6-3}$ is independently —C(=O)—$C_1$-$C_6$ alkyl;

$R^{2-6-1-1}$ is independently halogen;

$R^{2-7}$ is $C_1$-$C_6$ alkyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{2-10}$ is independently $C_1$-$C_6$ alkyl or oxo.

In some embodiments, in the fused ring compound represented by formula I, wherein, 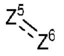 is a double bond;

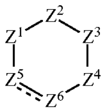

is benzene ring, "6-membered heteroaromatic ring with 1, 2 or 3 heteroatoms selected from one or more of N, O and S" or "6-membered heterocycloalkene with 1, 2 or 3 heteroatoms selected from one or more of N, O and S";

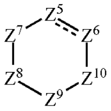

is benzene ring;

$R^1$ is

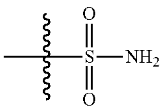 or 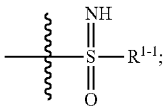

$R^{1-1}$ is $C_1$-$C_6$ alkyl;

$R^3$ is

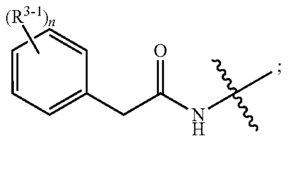

n is 1, 2 or 3;

$R^{3-1}$ is independently halogen, cyano or hydroxyl;

m is 0 or 1;

$R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heterocycloalkyl with 1, 2 or 3 heteroatoms selected from one or more of N, O and S", "5- to 6-membered heteroaryl with 1, 2 or 3 heteroatoms selected from one or more of N, O and S", —$OR^{2-6}$, —C(=O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$.

$R^{2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently halogen, hydroxyl, $C_3$-$C_6$ cycloalkyl, or, $C_6$-$C_{10}$ aryl substituted by one or more $R^{2-6-1-1}$.

$R^{2-6-2}$ is independently halogen, $C_1$-$C_6$ alkyl or $C_1$-$C_6$ alkoxy;

$R^{2-6-3}$ is independently —C(=O)—$C_1$-$C_6$ alkyl;

$R^{2-6-1-1}$ is independently halogen;

$R^{2-7}$ is $C_1$-$C_6$ alkyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{21-0}$ is independently $C_1$-$C_6$ alkyl or oxo. In some embodiments, in the fused ring compound represented by formula I, wherein, 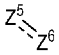 is a double bond;

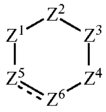

is benzene ring, "6-membered heteroaromatic ring with 1, 2 or 3 heteroatoms selected from one or more of N, O and S" or "6-membered heterocycloalkene with 1, 2 or 3 heteroatoms selected from one or more of N, O and S";

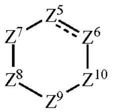

is benzene ring;

$R^1$ is

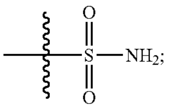 [SMILES: *S(N)(=O)=O]

$R^3$ is

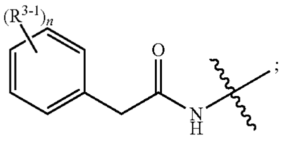

n is 1, 2 or 3;

$R^{3-1}$ is independently halogen, cyano or hydroxyl;

m is 0 or 1;

$R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heteroaryl with 1, 2 or 3 heteroatoms selected from one or more of N, O and S", or, —$OR^{2-6}$.

$R^{2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently halogen, $C_3$-$C_6$ cycloalkyl, or, $C_6$-$C_{10}$ aryl substituted by one or more $R^{2-6-1-1}$; $R^{2-6-1-1}$ is independently halogen;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-10}$ is independently $C_1$-$C_6$ alkyl or oxo.

In some embodiments, in the fused ring compound represented by formula I,

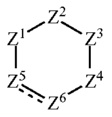

is benzene ring, or, "6-membered heteroaromatic ring with 1, 2 or 3 heteroatoms selected from one or more of N, O and S";

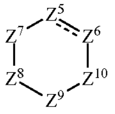

is benzene ring;

$R^1$ is

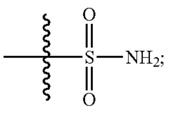 [SMILES: *S(N)(=O)=O]

$R^3$ is

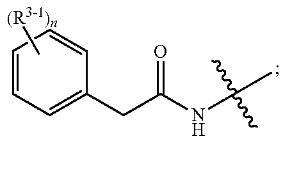

n is 1, 2 or 3;

$R^{3-1}$ is independently halogen, cyano or hydroxyl;

m is 0 or 1;

$R^2$ is oxo, halogen, cyano, $C_1$-$C_{10}$ alkyl or $C_1$-$C_{10}$ alkyl substituted by one or more $R^{2-1}$, $C_3$-$C_6$ cycloalkyl, "5- to 6-membered heteroaryl with 1, 2 or 3 heteroatoms selected from one or more of N, O and S", or, —$OR^{2-6}$.

$R^{2-1}$ is independently halogen;

$R^{2-6}$ is $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$.

$R^{2-6-1}$ is independently halogen, $C_3$-$C_6$ cycloalkyl, or, $C_6$-$C_{10}$ aryl substituted by one or more $R^{2-6-1-1}$; $R^{2-6-1-1}$ is independently halogen;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl.

In some embodiments, in the fused ring compound represented by formula I,

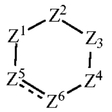

is benzene ring, or, "6-membered heteroaromatic ring with 1 heteroatom selected from one of N, O and S".

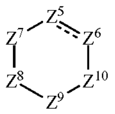

is benzene ring;

$R^1$ is

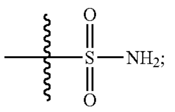

$R^3$ is

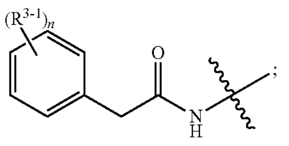

n is 1, 2 or 3;

$R^{3-1}$ is independently halogen, cyano or hydroxyl;

m is 0 or 1;

$R^2$ is chlorine, cyano, $C_1$-$C_{10}$ alkyl, $C_1$-$C_{10}$ alkyl substituted by one or more $R^{2-1}$, $C_3$-$C_6$ cycloalkyl, "5- to 6-membered heteroaryl with 1, 2 or 3 heteroatoms selected from one or more of N, O and S", or, —$OR^{2-6}$.

$R^{2-1}$ is independently halogen;

$R^{2-6}$ is $C_1$-$C_4$ alkyl, $C_1$-$C_2$ alkyl substituted by one or more $R^{2-6-1}$, $C_3$-$C_6$ cycloalkyl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$; and when $R^2$ is chlorine, $R^2$ is located on $Z^1$ or $Z^4$;

$R^{2-6-1}$ is independently halogen, $C_3$-$C_6$ cycloalkyl, or, $C_6$-$C_{10}$ aryl substituted by one or more $R^{2-6-1-1}$.

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl.

In some embodiments, in the fused ring compound represented by formula I,

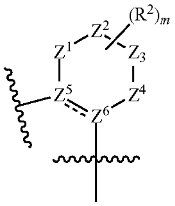

is

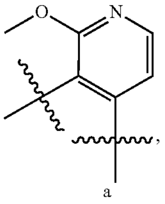

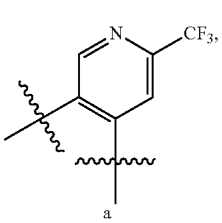

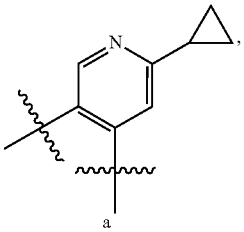

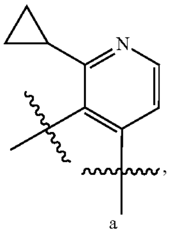

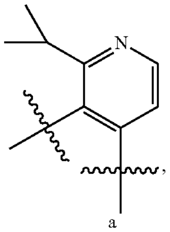

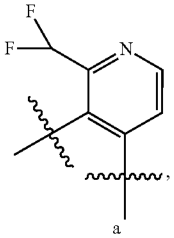

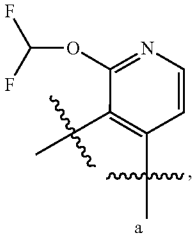

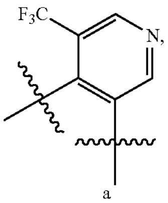

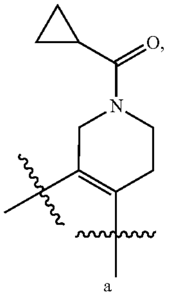

-continued

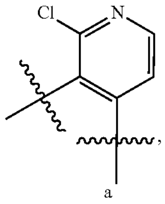

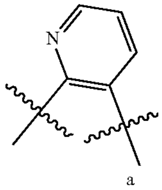

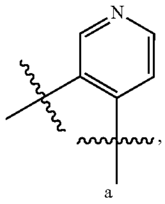

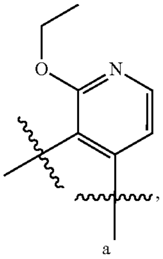

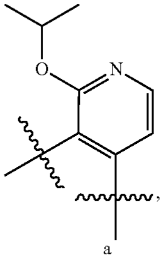

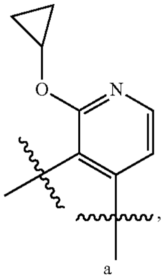

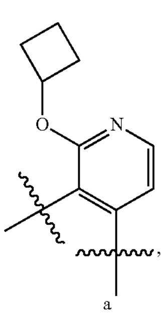

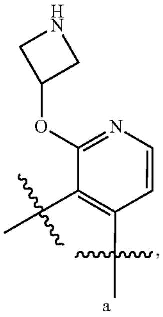

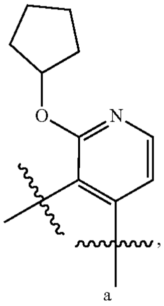

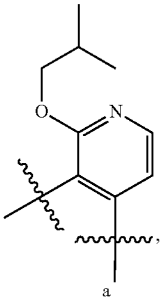

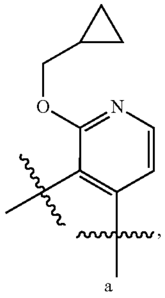

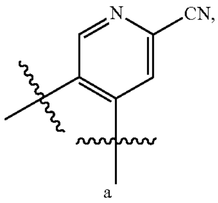

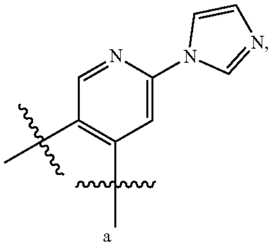

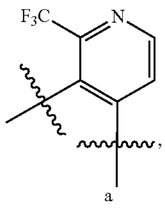

-continued
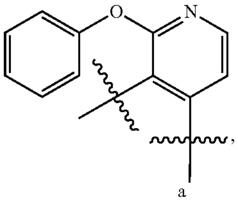
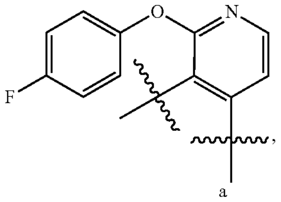
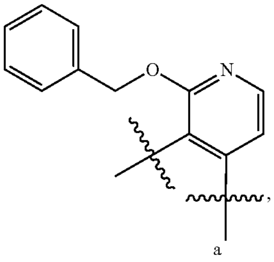
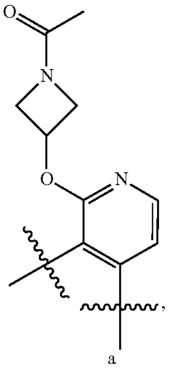
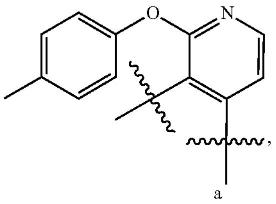
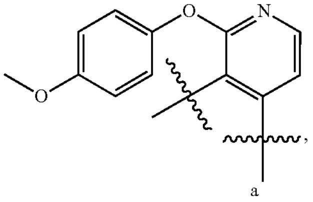
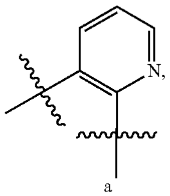
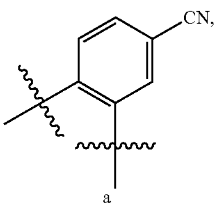
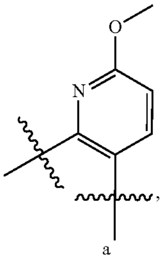
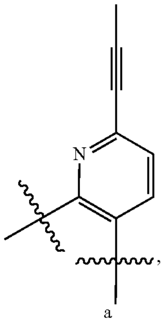
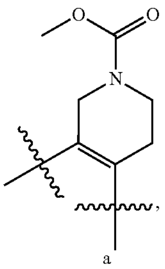
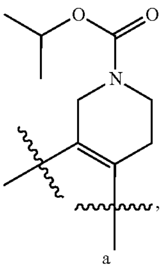
-continued
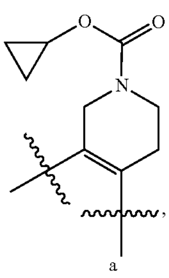
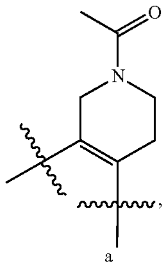
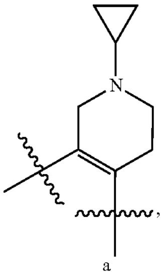
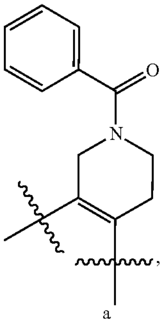
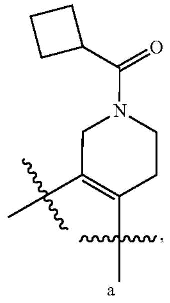
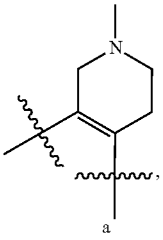
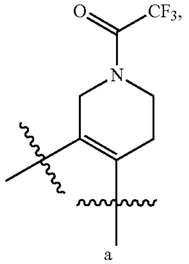
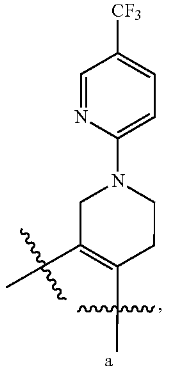
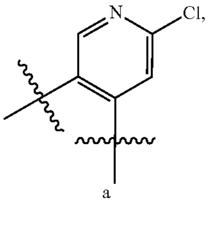
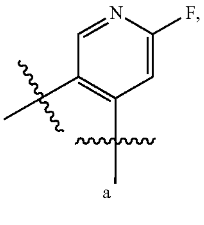

-continued
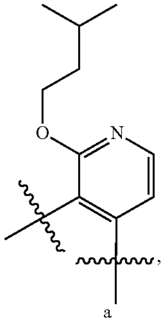
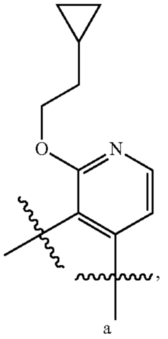
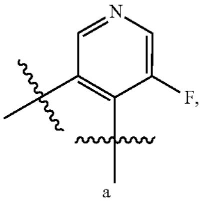
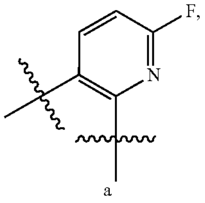
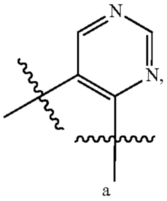
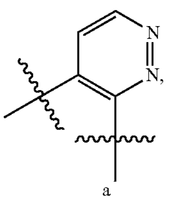
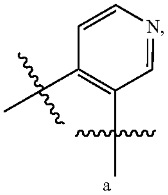
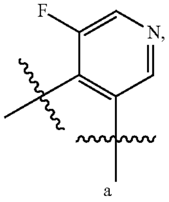
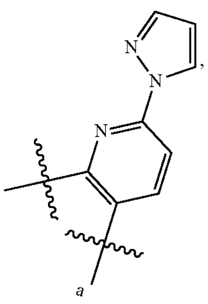
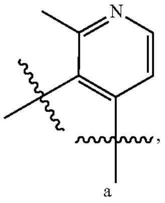
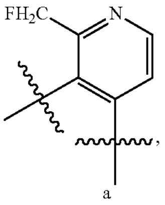
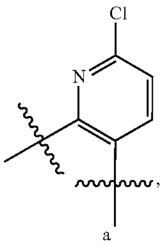
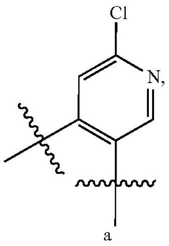
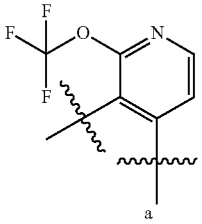
-continued
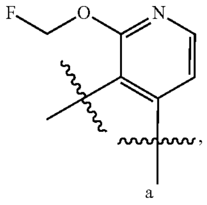
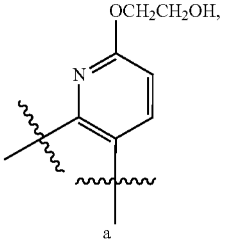
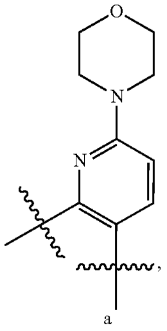
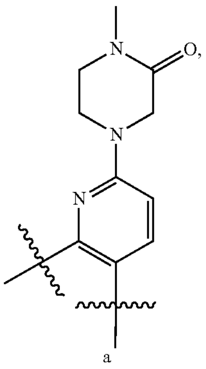
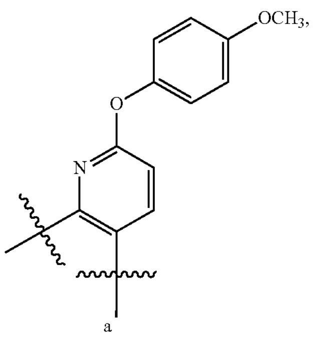
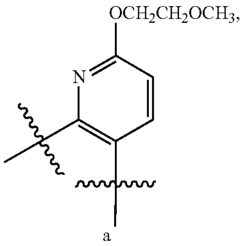
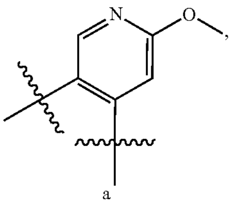
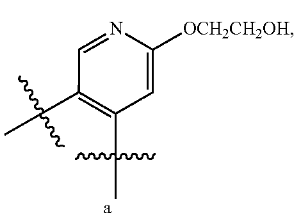

-continued
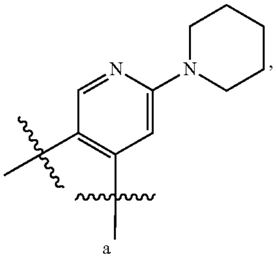
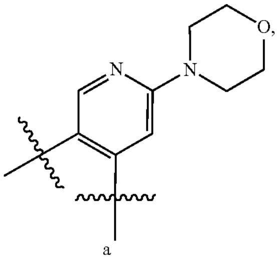
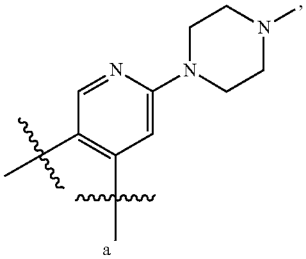
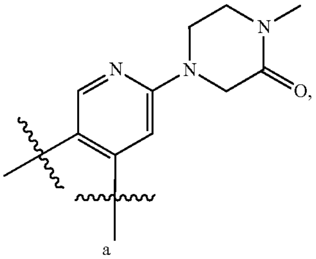
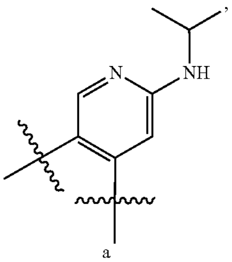
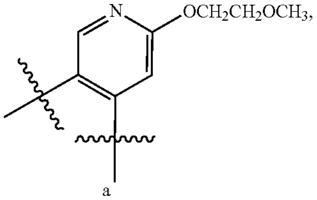
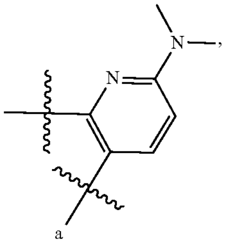
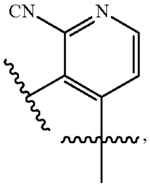
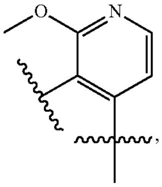
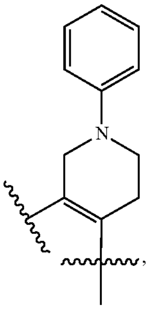
-continued
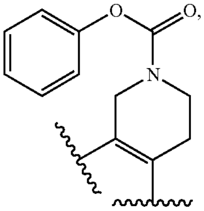
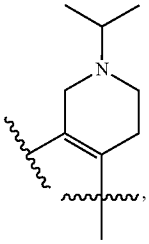
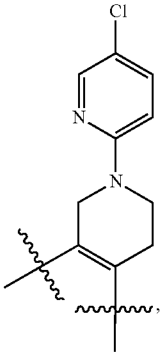
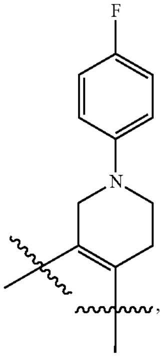
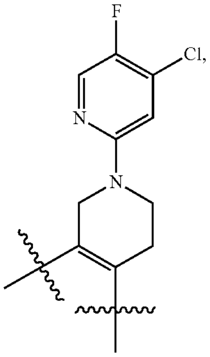
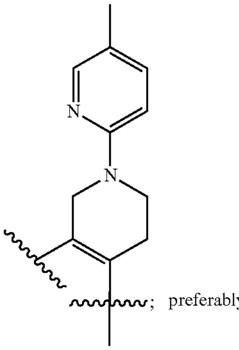
; preferably
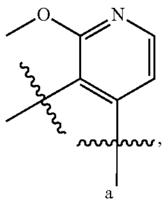
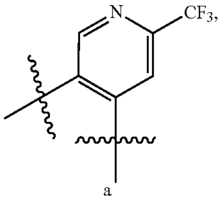
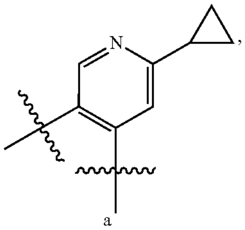

-continued
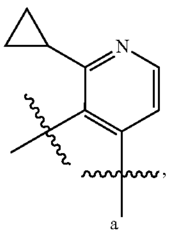,
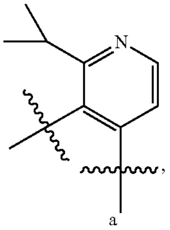,
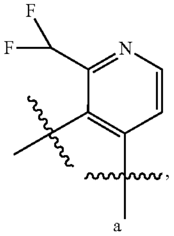,
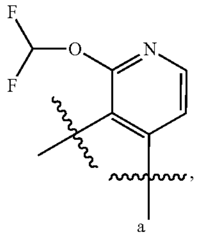,
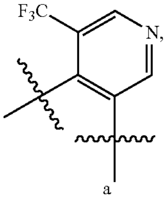,
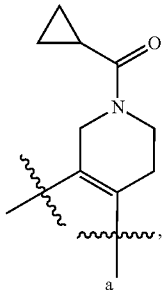,
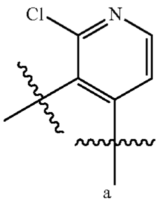
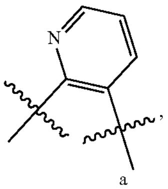,
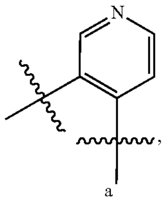,
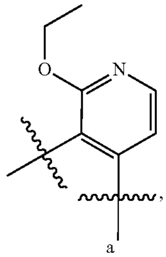,
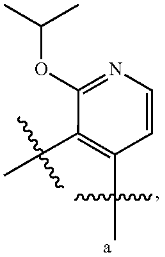,
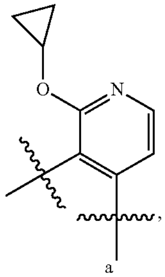,
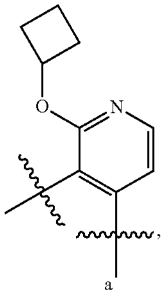,
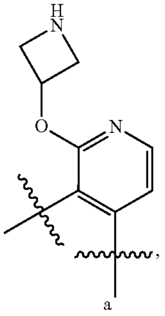,
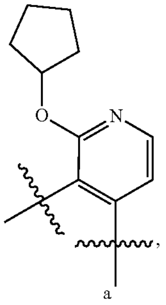,
-continued
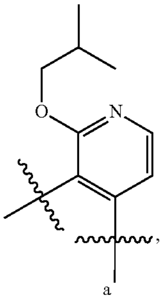,
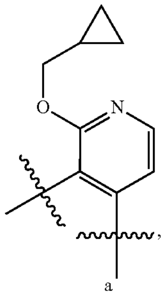,
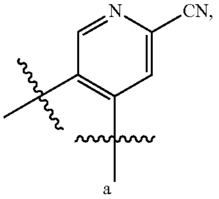,
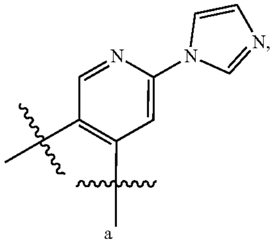,
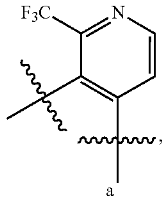,
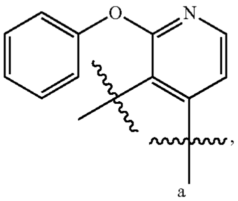,
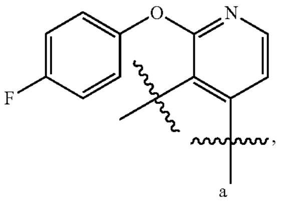,
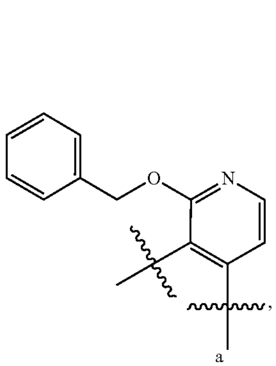,
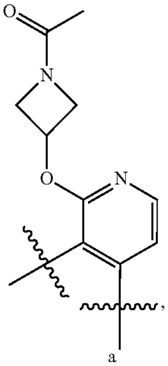,
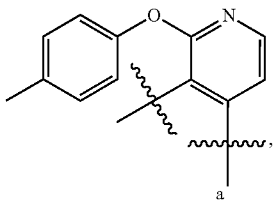, -continued
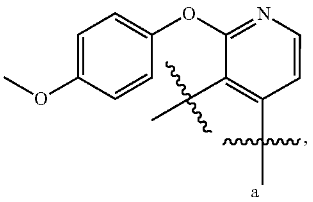
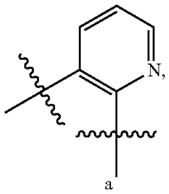
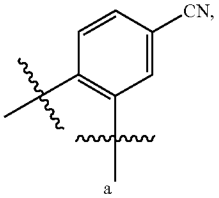
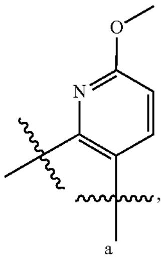
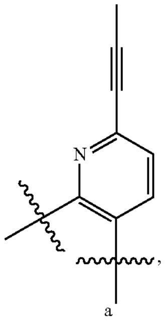
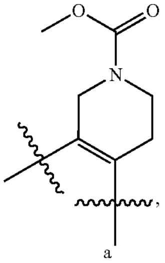
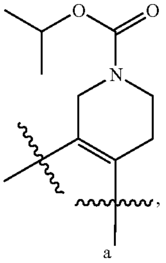
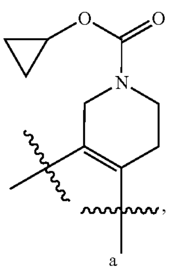
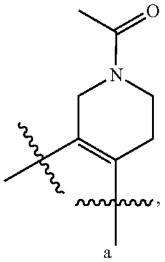
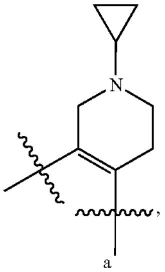
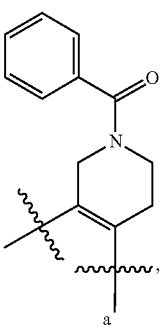
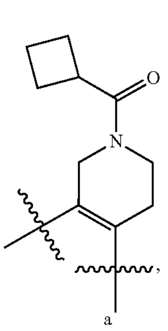
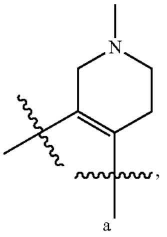
-continued
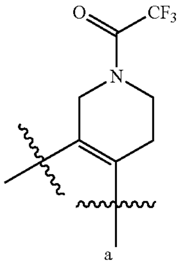
or
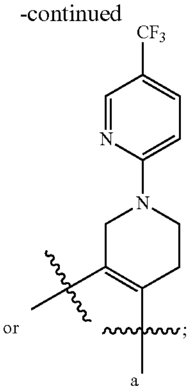
more preferably
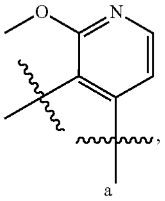
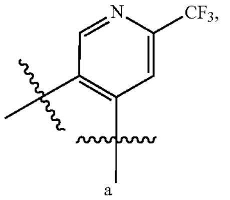
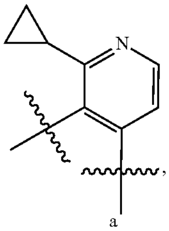
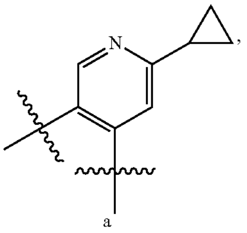
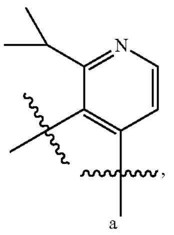
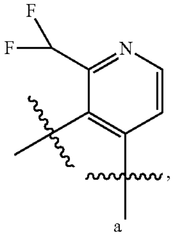
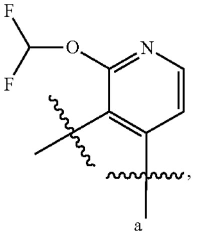
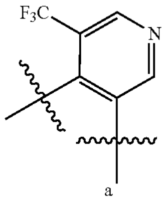
or
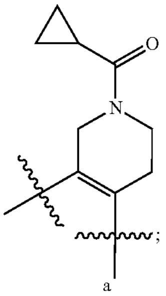
a end represents the position connected to $Z^{10}$.
In some embodiments, the compound represented by formula I is any of the following compound:

1
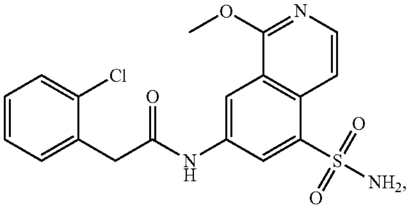
2
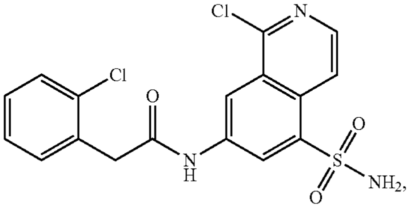
3
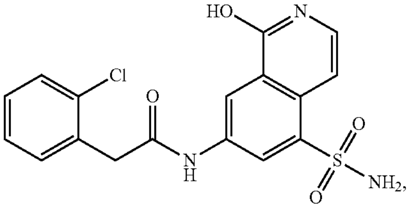
4
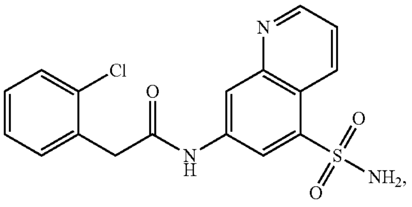
5
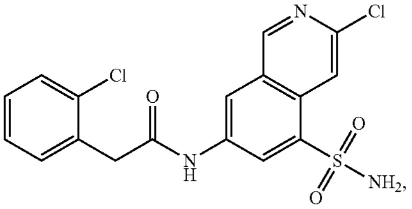
6
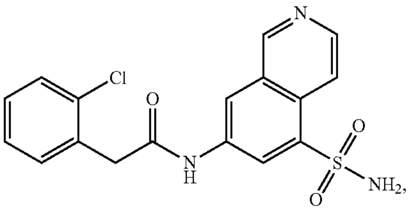
7
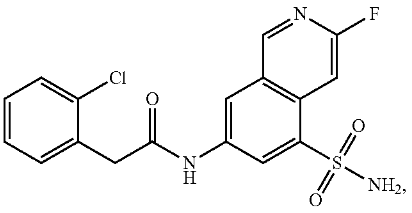
-continued
8
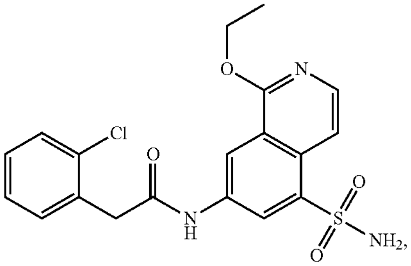
9
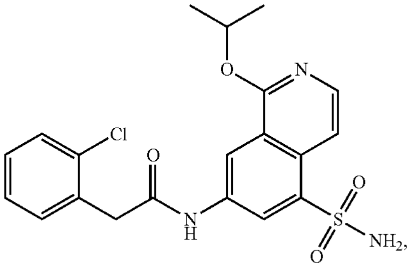
10
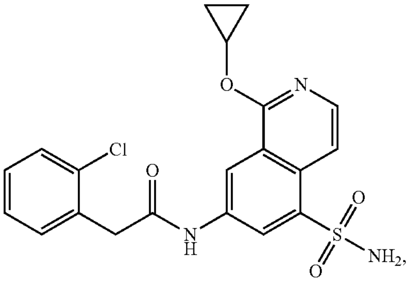
11
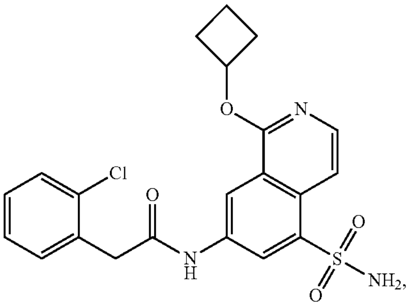
12
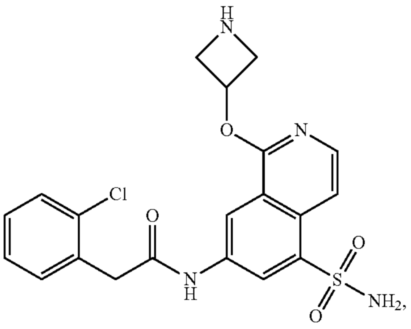

13
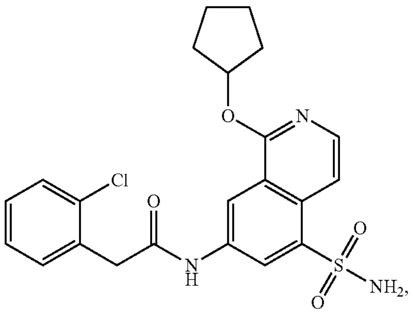
14
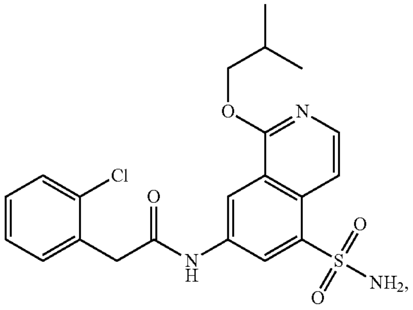
15
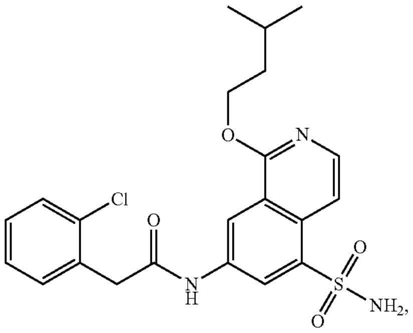
16
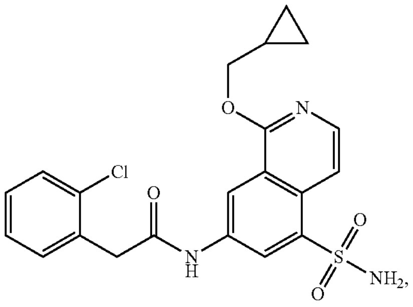
17
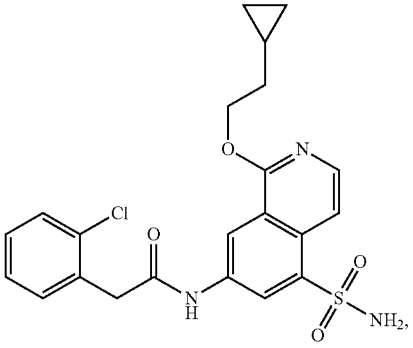
18
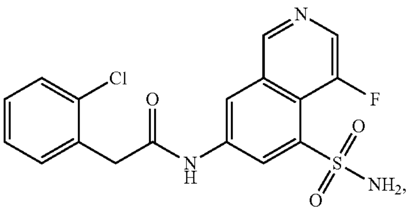
19
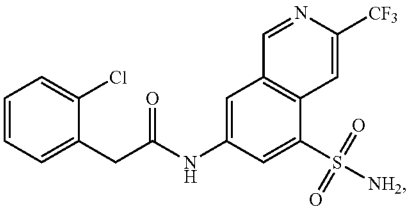
20
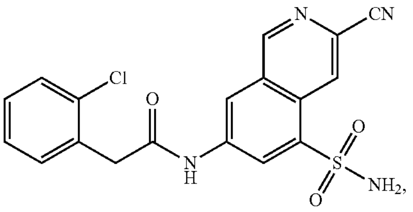
21
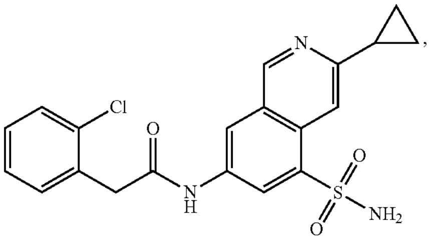
22
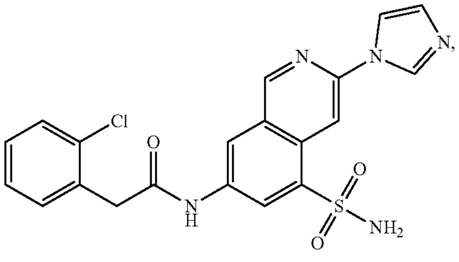
23
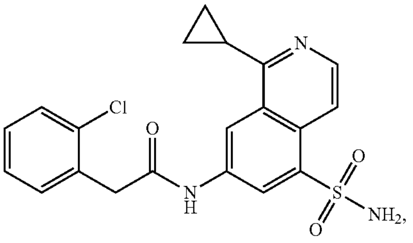

-continued
24
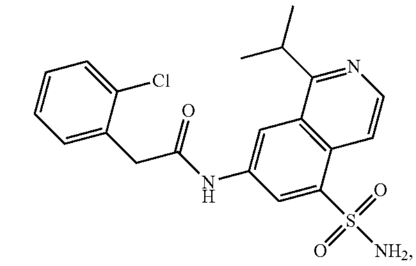
25
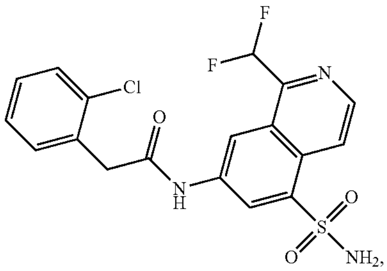
26
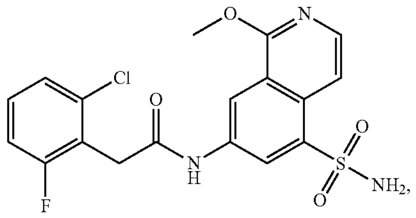
27
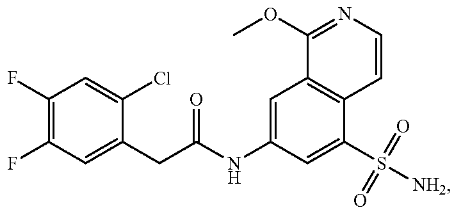
28
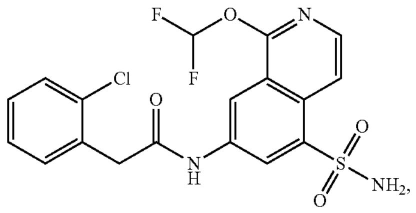
29
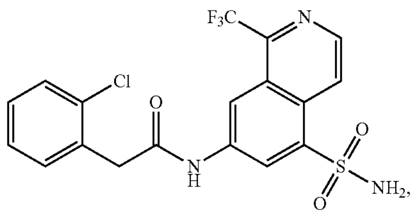
-continued
30
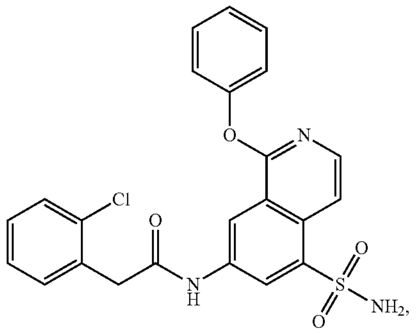
31
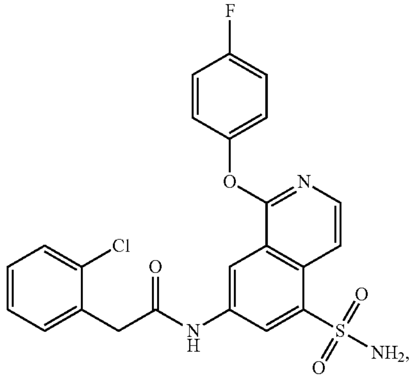
32
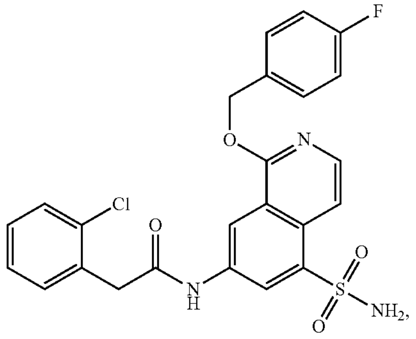
33
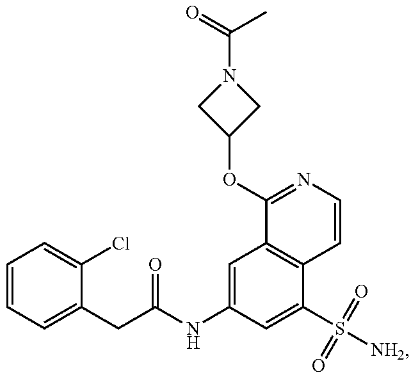

-continued
34
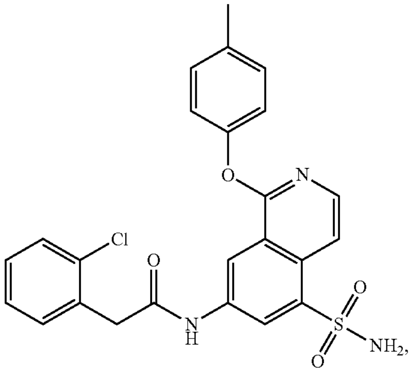
35
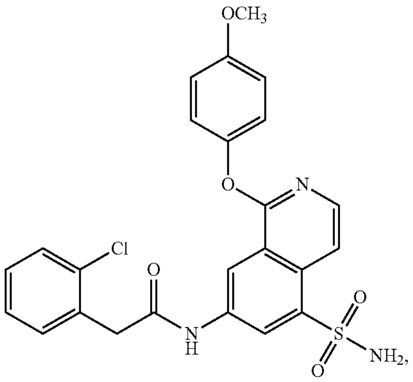
36
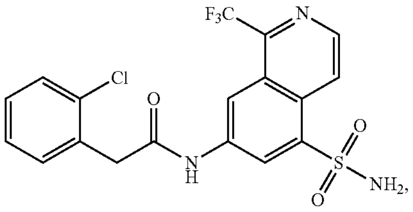
37
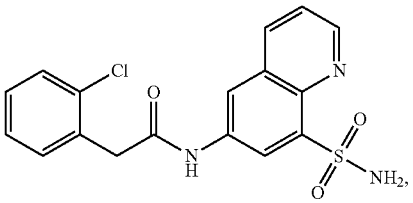
38
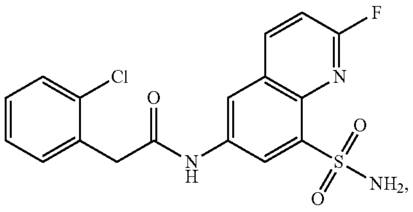
-continued
39
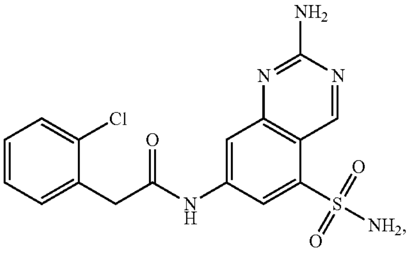
40
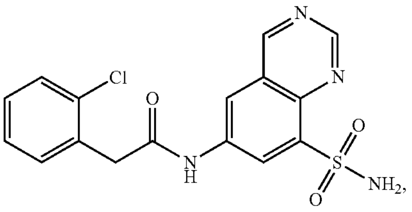
41
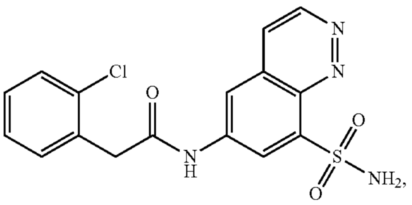
42
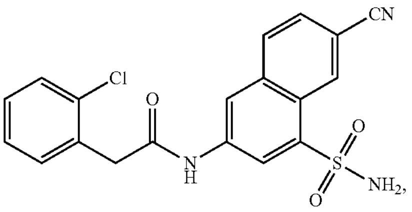
43
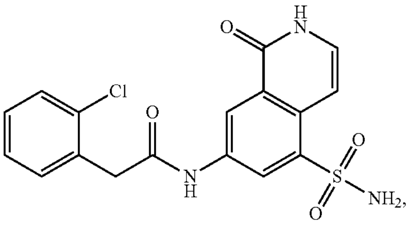
44
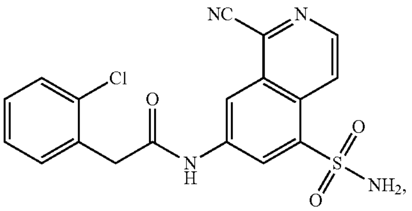
45
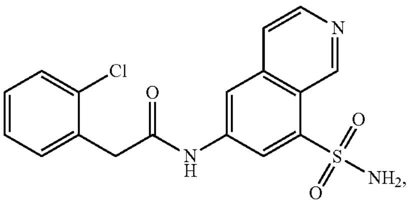

-continued
46
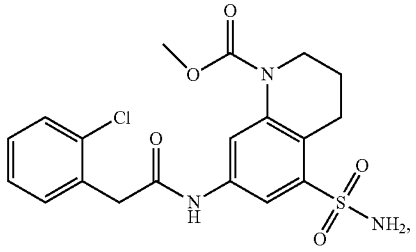
47
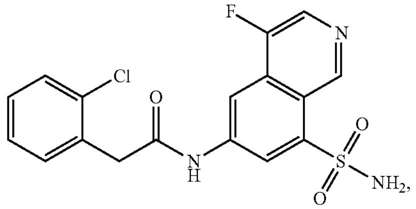
48
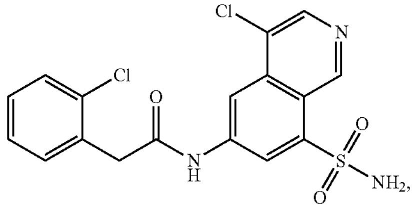
49
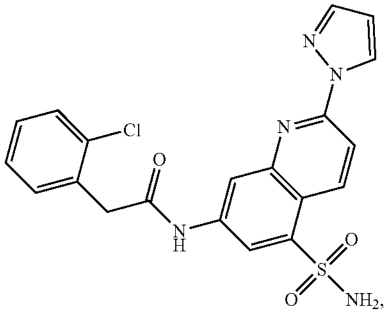
50
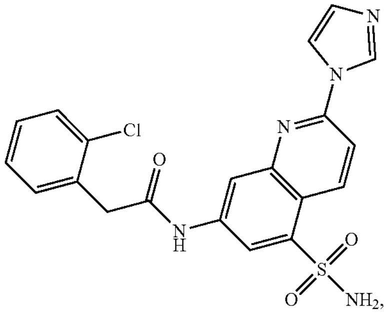
51
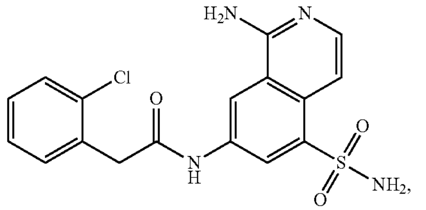
-continued
52
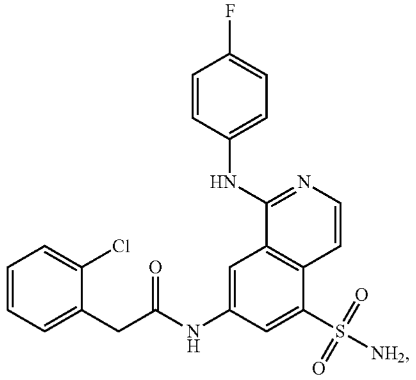
53
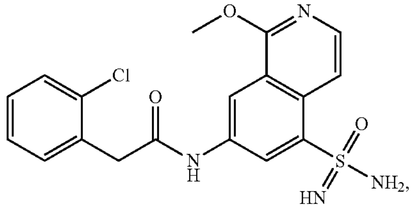
54
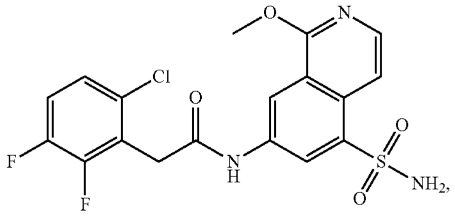
55
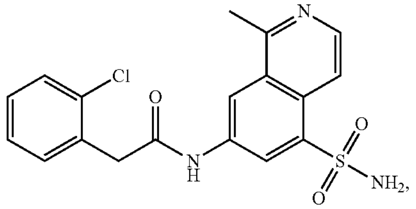
56
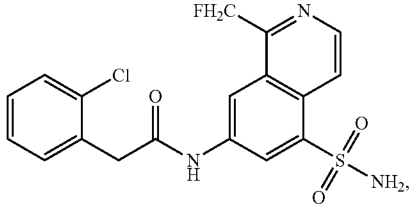
57
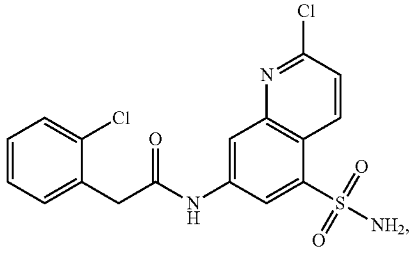

-continued
58
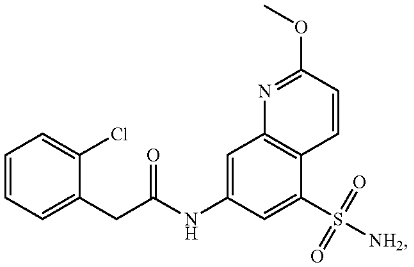
59
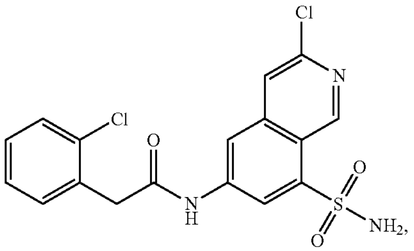
60
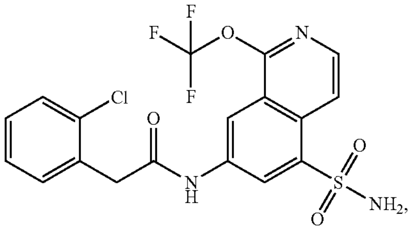
61
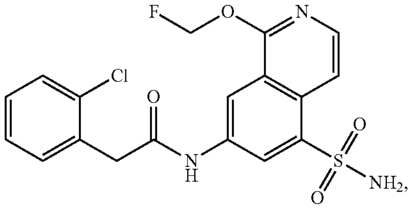
62
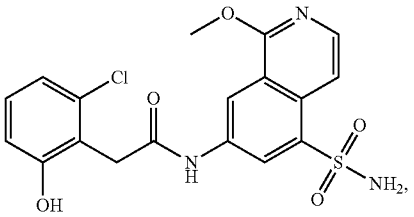
63
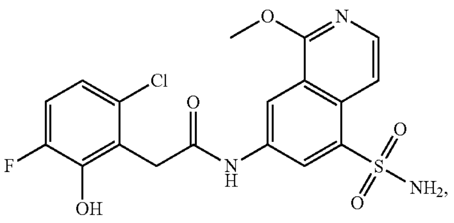
-continued
64
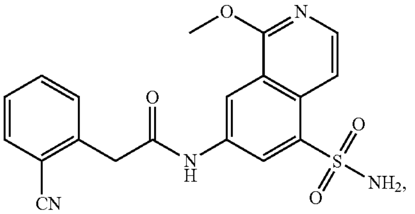
65
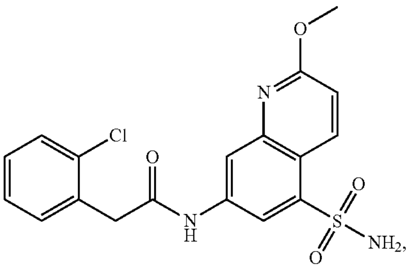
66
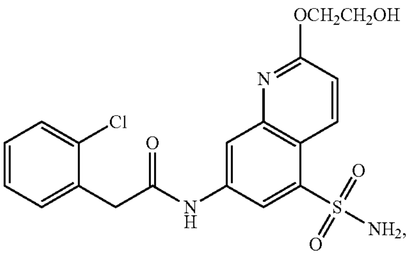
67
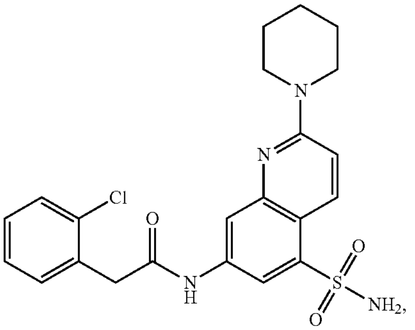
68
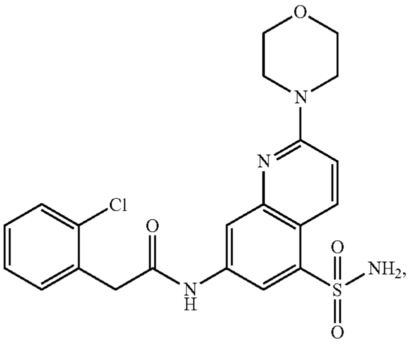

-continued
69
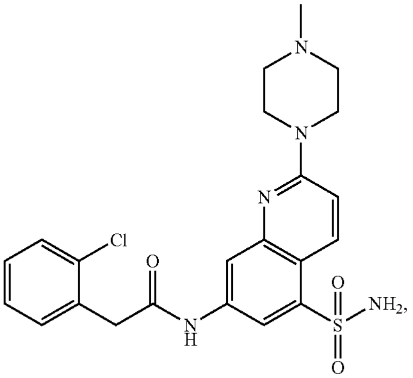
70
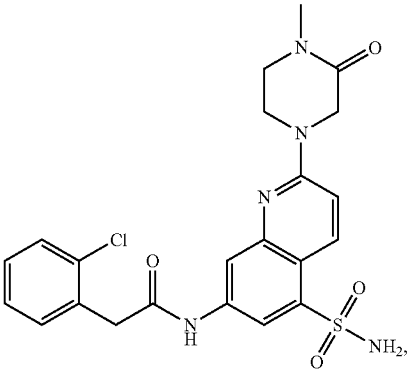
71
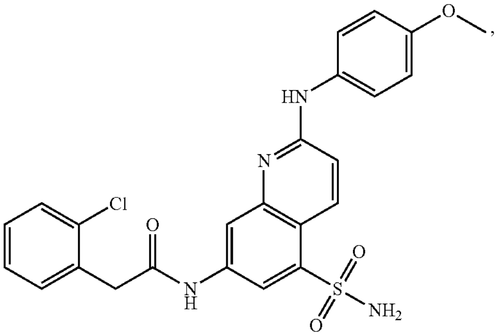
72
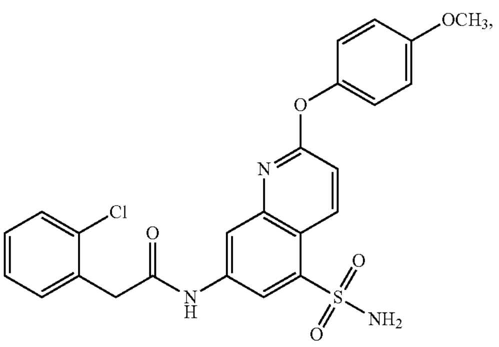
-continued
73
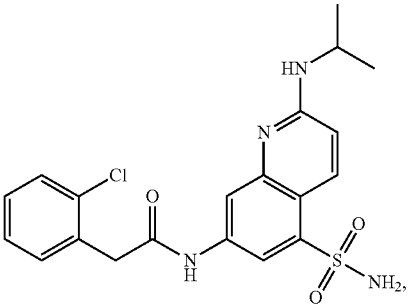
74
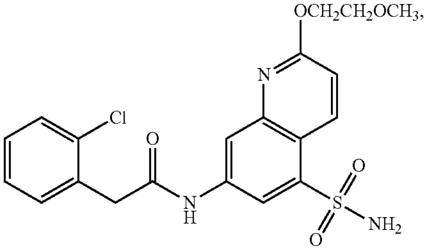
75
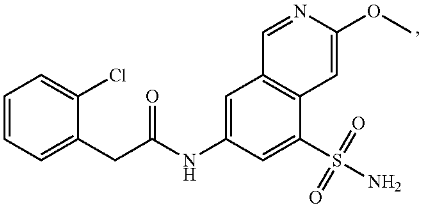
76
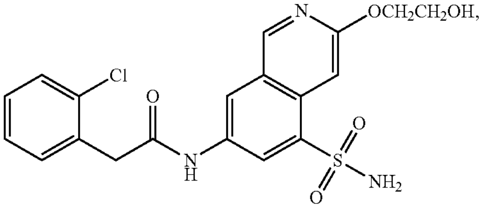
77
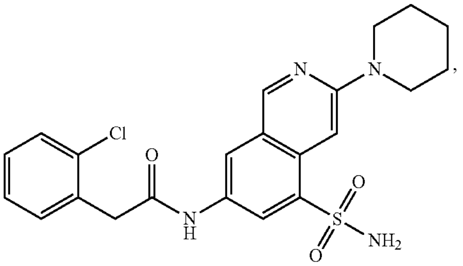
78
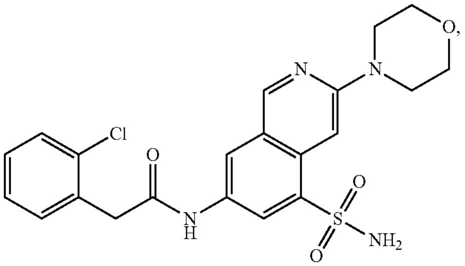

-continued
79
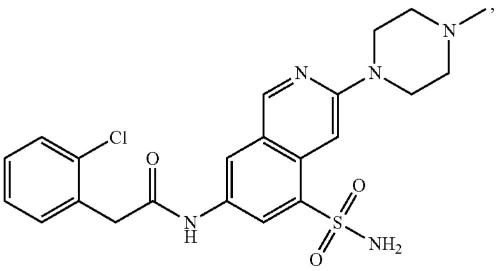
80
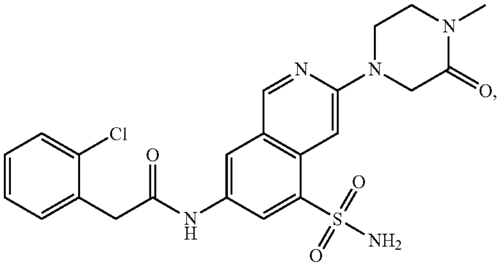
81
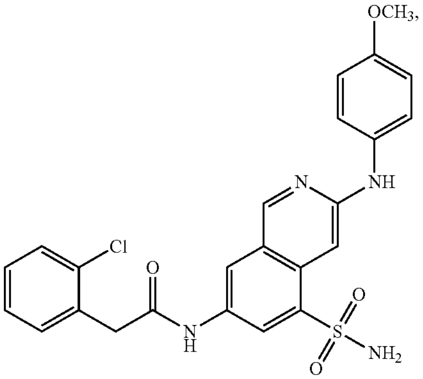
82
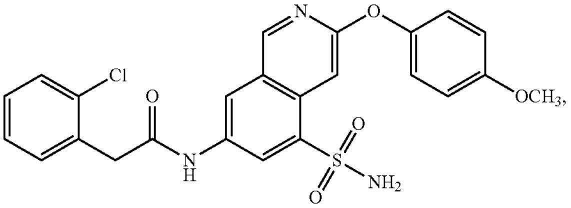
83
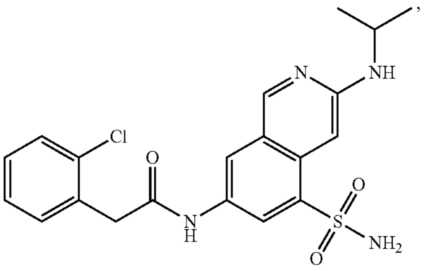
-continued
84
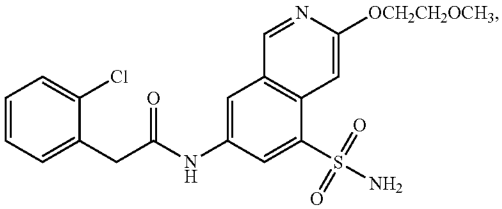
85
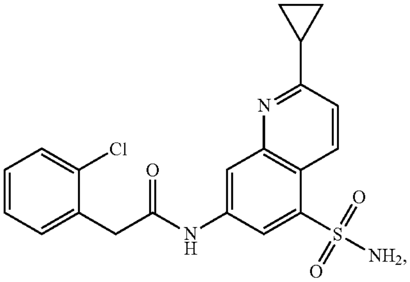
86
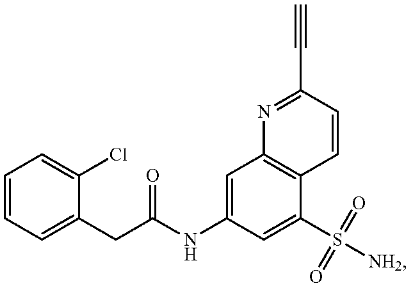
87
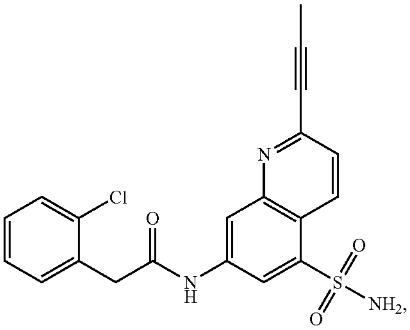
88
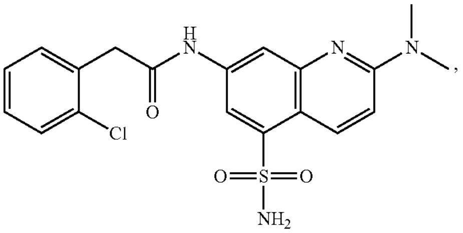
89
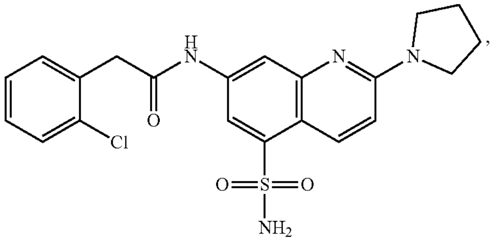

-continued
91
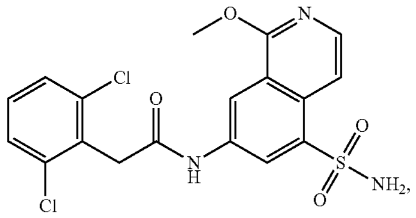
92
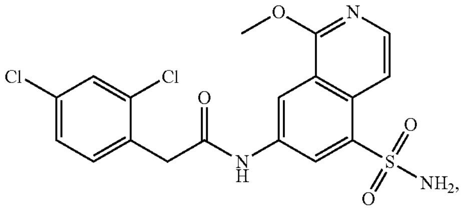
93
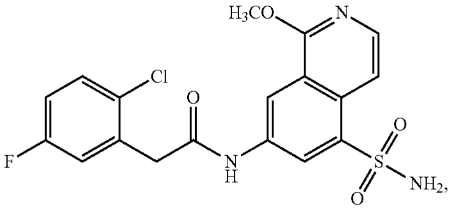
94
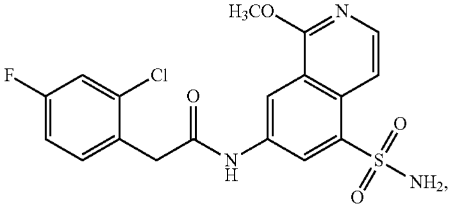
95
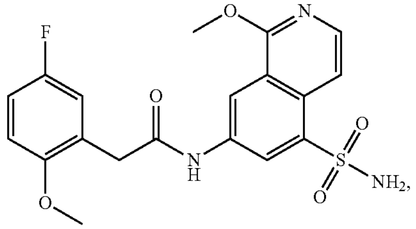
96
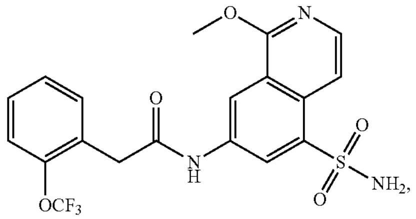
97
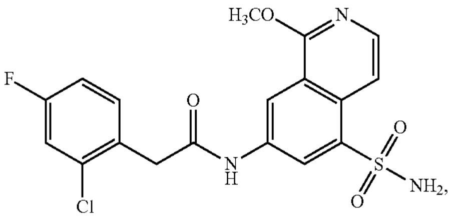
-continued
98
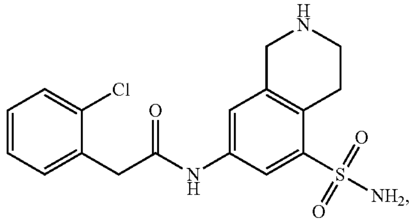
99
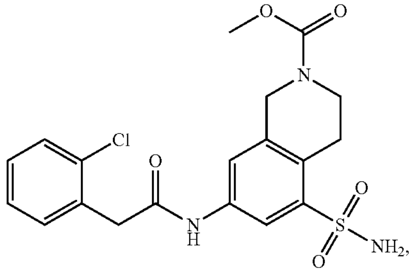
100
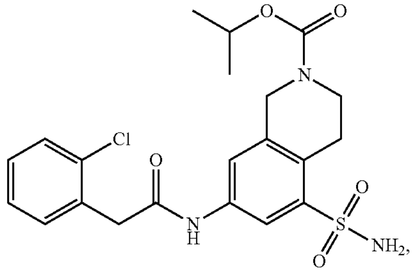
101
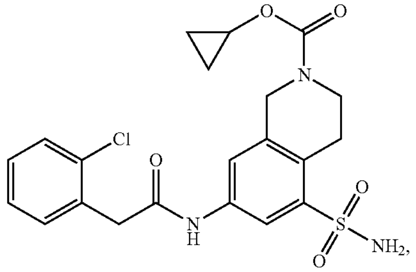
102
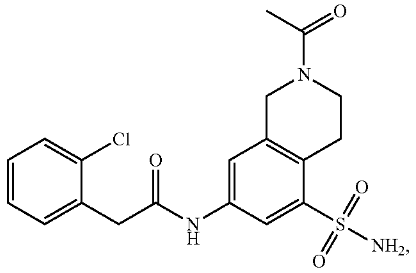
103
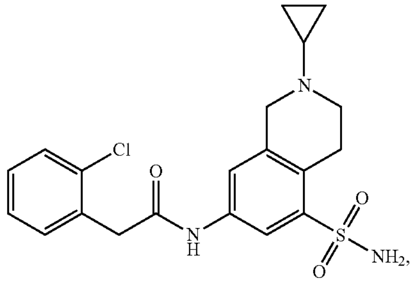

104
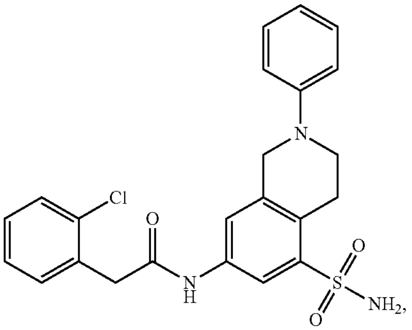
105
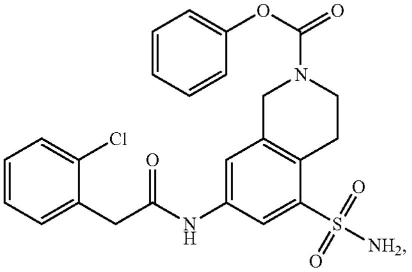
106
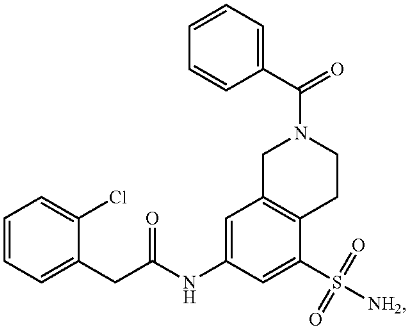
107
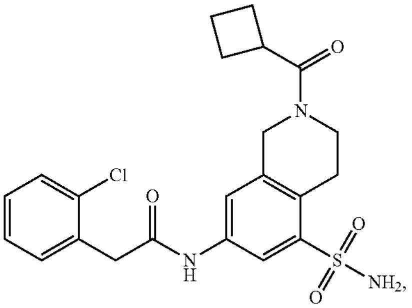
108
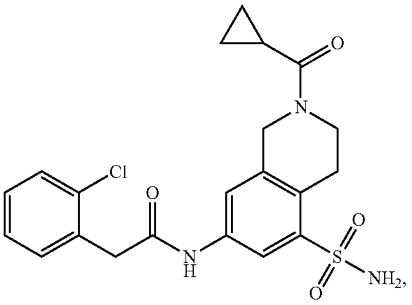
109
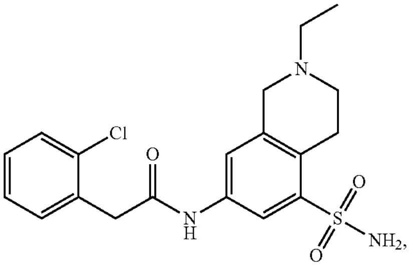
110
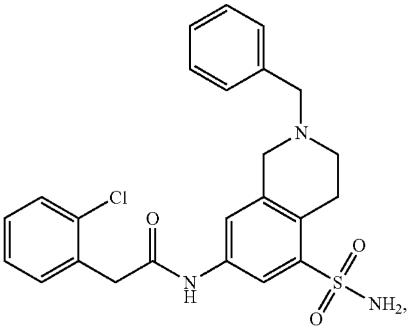
111
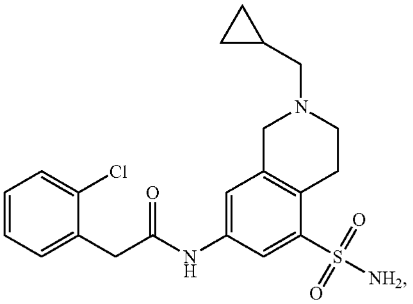
112
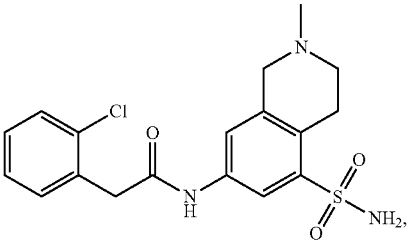
113
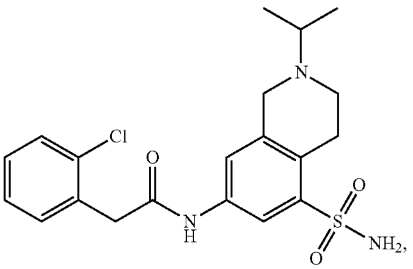

-continued
114
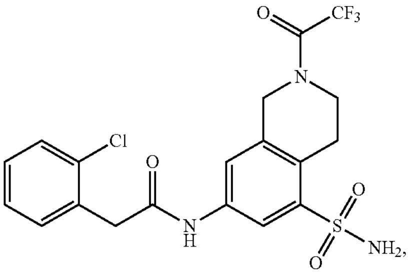
115
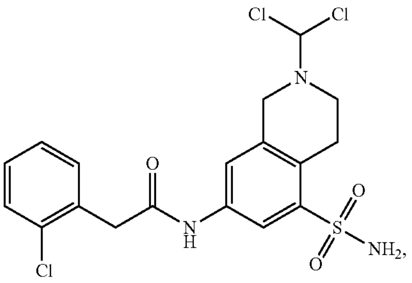
116
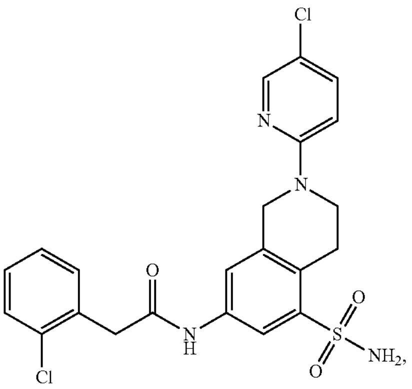
117
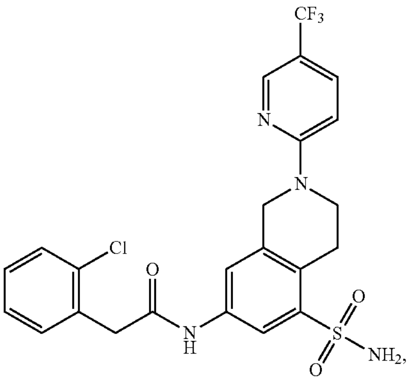
-continued
118
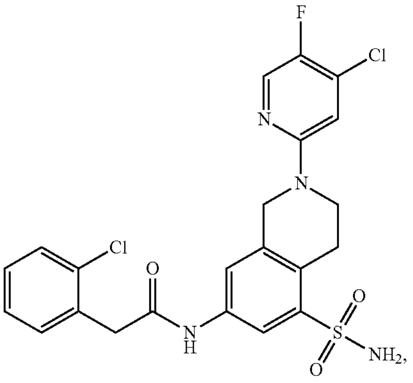
119
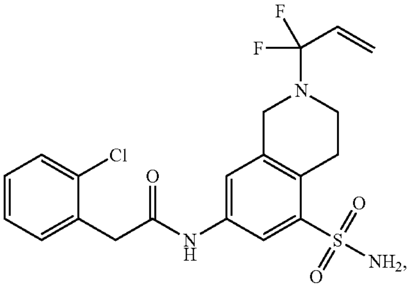
120
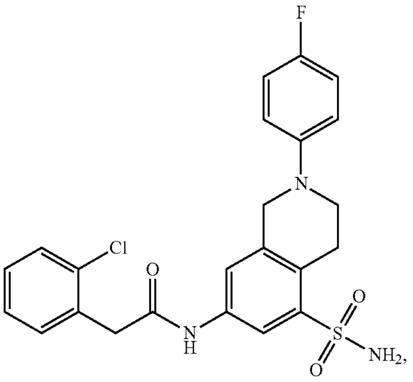
121
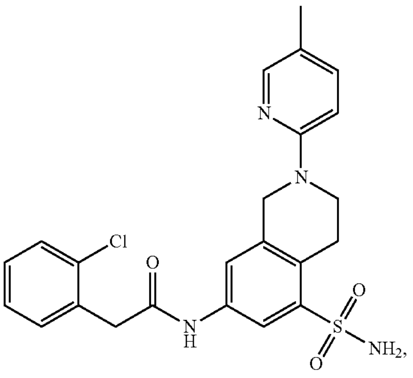

-continued

122

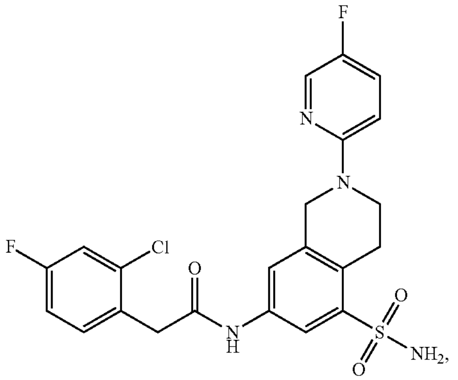

123

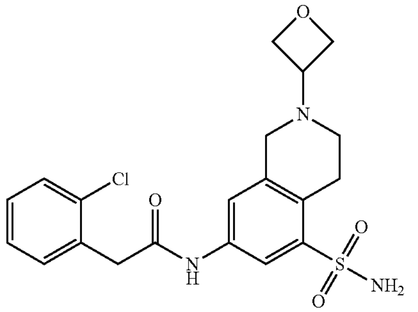

or 85-1

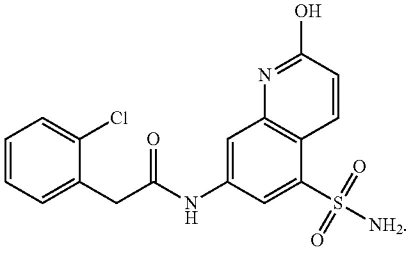

In some embodiments, the pharmaceutically acceptable salt of the compound represented by formula I is the following compound:

trifluoroacetate of

71

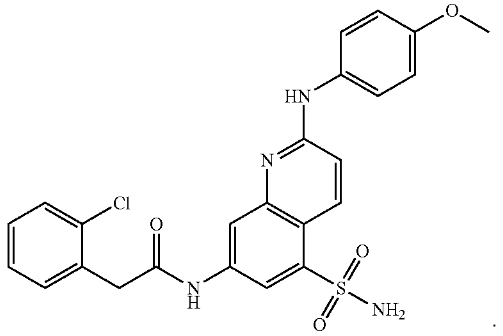

The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as described in the present disclosure can be synthesized by similar methods known in the chemical field, or by the method described in the present disclosure.

The present disclosure provides a preparation method of the compound represented by formula I, and the method is any of the following schemes:

scheme 1: in solvent, under the action of a base, a compound represented by formula II is subjected to the following reaction to obtain the compound represented by formula I,

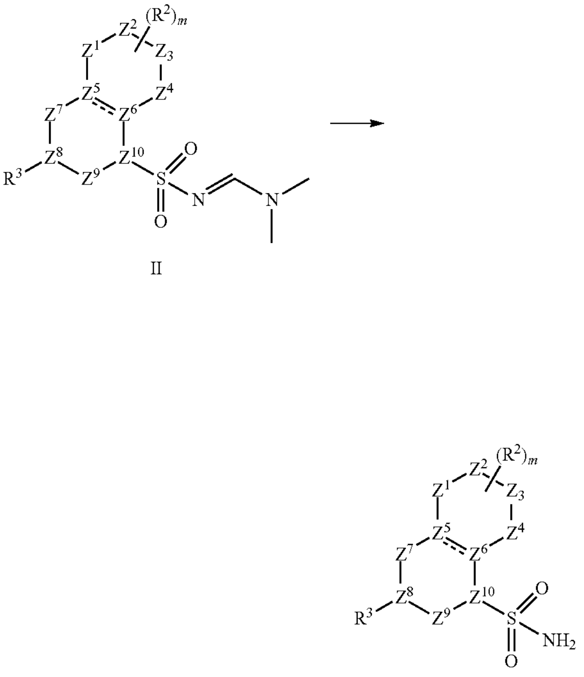

II

I wherein, the base can be sodium ethoxide, ammonia or water hydrazine;

scheme 2: in solvent, a compound represented by formula III and ammonia are subjected to the following reaction to obtain the compound represented by formula I,

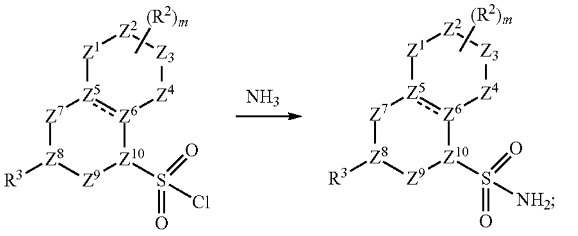

III

I scheme 3: in solvent, under the action of trifluoroacetic acid, a compound represented by formula IV is subjected to the following reaction to obtain the compound represented by formula

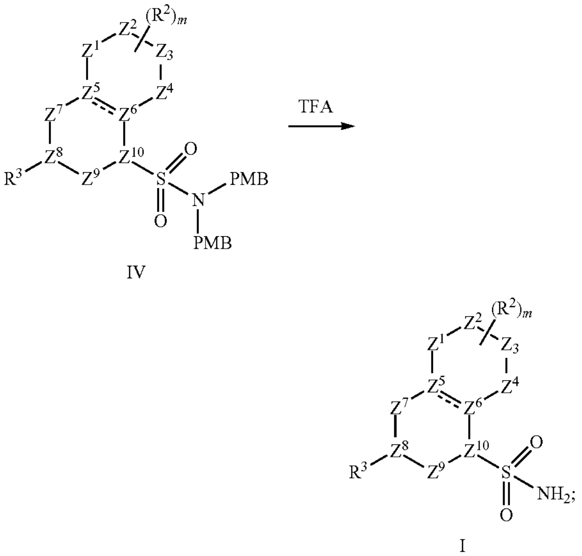
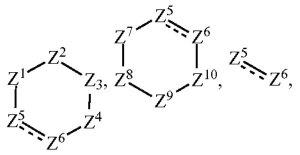
m, $R^2$ and $R^3$ are defined as above.
The preparation conditions of the compound represented by formula I can be conventional in the art.
The present disclosure also provides a compound represented by formula II, III or IV,
II
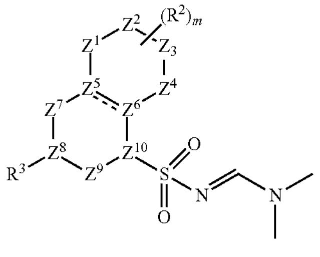
III
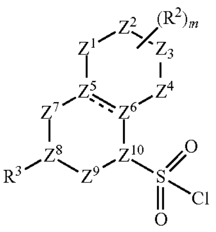
-continued
IV
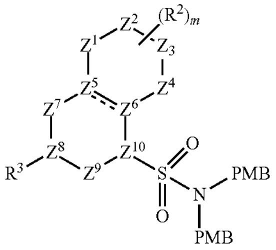
wherein, 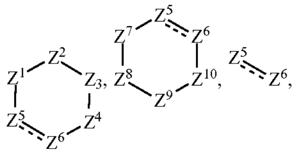
m, $R^2$ and $R^3$ are defined as above.
In some embodiments, the compound represented by formula II is
1-8
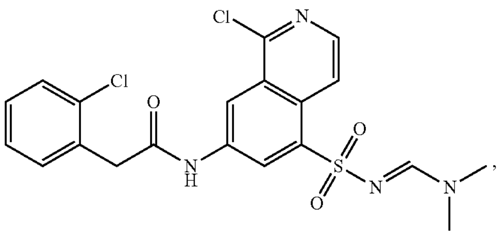
3-1
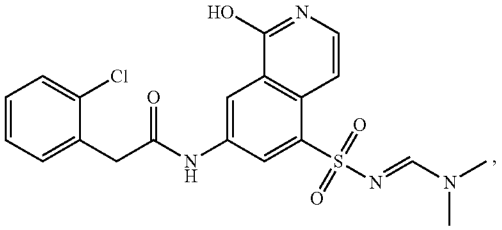
5-8
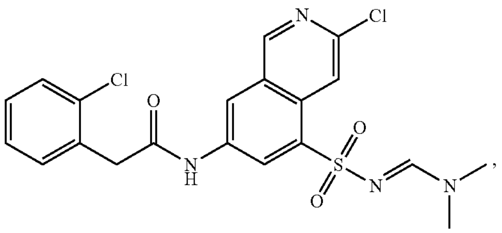
26-2
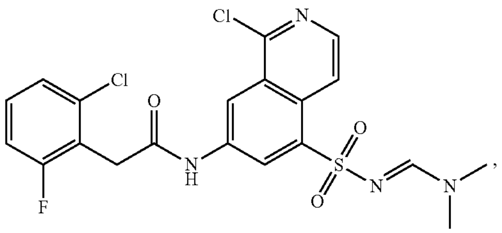

-continued
31-1
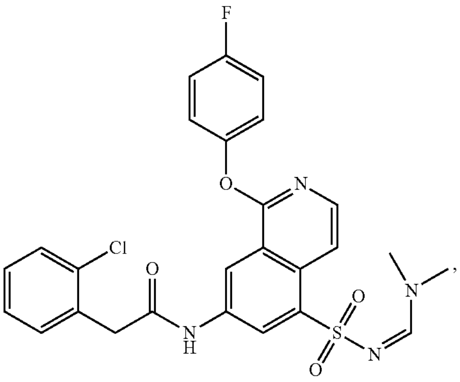
71-1
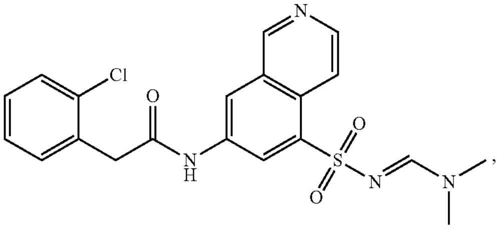
71-2
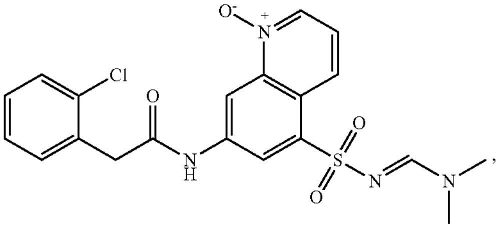
71-3
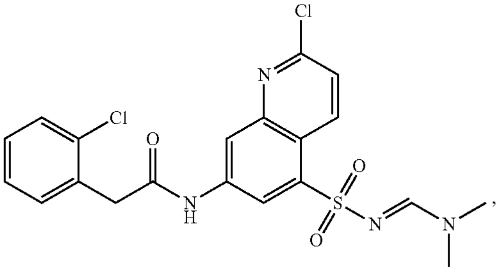
71-5
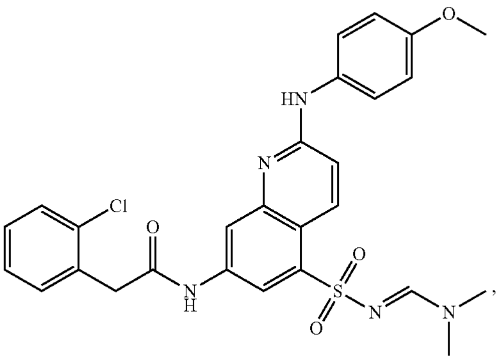
-continued
85-2
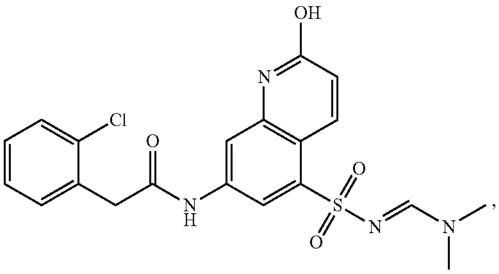
85-3
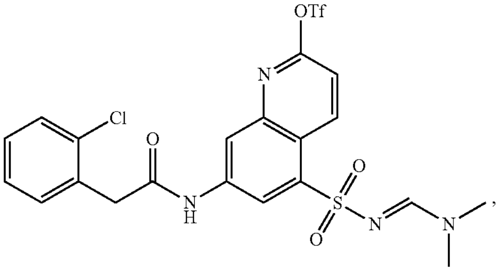
85-4
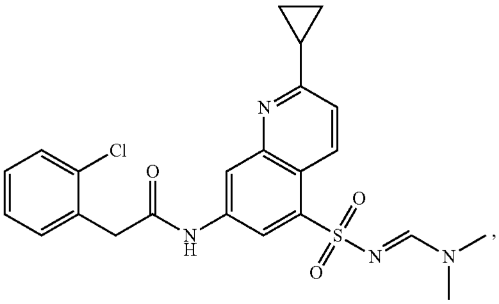
86-1
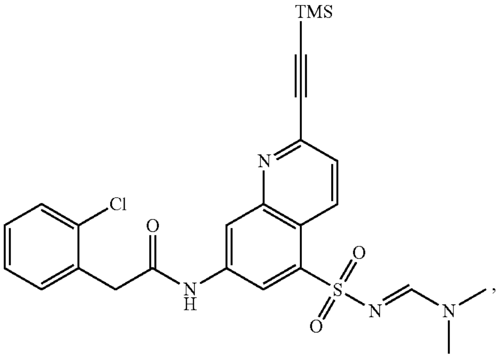
86-2
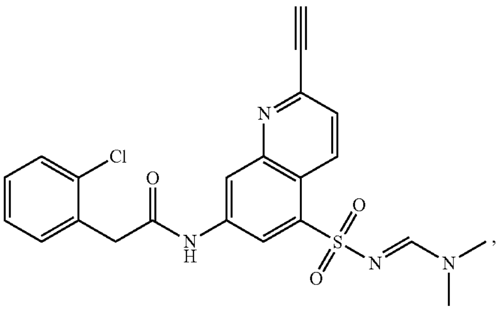

-continued
87-2
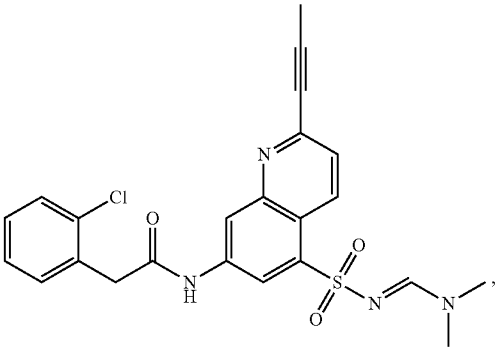
98-5
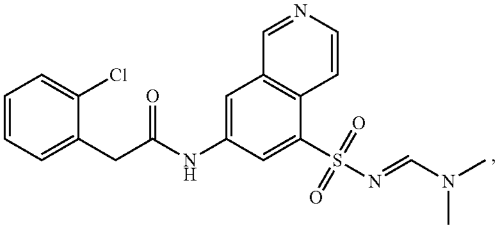
98-6
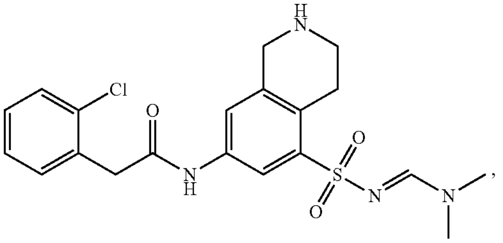
99-2
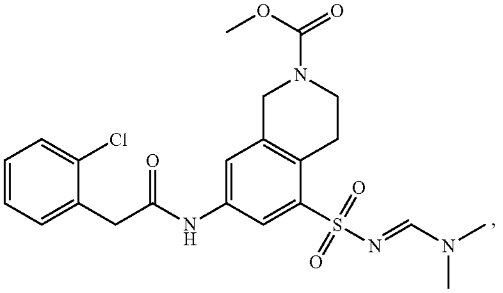
103-2
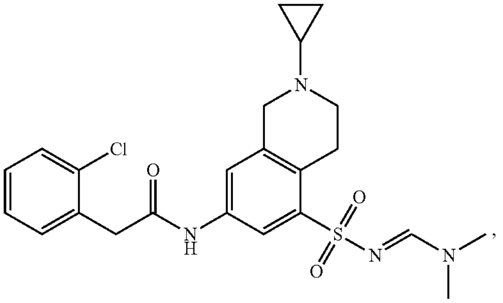
-continued
106-2
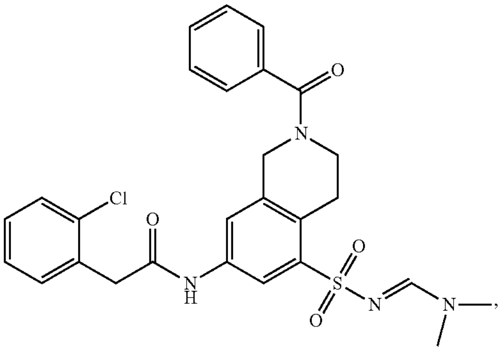
107-2
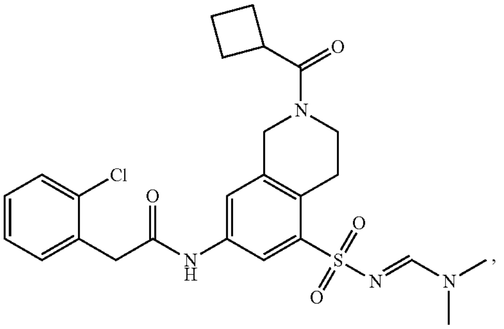
108-2
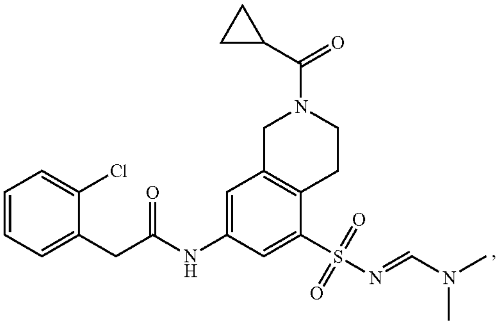
109-1
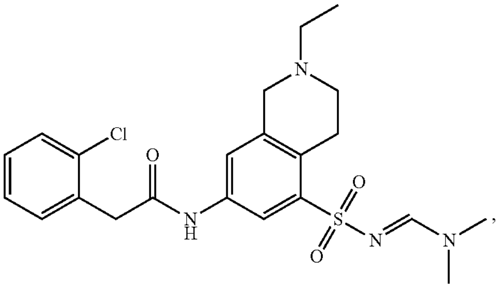

-continued
110-1
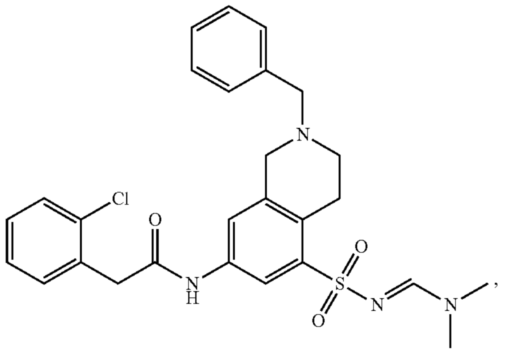
111-2
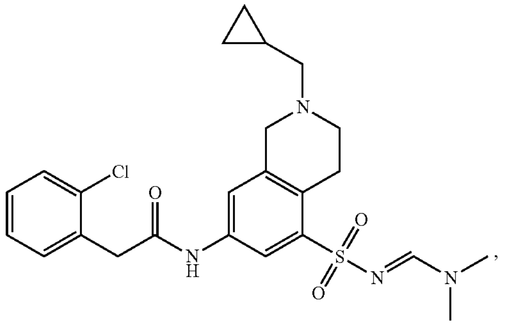
112-1
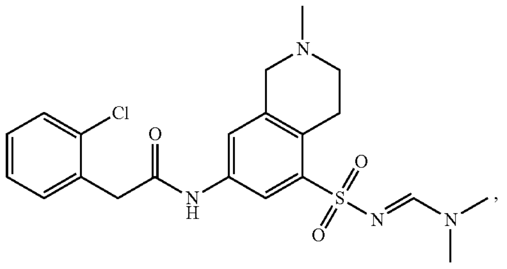
113-1
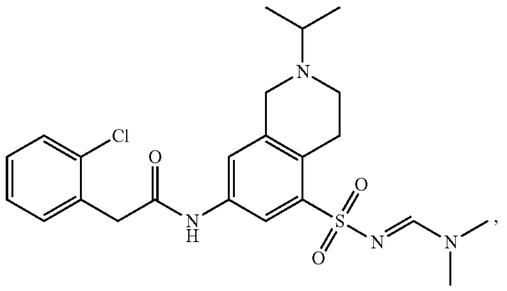
115-1
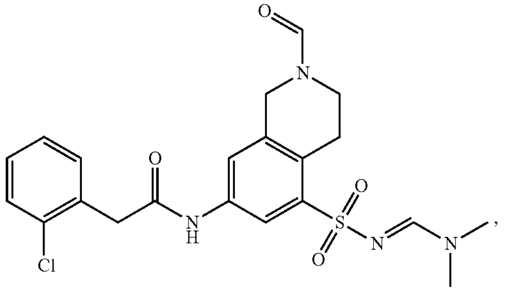
-continued
115-2
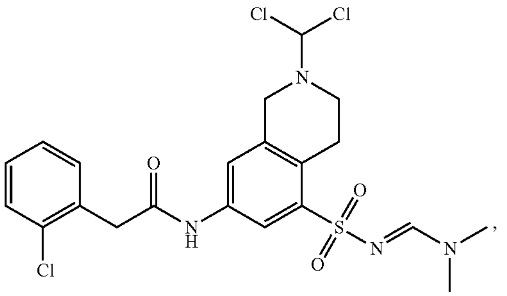
116-2
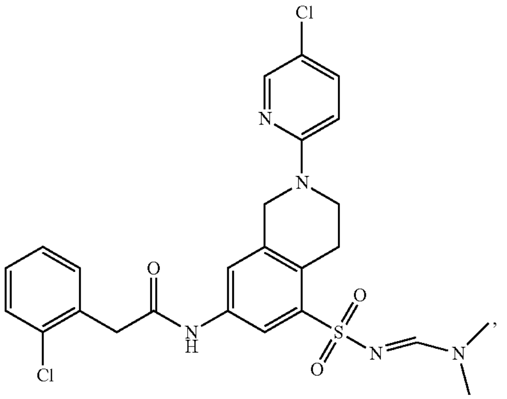
117-2
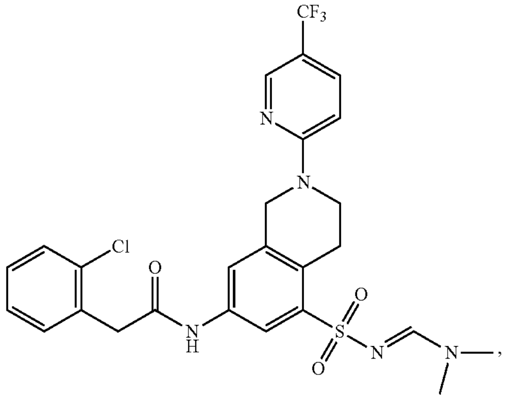
118-2
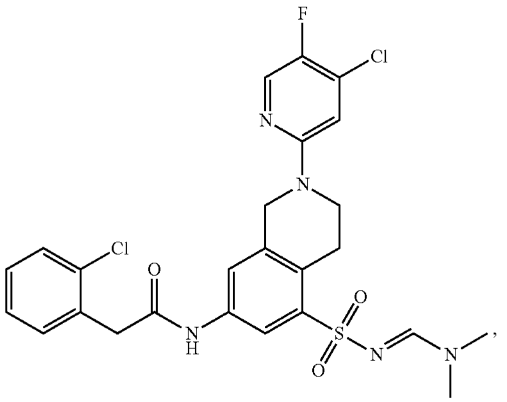

-continued
119-2
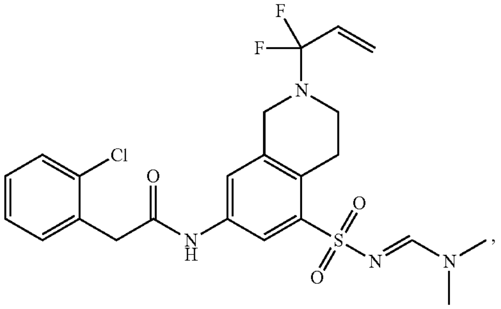
120-2
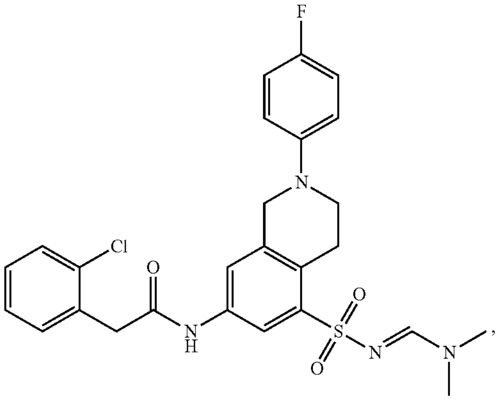
121-2
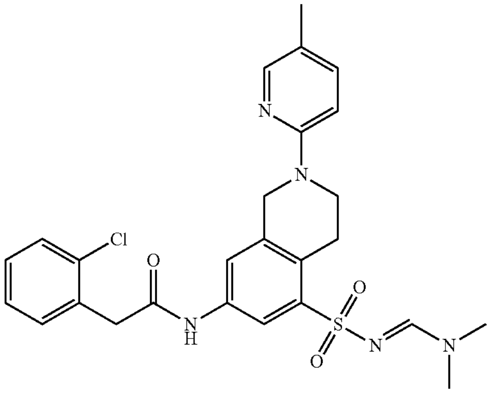
or
123-2
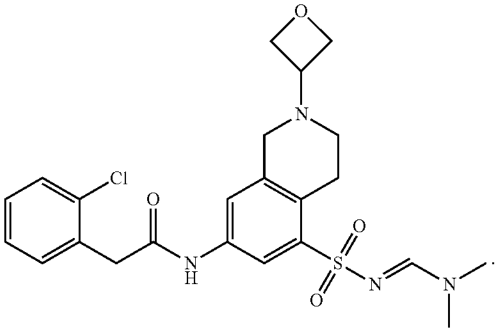
In some embodiments, the compound represented by formula III is
4-9
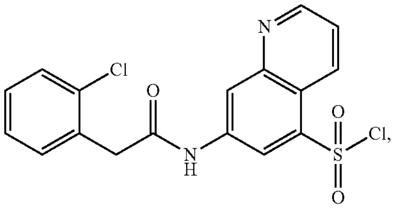
65-7
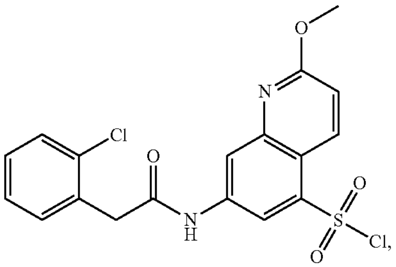
68-5
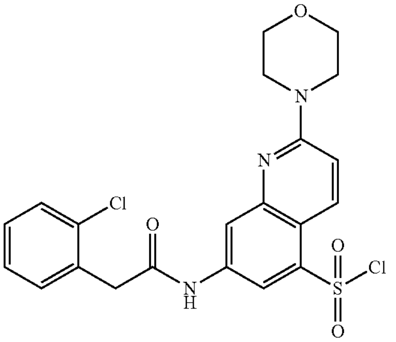
or
69-3
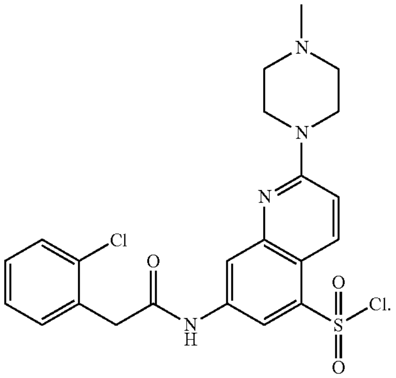
In some embodiments, the compound represented by formula IV is
6-5
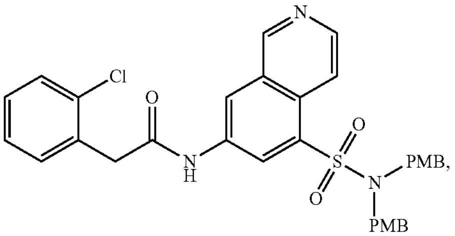

-continued
24-6
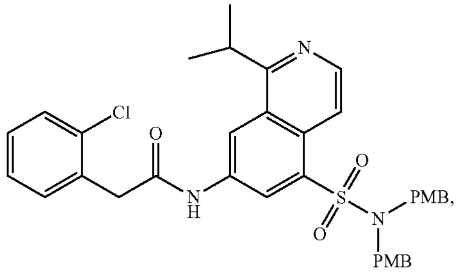
25-5
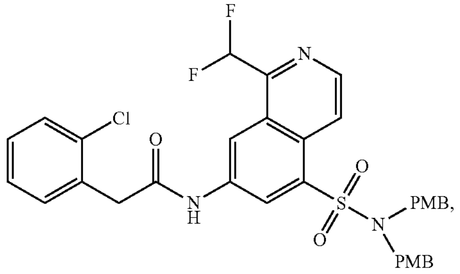
28-4
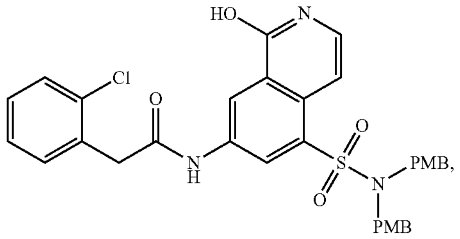
28-6
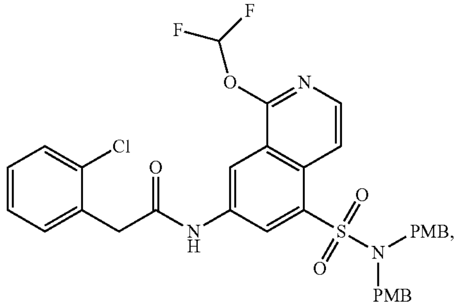
37-4
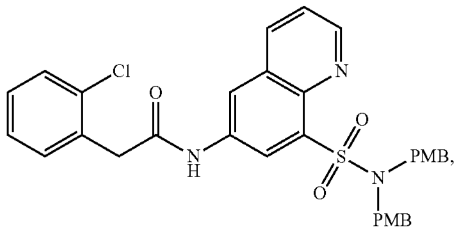
42-10
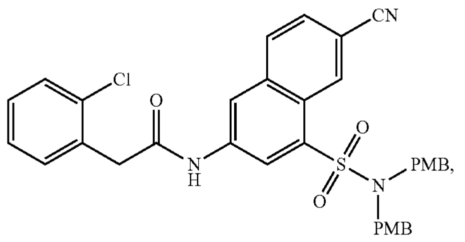
-continued
54-3
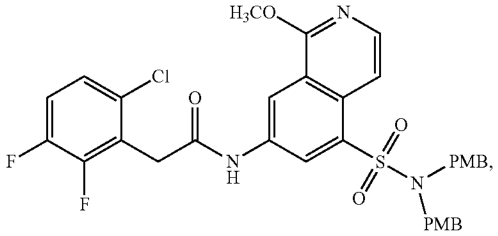
55-6
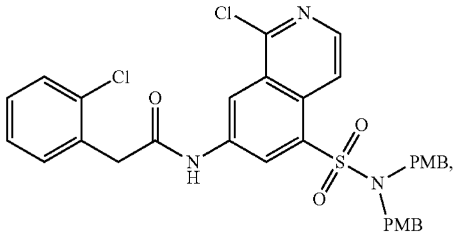
55-7
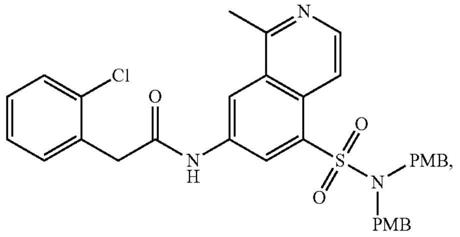
57-1
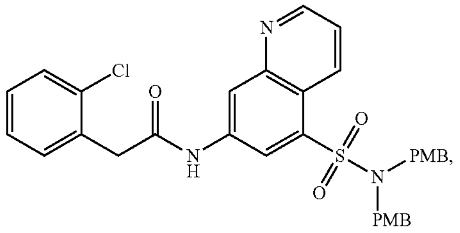
57-2
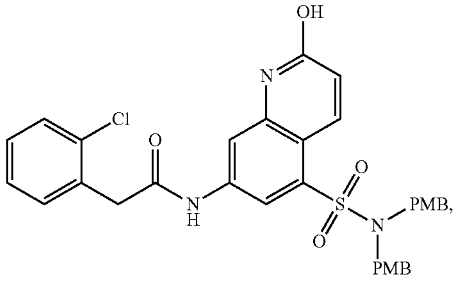
57-3
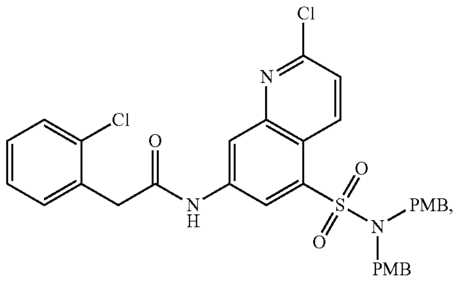

-continued
90-4
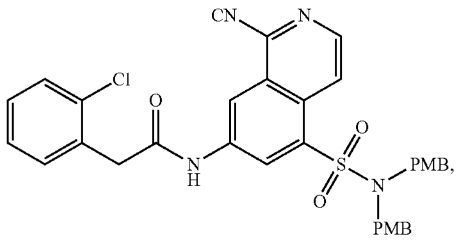
92-2
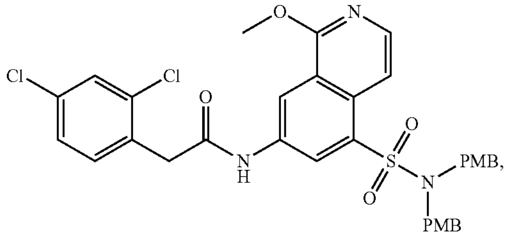
93-1
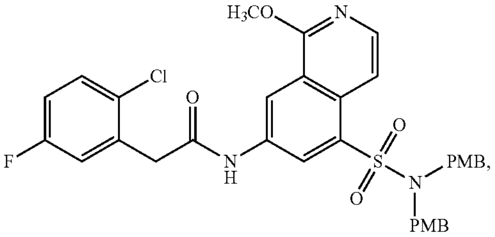
94-1
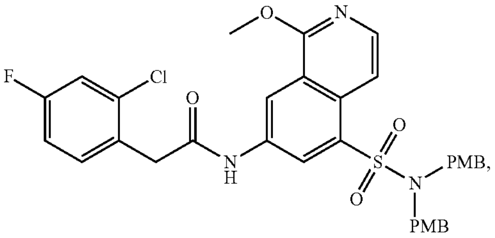
95-1
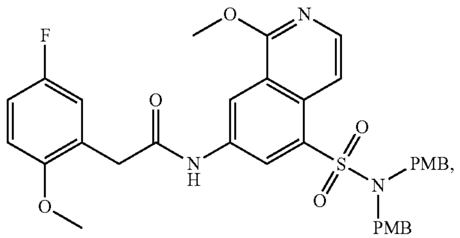
96-2
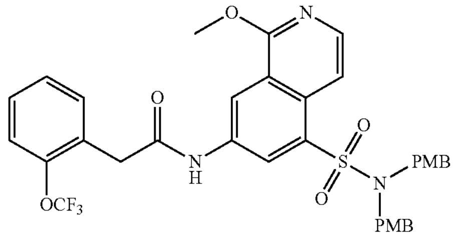
or
-continued
97-2
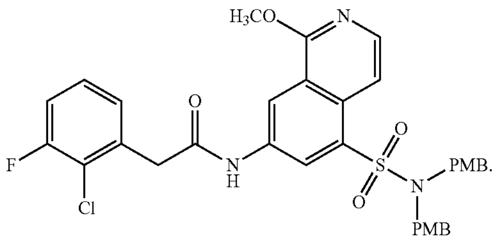
The present disclosure also provides a compound represented by the following formula,
1-3
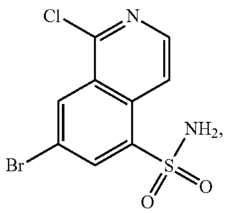
1-4
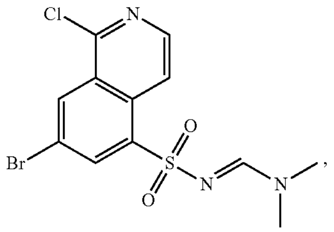
1-5
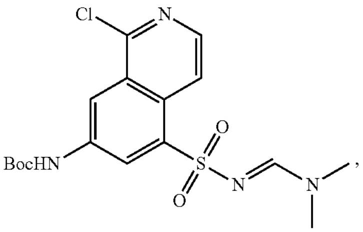
1-6
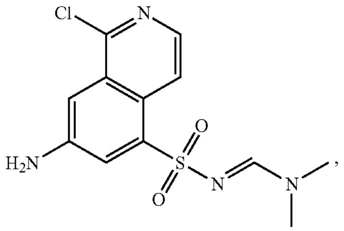
4-4
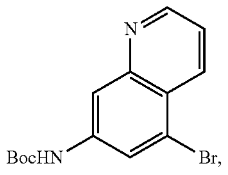

-continued
4-6
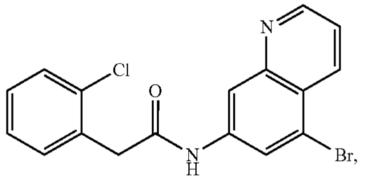
4-8
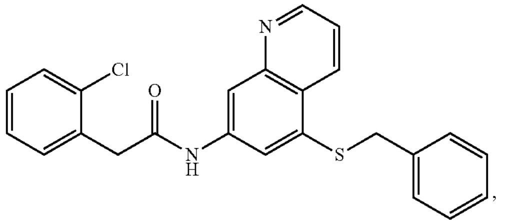
5-2
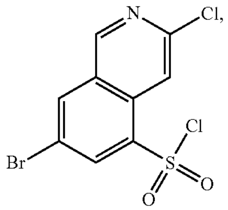
5-3
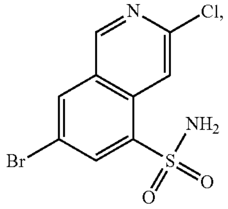
5-4
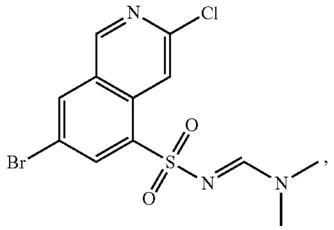
5-5
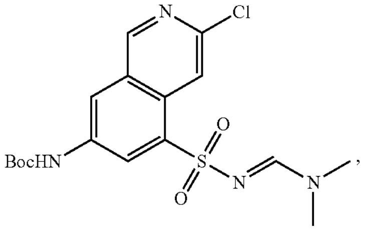
5-6
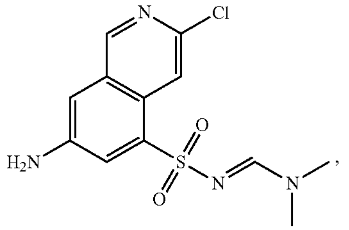
-continued
6-3
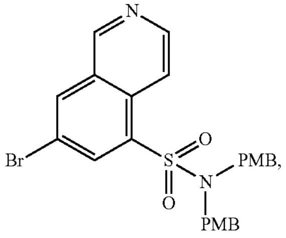
24-3
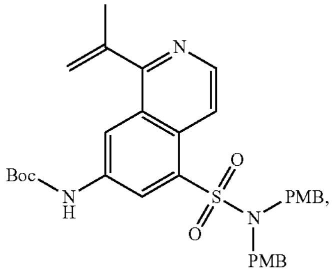
24-4
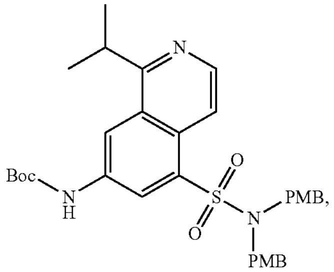
24-5
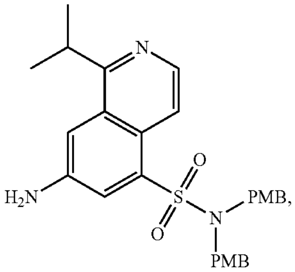
25-1
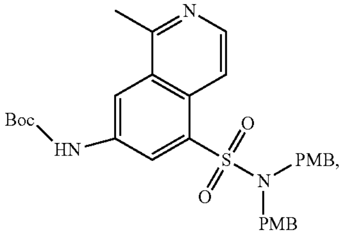
25-2
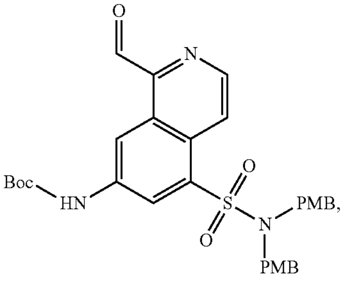

-continued
25-3
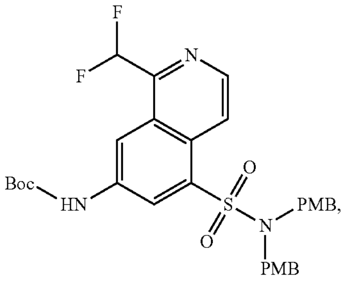
25-4
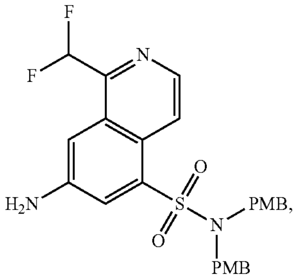
28-1
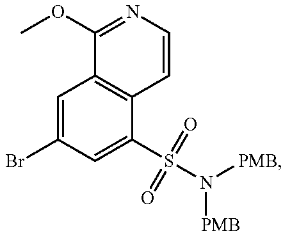
28-2
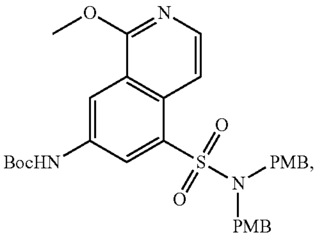
28-3
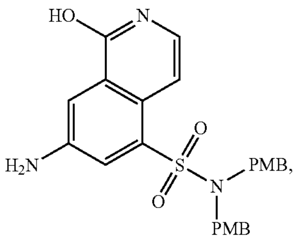
28-4
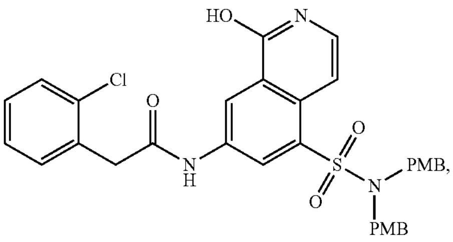
-continued
37-3
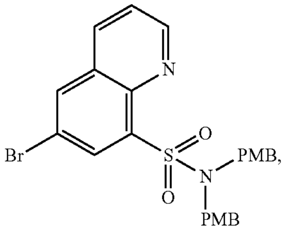
42-5
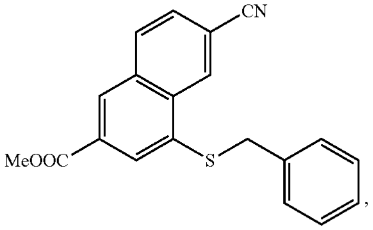
42-6
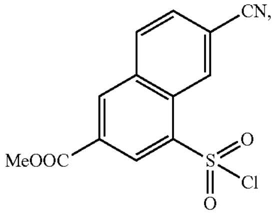
42-7
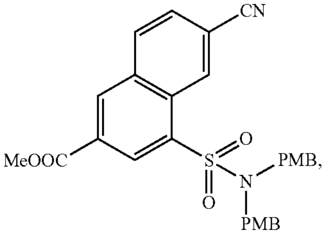
42-8
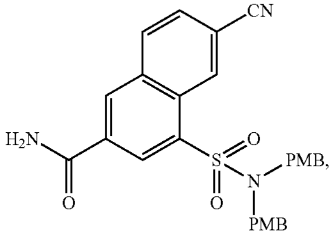
42-9
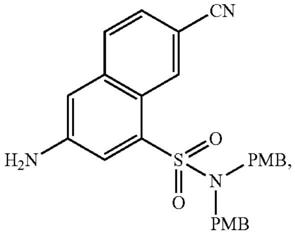

-continued
54-1
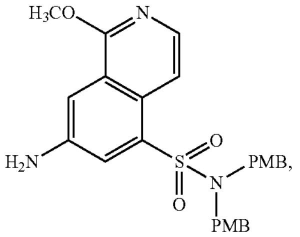
55-1
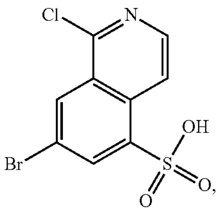
55-2
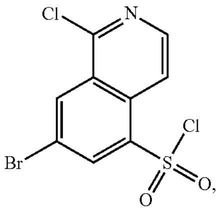
55-3
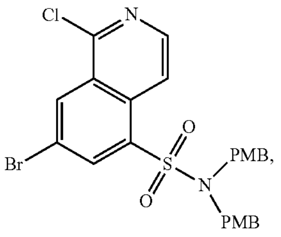
55-4
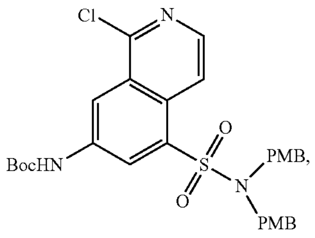
55-5
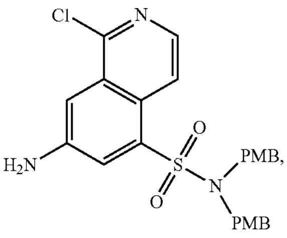
65-1
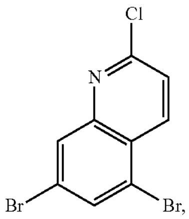
-continued
65-2
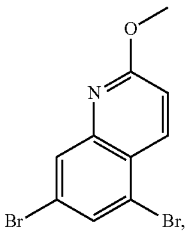
65-3
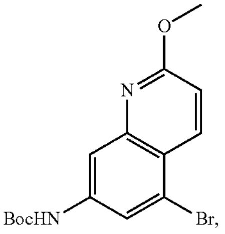
65-4
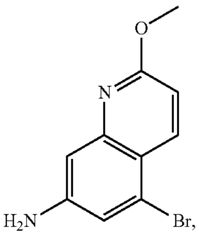
65-5
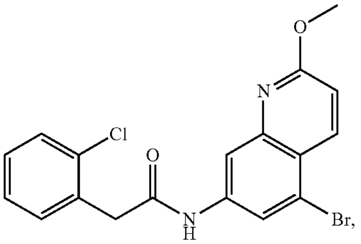
65-6
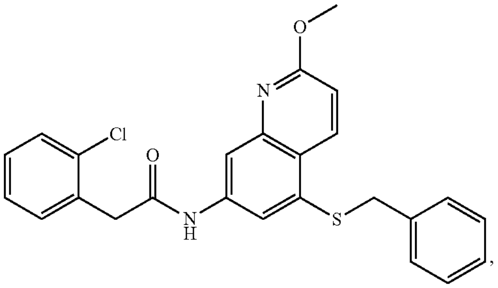
68-1
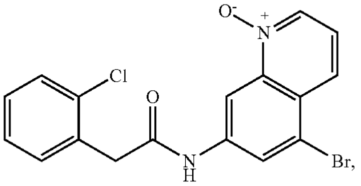

-continued
68-2
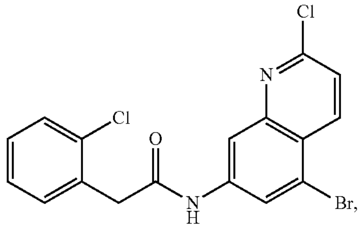
68-3
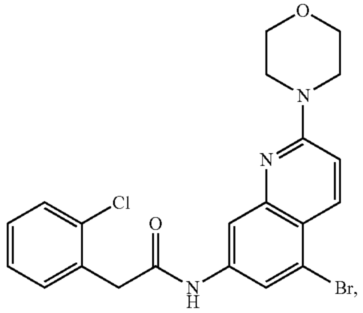
68-4
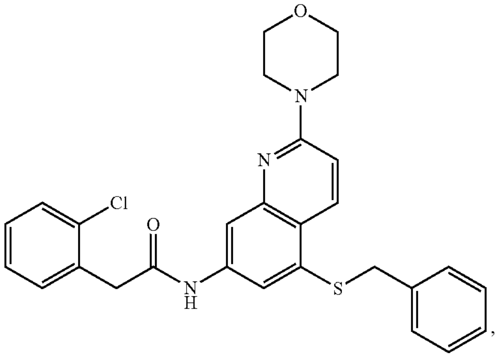
69-1
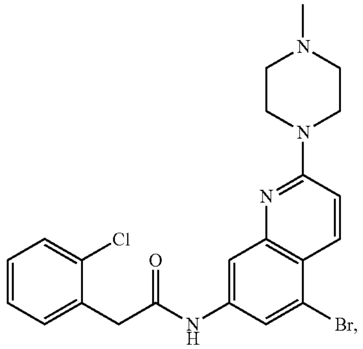
-continued
69-2
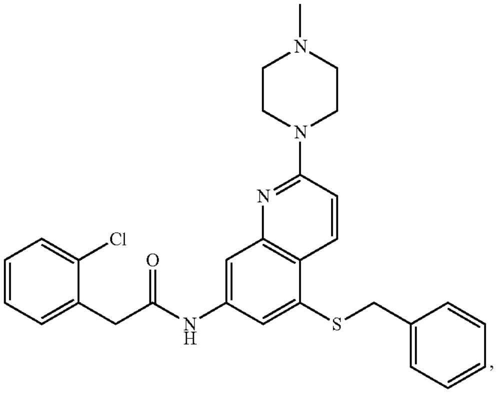
90-1
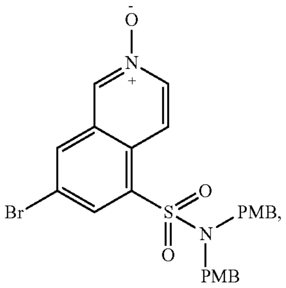
90-3
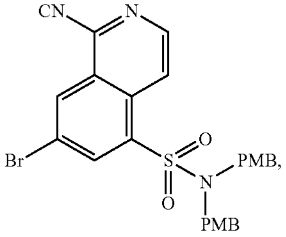
98-1
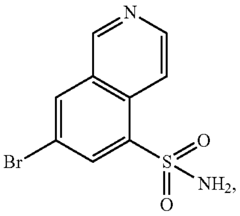
98-2
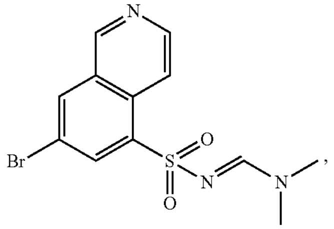
98-3
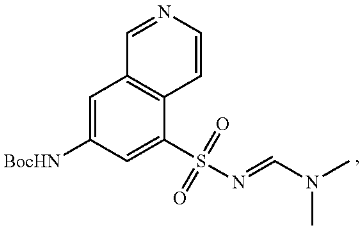

-continued 98-4

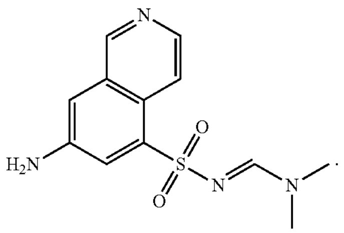

The fused ring compound represented by formula I, the pharmaceutically acceptable salt thereof, the stereoisomer thereof, the tautomer thereof or the isotopic compound thereof as described in the present disclosure can be synthesized by similar methods known in the chemical field, or by the method described in the present disclosure.

The present disclosure provides a pharmaceutical composition comprising substance A and at least one of pharmaceutical excipients;

the substance A is the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof.

In the pharmaceutical composition, the amount of the substance A can be in a therapeutically effective amount.

The present disclosure also provides use of the substance A in the manufacture of a P2X4 receptor antagonist or a medicament;

the substance A is the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof.

In some embodiments, the medicament can be used for the treatment or prevention of urinary tract disease, respiratory disease, pain, autoimmune disease, inflammation, alzheimer's disease, parkinson's, sleep disorder, epilepsy, mental illness, arthritis, neurodegeneration, traumatic brain injury, myocardial infarction, rheumatoid arthritis, stroke, thrombosis, atherosclerosis, colon syndrome, inflammatory bowel disease, digestive tract disease, gastric bowel dysfunction, respiratory failure, sexual dysfunction, cardiovascular disease, heart failure, hypertension, urinary incontinence, cystitis, arthritis, endometriosis, blood disease, musculoskeletal and connective tissue developmental disorder, or, systemic disorder of animals (such as humans). The urinary tract disease such as urinary incontinence, overactive bladder, dysuria or cystitis. The respiratory diseases such as breathing disorders comprising idiopathic pulmonary fibrosis, chronic obstructive pulmonary disease, asthma, bronchospasm or cough (e.g., chronic cough). The pain such as inflammatory pain, surgical pain, visceral pain, dental pain, premenstrual pain, central pain, pain due to burns, migraine, cluster headache or chronic pain.

In some embodiments, the medicament can be used for the treatment or prevention of diseases of animals (such as humans) at least partially mediated by P2X4.

The diseases at least partially mediated by P2X4 such as urinary tract disease, respiratory disease, pain, autoimmune disease, inflammation, alzheimer's disease, parkinson's, sleep disorders, epilepsy, mental illness, arthritis, neurodegeneration, traumatic brain injury, myocardial infarction, rheumatoid arthritis, stroke, thrombosis, atherosclerosis, colon syndrome, inflammatory bowel disease, digestive tract disease, gastric bowel dysfunction, respiratory failure, sexual dysfunction, cardiovascular disease, heart failure, hypertension, urinary incontinence, cystitis, arthritis, endometriosis, blood disease, musculoskeletal and connective tissue developmental disorder, or, systemic disorder. The urinary tract diseases such as urinary incontinence, overactive bladder, dysuria or cystitis. The respiratory diseases, such as breathing disorder comprising idiopathic pulmonary fibrosis, chronic obstructive pulmonary disease, asthma, bronchospasm or cough (e.g., chronic cough). The pain such as inflammatory pain, surgical pain, visceral pain, dental pain, premenstrual pain, central pain, pain due to burns, migraine, cluster headache or chronic pain.

The present disclosure also provides a method for treating or preventing disease comprising administering a therapeutically effective amount of the substance A to a patient.

The diseases is urinary tract disease, respiratory disease, pain, autoimmune disease, inflammation, alzheimer's disease, parkinson's, sleep disorder, epilepsy, mental illness, arthritis, neurodegeneration, traumatic brain injury, myocardial infarction, rheumatoid arthritis, stroke, thrombosis, atherosclerosis, colon syndrome, inflammatory bowel disease, digestive tract disease, gastric bowel dysfunction, respiratory failure, sexual dysfunction, cardiovascular disease, heart failure, hypertension, urinary incontinence, cystitis, arthritis, endometriosis, blood disease, musculoskeletal and connective tissue developmental disorder, or, systemic disorder;

the substance A is the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof.

In some embodiments, the urinary tract disease such as urinary incontinence, overactive bladder, dysuria or cystitis.

In some embodiments, the respiratory diseases such as breathing disorder comprising idiopathic pulmonary fibrosis, chronic obstructive pulmonary disease, asthma, bronchospasm or cough (e.g., chronic cough).

In some embodiments, the pain such as inflammatory pain, surgical pain, visceral pain, dental pain, premenstrual pain, central pain, pain due to burns, migraine, cluster headache or chronic pain.

The present disclosure also provides a method for treating or preventing diseases at least partially mediated by P2X4 comprising administering a therapeutically effective amount of the substance A to a patient (such as human);

the substance A is the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof.

In some embodiments, the diseases can be urinary tract disease, respiratory disease, pain, autoimmune disease, inflammation, alzheimer's disease, parkinson's, sleep disorder, epilepsy, mental illness, arthritis, neurodegeneration, traumatic brain injury, myocardial infarction, rheumatoid arthritis, stroke, thrombosis, atherosclerosis, colon syndrome, inflammatory bowel disease, digestive tract disease, gastric bowel dysfunction, respiratory failure, sexual dysfunction, cardiovascular disease, heart failure, hypertension, urinary incontinence, cystitis, arthritis, endometriosis, blood disease, musculoskeletal and connective tissue developmental disorder, or, systemic disorder.

In some embodiments, the urinary tract disease such as urinary incontinence, overactive bladder, dysuria or cystitis.

In some embodiments, the respiratory diseases such as breathing disorder comprising idiopathic pulmonary fibrosis, chronic obstructive pulmonary disease, asthma, bronchospasm or cough (eg, chronic cough).

In some embodiments, the pain is, such as inflammatory pain, surgical pain, visceral pain, dental pain, premenstrual pain, central pain, pain due to burns, migraine, cluster headache or chronic pain.

All patents and publications referred to herein are incorporated by reference in their entirety.

General principles of organic chemistry can be found in the description of "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are incorporated herein by reference.

Unless otherwise specified, terms used in the present disclosure have the following definitions, and the definitions of terms not mentioned below are as commonly understood by those skilled in the art to which the present disclosure belongs.

The term "more" means 2, 3, 4 or 5.

The term "pharmaceutically acceptable salt" refers to the salt prepared by the compound of the present disclosure and a relatively nontoxic and pharmaceutically acceptable acid or base. When compound of the present disclosure contains a relatively acidic functional group, a base addition salt can be obtained by bringing the neutral form of the compound into contact with a sufficient amount of pharmaceutically acceptable base in a pure solution or a suitable inert solvent. Pharmaceutically acceptable base addition salts include, but are not limited to, lithium, sodium, potassium, calcium, aluminum, magnesium, zinc, bismuth, ammonium, diethanolamine. When compound of the present disclosure contains a relatively basic functional group, an acid addition salt can be obtained by bringing the neutral form of the compound into contact with a sufficient amount of pharmaceutically acceptable acid in a pure solution or a suitable inert solvent. The pharmaceutically acceptable acids include inorganic acids, and the inorganic acids include but are not limited to: hydrochloric acid, hydrobromic acid, hydroiodic acid, nitric acid, carbonic acid, phosphoric acid, phosphorous acid, sulfuric acid, etc. The pharmaceutically acceptable acid includes organic acid, and the organic acid includes but is not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, hydrogen tartrate, ascorbic acid, gentisic acid, fumaric acid, gluconic acid, sugar acid, formic acid, ethanesulfonic acid, pamoic acid (i.e., 4,4'-methylene-bis(3-hydroxy-2-naphthoic acid)), amino acid (such as glutamic acid, arginine), etc. When compounds of the present disclosure contain relatively acidic and relatively basic functional groups, they can be converted into base addition salts or acid addition salts. For details, see Berge et al., "Pharmaceutical Salts", Journal of Pharmaceutical Science 66: 1-19 (1977), or, Handbook of Pharmaceutical Salts: Properties, Selection, and Use (P. Heinrich Stahl and Camille G. Wermuth, ed., Wiley-VCH, 2002).

The term "solvate" refers to a substance formed by combining a compound of the present disclosure with a stoichiometric or non-stoichiometric solvent. Solvent molecules in solvates can exist in an ordered or unordered arrangement. The solvent includes, but is not limited to, water, methanol, ethanol, etc.

In the term "solvate of pharmaceutically acceptable salt", the "pharmaceutically acceptable salt" and the "solvate" are as described above, and the "solvate of the pharmaceutically acceptable salt" refers to a substance formed by combining the compound of the present disclosure, a relatively nontoxic and pharmaceutically acceptable acid or alkali of 1 with a stoichiometric or non-stoichiometric amount of solvent of 2. The "solvate of pharmaceutically acceptable salt" includes, but is not limited to, a hydrochloric acid monohydrate of the compound of the present disclosure.

The term "stereoisomer" refers to the isomers caused by the atoms or atomic groups in the molecule being connected to each other in the same order but with different spatial arrangements, such as cis-trans isomers, optical isomers or atropisomers. These stereoisomers can be separated, purified and enriched by asymmetric synthesis methods or chiral separation methods (including but not limited to thin layer chromatography, rotary chromatography, column chromatography, gas chromatography, high pressure liquid chromatography, etc.), and can also be obtained by chiral resolution by bonding (chemical combination, etc.) or salifying (physical combination, etc.) with other chiral compounds.

The term "tautomer" refers to a functional group isomer generated by the rapid movement of a certain atom in a molecule between two positions. For example, acetone and 1-propen-2-ol can be converted into each other by the rapid movement of a hydrogen atom between oxygen and α-carbon.

The term "isotopic compound" means that one or more atoms in a compound are replaced by one or more atoms with specific atomic mass or mass number. Examples of isotopes that can be incorporated into the compounds of the present disclosure include, but are not limited to, isotopes of hydrogen, carbon, nitrogen, oxygen, fluorine, sulfur and chlorine (e.g., $^{2}H$, $^{3}H$, $^{13}C$, $^{14}C$, $^{15}N$, $^{18}O$, $^{17}O$, $^{18}F$, $^{35}S$ and $^{36}Cl$). Isotopic compounds of the present disclosure can generally be prepared according to the methods described herein by replacing non-isotopically labeled reagents with isotopically labeled reagents.

The term "crystal form" refers to a crystal form in which ions or molecules are strictly and periodically arranged in a three-dimensional space in a certain way, and have a regular repetition interval at a certain interval; due to the difference in the periodic arrangement, a plurality of crystal forms, i.e., polymorphism phenomena, may exist.

The term "nitrogen oxide" means that when compound contains several amine functional groups, one or more nitrogen atoms can be oxidized to form an N-oxide. Particular examples of N-oxides are N-oxides of tertiary amines or N-oxides containing nitrogen atoms of nitrogen heterocycles. The corresponding amine can be treated with oxidant such as hydrogen peroxide or peracid (such as peroxycarboxylic acid) to form N-oxide (see Advanced Organic Chemistry, Wiley Interscience, 4th Edition, Jerry March, pages). In particular, N-oxides can be prepared by the method of L. W. Deady (Syn. Comm. 1977, 7, 509-514) in which, for example, an amine compound is reacted with m-chloroperoxybenzoic acid (MCPBA) in an inert solvent such as dichloromethane.

When an arbitrary variable (e.g., $R^{1-1-1}$) appears many times in the definition of a compound, the definition of each occurrence of the variable has nothing to do with the definitions of other occurrences, and their meanings are independent of each other and have no influence on each other. Therefore, if a group is substituted by 1, 2 or 3 $R^{1-1-1}$, that is, the group may be substituted by up to 3 $R^{1-1-1}$ groups, the definition of this position $R^{1-1-1}$ is independent of the definition of the remaining position $R^{1-1-1}$. Additionally, combinations of substituents and/or variables are permissible only if such combinations result in stable compounds.

The "" used in the structural formula of a group described in the present disclosure means that the corresponding group is connected to other fragments and groups in the compound through this site.

In various parts of the present disclosure, linking substituents are described. When the structure clearly requires a linking group, the Markush variables listed for that group should be understood to be the linking group. For example, $C_1$-$C_6$ alkyl in the group "halogenated-$C_1$-$C_6$ alkyl" should be understood as $C_1$-$C_6$ alkylene.

Unless otherwise stated, the abbreviations of any protecting groups, amino acids and other compounds used in the present disclosure shall be based on their commonly used and recognized abbreviations, or refer to IUPAC-IUB Commission on Biochemical Nomenclature (see Biochem. 1972, 11: 942-944).

The term "oxo" refers to the replacement of two hydrogens on a methylene group with oxygen, that is, methylene is replaced by carbonyl.

The term "halogen" refers to fluorine, chlorine, bromine or iodine.

The term "alkyl" refers to a straight or branched chain alkyl having the indicated number of carbon atoms. Examples of alkyl include methyl, ethyl, n-propyl, isopropyl, n-butyl, tert-butyl, isobutyl, sec-butyl, n-pentyl, n-hexyl, n-heptyl, n-octyl and similar alkyl groups.

The term "alkoxy" refers to the group —O—$R^X$, wherein $R^X$ is an alkyl as defined above.

The term "cycloalkyl" refers to a monovalent saturated cyclic alkyl, preferably a monovalent saturated cyclic alkyl having 3 to 6 ring carbon atoms, such as cyclopropyl, cyclobutyl, cyclopentyl or cyclohexyl.

The term "alkenyl" means a hydrocarbon chain group of straight or branched chains consisting only of carbon atoms and hydrogen atoms, containing at least one carbon-carbon double bond and no carbon-carbon triple bond, having, for example, 2-10 (preferably 2-6, more preferably 2-4) carbon atoms and being connected to the rest of the molecule by a single bond. The one or more carbon-carbon double bonds can be internal (e.g., in 2-butenyl) or terminal (e.g., in 1-butenyl). In some embodiments, the alkenyl has 2 to 4 carbon atoms ("$C_2$-$C_4$ alkenyl"). Preferably one carbon-carbon double bond is present. Examples of $C_2$-$C_4$ alkenyl include vinyl ($C_2$;

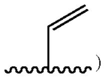
)

1-propenyl (C3;

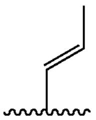
or
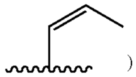
)

2-propenyl or isopropenyl (C3

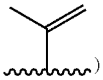
)

allyl (C3;

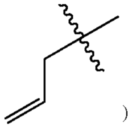 [SMILES: *CC=C]
)

1-butenyl ($C_4$;

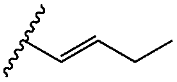
or
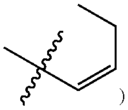
)

2-butenyl ($C_4$

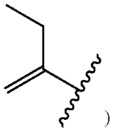 [SMILES: *C(=C)CC]
)

(crotonyl), 2-methylallyl ($C_4$;

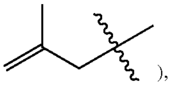 [SMILES: *CC(=C)C]
), 2-methylprop-1-en-1-yl ($C_4$;

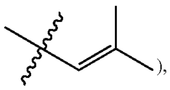 [SMILES: *C=C(C)C]
), but-3-ene-1-yl ($C_4$;

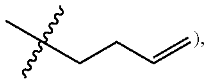 [SMILES: *CCC=C]
), butadiene {$C_4$; for example (E)-but-1,3-diene-1-yl benzene (
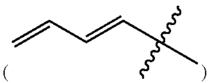 [SMILES: */C=C/C=C]
)

and isomers (e.g., cis-trans isomers or stereoisomers).

The term “alkynyl” refers to a straight or branched chain hydrocarbon group (“$C_2$-$C_{10}$ alkynyl”) with 2 to 10 carbon atoms, one or more carbon-carbon triple bonds and optionally one or more carbon-carbon double bonds. The one or more carbon-carbon triple bonds may be internal (e.g., in 2-butynyl) or terminal (e.g., in 1-butynyl). In some embodiments, the alkynyl has 2 to 4 carbon atoms (“$C_2$-$C_4$ alkynyl”), e.g., ethynyl ($C_2$), prop-1-ynyl

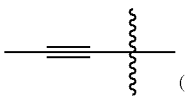

( ($C_3$), prop-2-ynyl

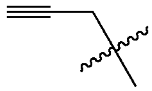

$C_3$), but-1-ynyl

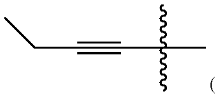 [SMILES: *C#CCC]

( $C_4$), but-2-ynyl

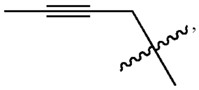 [SMILES: *CC#CC]

, $C_4$), but-3-ynyl

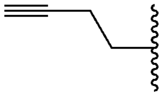 [SMILES: *CCC#C]

$C_4$) or 1-methylprop-2-ynyl ($C_4$).

The term “heterocycloalkyl” or “heterocycloalkane” refers to a saturated monocyclic group with heteroatoms, preferably a saturated monocycle containing 1, 2 or 3 ring heteroatoms independently selected from N, O and S. Examples of heterocycloalkyl are pyrrolidinyl, tetrahydrofuryl, tetrahydropyranyl, tetrahydrothienyl, tetrahydropyridyl, tetrahydropyrrolyl, azetidinyl, thiazolidinyl, oxazolidinyl, piperidinyl, morpholinyl, thiomorpholinyl, piperazinyl, azepanyl, diazepanyl, oxazacycloheptyl, etc.

The term “heterocycloalkenyl” or “heterocycloalkene” refers to a monocyclic group with heteroatoms (this monocyclic group has a double bond but is not aromatic), preferably a monocycle containing 1, 2 or 3 ring heteroatoms independently selected from N, O and S. Examples of heterocycloalkenyl are dihydrofuryl, dihydrothienyl, dihydropyrrolyl, dioxolanyl, dihydroimidazolyl, dihydropyrazolyl, dihydrothiazolyl, dihydroisothiazolyl, dihydrooxadiazoly, dihydrothiadiazoly, dihydrotriazolyl, dihydrotetrazoly, tetrahydropyridinyl, 3,4-dihydro-2H-pyran, pyranyl, thiopyranyl, dihydropyridyl, dihydropyrazinyl, dihydropyrimidinyl, oxazinyl, dihydrotetrazolyl, etc.

In the present disclosure, as a part of a group or other groups, the term “aryl” refers to a group (“$C_6$-$C_{14}$”) of monocyclic or polycyclic (e.g., bicyclic or tricyclic) 4n+2 aromatic ring system with 6-14 ring atoms and zero heteroatoms provided in the aromatic ring system (e.g., 6, 10, or 14 shared p electrons in a cyclic array) (“$C_6$-$C_{14}$ aryl”). Examples of the aryl unit include phenyl, naphthyl, phenanthryl, or anthracyl.

The term “heteroaryl” or “heteroaromatic ring” refers to an aromatic group containing heteroatoms, preferably aromatic monocyclic rings with 1, 2 or 3 heteroatoms independently selected from nitrogen, oxygen and sulfur, such as furyl, pyridyl, pyridazinyl, pyrimidinyl, pyrazinyl, thienyl, isoxazolyl, oxazolyl, diazolyl, imidazolyl, pyrrolyl, pyrazolyl, triazolyl, tetrazolyl, thiazolyl, isothiazolyl, thiadiazolyl, etc.

The terms “moiety”, “structural moiety”, “chemical moiety”, “group”, “chemical group” as used herein refer to a specific fragment or functional group in a molecule. Chemical moieties are usually considered as chemical entities embedded or attached to molecules.

When listed substituent does not indicate through which atom it is attached to a compound included in the formula but not specifically mentioned, such substituent may be bonded through any of its atoms. A combination of the substituent and/or the variant thereof is allowed only when combination results in a stable compound.

In various parts of the present disclosure, linking substituents are described. When the structure clearly requires a linking group, the Markush variables listed for that group should be understood to be the linking group. For example, if the structure requires a linking group and “alkyl” or “aryl” is listed for the definition of Markush group of this variable, it should be understood that the “alkyl” or “aryl” represents the linked alkylene group or arylene group, respectively.

The term “alkylene” refers to a saturated divalent hydrocarbyl group obtained by removing two hydrogen atoms from a saturated straight or branched chain hydrocarbyl group. Examples of alkylene groups include methylene ($—CH_2—$), ethylene {including $—CH_2CH_2—$ or $—CH(CH_3)—$}, isopropylidene {including $—CH(CH_3)CH_2—$ or $—C(CH_3)_2—$}, ect.

Unless otherwise specified, all technical terms and scientific terms used herein have standard meanings in the field to which the claimed subject matter belongs. If more than one definition exists for a term, the definitions herein prevail.

It should be understood that singular forms such as “a” used in the present disclosure include plural referents unless stated otherwise. In addition, the term “comprise” is an open definition rather than a closed one, that is, it includes the contents specified in the present disclosure, but does not exclude other aspects.

Unless otherwise specified, the present disclosure adopts the conventional methods of mass spectrometry and elemental analysis, and the steps and conditions can be referred to the conventional operating steps and conditions in the field.

Unless otherwise specified, the present disclosure adopts standard nomenclature and standard laboratory procedures and techniques of analytical chemistry, organic synthetic chemistry and optics. In some cases, standard techniques are used in chemical synthesis, chemical analysis, and performance testing of light emitting devices.

Furthermore, it should be noted that, unless otherwise explicitly stated, the description mode “ . . . be independently” used in the present disclosure should be understood in a broad sense, which means that the described individuals are independent of each other and can be the same or different specific groups independently. More specifically, the description " . . . be independently" can mean that the specific options expressed by the same symbols in different groups do not affect each other; it can also mean that in the same group, the specific options expressed by the same symbols do not affect each other.

The term "pharmaceutical excipients" refers to the excipients and additives used in the manufacture of drugs and the formulation of prescriptions, which are all substances contained in pharmaceutical preparations except active ingredients. See Pharmacopoeia of the People's Republic of China (2015 Edition) Part IV, or, Handbook of Pharmaceutical Excipients (Raymond C Rowe, 2009 Sixth Edition).

The term "treatment" refers to a therapeutic therapy. Regarding to a specific disease, the treatment refers to: (1) alleviation of one or more biological manifestations of a disorder or disease, (2) interfering with (a) one or more points in the biological cascade leading to or causing a disease or (b) one or more biological manifestations of the disease, (3) improvement of one or more symptoms, effects or side effects associated with the disease, or one or more symptoms, effects or side effects associated with the disease or treatment thereof, or (4) slowdown of the progression of a disease or one or more biological manifestations of the disease.

The term "prevention" refers to the reduction of the risk of acquiring or developing diseases or disorders.

The term "therapeutically effective amount" refers to an amount of compound that, when administered to a patient in need thereof, is sufficient to effectively treat the disorders or diseases described herein. The "therapeutically effective amount" is changed according to the compound, the disease and its severity, and the age of the patient to be treated, but can be adjusted as needed by those skilled in the art.

The term "patient" refers to any animal, preferably a mammal, and most preferably a human, to whom the compound or composition will be or has been administered according to embodiments of the present disclosure. The term "mammal" includes any mammal. Examples of the mammal include, but are not limited to, cow, horse, sheep, pig, cat, dog, mouse, rat, rabbit, guinea pig, monkey, human, etc., and most preferably a human.

The biological activity of the compounds of the present disclosure can be assessed using any conventionally known method. Appropriate detection methods are well known in the art. For example, the P2X4 inhibitory activity, pharmacokinetic activity and/or liver microsomal stability of the compounds of the present disclosure can be detected by appropriate conventional methods. The detection method provided by the present disclosure is only presented as an example and does not limit the present disclosure. The compound of the present disclosure has activity in at least one detection method provided by the present disclosure.

On the basis of not violating the common sense in the field, the above-mentioned preferred conditions can be arbitrarily combined to obtain the preferred examples of the present disclosure.

The reagents and raw materials used in the present disclosure are commercially available.

The positive progressive effect of the present disclosure is that the fused ring compound of the present disclosure has high P2X4 antagonistic activity, good selectivity, low toxicity and good metabolic stability.

DETAILED DESCRIPTION OF THE PREFERRED EMBODIMENT

The present disclosure is further described below by way of embodiments, but the present disclosure is not thereby limited to the scope of the described embodiments. The experimental methods not specified in the specific conditions in the following embodiments are selected according to the conventional methods and conditions, or according to the commodity instructions.

The following abbreviations are used throughout the present disclosure:

Titanium (IV) ethoxide (titanium ethoxide), Xantphos (4,5-bis(diphenylphosphino)-9,9-dimethylxanthene), TEMPO (2,2,6,6-tetramethyl-1-piperidone), LDA (lithium diisopropylamide), DMF (N,N-dimethylformamide), DMA (N,N-dimethylacetamide), DCM (dichloromethane), DME (ethylene glycol dimethyl ether), PE (petroleum ether), EA (ethyl acetate), DIPEA (N,N-diisopropylethylamine), THF (tetrahydrofuran), Ac (acetyl), MeOH (methanol), Boc(tert-butoxycarbonyl), $B_2Pin_2$ (bis(pinacolato)diboron)), rt (room temperature), HATU (2-(7-oxobenzotriazole)-N,N,N',N'-tetramethyluronium hexafluorophosphate), reflux (reflux), eq refers to equivalent, Rf: ratio shift, g (gram), mg (milligram), mol (mole), mmol (millimole), h (hour), min (minute), mL (milliliter), L (microliter).

Overnight refers to 8 hours to 15 hours, for example 12 hours; room temperature refers to 10° C. to 30° C.; solvent ratio such as PE/EA refers to the volume ratio.

In the embodiments described below, unless otherwise indicated, all temperatures were set as degrees Celsius. Unless otherwise indicated, reagents were purchased from commercial suppliers such as Aldrich Chemical Company, Arco Chemical Company and Alfa Chemical Company, and the reagents were used without further purification; general reagents were purchased from Shantou Xilong Chemical Factory, Guangdong Guanghua Sci-Tech Co., Ltd, Guangzhou Chemical Reagent Factory, Tianjin Haoyuyu Chemical Co., Ltd., Qingdao Tenglong Chemical Reagent Co., Ltd., and Qingdao Haiyang Chemical Factory.

Anhydrous tetrahydrofuran, dioxane, toluene and ether were obtained by refluxing and drying with metal sodium. Anhydrous dichloromethane and chloroform were obtained by refluxing and drying with calcium hydride. Ethyl acetate, petroleum ether, n-hexane, N,N-dimethylacetamide and N,N-dimethylformamide were dried prior to use by anhydrous sodium sulfate.

The following reaction were generally carried out under the positive pressure of nitrogen or argon or in anhydrous solvent in a drying tube (unless otherwise indicated), and the reaction flasks were plugged with suitable rubber plugs, and the substrate was injected through a syringe. Glassware was dried.

The chromatographic column was a silica gel column. Silica gel (300-400 mesh) was purchased from Qingdao Haiyang Chemical Factory. NMR spectral data were determined by BrukerAvance 400 NMR spectrometer or BrukerAvanceIIIHD600 NMR spectrometer with $CDCl_3$, DMSO-$d_6$, $CD_3OD$ or Acetone-$d_6$ as solvent (reported in ppm), with TMS (0 ppm) or chloroform (7.25 ppm) as the reference standard. When multiplets are present, the following abbreviations are used: s (singlet), d (doublet), t (triplet), m (multiplet), br (broadened), dd (doublet of doublets), dt (doublet of triplets), ddd (doublet of doublet of doublets), ddt (doublet of doublet of triplets), dddd (doublet of doublet of doublet of doublets). Coupling constant, expressed in Hertz (Hz).

Low-resolution mass spectrometry (MS) data were determined by an Agilent 6320 series LC-MS spectrometer equipped with a G1312A binary pump and a G1316ATCC (column temperature maintained at 30° C.); G1329A autosampler and G1315BDAD detector were used for analysis, and ESI source was used for LC-MS spectrometer.

Both of the above spectrometers were equipped with an Agilent ZorbaxSB-C18 column with a size of 2.1×30 mm, 5 m. Injection volume was determined by sample concentration; flow rate was 0.6 mL/min; HPLC peaks were read by recording UV-Vis wavelengths at 210 nm and 254 nm.

Embodiment 1

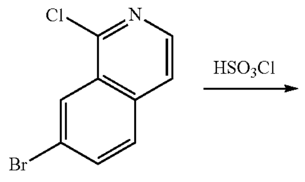

1-1

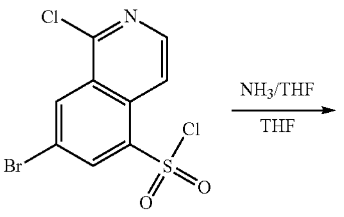

1-2

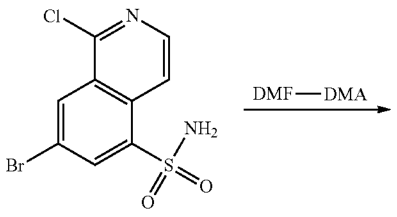

1-3

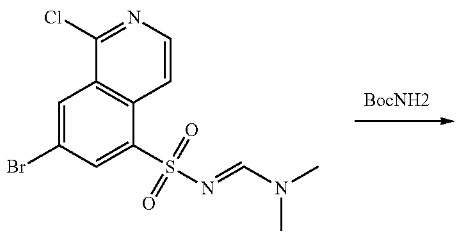

1-4

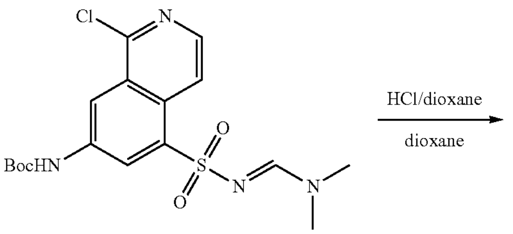

1-5

-continued

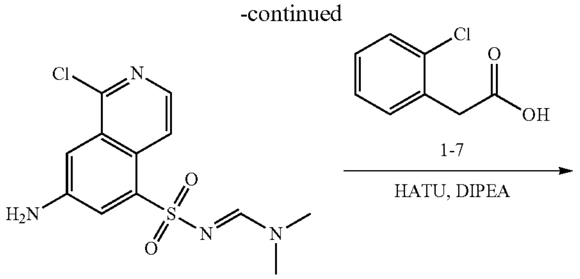

1-6

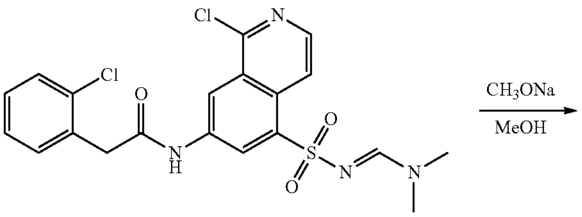

1-8

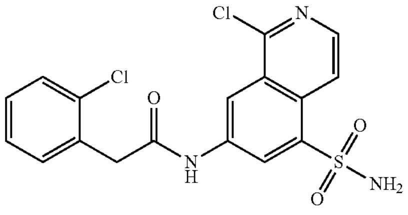

1

Step (1) Preparation of 7-bromo-1-chloroisoquinoline-5-sulfonyl chloride 1-2

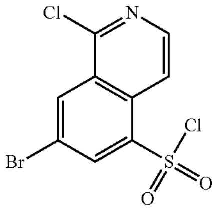

Compound 1-1 (5.0 g, 20.7 mmol) was weighed, and chlorosulfonic acid (50 mL) was added; the reaction system was replaced with $N_2$ for three times, and the mixture was warmed to 170° C. and stirred for 36 hours, and then the sample was taken, quenched with water and extracted with DCM, and TLC showed that about 30% of the raw materials were remained. The reaction solution was slowly added dropwise to ice water (200 mL), extracted with DCM (200 mL) for three times; the organic phases were combined, washed with saturated brine, dried over anhydrous sodium sulfate, filtered, and the filtrate was concentrated under reduced pressure to obtain a crude product of intermediate 1-2 as a yellow oil (5.6 g). LC-MS: $[M+H]^+$=339.9.

Step (2) Preparation of 7-bromo-1-chloroisoquinoline-5-sulfonamide 1-3

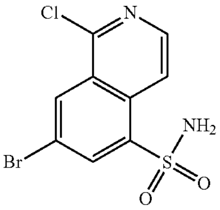

Intermediate 1-2 (5.6 g, crude product) was sequentially dissolved in THF (50 mL), and then slowly added dropwise to 0.5 M $NH_3$/THF (100 mL) solution, and the mixture was stirred at room temperature for 1 hour. The sample was taken and sent to LCMS to show that raw materials were reacted completely. The reaction mixture was concentrated under reduced pressure at 40° C., then the residue was slurried for 10 min with PE:EA=5:1 (50 mL), filtered, and the filter cake was dried under reduced pressure to obtain intermediate 1-3 as an off-white solid (3.2 g, the purity was 93%). LC-MS: $[M+H]^+$=322.

Step (3) Preparation of (E)-N'-(((7-bromo-1-chloroisoquinolin-5-yl)-sulfonyl)-N,N-dimethylformamide 1-4

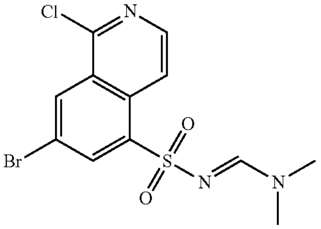

Intermediate 1-3 (3.2 g, 10 mmol) was dissolved in DMF (10 mL), then DMF-DMA (1.43 g, 12 mmol) was added, and the mixture was stirred at 70° C. for 3 hours. The sample was taken and LCMS showed that raw materials were reacted completely. After cooling down, the reaction solution was slowly added dropwise to ice water (50 mL), and the solid was precipitated, and the mixture was continued to stir for 10 minutes then filtered, and the filter cake was washed with water, and then evaporated twice with acetonitrile (20 mL) to obtain intermediate 1-4 as a yellow solid (3.0 g, the purity was 92%), LC-MS: $[M+H]^+$=375.

Step (4) Preparation of tert-butyl (E)-(1-chloro-5-(N-(((dimethylamino)methylene)sulfamoyl)isoquinolin-7-yl)carbamate 1-5

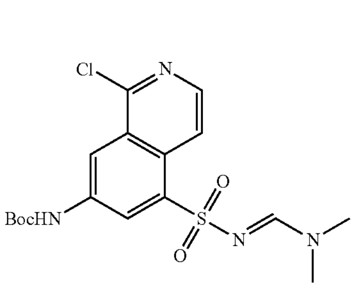

Intermediate 1-4 (2.9 g, 7.73 mmol), $BocNH_2$ (1.36 g, 11.6 mmol), $Cs_2CO_3$ (3.8 g, 11.6 mmol) were added to 1,4-dioxane (30 mL) and stirred to dissolve, and then $PdCl_2$(dppf) (0.63 g) and Xantphos (0.45 g) were added; the reaction system was replaced with $N_2$ for three times, and the mixture was stirred at 85° C. for 16 hours. The sample was taken, quenched with water, extracted with EA, sent to LCMS to show that raw materials were reacted completely; water (50 mL) and DCM (100 mL) were added after cooling, and the mixture was stirred, then the phases were separated, and the aqueous phase was filtered, and concentrated under reduced pressure, purified by silica gel column, concentrated under reduced pressure at 45° C. to obtain intermediate 1-5 as a yellow solid (1.2 g, the purity was 80%), LC-MS: $[M+H]^+$=413.

Step (5) Preparation of (E)-N'-(((7-amino-1-chloroisoquinolin-5-yl)sulfonyl)-N,N-dimethylformamide 1-6

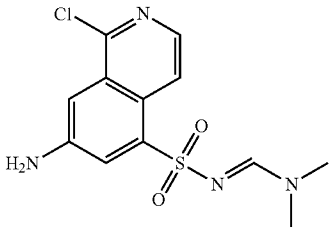

Intermediate 1-5 (200 mg, 0.5 mmol) was dissolved in DCM (5 mL), then 3M HCl/EA (5 mL) was added thereto, and the mixture was stirred at room temperature for 3 hours; the sample was taken, and TLC showed that the reaction of raw materials was completed, and $H_2O$ (10 mL) and DCM (20 mL) were added; the pH was adjusted to 8 to 9 with saturated $NaHCO_3$ solution, and the phases were separated, and the organic phase was washed with saturated brine, dried over anhydrous sodium sulfate, filtered and concentrated to obtain intermediate 1-6 as a yellow solid (100 mg). LC-MS: $[M+H]^+$: =313.0.

Step (6) Preparation of (E)-N-(1-chloro-5-(N-((dimethylamino)methylene)sulfamoyl)isoquinolin-7-yl)-2-(2-chlorophenyl)acetamide 1-8

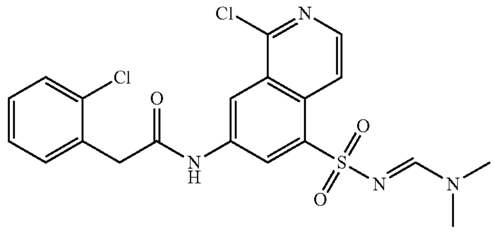

2-Chlorophenylacetic acid (80 mg, 0.05 mmol) and HATU (180 mg, 0.05 mmol) were dissolved in DMF (5 mL), and the mixture was stirred at room temperature for 1 hour, and then intermediate 1-6 (100 mg, 0.03 mmol) and DIPEA (160 mg, 0.12 mmol) were added, and the mixture was continued to stir for 12 hours. The sample were taken, TLC (PE:EA=1:2) showed raw material:product=1:4, then DCM (20 mL) and $H_2O$ (10 mL) were added to the reaction solution, and the phases were separated, and the organic phase was washed with brine, dried over anhydrous sodium sulfate, filtered then concentrated under reduced pressure at 40° C. to obtain a crude product, and the crude product was purified by prep-HPLC with $H_2O/CH_3CN$ system, and lyophilized to obtain intermediate 1-8 as a yellow solid (40 mg). LC-MS: $[M+H]^+$: =465.0.

Step (7) Preparation of 2-(2-chlorophenyl)-N-(1-methoxy-5-sulfamoylisoquinolin-7-yl)acetamide

1

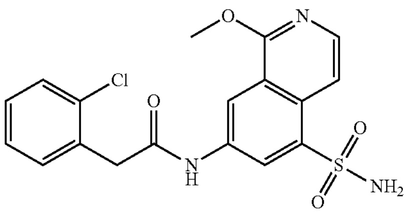

Intermediate 1-8 (20 mg, 0.043 mmol) was dissolved in DCM (0.5 mL), and then a solution of 30% mass sodium methoxide in methanol (0.1 mL) was added, and the mixture was stirred at room temperature for 16 hours; the sample was taken and sent to LCMS to show that raw materials were reacted completely, and the reaction mixture was diluted with DCM (10 mL), filtered, and the filtrate was concentrated to obtain a crude product. The crude product was purified by prep-HPLC with $H_2O/CH_3CN$ system, and then lyophilized to obtain compound 1 as a white solid (5.8 mg, the purity was 97.01%). LC-MS: $[M+H]^+$=406.

$^1$H NMR (400 MHz, DMSO): δ10.88 (s, 1H), 8.86 (d, J=1.3 Hz, 1H), 8.54 (d, J=2.2 Hz, 1H), 8.06 (d, J=6.2 Hz, 1H), 7.92-7.89 (m, 1H), 7.75 (s, 2H), 7.48-7.44 (m, 2H), 7.35-7.32 (m, 2H), 4.06 (s, 3H), 3.92 (s, 2H).

Embodiment 2

Preparation of N-(1-chloro-5-sulfamoylisoquinolin-7-yl)-2-(2-chlorophenyl)acetamide

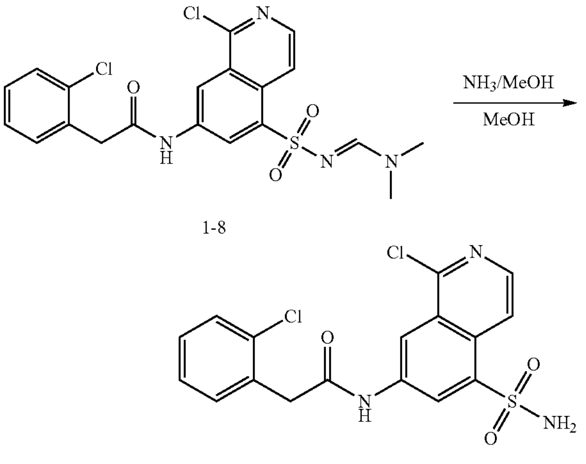

1-8

2

Intermediate 1-8 (20 mg, 0.043 mmol) was dissolved in DCM (0.5 mL), and then a solution of 30% mass sodium methoxide in methanol (0.1 mL) was added, and the mixture was stirred at room temperature for 16 hours; the sample was taken and sent to LCMS to show that raw materials were reacted completely, and the reaction mixture was diluted with DCM (10 mL), filtered, and the filtrate was concentrated to obtain a crude product. The crude product was purified by prep-HPLC with $H_2O/CH_3CN$ system, and then lyophilized to obtain compound 2 as a white solid (3.6 mg) with a purity of 97.38%. LC-MS: $[M+H]^+$=409.95.

$^1$H NMR (400 MHz, DMSO): δ11.09 (s, 1H), 9.02 (s, 1H), 8.66 (s, 1H), 8.38 (s, 2H), 7.93 (s, 2H), 7.50-7.45 (m, 2H), 7.37-7.32 (m, 2H), 3.96 (s, 2H).

Embodiment 3

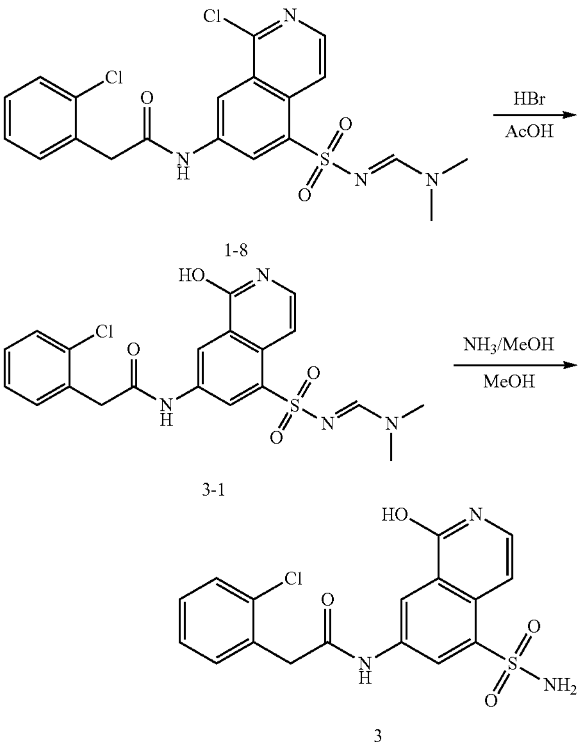

1-8

3-1

3

Step (1) Preparation of (E)-2-(2-chlorophenyl)-N-(5-(N-((dimethylamino)methylene)sulfamoyl)-1-hydroxyisoquinolin-7-yl)acetamide 3-1

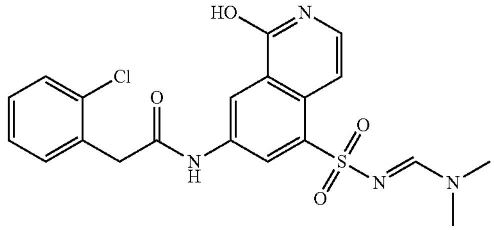

Intermediate 1-8 (70 mg, 0.15 mmol) was dissolved in AcOH (1 mL), and then HBr (0.1 mL) was added, and the mixture was stirred at room temperature for 16 hours, and the sample was taken and sent to LCMS to show that raw materials were reacted completely; the reaction mixture was filtered, and the filtrate was concentrated to obtain a crude product of intermediate 3-1 as a yellow solid (35 mg).

Step (2) preparation of 2-(2-chlorophenyl)-N-(1-hydroxy-5-sulfamoylisoquinolin-7-yl)acetamide

3

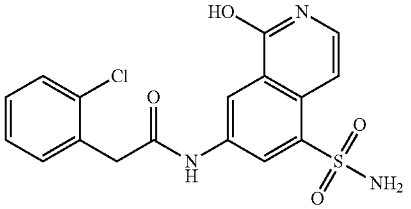

Intermediate 3-1 (35 mg, 0.078 mmol) was dissolved in DMF (2.5 mL), then a solution of 7M ammonia in methanol (1 mL) was added, and the mixture was stirred at room temperature for 16 hours; the sample was taken and sent to LCMS to show that 5% of the raw materials remained, and the reaction solution was purified by prep-HPLC with $H_2O$/$CH_3CN$ system, and lyophilized to obtain compound 3 as an off-white solid (5.3 mg, the purity was 98.06%).

LC-MS: $[M+H]^+$=391.95. $^1H$ NMR (400 MHz, DMSO) δ 11.46 (d, J=4.9 Hz, 1H), 10.74 (s, 1H), 8.71 (s, 1H), 8.56 (d, J=1.5 Hz, 1H), 7.64 (s, 2H), 7.49-7.38 (m, 2H), 7.35-7.27 (m, 2H), 7.24-7.18 (m, 1H), 7.08 (d, J=7.3 Hz, 1H), 3.87 (s, 2H).

Embodiment 4

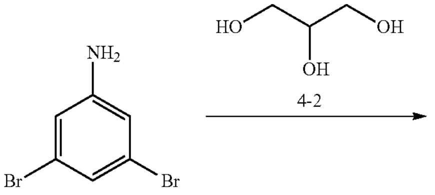

4-1

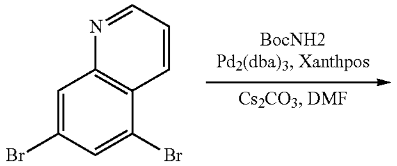

4-3

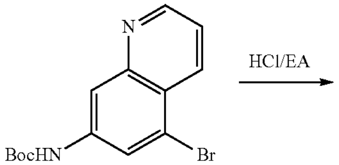

4-4

-continued

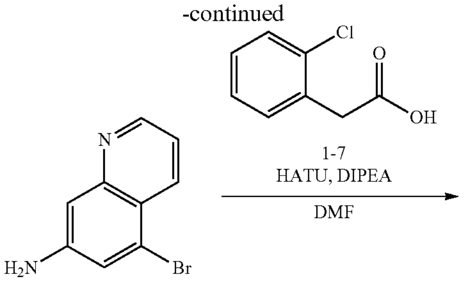

4-5

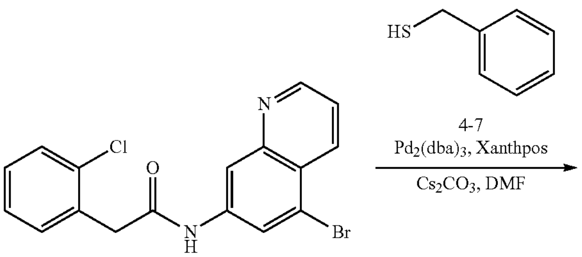

4-6

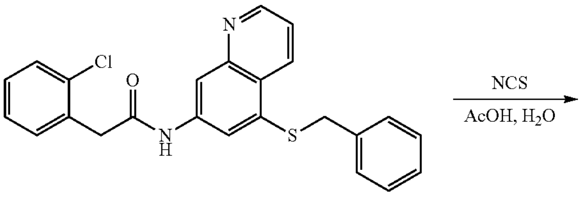

4-8

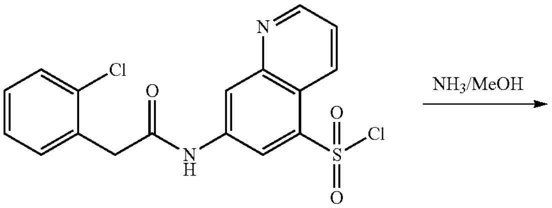

4-9

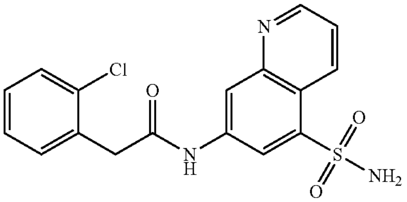

4

Step (1) Preparation of 5,7-dibromoquinoline 4-3

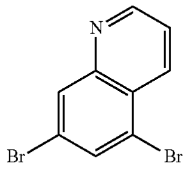

Compound 4-1 (3.0 g, 11.96 mmol) was dissolved in $CH_3SO_3H$ (20 mL), and glycerol (1.32 g, 14.35 mmol), ferric sulfate heptahydrate (0.66 g, 2.39 mmol) and sodium m-nitrobenzenesulfonate (0.54 g, 2.39 mmol) were added at room temperature, and the reaction solution was reacted at 140° C. overnight. TLC showed that the raw materials were reacted completely. The reaction solution was slowly added with water (200 mL) and DCM (200 mL), and the aqueous phase was extracted with DCM (150 mL×3), and the organic phases were combined, washed with saturated brine (100 mL), dried over anhydrous sodium sulfate, filtered, and the filtrate was concentrated to obtain intermediate 4-3 as a yellow solid (2.0 g). LC-MS: $[M+H]^+$=286.04.

Step (2) Preparation of tert-butyl (5-bromoquinolin-7-yl)carbamate 4-4

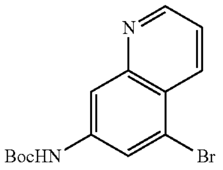

Intermediate 4-3 (1.0 g, 3.48 mmol), $BocNH_2$ (0.5 g, 4.18 mmol), $Cs_2CO_3$ (0.57 g, 4.18 mmol), Xant-phos (0.1 g, 0.17 mmol) and $Pd_2(dba)_3$ (0.09 g, 0.17 mmol) were dissolved in DMF (10 mL), and the reaction solution was stirred at 85° C. overnight. TLC showed that the reaction was completed. The reaction solution was added with water (100 mL), and the aqueous phase was extracted with EA (150 mL×3), and the organic phases were combined, washed with saturated brine (100 mL), dried over anhydrous sodium sulfate, filtered, and the filtrate was concentrated to obtain a crude product, and the crude product was washed out with silica gel column chromatography to obtain intermediate 4-4 as a yellow solid (0.8 g). LC-MS: $[M+H]^+$=323.15.

Step (3) Preparation of 5-bromoquinolin-7-amine 4-5

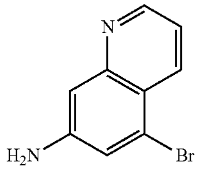

Intermediate 4-4 (1.2 g, 3.71 mmol) was dissolved in EA (2 mL), then HCl/EA (20 mL) was added, and the reaction solution was reacted at room temperature for 2 hours. TLC showed that the reaction was completed. The reaction solution was concentrated to obtain a crude product, and the crude product was washed with EA (2 mL) to obtain intermediate 4-5 as a yellow solid (1.0 g). LC-MS: $[M+H]^+$=223.35.

Step (4) Preparation of N-(5-bromoquinolin-7-yl)-2-(2-chlorophenyl)acetamide 4-6

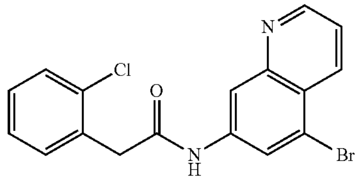

o-Chlorophenylacetic acid (0.46 g, 2.69 mmol), DIPEA (0.87 g, 6.72 mmol) and HATU (1.27 g, 3.36 mmol) were dissolved in DMF (5 mL), and the reaction solution was stirred at room temperature for 0.5 hours, and then intermediate 4-5 (0.5 g, 2.24 mmol) was added, and the reaction solution was reacted at room temperature overnight. TLC showed that the reaction was completed. The reaction solution was added with water (100 mL), and the aqueous phase was extracted with EA (150 mL×3), and then the organic phases were combined, washed with saturated brine (100 mL), dried over anhydrous sodium sulfate, filtered, and the filtrate was concentrated to obtain a crude product, and the crude product was subjected to silica gel column chromatography to obtain intermediate 4-6 as a yellow solid (0.4 g). LC-MS: $[M+H]^+$=375.16.

Step (5) Preparation of N-(5-(benzylthio)quinolin-7-yl)-2-(2-chlorophenyl)acetamide 4-8

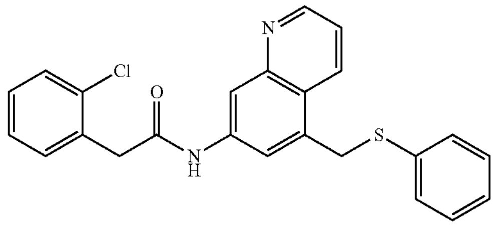

Intermediate 4-6 (0.4 g, 1.06 mmol), benzyl mercaptan (0.16 g, 1.28 mmol), $Cs_2CO_3$ (0.42 g, 1.28 mmol), Xant-phos (0.03 g, 0.053 mmol) and $Pd_2(dba)_3$ (0.048 g, 0.053 mmol) were dissolved in DMF (10 mL), and the reaction solution was stirred and reacted at 85° C. overnight. TLC showed that the reaction was completed. The reaction solution was added with water (100 mL), and the aqueous phase was extracted with EA (200 mL×3), and then the organic phases were combined, washed with saturated brine (100 mL), dried over anhydrous sodium sulfate, filtered, and the filtrate was concentrated to obtain a crude product, and the crude product was subjected to silica gel column chromatography to obtain intermediate 4-8 as a yellow solid (0.3 g). LC-MS: $[M+H]^+$=419.23.

Step (6) Preparation of 7-(2-(2-chlorophenyl)acetamido)quinoline-5-sulfonyl chloride 4-9

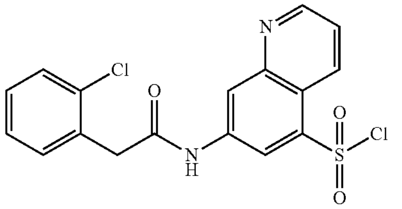

Intermediate 4-8 (0.3 g, 0.72 mmol) was dissolved in $CH_3COOH$ (1.0 mL) and water (0.3 mL), and NCS (0.48 g, 3.58 mmol) was slowly added to the reaction solution at 0° C., and the reaction solution was continued to react at 0° C. for 4 hours. TLC showed that the reaction was completed. LCMS showed that the raw materials were reacted completely. The reaction solution was added with water (100 mL), and the aqueous phase was extracted with EA (150 mL×3), and then the organic phases were combined, washed with saturated brine (100 mL), dried over anhydrous sodium sulfate, filtered, and the filtrate was concentrated to obtain a crude product, and the crude product was subjected to silica gel column chromatography to obtain intermediate 4-9 as a yellow solid (0.2 g). LC-MS: $[M+H]^+$=395.24.

Step (7) Preparation of 2-(2-chlorophenyl)-N-(5-sulfamoylquinolin-7-yl)acetamide

4

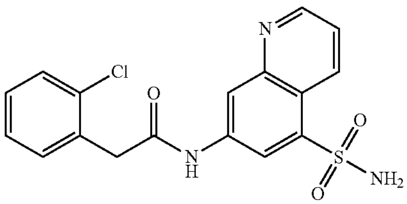

Intermediate 4-9 (0.2 g, 0.5 mmol) was dissolved in $NH_3$/MeOH (20 mL), and the reaction solution was stirred and reacted at room temperature for 2 hours. TLC showed that the reaction was completed. LCMS showed that the raw materials were reacted completely. The reaction solution was purified by prep-HPLC with $H_2O$/MeCN system, and then lyophilized to obtain compound 4 as a white solid (14.5 mg, the purity was 99.51%). LC-MS: $[M+H]^+$=375.95.

$^1H$ NMR (400 MHz, DMSO) δ 10.88 (s, 1H), 8.94 (d, J=4.0 Hz, 1H), 8.90 (d, J=8.6 Hz, 1H), 8.61 (s, 1H), 8.44 (d, J=1.6 Hz, 1H), 7.74 (s, 2H), 7.57 (dd, J=8.6, 4.2 Hz, 1H), 7.46 (s, 2H), 7.34 (d, J=3.8 Hz, 2H), 3.95 (s, 2H).

Embodiment 5

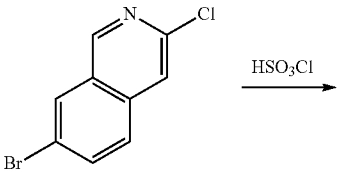

5-1

-continued

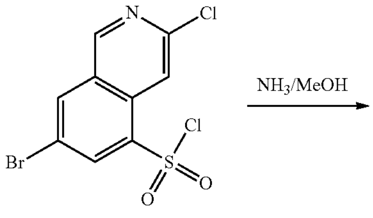

5-2

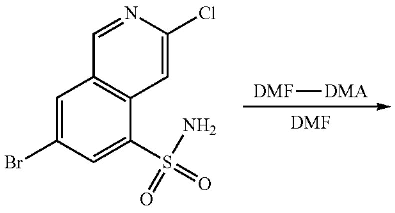

5-3

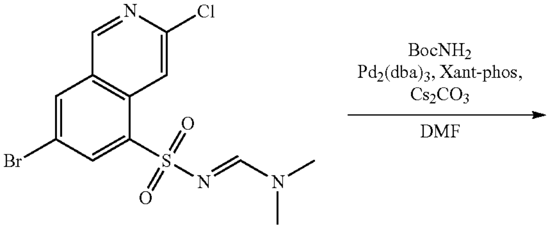

5-4

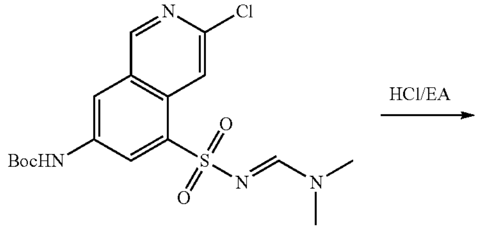

5-5

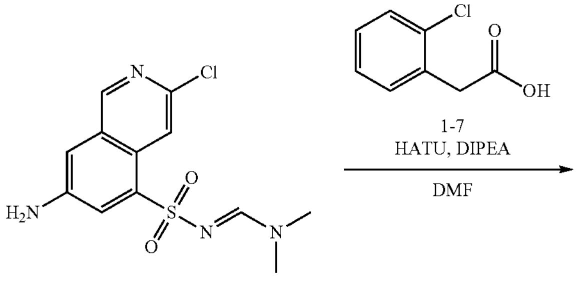

5-6

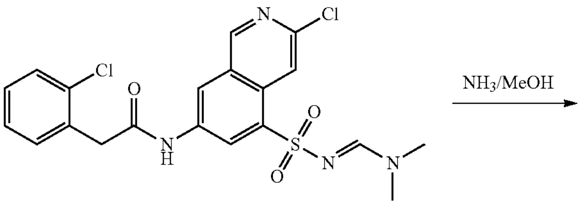

5-8

-continued

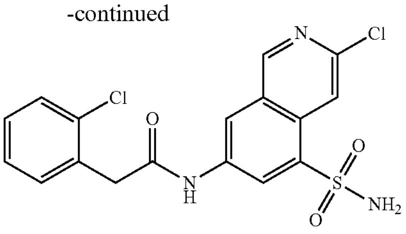

5

Step (1) Preparation of 7-bromo-3-chloroisoquinoline-5-sulfonyl chloride 5-2

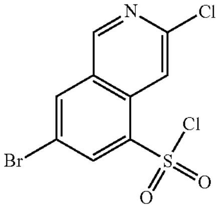

Compound 5-1 (4.0 g, 16.49 mmol) was dissolved in $HSO_3Cl$ (20 mL), and the reaction solution was reacted at 170° C. for 24 hours. TLC showed that the reaction was completed. The reaction solution was slowly added dropwise to DCM (200 mL) and water (200 mL), and the aqueous phase was extracted with DCM (150 mL×3), and then the organic phases were combined, washed with saturated brine (100 mL), dried over anhydrous sodium sulfate, filtered, and the filtrate was concentrated to obtain intermediate 5-2 as a yellow solid (3.0 g). LC-MS: $[M+H]^+$=340.05.

Step (2) Preparation of 7-bromo-3-chloroisoquinoline-5-sulfonamide 5-3

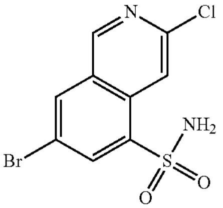

Intermediate 5-2 (3.0 g, 8.8 mmol) was added dropwise to $NH_3$/MeOH (30 mL), and the reaction solution was stirred and reacted at room temperature for 2 hours. TLC showed that the reaction was completed. The reaction solution was concentrated to obtain intermediate 5-3 as a yellow solid (3.0 g of crude product). LC-MS: $[M+H]^+$=320.12.

Step (3) Preparation of (E)-N'(((7-bromo-3-chloroisoquinolin-5-yl)-sulfonyl)-N,N-dimethylformamide 5-4

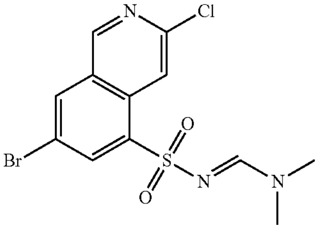

Intermediate 5-3 (3.0 g, 9.33 mmol) was dissolved in DMF (5 mL), then DMF-DMA (20 mL) was added, and the reaction solution was reacted at room temperature for 4 hours. TLC showed that the reaction was completed. EA (200 mL) and water (50 mL) were added to the reaction solution, and then the aqueous phase was extracted with EA (150 mL×3), and the organic phases were combined, washed with saturated brine (100 mL×3), dried over anhydrous sodium sulfate, filtered, and the filtrate was concentrated to obtain intermediate 5-4 as a yellow solid (3.0 g). LC-MS: $[M+H]^+$=376.05.

Step (4) Preparation of tert-butyl (E)-(3-chloro-5-(N-(((dimethylamino)methylene)sulfamoyl)isoquinolin-7-yl)carbamate 5-5

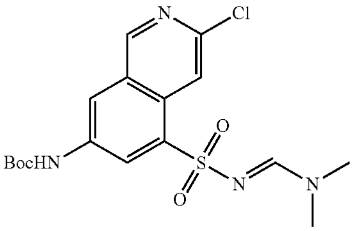

Intermediate 5-4 (2.5 g, 6.64 mmol), $BocNH_2$ (0.93 g, 7.96 mmol), $Cs_2CO_3$ (2.59 g, 7.96 mmol), Xant-phos (0.192 g, 0.33 mmol) and $Pd_2(dba)_3$ (0.18 g, 0.33 mmol) were dissolved in DMF (30 mL), and the reaction solution was stirred and reacted at 85° C. overnight. TLC showed that the reaction was completed. The reaction solution was added to water (100 mL), and the aqueous phase was extracted with EA (200 mL×3), and then the organic phases were combined, washed with saturated brine (100 mL), dried over anhydrous sodium sulfate, filtered, and the filtrate was concentrated to obtain a crude product, and the crude product was purified by silica gel column chromatography to obtain intermediate 5-5 as a yellow solid (2.2 g). LC-MS: $[M+H]^+$=413.10.

Step (5) Preparation of (E)-N'-(((7-amino-3-chloroisoquinolin-5-yl)sulfonyl)-N,N-dimethylformamide 5-6

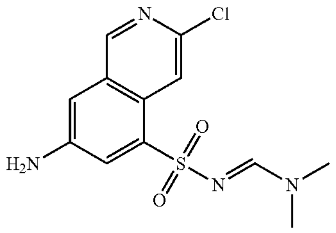

Intermediate 5-5 (2.2 g, 5.33 mmol) was dissolved in EA (4 mL), then HCl/EA (20 mL) was added, and the reaction solution was reacted at room temperature for 2 hours. TLC showed that the reaction was completed. The reaction solution was concentrated to obtain a crude product, and the crude product was washed with EA (4 mL) to obtain intermediate 5-6 as a yellow solid (1.0 g). LC-MS: $[M+H]^+=313.04$.

Step (6) Preparation of (E)-N-(3-chloro-5-(N-((dimethylamino)methylene)sulfamoyl)isoquinolin-7-yl)-2-(2-chlorophenyl)acetamide 5-8

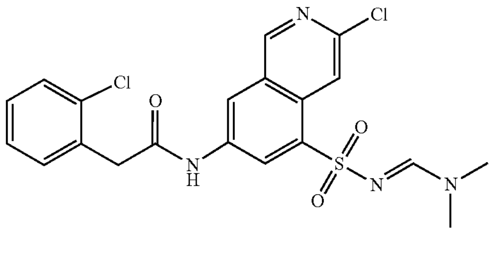

o-Chlorophenylacetic acid (0.33 g, 1.92 mmol), DIPEA (0.62 g, 4.8 mmol) and HATU (0.91 g, 2.4 mmol) were dissolved in DMF (5 mL), and the reaction solution was stirred and reacted at room temperature for 0.5 hours, and then intermediate 5-6 (0.5 g, 1.6 mmol) was added thereto, and the reaction solution was warmed to room temperature and reacted at room temperature overnight. TLC showed that the reaction was completed. The reaction solution was added with water (100 mL), and the aqueous phase was extracted with EA (150 mL×3), and then the organic phases were combined, washed with saturated brine (100 mL), dried over anhydrous sodium sulfate, filtered, and the filtrate was concentrated to obtain a crude product, and the crude product was subjected to silica gel column chromatography to obtain intermediate 5-8 as a yellow solid (0.5 g). LC-MS: $[M+H]^+=465.05$.

Step (7) Preparation of N-(3-chloro-5-sulfamoylisoquinolin-7-yl)-2-(2-chlorophenyl)acetamide

5

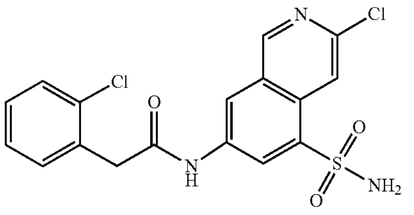

Intermediate 5-8 (0.5 g, 1.07 mmol) was dissolved in $NH_3$/MeOH (20 mL), and the reaction solution was warmed to room temperature and reacted at room temperature overnight. TLC showed that the reaction was completed. LCMS showed that the raw materials were reacted completely. The reaction solution was purified by prep-HPLC with $H_2O$/MeCN system, and then lyophilized to obtain compound 5 as a white solid (38 mg, the purity was 99.54%). LC-MS: $[M+H]^+=409.95$.

$^1$H NMR (400 MHz, DMSO) δ 10.97 (s, 1H), 9.26 (s, 1H), 8.76 (d, J=1.2 Hz, 1H), 8.56 (d, J=2.2 Hz, 1H), 8.40 (s, 1H), 7.91 (s, 2H), 7.47 (d, J=9.2 Hz, 2H), 7.34 (dd, J=6.6, 2.4 Hz, 2H), 3.94 (s, 2H).

Embodiment 6

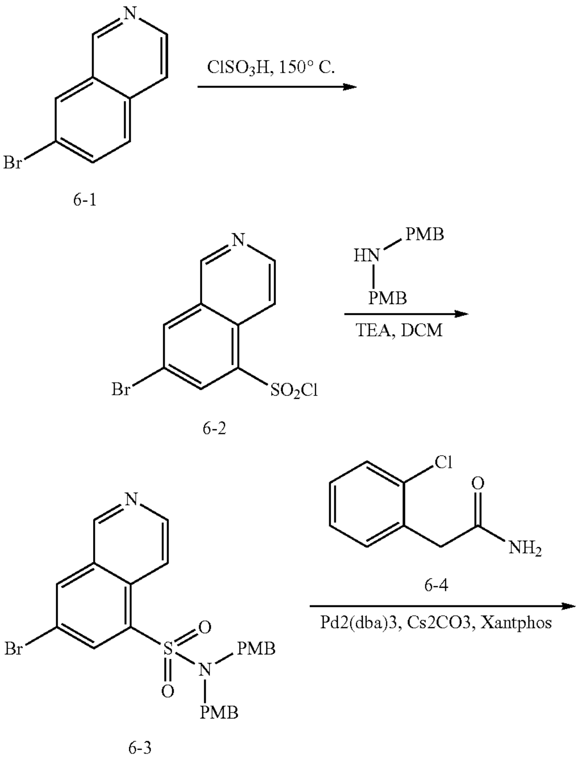

6-1

6-2

6-3

6-4

-continued

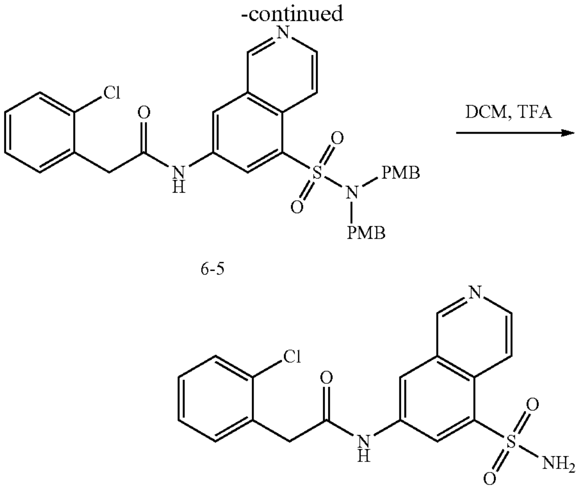

6-5

6

Step (1) Preparation of 7-bromoisoquinoline-5-sulfonyl chloride 6-2

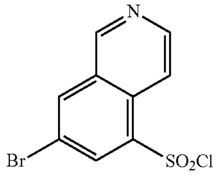

7-Bromoisoquinoline (4.0 g, 19.2 mmol) was dissolved in chlorosulfonic acid (60 mL), and the mixture was heated to 150° C., and stirred for 22 hours. After the reaction solution was cooled to room temperature, the reaction solution was slowly added to ice brine. The temperature of the dropping process was kept <−10° C., and after the dropping, 5N sodium hydroxide solution was added to adjust the pH to 9 to 10. The mixture was filtered, washed with cold water, and the solid was collected, and dried to obtain intermediate 6-2 as a yellow solid (20 g, the purity was 10%, the yield was 34%). LC-MS: $[M+H]^+$=307.9.

Step (2) Preparation of 7-bromo-N,N-bis(4-methoxybenzyl)isoquinoline-5-sulfonamide 6-3

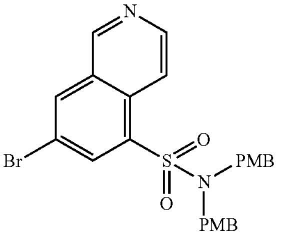

Bis-(4-methoxybenzyl)-amine (403 mg, 1.6 mmol) and triethylamine (396 mg, 3.9 mmol) were dissolved in dichloromethane (30 mL), and the mixture was stirred at room temperature, then intermediate 6-2 (4.0 g, 1.3 mmol) was added in batches, and the mixture was stirred at room temperature overnight. The mixture was diluted with dichloromethane (20 mL), then sequentially washed with saturated sodium bicarbonate solution (30 mL) and saturated brine (30 mL). The organic phase was dried over anhydrous sodium sulfate, filtered and concentrated, and the crude product was purified by silica gel chromatography to obtain intermediate 6-3 as a white solid (300 mg, the purity was 75%, the yield was 33%). LC-MS: $[M+H]^+$=527.1.

Step (3) Preparation of N-(5-(N,N-bis(4-methoxybenzyl)sulfamoyl)isoquinolin-7-yl)-2-(2-chlorophenyl)acetamide 6-5

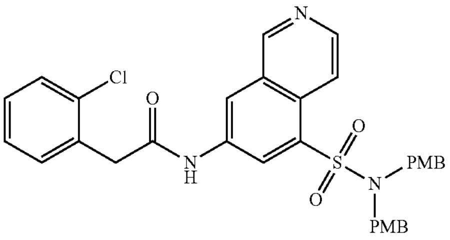

Under the protection of nitrogen, intermediate 6-3 (80 mg, 0.51 mmol), 2-(2-chlorophenyl)acetamide (38 mg, 0.23 mmol), cesium carbonate (147 mg, 0.45 mmol), tris(dibenzylideneacetone)dipalladium (14 mg, 0.015 mmol) and 4,5-bis(diphenylphosphino)-9,9-dimethylxanthene (17 mg, 0.03 mmol) were added to dioxane (10 mL), and the mixture was reacted at 110° C. for 16 hours. The mixture was returned to room temperature, filtered, and the filtrate was concentrated by rotary evaporation, and the crude product was purified by silica gel column chromatography to obtain intermediate 6-5 as a yellow solid (120 mg, the purity was 70%, the yield was 91%). LC-MS: $[M+H]^+$=616.1.

Step (4) Preparation of N-(5-(N,N-bis(4-methoxybenzyl)sulfamoyl)isoquinolin-7-yl)-2-(2-chlorophenyl)acetamide

6

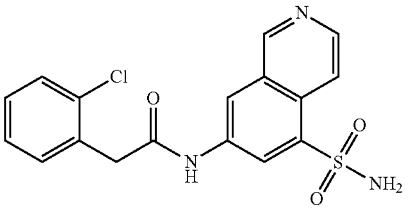

Intermediate 6-5 (120 mg, 0.14 mmol) was dissolved in dichloromethane (2 mL), then trifluoroacetic acid (8 mL) was added, and the mixture was stirred at 45° C. for 24 hours. The mixture was concentrated by rotary evaporation and then dissolved in dichloromethane (30 mL), and the pH of the mixture was adjusted to 8 with saturated sodium bicarbonate solution, then the phases were separated, and the organic phase was dried over anhydrous sodium sulfate, filtered and concentrated. The crude product was purified by silica gel column chromatography to obtain compound 6 as a white solid (20 mg, the yield was 38%). LC-MS: $[M+H]^+$ =375.7.

$^1$H NMR (400 MHz, $d_6$-DMSO) δ 11.01 (s, 1H), 9.49 (s, 1H), 8.81 (d, J=1.6 Hz, 1H), 8.62 (s, 1H), 8.59 (d, J=2.1 Hz, 1H), 8.43 (d, J=6.0 Hz, 1H), 7.89 (s, 2H), 7.55-7.43 (m, 2H), 7.42-7.26 (m, 2H), 3.96 (s, 2H).

Embodiment 7

Preparation of 2-(2-chlorophenyl)-N-(3-fluoro-5-sulfamoylisoquinolin-7-yl)acetamide

7

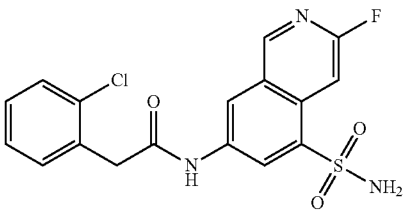

The compound was prepared by reference to the preparation method of embodiment 5. LC-MS: $[M+H]^+$=394.0.

Embodiment 8

Preparation of 2-(2-chlorophenyl)-N-(1-ethoxy-5-sulfamoylisoquinolin-7-yl)acetamide

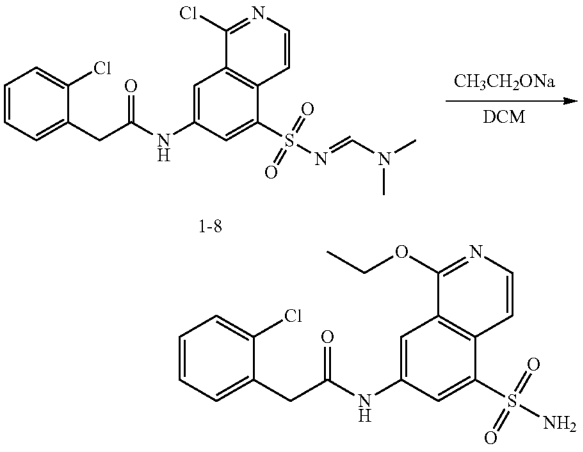

1-8

8

Intermediate 1-8 (200 mg, 0.43 mmol) was dissolved in DCM (2 mL), and then a solution of 10% mass sodium ethoxide in ethanol (4 mL) was added thereto, and the mixture was stirred at room temperature for 16 hours, and the sample was taken and sent to TLC to show that raw materials were reacted completely; DCM (10 mL) was added to dilute, and the mixture was filtered, and the filtrate was concentrated to obtain a crude product, and the crude product was purified by prep-HPLC, and lyophilized to obtain compound 8 as a white solid (4.0 mg, the purity was 99.4%), LC-MS: $[M+H]^+$=420.05.

$^1$H NMR (400 MHz, DMSO) δ 10.87 (s, 1H), 8.82 (d, J=1.6 Hz, 1H), 8.59 (d, J=2.2 Hz, 1H), 8.04 (d, J=6.2 Hz, 1H), 7.89 (dd, J=6.2, 0.6 Hz, 1H), 7.74 (s, 2H), 7.50-7.44 (m, 2H), 7.36-7.30 (m, 2H), 4.52 (q, J=7.0 Hz, 2H), 3.92 (s, 2H), 1.42 (t, J=7.0 Hz, 3H).

Embodiment 9

Preparation of 2-(2-chlorophenyl)-N-(1-isopropoxy-5-sulfamoylisoquinolin-7-yl)acetamide

9

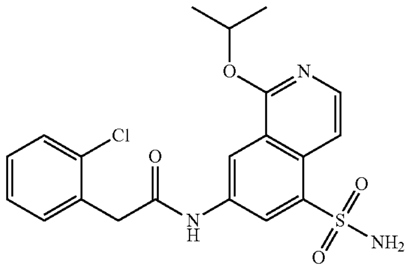

The compound was prepared by reference to the preparation method of embodiment 1. LC-MS: $[M+H]^+$=434.1.

Embodiment 10

Preparation of 2-(2-chlorophenyl)-N-(1-cyclopropoxy-5-sulfamoylisoquinolin-7-yl)acetamide

10

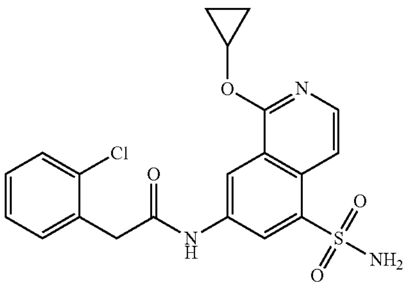

The compound was prepared by reference to the preparation method of embodiment 1. LC-MS: $[M+H]^+$=432.1.

Embodiment 11

Preparation of 2-(2-chlorophenyl)-N-(1-cyclobutoxy-5-sulfamoylisoquinolin-7-yl)acetamide

11

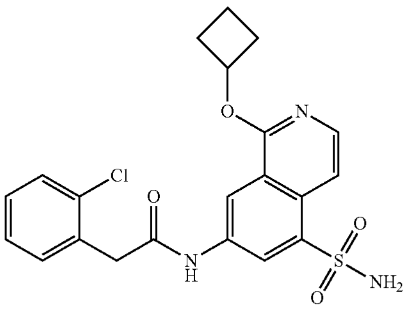

The compound was prepared by reference to the preparation method of embodiment 1. LC-MS: $[M+H]^+$=446.1.

Embodiment 12

Preparation of N-(1-(azetidin-3-oxy)-5-sulfamoylisoquinolin-7-yl)-2-(2-chlorophenyl)acetamide

12

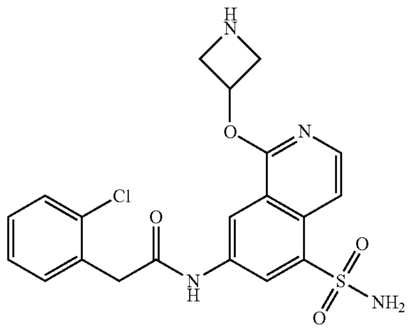

The compound was prepared by reference to the preparation method of embodiment 1. LC-MS: $[M+H]^+$=447.1.

Embodiment 13

Preparation of 2-(2-chlorophenyl)-N-(1-cyclopentyloxy)-5-sulfamoylisoquinolin-7-yl)acetamide

13

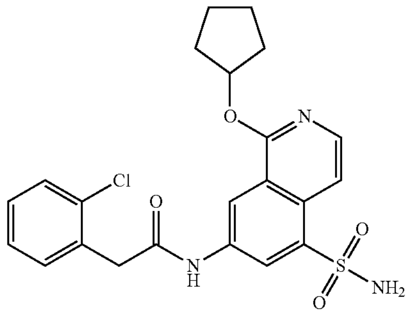

The compound was prepared by reference to the preparation method of embodiment 1. LC-MS: $[M+H]^+$=460.1.

Embodiment 14

Preparation of 2-(2-chlorophenyl)-N-(1-isobutoxy-5-sulfamoylisoquinolin-7-yl)acetamide

14

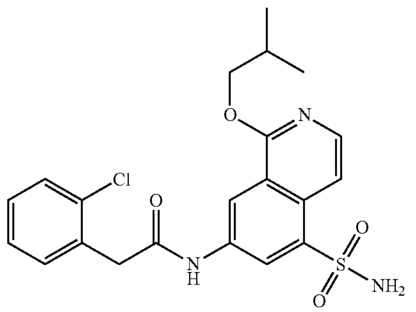

The compound was prepared by reference to the preparation method of embodiment 1. LC-MS: $[M+H]^+$=448.1.

Embodiment 15

Preparation of 2-(2-chlorophenyl)-N-(1-(isopentyloxy)-5-sulfamoylisoquinolin-7-yl)acetamide

15

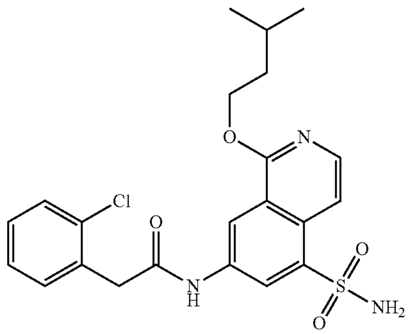

The compound was prepared by reference to the preparation method of embodiment 1. LC-MS: $[M+H]^+$=462.1.

Embodiment 16

Preparation of 2-(2-chlorophenyl)-N-(1-cyclopropylmethoxy)-5-sulfamoylisoquinolin-7-yl)acetamide

16

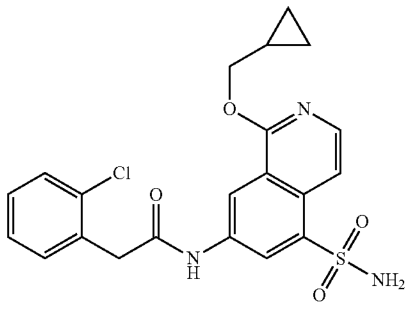

The compound was prepared by reference to the preparation method of embodiment 1. LC-MS: $[M+H]^+$=446.1.

Embodiment 17

Preparation of 2-(2-chlorophenyl)-N-(1-(2-cyclopropylethoxy)-5-sulfamoylisoquinolin-7-yl)acetamide

17

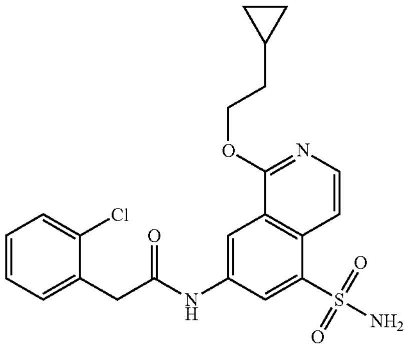

The compound was prepared by reference to the preparation method of embodiment 1. LC-MS: $[M+H]^+$=460.1.

Embodiment 18

Preparation of 2-(2-chlorophenyl)-N-(4-fluoro-5-sulfamoylisoquinolin-7-yl)acetamide

18

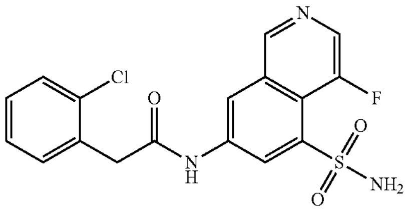

The compound was prepared by reference to the preparation method of embodiment 5. LC-MS: $[M+H]^+$=394.0.

Embodiment 19

Preparation of 2-(2-chlorophenyl)-N-(–5-sulfamoyl-3-(trifluoromethyl)isoquinolin-7-yl)acetamide

19

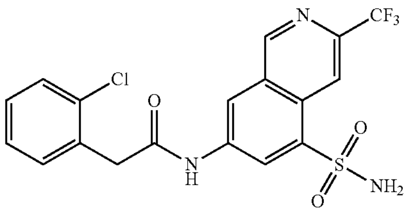

The compound was prepared by reference to the preparation method of embodiment 5. LC-MS: $[M+H]^+$=444.0.

Embodiment 20

Preparation of 2-(2-chlorophenyl)-N-(3-cyano-5-sulfamoylisoquinolin-7-yl)acetamide

20

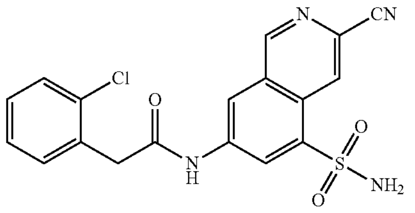

The compound was prepared by reference to the preparation method of embodiment 5. LC-MS: $[M+H]^+$=401.0.

Embodiment 21

Preparation of 2-(2-chlorophenyl)-N-(3-cyclopropyl-5-sulfamoylisoquinolin-7-yl)acetamide

21

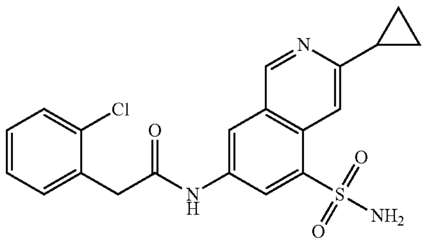

The compound was prepared by reference to the preparation method of embodiment 5. LC-MS: $[M+H]^+$=416.1.

Embodiment 22

Preparation of N-(3-(1H-imidazol-1-yl)-5-sulfamoylisoquinolin-7-yl)-2-(2-chlorophenyl)acetamide

22

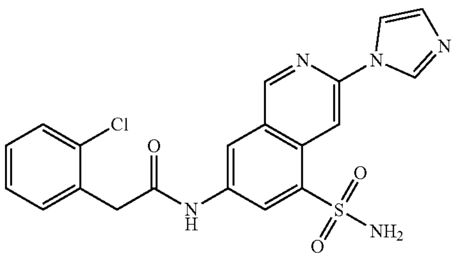

The compound was prepared by reference to the preparation method of embodiment 5. LC-MS: $[M+H]^+$=442.1.

Embodiment 23
Preparation of 2-(2-chlorophenyl)-N-(1-cyclopropyl-5-sulfamoylisoquinolin-7-yl)acetamide
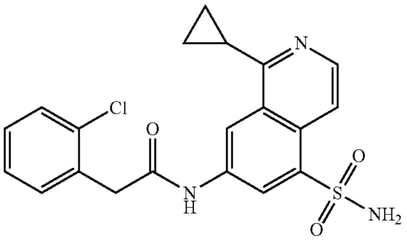 [SMILES: NS(=O)(=O)c1cc(NC(=O)Cc2ccccc2Cl)cc2c(C3CC3)nccc12]
The compound was prepared by reference to the preparation method of embodiment 1. LC-MS: $[M+H]^+$=416.1.
Embodiment 24
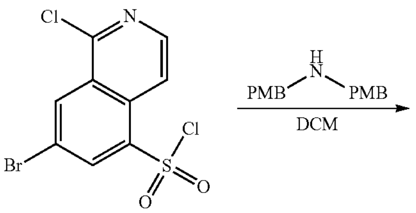
1-3
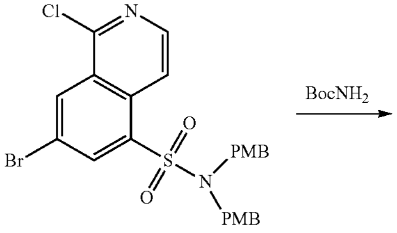
24-1
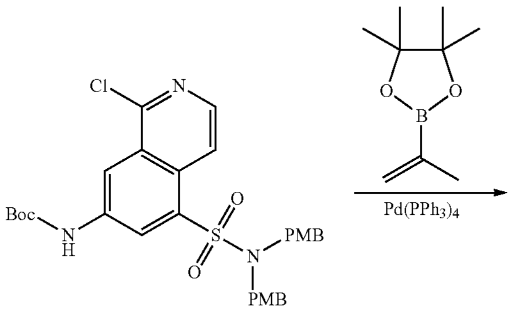
24-2
-continued
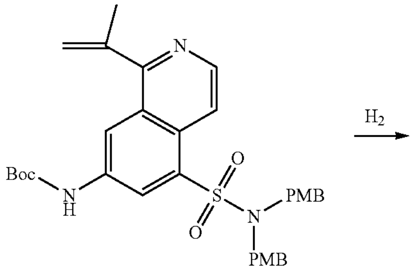
24-3
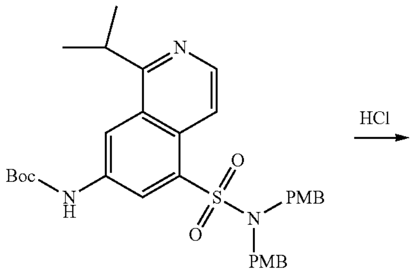
24-4
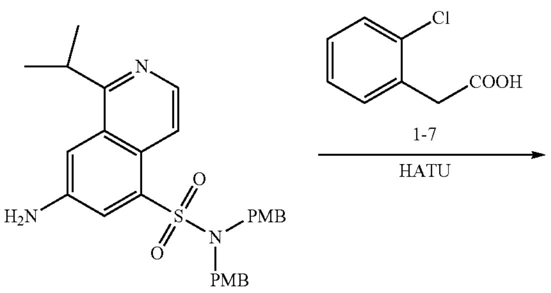
24-5
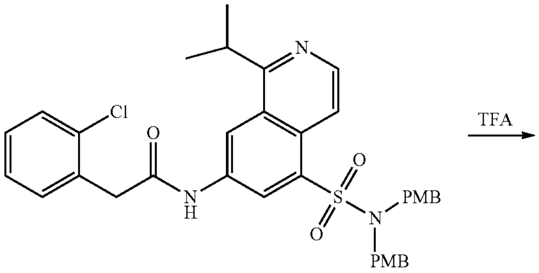
24-6
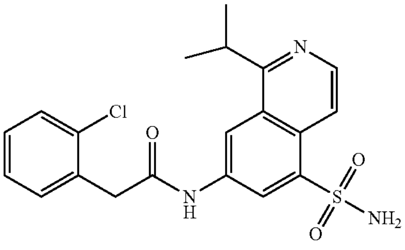
24

Step (1) Preparation of 7-bromo-1-chloro-N,N-bis(4-methoxybenzyl)isoquinoline-5-sulfonamide 24-1

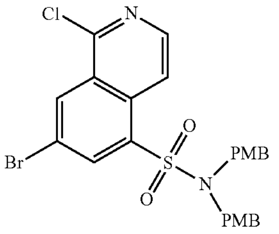

Intermediate 1-3 (20 g, 59 mmol) was dissolved in DCM (150 mL), and $NH(PMB)_2$ (15.2 g, 59 mmol) was weighed and dissolved in DCM (150 mL), and then a solution of intermediate 1-3 was slowly added dropwise to the $NH(PMB)_2$ solution; the mixture was stirred at room temperature for 1 hour after the dropwise addition, and the sample was taken, TLC showed that raw materials were reacted completely and the reaction solution was concentrated under reduced pressure, then the residue was mixed with silica gel and purified by column chromatography to obtain intermediate 24-1 as a yellow solid (32 g). LC-MS: $[M+H]^+$=561.0.

Step (2) Preparation of tert-butyl 5-(N,N-bis(4-methoxybenzyl)sulfamoyl)-1-chloroisoquinolin-7-yl) carbamate 24-2

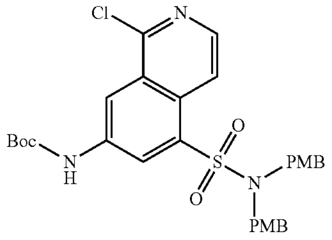

Intermediate 24-1 (11.5 g, 20.5 mmol), $BocNH_2$ (3.6 g, 30.8 mmol), $Cs_2CO_3$ (10.03 g, 30.8 mmol) were weighed, then DMF (100 mL) was added, and the mixture was stirred to dissolve, and then $PdCl_2$(dppf) (1.5 g, 2.05 mmol) and Xantphos (1.18 g, 2.05 mmol) were added thereto; the reaction system was replaced with $N_2$ for three times, and the mixture was stirred at 85° C. for 2 hours. The sample was taken, quenched with water and extracted with EA; TLC showed that about 30% of intermediate 24-1 remained, and water (100 mL) and EA (300 mL) were added to the mixture after cooling, and the mixture was stirred then the phases were separated; the aqueous phase was extracted with EA (100 mL) for three times, and the organic phases were combined, washed with brine (300 mL), dried over anhydrous sodium sulfate, filtered, and the filtrate was concentrated under reduced pressure and then purified by subjecting to column chromatography, concentrated under reduced pressure at 45° C. to obtain intermediate 24-2 as a yellow solid (2.5 g). LC-MS: $[M+H]^+$=598.1.

Step (3) Preparation of tert-butyl (5-(N,N-bis(4-methoxybenzyl)sulfamoyl)-1-(prop-1-en-2-yl)isoquinolin-7-yl)carbamate 24-3

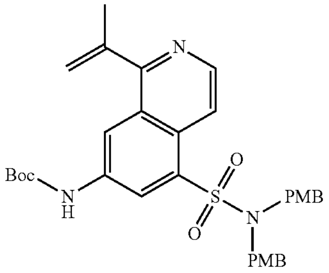

Intermediate 24-2 (240 mg, 0.4 mmol), isopropenyl boronate (100 mg, 0.6 mmol), $Pd(PPh_3)_4$ (46 mg, 0.04 mmol), cesium carbonate (388 mg, 1.2 mmol) were dissolved in DMF (16 mL), and the mixture was stirred under the protection of $N_2$ at 85° C. for 4 hours. TLC showed that the reaction was completed, then the reaction solution was added with water (50 mL), then extracted with ethyl acetate (30 mL) for two times; the organic phases were combined, washed sequentially with saturated brine, dried over anhydrous sodium sulfate, and filtered, and the filtrate was concentrated under reduced pressure and subjected to column chromatography to obtain intermediate 24-3 as a pale-yellow oil (120 mg, the purity was 95%, the yield was 41%). LC-MS: $[M+1]^+$=604.

Step (4) Preparation of tert-butyl (5-(N,N-bis(4-methoxybenzyl)sulfamoyl)-1-isopropylisoquinolin-7-yl)carbamate 24-4

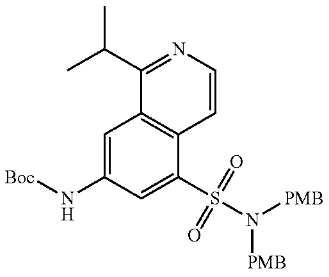

Intermediate 24-3 (110 mg, 0.18 mmol) was dissolved in THF (7 mL), then Pd/C (20 mmol) was added thereto, and the mixture was stirred at room temperature for 2 hours under the protection of $H_2$. LCMS showed that the reaction was completed, and the reaction solution was directly filtered with diatomite and concentrated to obtain intermediate 24-4 as a pale-yellow oil (120 mg, the purity was 92%, the yield was 100%). LC-MS: $[M+1]^+$=606.

Step (5) Preparation of 7-amino-1-isopropyl-N,N-bis(4-methoxybenzyl)isoquinoline-5-sulfonamide 24-5

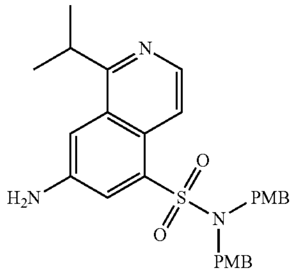

Intermediate 24-4 (120 mg, 0.198 mmol) was dissolved in DCM (0.1 mL), and HCl-1,4-dioxane (0.5 mL, 1.98 mmol, 4 M) was added, and then the mixture was reacted at room temperature for 2 hours. LCMS showed that the reaction was completed, but impurities were formed in the reaction. After the reaction solution was concentrated, water (10 mL) was added, and the pH of the mixture was adjusted to 8 with saturated sodium bicarbonate solution, then the mixture was extracted with ethyl acetate (5 mL) for two times; the organic phases were combined, washed sequentially with saturated brine, dried over anhydrous sodium sulfate, and filtered; the filtrate was concentrated under reduced pressure to obtain a crude product of intermediate 24-5 as a pale-yellow oil (92 mg, the purity was 60%, the yield was 92%), LC-MS: $[M+1]^+=506$. The crude product was used directly for the next reaction without purification.

Step (6) Preparation of N-(5-(N,N-bis(4-methoxybenzyl)sulfamoyl)isopropylisoquinolin-7-yl)-2-(2-chlorophenyl)acetamide 24-6

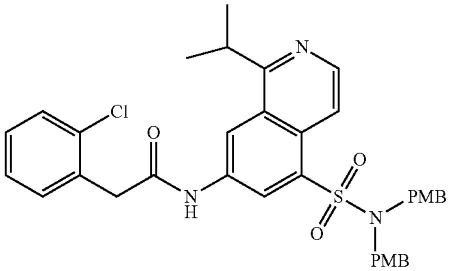

Intermediate 24-5 (80 mg, 0.16 mmol), 2-chloropheny-lacetic acid (41 mg, 0.24 mmol), HATU (100 mg, 0.24 mmol) and DIEA (62 mg, 0.48 mmol) were dissolved in DMF (5 mL), and the mixture was stirred overnight at room temperature. TLC showed that the reaction was completed, then the reaction solution was added with water (20 mL) then extracted with ethyl acetate (5 mL) for two times; the organic phases were combined, dried, and concentrated under reduced pressure and subjected to column chromatography to obtain intermediate 24-6 as a pale-yellow oil (31 mg, the purity was 95%, the yield was 31%). LC-MS: $[M+1]^+=658$.

Step (7) Preparation of 2-(2-chlorophenyl)-N-(1-isopropyl-5-sulfamoylisoquinolin-7-yl)acetamide

24

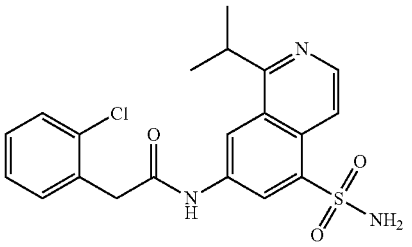

Intermediate 24-6 (31 mg, 0.048 mmol) was dissolved in DCM (1 mL), then TFA (2 mL) was added, and the mixture was stirred at 55° C. for 2 hours. TLC showed that the reaction was completed, and the reaction solution was concentrated under reduced pressure to obtain a crude product. The crude product was purified by prep-HPLC, and then lyophilized to obtain compound 24 as a white solid (8.2 mg, the purity was 97.91%, the yield was 41.8%). LC-MS: $[M+1]^+=418$.

$^1H$ NMR (400 MHz, DMSO) δ 10.90 (s, 1H), 8.98 (s, 1H), 8.54 (d, J=1.9 Hz, 1H), 8.47 (d, J=6.0 Hz, 1H), 8.18 (m, 1H), 7.75 (s, 2H), 7.52-7.41 (m, 2H), 7.37-7.26 (m, 2H), 3.93 (s, 2H), 3.80 (dt, J=13.5, 6.6 Hz, 1H), 1.32 (d, J=6.7 Hz, 6H).

Embodiment 25

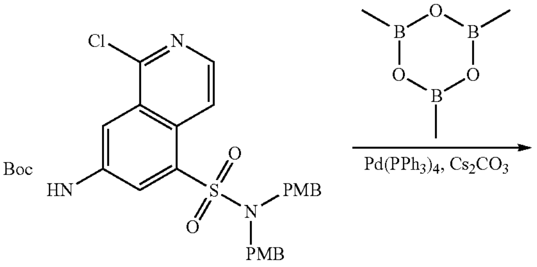

24-2

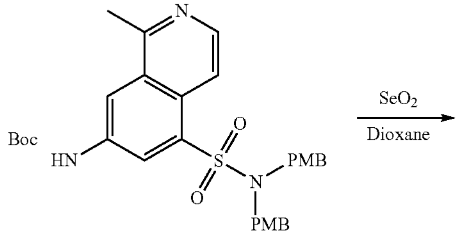

25-1

-continued

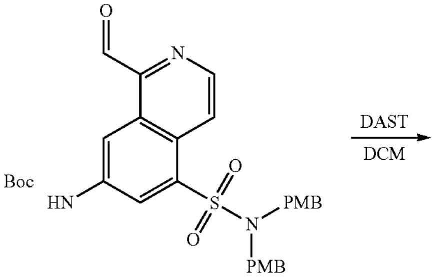

25-2

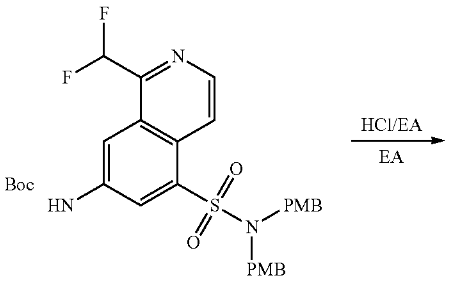

25-3

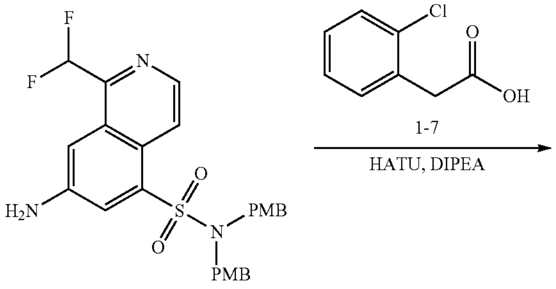

25-4

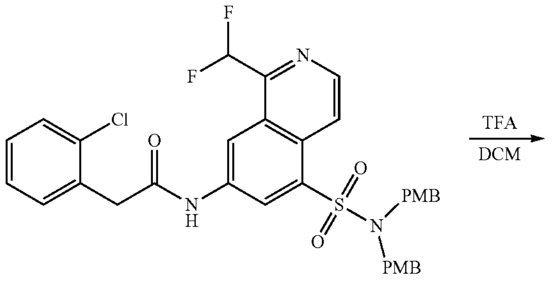

25-5

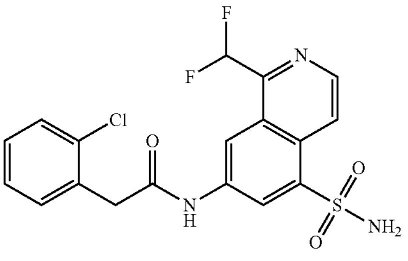

25

Step (1) Preparation of tert-butyl 5-(N,N-bis(4-methoxybenzyl)sulfamoyl)-1-methylisoquinolin-7-yl)carbamate 25-1

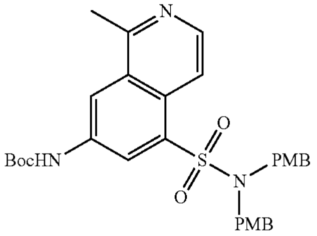

Intermediate 24-2 (2.5 g, 4.2 mmol), trimethylboron (1.57 g, 6.3 mmol), $Cs_2CO_3$ (2.73 g, 8.4 mmol), $Pd(PPh_3)_4$ (0.48 g, 0.42 mmol) were weighed and dissolved in DMF (20 mL), and the reaction system was replaced with $N_2$ for three times and the mixture was stirred at 85° C. for 40 hours. The sample was taken, and TLC showed that raw material: product=1:1, and the reaction solution was cooled to 30° C.; water (50 mL) and EA (100 mL) were added, and the mixture was stirred, then the phases were separated; the aqueous phase was extracted with EA (30 mL) for two times, and the organic phases were combined, then washed with brine, dried over anhydrous sodium sulfate, filtered, and concentrated to obtain a crude product, and the crude product was purified by column chromatography to obtain intermediate 25-1 as a yellow solid (0.9 g). LC-MS: $[M+H]^+$ =578.2.

Step (2) Preparation of tert-butyl 5-(N,N-bis(4-methoxybenzyl)sulfamoyl)-1-formylisoquinolin-7-yl)carbamate 25-2

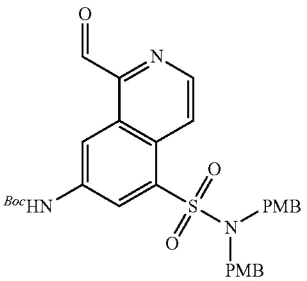

Intermediate 25-1 (0.9 g, 1.56 mmol) and selenium dioxide (0.52 g, 4.68 mmol) were weighed and dissolved in 1,4-dioxane (10 mL), and the reaction system was replaced with $N_2$ for three times and the mixture was stirred at 80° C. for 1 hour. The sample was taken, and TLC showed that raw materials were reacted completely, and the reaction solution was cooled to 30° C.; $H_2O$ (50 mL) and EA (100 mL) were added, and the mixture was stirred then the phases were separated; the aqueous phase was extracted with EA (30 mL) for two times, and the organic phases were combined, then washed with brine, dried over anhydrous sodium sulfate, filtered, and concentrated to obtain a crude product, and intermediate 25-2 as a yellow solid (400 mg) was obtained form the crude product. LC-MS: $[M+H]^+$=592.2.

Step (3) Preparation of tert-butyl 5-(N,N-bis(4-methoxybenzyl)sulfamoyl)-1-(difluoromethyl)isoquinolin-7-yl)carbamate 25-3

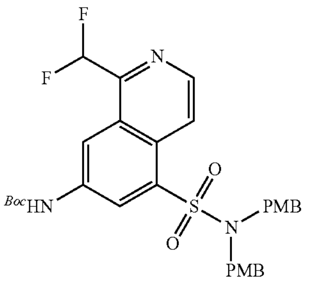

Intermediate 25-2 (400 mg, 0.67 mmol) was weighed and dissolved in DCM (10 mL), and the mixture was cooled to 0° C., then DAST (0.22 g, 1.35 mmol) was slowly added dropwise; after the dropwise addition was completed, the mixture was stirred at room temperature for 1 hour; the sample was taken, and TLC showed that raw materials were reacted completely; DCM (20 mL) and $H_2O$ (10 mL) were added to the reaction solution, and the mixture was stirred and then the phases were separated; the aqueous phase was extracted with DCM (10 mL) for three times, and the organic phases were combined, washed with brine, dried over anhydrous sodium sulfate, filtered, and the filtrate was concentrated under reduced pressure at 45° C. to obtain intermediate 25-3 as a red solid (370 mg). LC-MS: $[M+H]^+$=614.2.

Step (4) Preparation of 7-amino-1-(difluoromethyl)-N,N-bis(4-methoxybenzyl)isoquinoline-5-sulfonamide 25-4

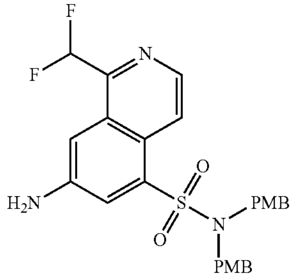

Intermediate 25-3 (370 mg, 0.6 mmol) was weighed and dissolved in EA (5 mL), then 3M HCl/EA solution (20 mL) was added thereto, and the mixture was stirred at 25° C. for 3 hours, and the sample was taken, then TLC showed that raw materials were reacted completely; the reaction mixture was diluted with EA (50 mL), and the pH of the mixture was adjusted to 8 to 9 with saturated sodium carbonate solution, and the phases were separated; the aqueous phase was extracted with EA (20 mL) for three times, and the organic phases were combined, washed with brine, dried over anhydrous sodium sulfate, filtered, and then concentrated under reduced pressure at 40° C. to obtain a crude product of intermediate 25-4 as a green solid (320 mg). LC-MS: $[M+H]^+$=514.1.

Step (5) N-(5-(N,N-bis(4-methoxybenzyl)sulfamoyl)-1-(difluoromethyl)isoquinolin-7-yl)-2-(2-chlorophenyl)acetamide 25-5

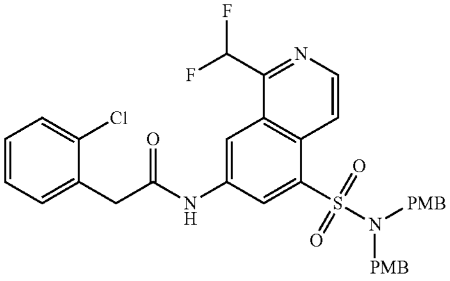

2-Chlorophenylacetic acid (0.16 g, 0.93 mmol) and HATU (0.35 g, 0.93 mmol) were dissolved in DMF (20 mL), and the mixture was stirred at room temperature for 1 hour, and then intermediate 25-4 (0.32 g, 0.62 mmol) and DIPEA (0.16 g, 1.24 mmol) were added, and the mixture was stirred at 40° C. for 40 hours. The sample was taken, and TLC showed that raw materials were reacted completely, and the reaction solution was cooled to 25° C.; EA (100 mL) and $H_2O$ (50 mL) were added to the reaction mixture, and the mixture was stirred then the phases were separated; the aqueous phase was extracted with EA (50 mL) for three times, and the organic phases were combined, then washed with brine, dried over anhydrous sodium sulfate, filtered, and the filtrate was concentrated under reduced pressure, then purified by column chromatography to obtain intermediate 25-5 as a yellow solid (290 mg). LC-MS: $[M+H]^+$=666.1.

Step (6) Preparation of 2-(2-chlorophenyl)-N-(1-(difluoromethyl)-5-sulfamoylisoquinolin-7-yl)acetamide

25

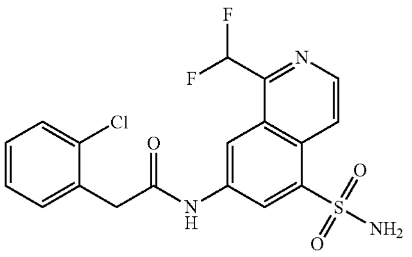

Intermediate 25-5 (290 mg, 0.436 mmol) was dissolved in DCM (10 mL), then TFA (20 mL) was added, and the mixture was stirred at 40° C. for 16 hours; the sample was taken, and LCMS showed that raw materials were reacted completely; DCM (50 mL) and $H_2O$ (20 mL) were added to the reaction solution, and the mixture was stirred and then the phases were separated; the aqueous phase was extracted with DCM (20 mL) for three times, and the organic phases were combined, washed with saturated sodium carbonate solution and saturated brine, and dried over anhydrous sodium sulfate, filtered, and the filtrate was concentrated to obtain a crude product. The crude product was purified by prep-HPLC, and lyophilized to obtain compound 25 as a white solid (43 mg, the purity was 99.53%).

LC-MS: $[M+H]^+$=426. $^1H$ NMR (400 MHz, DMSO) δ 11.05 (s, 1H), 9.09 (s, 1H), 8.70 (d, J=1.9 Hz, 1H), 8.64 (d, J=6.0 Hz, 1H), 8.56 (d, J=6.0 Hz, 1H), 7.92 (s, 2H), 7.50-7.45 (m, 2H), 7.44 (s, 1H), 7.34 (dt, J=10.2, 3.0 Hz, 2H), 7.30 (s, 1H), 7.17 (s, 1H), 3.96 (s, 2H).

Embodiment 26

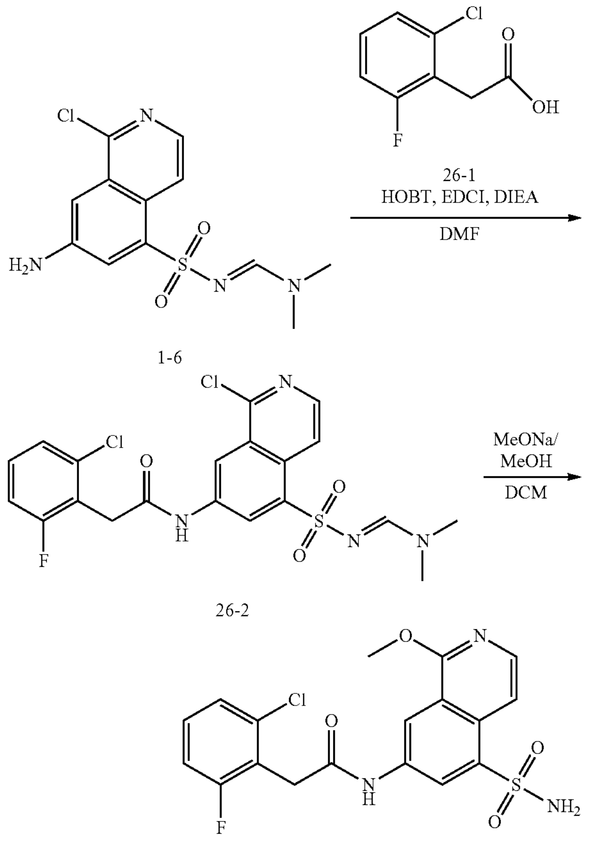

1-6

26-2

26

Step (1) Preparation of (E)-N-(1-chloro-5-(N-((dimethylamino)methylene)sulfamoyl)isoquinolin-7-yl)-2-(2-chloro-6-fluorophenyl)acetamide 26-2

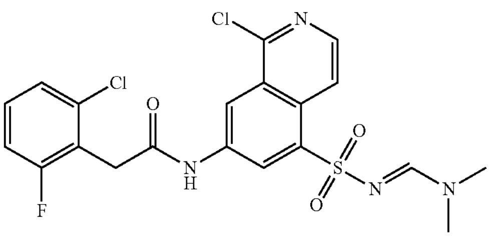

Intermediate 1-6 (150 mg, 0.481 mmol) and intermediate 26-1 (136 mg, 0.721 mmol) were dissolved in DMF (3 mL), then HOBT (77.9 mg, 0.577 mmol), EDCI (111 mg, 0.577 mmol) and DIEA (124 mg, 0.962 mmol) were added. The reaction solution was stirred at room temperature overnight. After the reaction was completed, the reaction solution was poured into water and extracted with EA. The organic phase was concentrated by rotary evaporation to obtain a crude product of intermediate 26-2 as a yellow oil (105 mg, the yield was 45.3%). LC-MS: $[M+H]^+$=482.90.

Step (2) Preparation of 2-(2-chloro-6-fluorophenyl)-N-(1-methoxy-5-sulfamoylisoquinolin-7-yl)acetamide

26

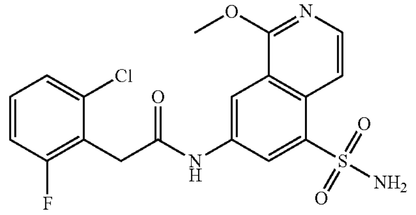

Intermediate 26-2 (100 mg, 0.207 mmol) was dissolved in DCM (2 mL), then MeONa/MeOH (30%, 186 mg, 1.04 mmol) solution was added, and the reaction solution was stirred at room temperature for 3 hours. The reaction was completed. The reaction solution was poured into water, extracted with EA, and the organic phase was concentrated by rotary evaporation to obtain 100 mg of crude product, and the crude was prepared by prep-HPLC to obtain compound 26 as a white solid (11.8 mg).

LC-MS: $[M+H]^+$=423.95. $^1H$ NMR (400 MHz, DMSO-$d_6$) δ 10.97 (s, 1H), 8.84 (s, 1H), 8.53 (d, J=2.4 Hz, 1H), 8.07 (d, J=6.4 Hz, 1H), 7.91 (d, J=6.4 Hz, 1H), 7.76 (s, 2H), 7.44-7.36 (m, 2H), 7.30-7.24 (m, 1H), 4.06 (s, 3H), 3.97 (s, 2H).

Embodiment 27

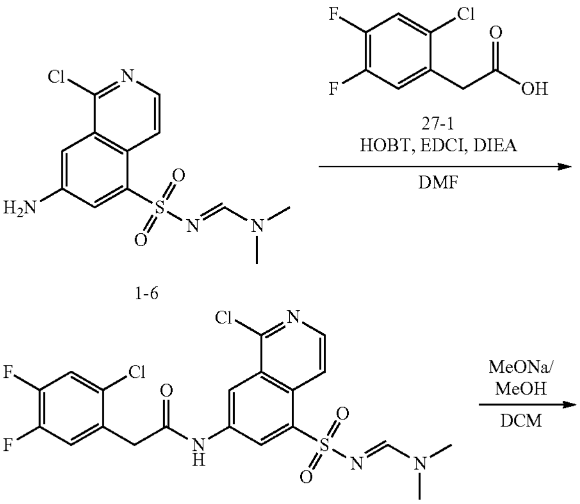

1-6

27-2

-continued

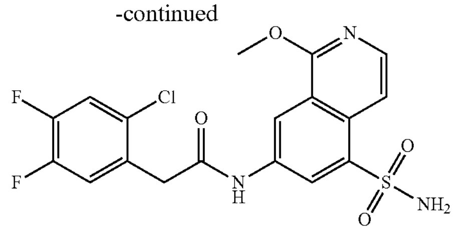

27

Step (1) Preparation of (E)-N-(1-chloro-5-(N-((dimethylamino)methylene)sulfamoyl)isoquinolin-7-yl)-2-(2-chloro-4,5-difluorophenyl)acetamide 27-2

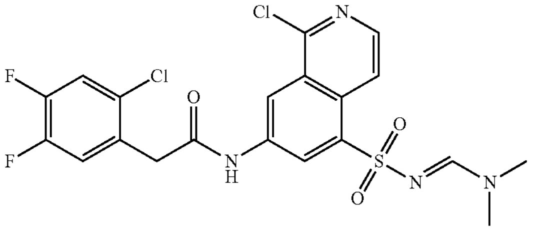

Intermediate 1-6 (150 mg, 0.481 mmol) and intermediate 27-1 (149 mg, 0.721 mmol) were dissolved in DMF (3 mL), then HOBT (77.9 mg, 0.577 mmol), EDCI (111 mg, 0.577 mmol) and DIEA (124 mg, 0.962 mmol) were added. The reaction solution was stirred at room temperature overnight. After the reaction was completed, the reaction solution was poured into water and extracted with EA. The organic phase was concentrated by rotary evaporation to obtain a crude product of intermediate 27-2 as a yellow oil (165 mg, the yield was 68.6%). LC-MS: $[M+H]^+=500.90$.

Step (2) Preparation of 2-(2-chloro-4,5-difluorophenyl)-N-(1-methoxy-5-sulfamoylisoquinolin-7-yl)acetamide

27

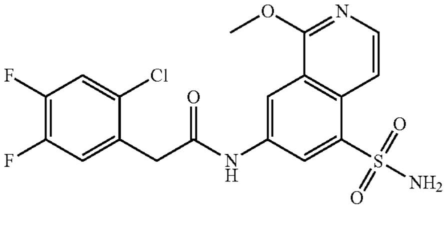

Intermediate 27-2 (160 mg, 0.319 mmol) was dissolved in DCM (2 mL), then MeONa/MeOH (30%, 286 mg, 1.59 mmol) solution was added, and the reaction solution was stirred at room temperature for 72 hours. The reaction was completed. The reaction solution was poured into water, extracted with EA, and the organic phase was concentrated by rotary evaporation to obtain 100 mg of crude product, and the crude product was prepared by prep-HPLC to obtain compound 27 as a white solid (27 mg).

LC-MS: $[M+H]^+=441.95$. $^1H$ NMR (400 MHz, MeOD-$d_4$) δ 8.84 (d, J=2.4 Hz, 1H), 8.63 (d, J=2.0 Hz, 1H), 8.06 (d, J=6.4 Hz, 1H), 7.98 (d, J=6.4 Hz, 1H), 7.51-7.40 (m, 2H), 4.14 (s, 3H), 3.96 (s, 2H).

Embodiment 28

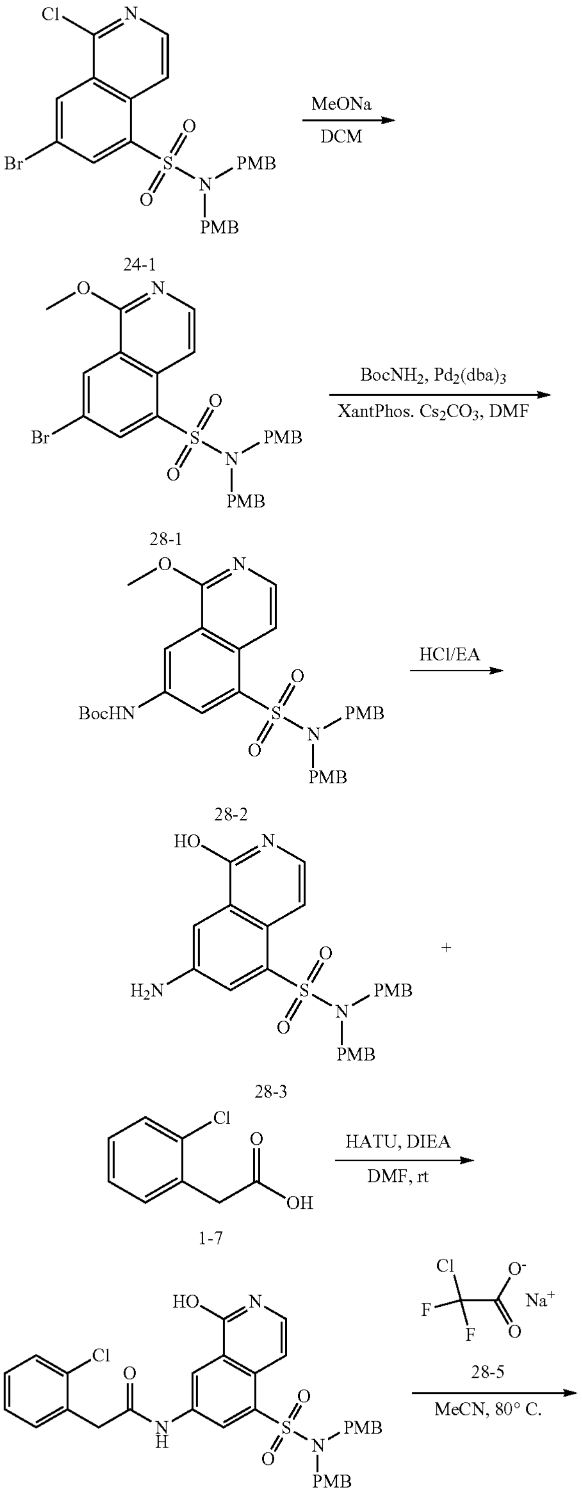

24-1

28-1

28-2

28-3

1-7

28-5

28-4

-continued

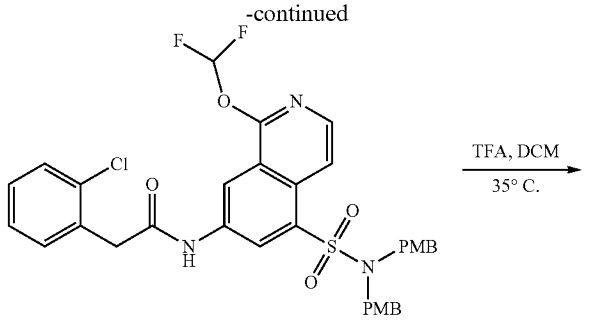

28-6

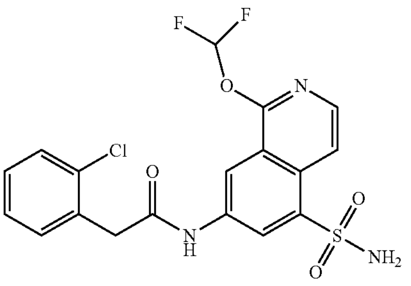

28

Step (1) Preparation of 7-bromo-1-methoxy-N,N-bis(4-methoxybenzyl)isoquinoline-5-sulfonamide 28-1

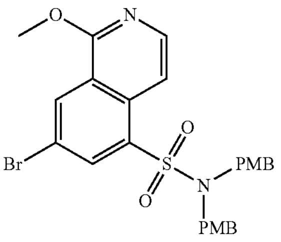

Intermediate 24-1 (2 g, 3.56 mmol) was dissolved in DCM (30 mL), then sodium methoxide solution (5 mol/L, 4.3 mL, 21.4 mmol) was added. The reaction solution was stirred at room temperature overnight. After the reaction was completed, the reaction solution was poured into water, and the pH was adjusted to 8 with HCl (1M), and the mixture was extracted with EA. The organic phase was concentrated by rotary evaporation to obtain a crude product, and the crude product was purified by silica gel column to obtain intermediate 28-1 as a yellow solid (1.2 g, the yield was 60.5%). LC-MS: $[M+H]^+$=557.1.

Step (2) Preparation of tert-butyl 5-(N,N-bis(4-methoxybenzyl)sulfonamide)1-methoxyisoquinolin-7-yl)carbamate 28-2

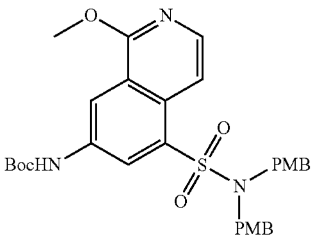

Intermediate 28-1 (1 g, 1.78 mmol) and $BocNH_2$ (312 mg, 2.67 mmol) were dissolved in DMF (30 mL), then $Pd_2(dba)_3$ (81.4 mg, 89 μmol), XantPhos (51.4 mg, 89 μmol) and $Cs_2CO_3$ (1.16 g, 3.56 mmol) were added thereto, and the reaction was stirred at 85° C. for 4 hours. The reaction was completed. The reaction solution was poured into water, extracted with EA, and the organic phase was concentrated by rotary evaporation to obtain a crude product, and the crude product was purified by silica gel column to obtain intermediate 28-2 as a yellow solid (1.1 g, the yield was 100%). LC-MS: $[M+H]^+$=594.2.

Step (3) Preparation of 7-amino-1-hydroxy-N,N-bis(4-methoxybenzyl)isoquinoline-5-sulfonamide 28-3

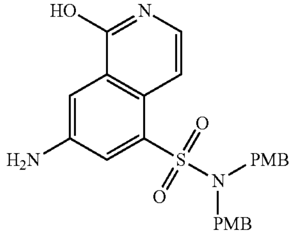

Intermediate 28-2 (1.1 g, 1.84 mmol) was added to HCl/EA (3 M), and the mixture was stirred at room temperature for 2 hours, then the reaction was completed; the reaction solution was diluted with EA, and then the pH was adjusted to 6 with NaOH (1 M), and the phases were separated; the organic phase was concentrated by rotary evaporation to obtain a crude product of intermediate 28-3 as a yellow oil (600 mg, the yield was 100%). LC-MS: $[M+H]^+$=480.2.

Step (4) Preparation of N-(5-(N,N-bis(4-methoxybenzyl)sulfamoyl)-1-hydroxyisoquinolin-7-yl)-2-(2-chlorophenyl)acetamide 28-4

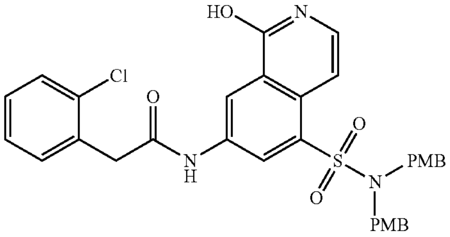

Intermediate 28-3 (550.0 mg, 1.15 mmol) was dissolved in DMF (15 mL), and then intermediate 1-7 (234.8 mg, 1.38 mmol), HATU (1.72 mmol), DIEA (296.5 mg, 2.29 mmol) were added, and the reaction was stirred overnight at room temperature. TLC (EA:PE=1:2) showed that the raw materials were reacted completely, and the reaction solution was diluted with water (50 mL), extracted with ethyl acetate (50 mL×3); the organic phases were combined, washed with saturated brine, dried over anhydrous $Na_2SO_4$; the solvent was removed by rotary evaporation, and the residue was separated by column chromatography to obtain intermediate 28-4 as a beige solid (600 mg, the yield was 82.8%). LC-MS: $[M+H]^+$=632.

Step (5) Preparation of N-(5-(N,N-bis(4-methoxybenzyl)sulfamoyl)-1-(difluoromethoxy)isoquinolin-7-yl)-2-(2-chlorophenyl)acetamide 28-6

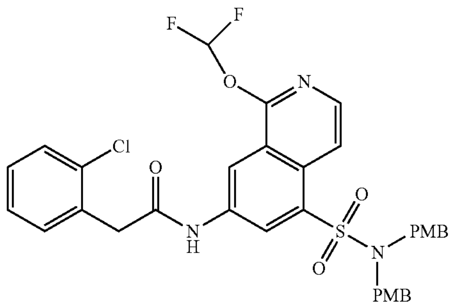

Intermediate 28-4 (500.0 mg, 790.98 μmol) was dissolved in MeCN (15 mL), and intermediate 28-5 (241.2 mg, 1.58 mmol) was added. The temperature was heated to 80° C. and the reaction was stirred overnight. TLC showed that the raw materials were reacted completely. The solvent was removed by rotary evaporation, and the residue was separated by column chromatography to obtain intermediate 28-6 as a beige solid (200.2 mg). LC-MS: $[M+H]^+$=682.

Step (6) Preparation of 2-(2-chlorophenyl)-N-(1-(difluoromethoxy)-5-sulfamoylisoquinolin-7-yl)acetamide

28

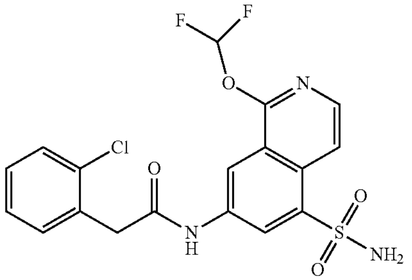

Intermediate 28-4 (490.0 mg, 718.33 μmol) was dissolved in DCM (8 mL), then TFA (8 mL) was added, and the reaction was stirred at 35° C. overnight. TLC showed that the raw materials were reacted completely and the reaction was stopped. The solvent was removed by rotary evaporation to obtain a crude product. The crude product was purified by prep-HPLC, and lyophilized to obtain compound 28 as a white solid (115.3 mg, the purity was 99.927%).

LC-MS: $[M+H]^+$=441.90. $^1$H NMR (400 MHz, DMSO-$d_6$) δ 11.02 (s, 1H), 8.82 (d, J=1.4 Hz, 1H), 8.66 (d, J=2.0 Hz, 1H), 8.17 (dd, J=13.5, 6.2 Hz, 2H), 8.11 (s, 1H), 7.93 (s, 1H), 7.87 (s, 2H), 7.74 (s, 1H), 7.47 (dd, J=5.2, 4.0 Hz, 2H), 7.37-7.30 (m, 2H), 3.94 (s, 2H).

Embodiment 29

Preparation of 2-(2-chlorophenyl)-N-(-5-sulfamoyl-1-(trifluoromethyl)isoquinolin-7-yl)acetamide

29

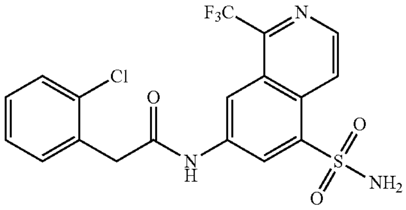

The compound was prepared by reference to the preparation method of embodiment 1. LC-MS: $[M+H]^+$=440.0.

Embodiment 30

Preparation of 2-(2-chlorophenyl)-N-(1-phenoxy-5-sulfamoylisoquinolin-7-yl)acetamide

30

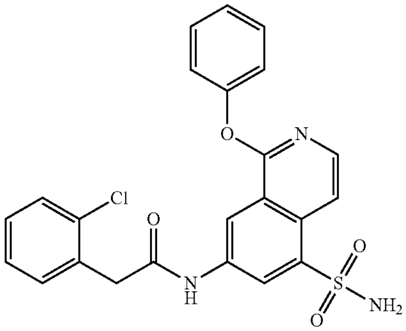

The compound was prepared by reference to the preparation method of embodiment 1. LC-MS: $[M+H]^+$=468.1.

Embodiment 31

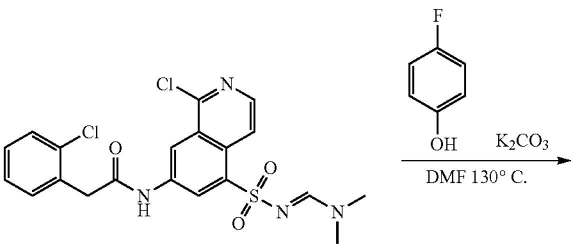

1-8

-continued

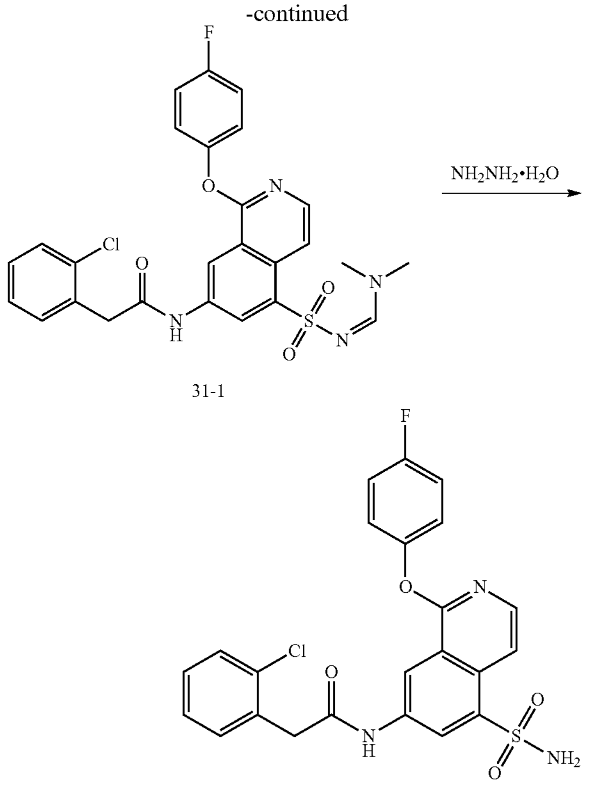

31-1

31

Step (1) Preparation of (Z)-2-(2-chlorophenyl)-N-(5-(N-(((dimethylamino)methylene)sulfamoyl)-1-(4-fluorophenoxy)isoquinolin-7-yl)acetamide 31-1

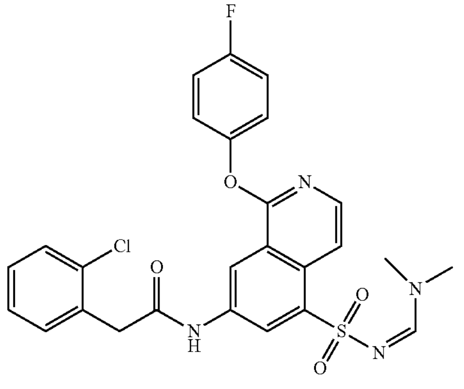

Intermediate 1-8 (160 mg, 0.35 mmol), p-fluorophenol (118 mg, 1.05 mmol) and potassium carbonate (145 mg, 1.05 mmol) were dissolved in DMF and the reaction was stirred at room temperature overnight. The sample was taken, then TLC showed that raw materials were reacted completely. The reaction solution was slowly added with water (5 mL), extracted with EA for three times, then EA phases were combined, washed with saturated brine, dried over anhydrous sodium sulfate, filtered, and the filtrate was concentrated to obtain a product of intermediate 31-1 (100 mg). LC-MS: $[M+H]^+=541$.

Step (2) Preparation of 2-(2-chlorophenyl)-N-(1-(4-fluorophenoxy)-5-sulfamoylisoquinolin-7-yl)acetamide

31

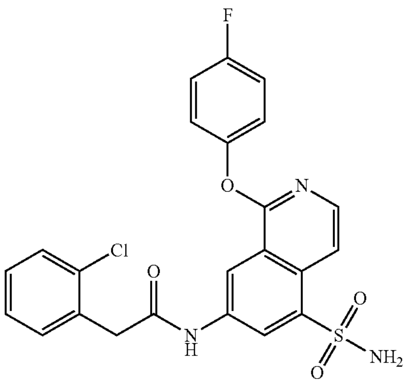

Intermediate 31-1 (100 mg, 0.28 mmol) was dissolved in hydrazine hydrate (15 mL), and the reaction was stirred at room temperature for 2 hours. The sample was taken, and TLC showed that raw materials were reacted completely. The reaction solution was concentrated by rotary evaporation and purified by preparative chromatography, then the preparation solution was lyophilized to obtained compound 31 as a white solid (35 mg).

LC-MS: $[M+H]^+=486.1$. $^1H$ NMR (400 MHz, DMSO) δ:10.96 (s, 1H), 9.04 (s, 1H), 8.62 (d, J=2.0 Hz, 1H), 8.02 (s, 1H), 7.97 (d, J=6.0 Hz, 1H), 7.82 (s, 2H), 7.46 (d, J=9.2 Hz, 2H), 7.34-7.26 (m, 6H), 3.94 (s, 2H).

Embodiment 32

Preparation of 2-(2-chlorophenyl)-N-(1-((4-fluorobenzyl)oxo)-5-sulfamoylisoquinolin-7-yl)acetamide

32

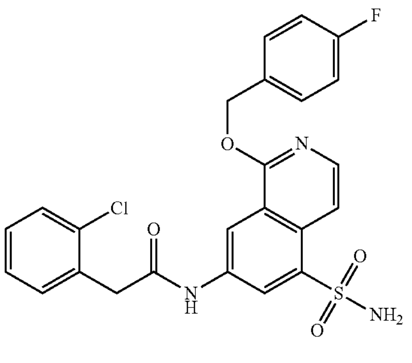

The compound was prepared by reference to the preparation method of embodiment 1. LC-MS: $[M+H]^+=500.1$.

Embodiment 33

Preparation of N-(1-((1-acetylazetidin-3-yl)oxo)-5-sulfamoylisoquinolin-7-yl)-2-(2-chlorophenyl)acetamide

33

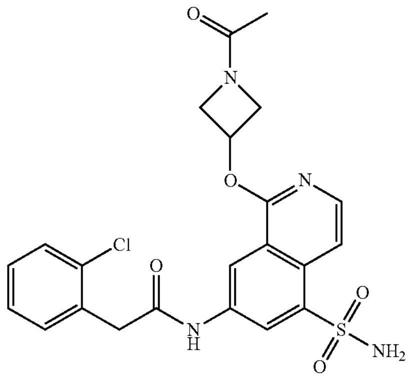

The compound was prepared by reference to the preparation method of embodiment 1. LC-MS: $[M+H]^+$=489.1.

Embodiment 34

Preparation of 2-(2-chlorophenyl)-N-(5-sulfamoyl-1-(p-tolyloxy)isoquinolin-7-yl)acetamide

34

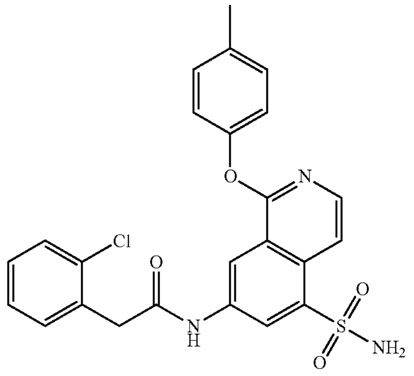

The compound was prepared by reference to the preparation method of embodiment 1. LC-MS: $[M+H]^+$=482.1.

Embodiment 35

Preparation of 2-(2-chlorophenyl)-N-(1-(4-methoxyphenoxy)-5-sulfamoylisoquinolin-7-yl)acetamide

35

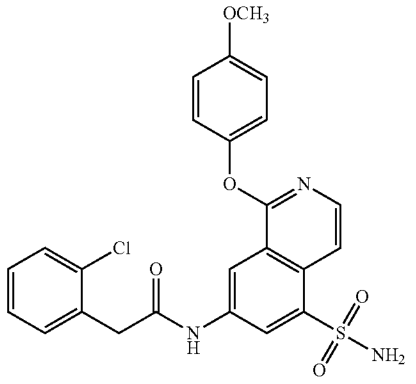

The compound was prepared by reference to the preparation method of embodiment 1. LC-MS: $[M+H]^+$=498.1.

Embodiment 36

Preparation of 2-(2-chlorophenyl)-N-(8-sulfamoyl-4-(trifluoromethyl)isoquinolin-6-yl)acetamide

36

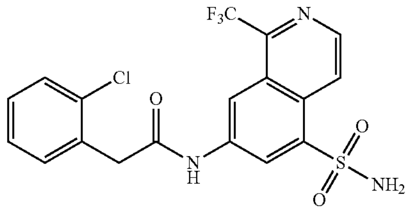

The compound was prepared by reference to the preparation method of embodiment 5. LC-MS: $[M+H]^+$=444.0.

Embodiment 37

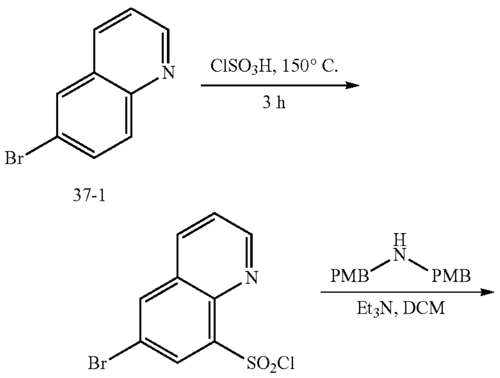

37-1

37-2

-continued

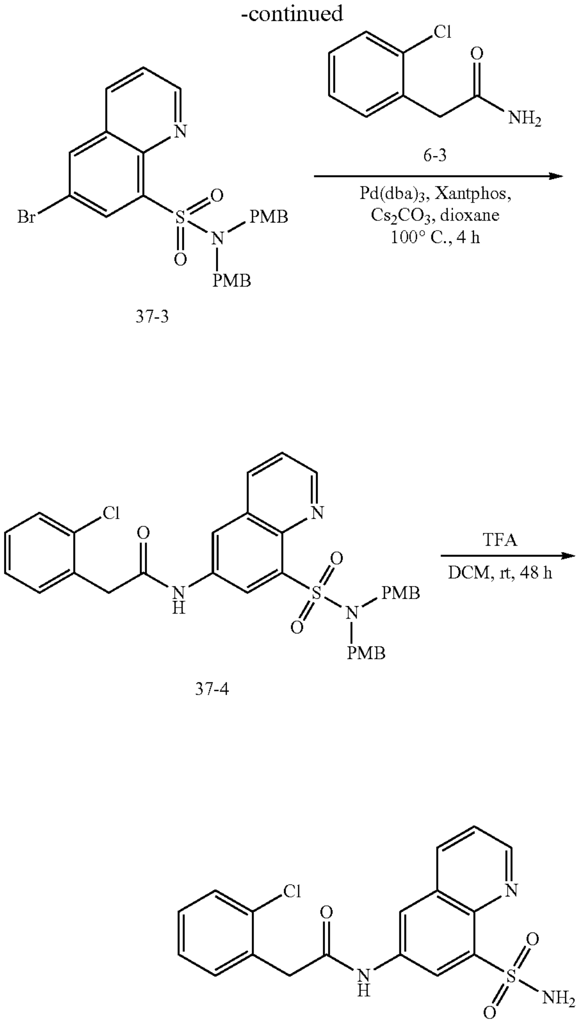

37-3 6-3 37-4 37

Step (1) Preparation of 6-bromoquinoline-8-sulfonyl chloride 37-2

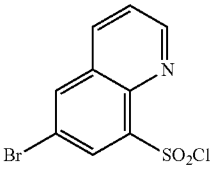

Under the protection of nitrogen, 6-bromoquinoline (3.0 g, 14.42 mmol) was slowly added to chlorosulfonic acid (10 mL), and the mixture was reacted at 150° C. for 3 hours, cooled to room temperature, and the reaction solution was slowly added dropwise to ice (50 g), and then extracted with ethyl acetate (50 mL×2); the organic phases were combined, washed with saturated brine (20 mL×2), dried over anhydrous sodium sulfate, filtered, and concentrated under reduced pressure to obtain a crude product of intermediate 37-2 as a brown solid (1.68 g). LC-MS: $[M+H]^+$=307.9.

Step (2) Preparation of 6-bromo-N,N-bis(4-methoxybenzyl)quinoline-8-sulfonamide 37-3

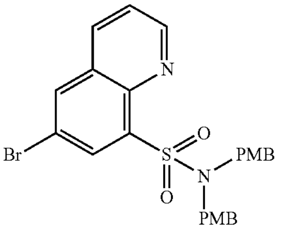

Under the protection of nitrogen, bis-(4-methoxybenzyl)-amine (1.27 g, 4.94 mmol) and triethylamine (2.22 g, 21.96 mmol) were dissolved in dichloromethane (16 mL) in an ice-water bath, then a dichloromethane (4 mL) solution of intermediate 37-2 (1.68 g, 5.49 mmol) was added dropwise and the mixture was stirred at room temperature overnight. The reaction solution was poured into water (30 mL), and extracted with dichloromethane (30 mL×2); the organic phases were combined, washed with saturated brine (30 mL), dried over anhydrous sodium sulfate, filtered, and the filtrate was concentrated, and the crude product was purified by silica gel column to obtain intermediate 37-3 as a pale-yellow solid (1.30 g) with a two-step yield of 17%. LC-MS: $[M+H]^+$=528.6.

Step (3) N-(8-(N,N-bis(4-methoxybenzyl)sulfamoyl)quinolin-6-yl)-2-(2-chlorophenyl)acetamide 37-4

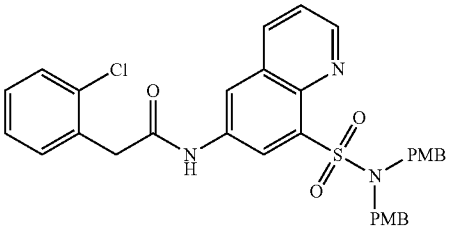

Intermediate 37-3 (1.25 g, 2.37 mmol) and 2-(2-chlorophenyl)acetamide (442 mg, 2.61 mmol) were dissolved in dioxane (20 mL), then 4,5-bis(diphenylphosphino)-9,9-dimethylxanthene (278 mg, 0.47 mmol), tris(dibenzylideneacetone)dipalladium (217 mg, 0.24 mmol) and cesium carbonate (1.93 g, 5.93 mmol) were sequentially added; under the protection of nitrogen, the mixture was reacted at 100° C. for 4 hours. The mixture was cooled to room temperature, filtered, concentrated under reduced pressure, and the crude product was purified by silica gel column to obtain intermediate 37-4 as a pale-yellow solid (957 mg, the yield was 63%). LC-MS: $[M+H]^+$=616.1.

Step (4) Preparation of 2-(2-chlorophenyl)-N-(8-sulfamoylquinolin-6-yl)acetamide

37

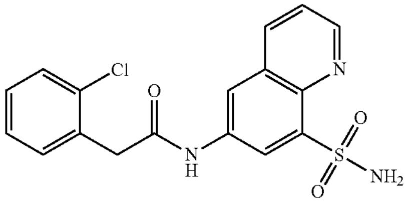

Intermediate 37-4 (950 mg, 1.54 mmol) was dissolved in dichloromethane (4 mL), then trifluoroacetic acid (4 mL) was added, and the reaction mixture was reacted at room temperature for 48 hours. The mixture was concentrated under reduced pressure, then dissolved in dichloromethane (40 mL), washed with saturated sodium bicarbonate solution (20 mL×2) and saturated brine (20 mL), dried over anhydrous sodium sulfate, filtered and concentrated to obtain 600 mg of crude product; 200 mg of the crude product was purified by preparative chromatography (acetonitrile (0.1% ammonia water)-water (0.1% ammonia water)) to obtain compound 37 as a white solid (73 mg, the yield was 38%).

LC-MS: $[M+H]^+$=376.1. $^1$H NMR (400 MHz, DMSO) δ 10.86 (s, 1H), 8.95 (dd, J=4.2, 1.7 Hz, 1H), 8.62 (d, J=2.4 Hz, 1H), 8.46 (dd, J=8.5, 1.9 Hz, 2H), 7.65 (dd, J=8.4, 4.2 Hz, 1H), 7.51-7.45 (m, 2H), 7.38-7.32 (m, 2H), 7.29 (s, 2H), 3.94 (s, 2H).

Embodiment 38

Preparation of 2-(2-chlorophenyl)-N-(2-fluoro-8-sulfamoylquinolin-6-yl)acetamide

38

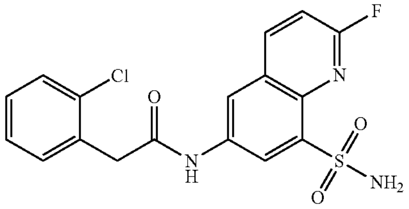

The compound was prepared by reference to the preparation method of embodiment 3. LC-MS: $[M+H]^+$=394.0.

Embodiment 39

Preparation of N-(2-amino-5-sulfamoylquinazolin-7-yl)-2-(2-chlorophenyl)acetamide

39

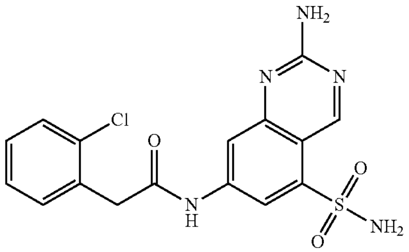

The compound was prepared by reference to the preparation method of embodiment 3. LC-MS: $[M+H]^+$=392.0.

Embodiment 40

Preparation of 2-(2-chlorophenyl)-N-(8-sulfamoylquinazolin-6-yl)acetamide

40

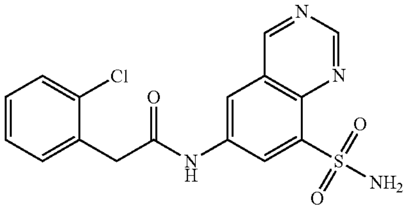

The compound was prepared by reference to the preparation method of embodiment 3. LC-MS: $[M+H]^+$=377.0.

Embodiment 41

Preparation of 2-(2-chlorophenyl)-N-(8-sulfamoylcinnolin-6-yl)acetamide

41

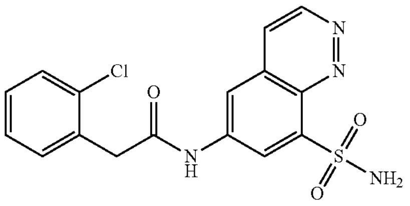

The compound was prepared by reference to the preparation method of embodiment 3. LC-MS: $[M+H]^+$=377.0.

Embodiment 42

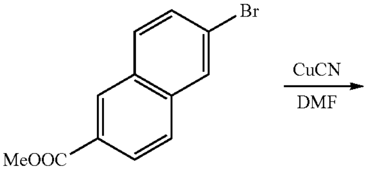

42-1

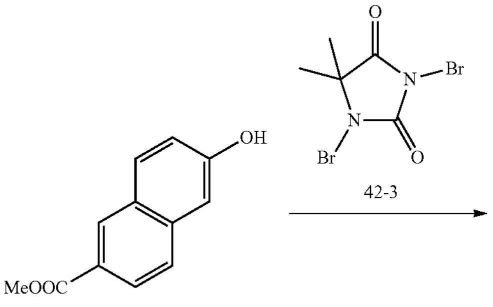

42-3

42-2

-continued

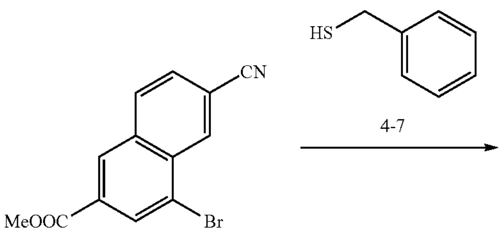

42-4

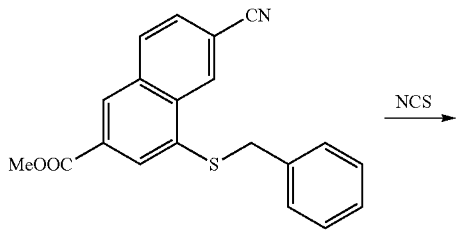

42-5

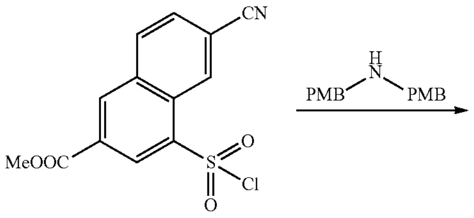

42-6

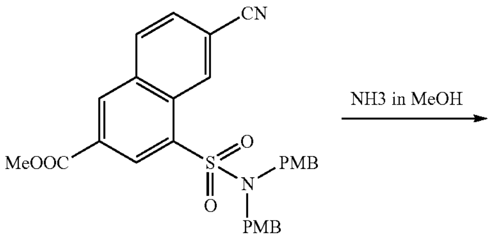

42-7

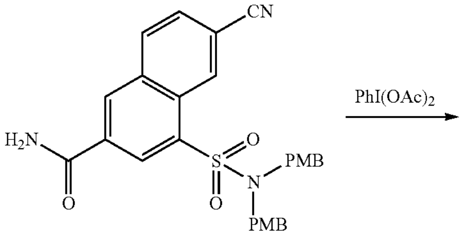

42-8

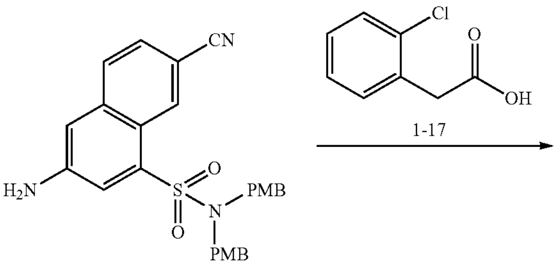

42-9

-continued

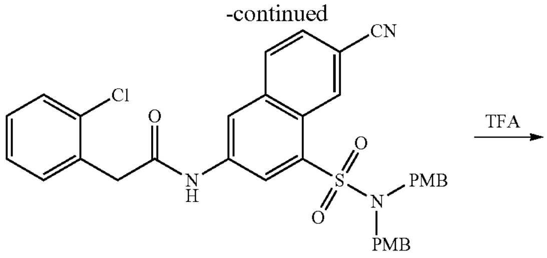

42-10

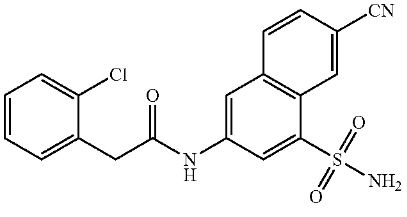

42

Step (1) Preparation of methyl 6-cyano-2-naphthoate 42-2

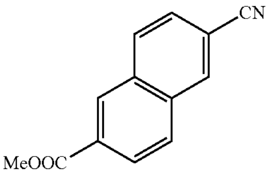

Intermediate 42-1 (5 g, 18.86 mmol) was weighed and then dissolved in DMF (100 mL), then CuCN (2.03 g, 22.63 mmol) was added, and the reaction mixture was reacted overnight at 150° C. reflux under the protection of $N_2$, then TLC showed that the raw materials were reacted completely. The reaction solution was cooled to room temperature, diluted with water (100 mL), extracted with dichloromethane (100 mL) for two times; the organic phase was concentrated by rotary evaporation, and purified by column chromatography to obtain intermediate 42-2 as a yellow-green solid (3.5 g). LC-MS: $[M+H]^+$=212.1.

Step (2) Preparation of methyl 4-bromo-6-cyano-2-naphthoate 42-4

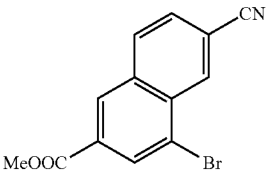

Intermediate 42-2 (6 g, 28.41 mmol) was weighed and then dissolved in DCM (200 mL), and the body of flask was covered with tin foil to avoid light; TfOH (4.7 g, 31.247 mmol) and DDH (6.5 g, 22.73 mmol) were added, and the reaction system was replaced with $N_2$; the mixture was reacted at room temperature overnight, and the completion of the reaction of the raw materials was monitored by TLC. The reaction solution was quenched with saturated $NaHSO_3$, and the pH was adjusted to about 7.0 with saturated $NaHCO_3$; the organic phase was separated and concentrated by rotary evaporation, slurried with methanol for two times and filtered, and the filter cake was dried by rotary evaporation to obtain intermediate 42-4 as a white solid (6.2 g). LC-MS: $[M+H]^+$=290.0.

Step (3) Preparation of methyl 4-(benzylthio)-6-cyano-2-naphthoate 42-5

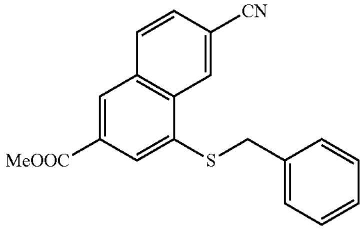

Intermediate 42-4 (6.2 g, 21.37 mmol), benzylthiol (3.5 g, 27.78 mmol), $Pd_2(dba)_3$ (1.9 g, 2.14 mmol), Xantphos (619 mg, 1.07 mmol) and DIEA (11 g, 84.48 mmol) were weighed and sequentially added to a single-necked flask containing 1,4-dioxane (150 mL), and the reaction system was replaced with $N_2$, and the mixture was reacted at 105° C. overnight; the completion of the reaction of the raw materials was monitored by TLC, and the reaction solution was cooled to room temperature, then water (100 mL) was added, and the mixture was extracted with EA (100 mL); the organic phase was concentrated by rotary evaporation, and purified by column chromatography to obtain intermediate 42-5 as a yellow solid (5.3 g). LC-MS: $[M+H]^+$=334.1.

Step (4) Preparation of methyl 4-(chlorosulfonyl)-6-cyano-2-naphthoate 42-6

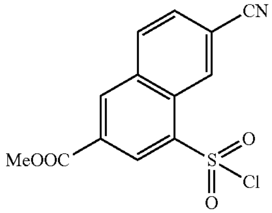

Intermediate 42-5 (4.3 g, 12.89 mmol) was weighed and dissolved in a mixture solution of glacial acetic acid (36 mL) and water (12 mL), and NCS (6.9 g, 51.59 mmol) was added in batches at room temperature; after the addition was completed, the reaction mixture was reacted at room temperature for 2 hours; the completion of the reaction of the raw materials was monitored by TLC, and the reaction solution was filtered, and the filter cake was washed with water for two times, and concentrated by rotary evaporation to obtain intermediate 42-6 as a pale-yellow solid (3.8 g). LC-MS: $[M+H]^+$=310.0.

Step (5) Preparation of methyl 4-(N,N-bis(4-methoxybenzyl)sulfamoyl)-6-cyano-2-naphthoate 42-7

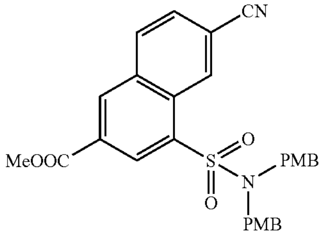

bis-(4-Methoxybenzyl)-amine (3.8 g, 14.75 mmol) was weighed and dissolved in DCM (120 mL), then TEA (3.7 g, 36.87 mmol) was added, and the mixture was stirred at room temperature for 10 min; intermediate 42-6 (3.8 g, 12.29 mmol) was added, and the reaction mixture was reacted at room temperature for 2 hours. The completion of the reaction of the raw materials was monitored by TLC, and water (100 mL) was added to the reaction solution; the organic phase was washed with dilute hydrochloric acid (0.1 N), dried over $Na_2SO_4$, and concentrated by rotary evaporation to obtain intermediate 42-7 as a yellow oily liquid (5.5 g). LC-MS: $[M+H]^+$=531.1.

Step (6) Preparation of 4-(N,N-bis(4-methoxybenzyl)sulfamoyl)-6-cyano-2-naphthylamide 42-8

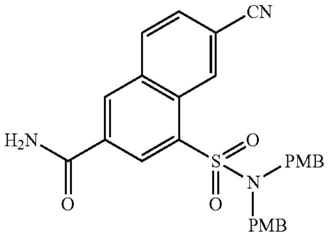

Intermediate 42-7 (1.2 g, 2.26 mmol) was weighed and placed in a stuffy jar, and a methanol solution of amine (7.0 M, 25 mL) was added; after sealing, the reaction mixture was reacted at 70° C. overnight, and the reaction solution was cooled to room temperature, and the completion of the reaction of the raw materials was monitored by TLC, and the mixture was directly concentrated by rotary evaporation and subjected to column chromatography to obtain intermediate 42-8 as an off-white solid (530 mg). LC-MS: $[M+H]^+$=516.1.

Step (7) Preparation of 3-amino-7-cyano-N,N-bis(4-methoxybenzyl)naphthalene-1-sulfonamide 42-9

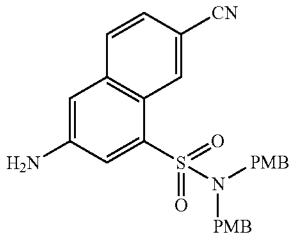

Intermediate 42-8 (600 mg, 1.16 mmol) and DBU (355 mg, 2.33 mmol) were weighed and dissolved in tetrahydrofuran (30 mL), and water (10 mL) was slowly added to ensure that the system was homogeneous (mutual dissolution without stratification); the mixture was cooled to 0° C., and iodobenzene acetate (450 mg, 1.39 mmol) was added, and the mixture was reacted at room temperature for 10 min after the addition was completed, and the completion of the reaction of the raw materials was monitored by TLC. Water (20 mL) was added to the reaction solution, and the mixture was extracted with EA (30 mL) for two times, and the organic phase was concentrated by rotary evaporation and purified by column chromatography to obtain intermediate 42-9 as a yellow oily liquid (500 mg). LC-MS: $[M+H]^+$=488.2.

Step (8) Preparation of N-(4-(N,N-bis(4-methoxybenzyl)sulfamoyl)-6-cyanonaphthalen-2-yl)-2-(2-chlorophenyl)acetamide 42-10

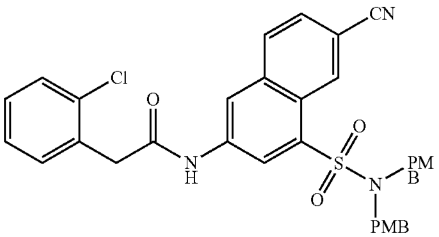

2-Chlorophenylacetic acid (263 mg, 1.54 mmol), HATU (585 mg, 1.54 mmol) and DIEA (531 mg, 4.102 mmol) were weighed and dissolved in DMF (20 mL), and the mixture was stirred at room temperature for 20 min, then intermediate 42-9 (500 mg, 1.11 mmol) was added, and the mixture was reacted at room temperature overnight; monitored by TLC, more than half of the raw materials were not reacted, and only a small amount of product appeared; 2-chlorophenylacetic acid (263 mg) and HATU (585 mg) were added, and the mixture was heated to 60° C. and reacted for 6 hours, and the completion of the reaction of the raw materials was monitored by TLC. The reaction solution was cooled and added with water (20 mL), extracted with EA (20 mL) for two times; the organic phase was concentrated by rotary evaporation and subjected to column chromatography to obtain intermediate 42-10 as a yellow solid (450 mg). LC-MS: $[M+H]^+$=640.2.

Step (9) Preparation of 2-(2-chlorophenyl)-N-(6-cyano-4-sulfamoylnaphthalen-2-yl)acetamide

42

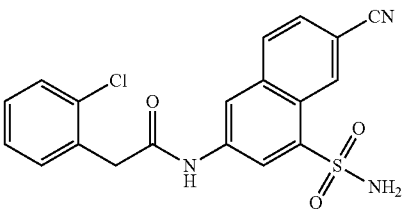

Intermediate 42-10 (450 mg, 0.72 mmol) was weighed and dissolved in DCM (15 mL), then TFA (15 mL) was added, and the reaction mixture was reacted at 40° C. overnight, and the completion of the reaction of the raw materials was monitored by TLC. The reaction solution was concentrated, and purified by Prep-HPLC to obtain compound 42 as a white solid (88.2 mg). LC-MS: $[M+H]^+$=400.0.

LC-MS: $[M+H]^+$=400.00. $^1H$ NMR (400 MHz, DMSO) δ 10.46 (s, 1H), 8.53 (s, 1H), 8.40 (d, J=6.5 Hz, 1H), 8.08 (s, 3H), 7.80 (dd, J=14.6, 8.4 Hz, 3H), 7.70 (d, J=8.6 Hz, 2H), 7.23 (s, 1H), 7.11 (d, J=5.1 Hz, 1H), 6.97 (s, 1H), 6.84 (d, J=6.5 Hz, 1H), 4.89 (s, 2H), 4.57 (s, 2H), 4.05 (s, 3H).

Embodiment 43

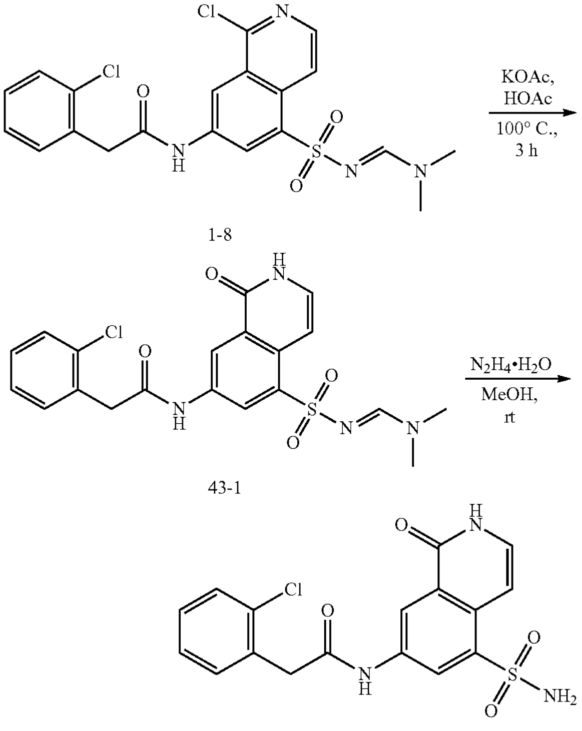

1-8

43-1

43

Step (1) Preparation of (E)-2-(2-chlorophenyl)-N-(5-(N-((dimethylamino)methylene)sulfamoyl)-1-oxo-1,2-dihydroisoquinolin-7-yl)acetamide 43-1

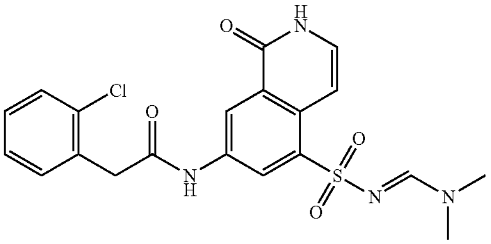

Intermediate 1-8 (200.0 mg, 429.78 μmol) was dissolved in HOAc (15 mL), and KOAc (421.8 mg, 4.30 mmol) was added. The temperature was warmed to 100° C., and the reaction was stirred for 3 hours. TLC showed that the raw materials were reacted completely. The solvent was removed by rotary evaporation, and the residue was separated by column chromatography to obtain intermediate 43-1 as a yellow solid (200 mg). LC-MS: $[M+H]^+$=447.

Step (2) Preparation of 2-(2-chlorophenyl)-N-(1-oxo-5-sulfamoyl-1,2-dihydroisoquinolin-7-yl)acetamide

43

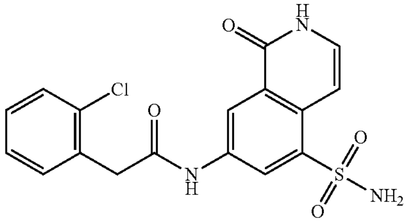

Intermediate 43-1 (190.0 mg, 425.15 μmol) was dissolved in MeOH (10 mL), then hydrazine hydrate (5 mL) was added, and the reaction was stirred for 1 hour at room temperature. TLC showed that the reaction was completed, and the reaction was stopped. The reaction solution was diluted with water (50 mL) and ethyl acetate (50 mL), and the phases were separated; the organic phase was collected, and the solvent was removed by rotary evaporation to obtain a crude product. The crude product was purified by prep-HPLC, and lyophilized to obtain compound 43 as a beige solid (5.0 mg, the purity was 97.123%).

LC-MS: $[M+H]^+$=391.95. $^1H$ NMR (400 MHz, DMSO) δ 11.46 (d, J=4.9 Hz, 1H), 10.74 (s, 1H), 8.71 (s, 1H), 8.56 (d, J=1.5 Hz, 1H), 7.64 (s, 2H), 7.49-7.38 (m, 2H), 7.35-7.27 (m, 2H), 7.24-7.18 (m, 1H), 7.08 (d, J=7.3 Hz, 1H), 3.87 (s, 2H).

Embodiment 44

Compound 44: Preparation of 2-(2-chlorophenyl)-N-(1-cyano-5-sulfamoylisoquinolin-7-yl)acetamide

44

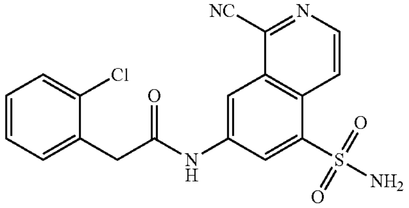

The compound was prepared by reference to the preparation method of embodiment 6. LC-MS: $[M+H]^+$=400.6

Embodiment 45

Compound 45: Preparation of 2-(2-chlorophenyl)-N-(8-sulfamoylisoquinolin-6-yl)acetamide

45

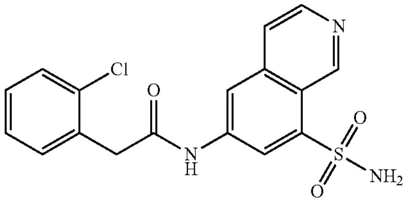

The compound was prepared by reference to the preparation method of embodiment 6. LC-MS: $[M+H]^+$=376.0

Embodiment 46

Compound 46: Preparation of methyl 7-(2-(2-chlorophenyl)acetamido)-5-sulfamoyl-3,4-dihydroquinoline-1(2H)-carboxylate

46

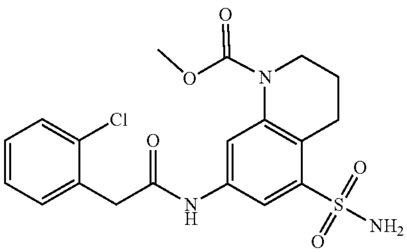

The compound was prepared by reference to the preparation method of embodiment 6. LC-MS: $[M+H]^+$=438.1

Embodiment 47

Compound 47: Preparation of 2-(2-chlorophenyl)-N-(4-fluoro-8-sulfamoylisoquinolin-6-yl)acetamide

47

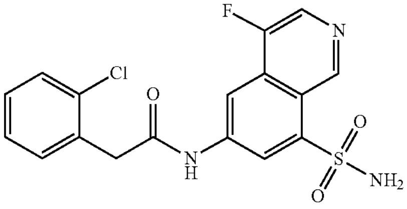

The compound was prepared by reference to the preparation method of embodiment 6. LC-MS: $[M+H]^+$=394.0.

Embodiment 48

Compound 48: Preparation of N-(4-chloro-8-sulfamoylisoquinolin-6-yl)-2-(2-chlorophenyl)acetamide

48

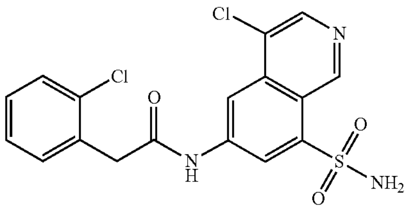

The compound was prepared by reference to the preparation method of embodiment 6. LC-MS: $[M+H]^+$=410.0

Embodiment 49

Compound 49: Preparation of N-(2-(1H-pyrazol-1-yl)-5-sulfamoylquinolin-7-yl)-2-(2-chlorophenyl) acetamide

49

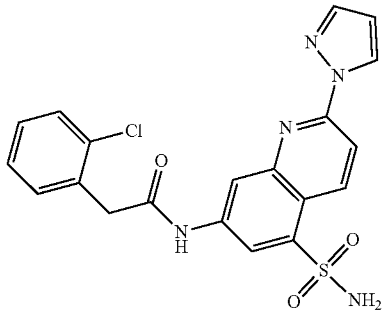

The compound was prepared by reference to the preparation method of Embodiment 5. LC-MS: $[M+H]^+$=442.1

Embodiment 50

Compound 50: Preparation of N-(3-(1H-imidazol-1-yl)-8-sulfamoylisoquinolin-6-yl)-2-(2-chlorophenyl) acetamide

50

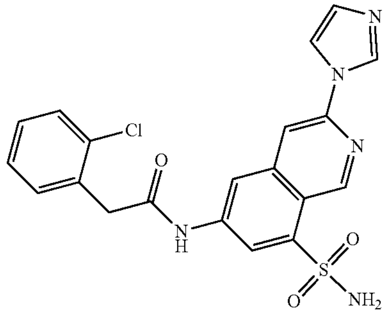

The compound was prepared by reference to the preparation method of embodiment 6. LC-MS: $[M+H]^+$=442.1

Embodiment 51

Compound 51: Preparation of N-(1-amino-5-sulfamoylisoquinolin-7-yl)-2-(2-chlorophenyl)acetamide

51

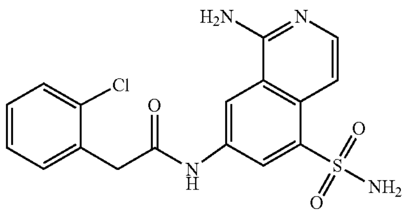

The compound was prepared by reference to the preparation method of embodiment 1. LC-MS: $[M+H]^+$=391.1

Embodiment 52

Compound 52: Preparation of 2-(2-chlorophenyl)-N-(1-((4-fluorophenyl)amino)-5-sulfamoylisoquinolin-7-yl)acetamide

52

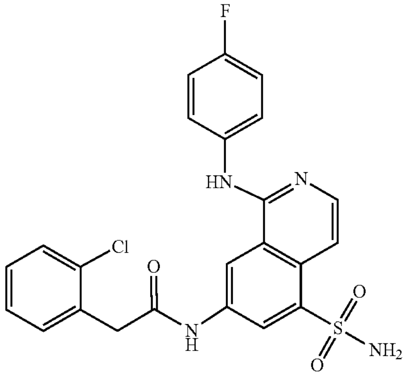

The compound was prepared by reference to the preparation method of embodiment 1. LC-MS: $[M+H]^+$=485.1

Embodiment 53

Compound 53: Preparation of 2-(2-chlorophenyl)-N-(1-methoxy-5-(S-methylsulfonimidoyl)isoquinolin-7-yl)acetamide

53

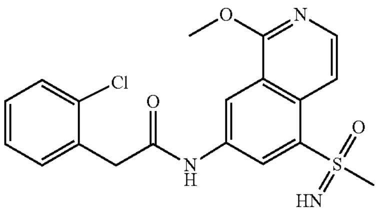

The compound was prepared by reference to the preparation method of embodiment 1. LC-MS: $[M+H]^+$=404.1

Embodiment 54

Compound 54: Preparation of 2-(6-chloro-2,3-difluorophenyl)-N-(1-methoxy-5-sulfamoylisoquinolin-7-yl)acetamide

54

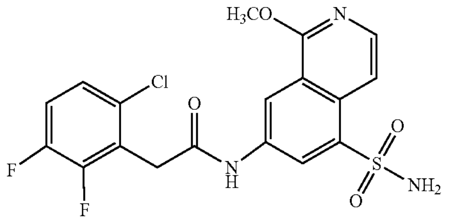

Synthetic Route:

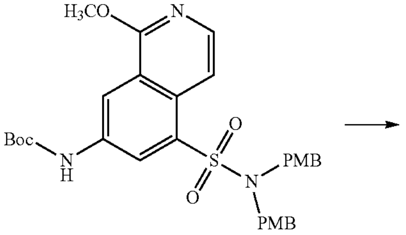

28-2

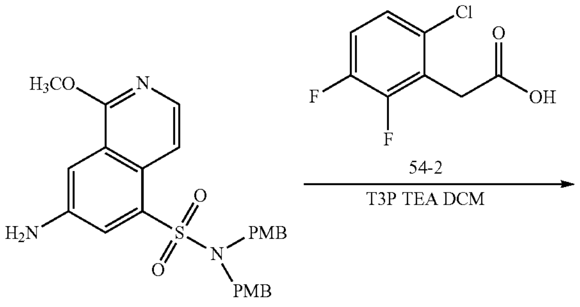

54-1

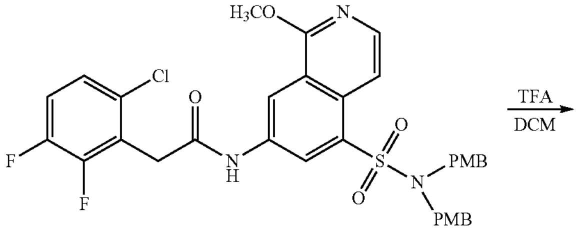

54-3

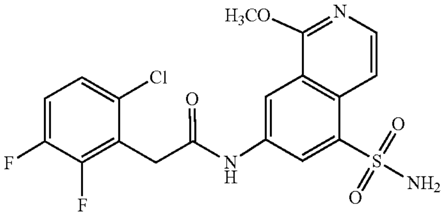

54

Step (1) Preparation of Intermediate 54-1

Intermediate 28-2 (600 mg) was weighed and dissolved in 18 mL of DCM, then 3 mL of TFA was added; after the addition was completed, and the mixture was reacted at room temperature for 1.5 hours; the completion of the reaction of the raw materials was monitored by TLC, and the reaction solution was quenched with saturated sodium bicarbonate solution, extracted with DCM, and the organic phase was washed with saturated brine, dried over sodium sulfate, and concentrated by rotary evaporation to obtain 690 mg of a crude product of intermediate 54-1 as a yellow oily liquid.

Step (2) Preparation of Intermediate 54-3

Intermediate 54-1 (80 mg), intermediate 54-2 (2-(6-chloro-2,3-difluorophenyl)acetic acid) (40 mg), T3P (103 mg) and TEA (49 mg) were accurately weighed and dissolved in DCM, and the reaction was stirred at room temperature for 1 hour. The sample was taken, and TCL showed that the raw materials were reacted completely. In post treatment, silica gel was directly added into the reaction solution, and subjected to column chromatography (PE/EA=4:1-2:1), and the obtained solution after column chromatography was concentrated by rotary evaporation to obtain the product. The reaction was successful, and 100 mg of intermediate 54-3 was obtained as a yellow oily liquid. LCMS: $[M+H]^+$=682.

Step (3) Preparation of Compound 54

Intermediates 54-3 (100 mg) and TFA (44.1 mg) were accurately weighed and dissolved in DCM, and the mixture was stirred at room temperature overnight. The sample was taken, and TLC showed that the raw materials were reacted completely; the reaction solution was concentrated by rotary evaporation, purified by preparative chromatography and the preparation solution was lyophilized to obtain the product. The reaction was successful to obtain 12 mg of compound 54 as a white foamy solid. LCMS: $[M+H]^+$=442.

$^1$H NMR (400 MHz, dmso) δ 10.99 (s, 1H), 8.81 (d, J=1.3 Hz, 1H), 8.51 (d, J=2.1 Hz, 1H), 8.05 (d, J=6.2 Hz, 1H), 7.89 (d, J=6.2 Hz, 1H), 7.74 (s, 1H), 7.50-7.36 (m, 2H), 4.04 (s, 3H), 4.00 (s, 2H).

Embodiment 55

Compound 55: Preparation of 2-(2-chlorophenyl)-N-(1-methyl-5-sulfamoylisoquinolin-7-yl)acetamide)

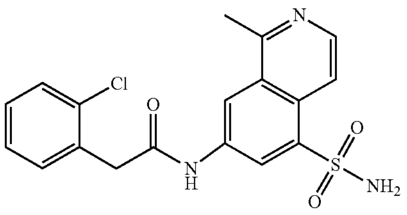 [SMILES: Cc1nccc2c(S(N)(=O)=O)cc(NC(=O)Cc3ccccc3Cl)cc12]

Synthetic Route:

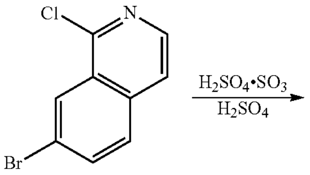

1-1

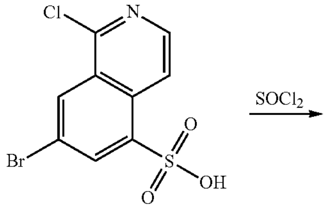

55-1

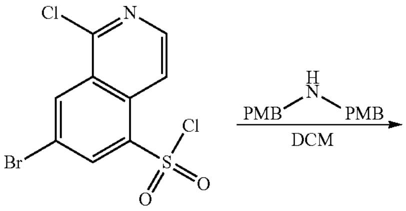

55-2

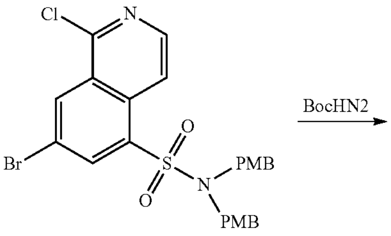

55-3

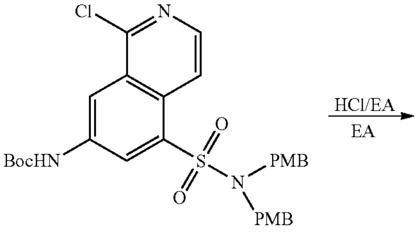

55-4

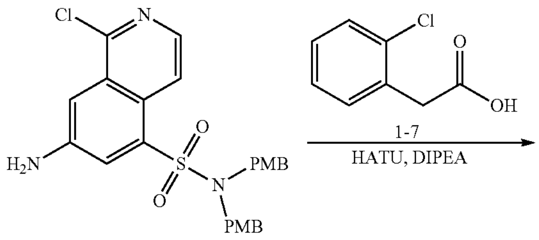

55-5

-continued

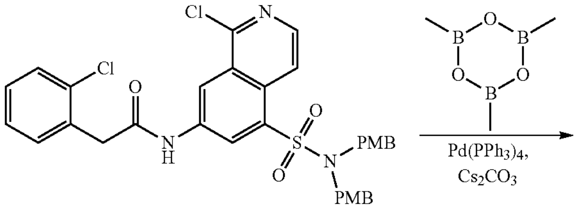

55-6

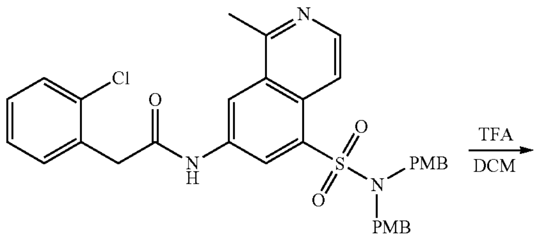

55-7

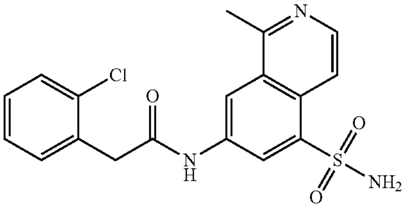

55

Step (1) Preparation of Intermediate 55-1

Intermediate 1-1 (10 g) was weighed, and concentrated sulfuric acid (10 mL) was added to dissolve, then oleum (50 mL) was added, and the mixture was warmed to 60° C. and stirred for 16 hours; the sample was taken, quenched with water, extracted with EA, and TLC (PE:EA=6:1) showed that about 10% of the raw material was remained. The reaction solution was slowly added dropwise to ice water (500 mL), and the internal temperature was controlled not to exceed 10° C.; after the dropwise addition was completed, the mixture was stirred for 30 min, and then settled for 1 hour, filtered, and the filter cake was evaporated with acetonitrile (200 mL) for three times, and slurried with PE:EA=10:1 (60 mL) for 20 min, filtered, and the filter cake was concentrated under reduced pressure to obtain intermediate 55-1 as a gray solid (16 g).

Step (2) Preparation of Intermediate 55-2

Intermediate 55-1 (12 g) was sequentially dissolved in thionyl chloride (120 mL), then DMF (1 mL) was added, and the mixture was stirred at 70° C. for 2 hours. The sample was taken, and TLC (PE:EA=2:1) showed that the raw materials were reacted completely. After cooling to 40° C., the mixture was concentrated under reduced pressure, and the filter cake was evaporated for three times with DCM (200 mL) to obtain intermediate 55-2 as an off-white solid (13 g).

Step (3) Preparation of Intermediate 55-3

Intermediate 55-2 (20 g) was dissolved in DCM (150 mL), then $NH(PMB)_2$ (15.2 g) was weighed and dissolved in DCM (150 mL), and the solution of intermediate 55-2 was slowly added dropwise to $NH(PMB)_2$ solution; the mixture was stirred at room temperature for 1 hour after the dropwise addition was completed, and the sample was taken, and TLC (PE:EA=2:1) showed that raw materials were reacted completely; the reaction solution was concentrated and dried, and then silica gel was added to mix with the sample, and the mixture was purified by column chromatography with PE:EA=5:1 to 2:1, and the purified solution was concentrated under reduced pressure to obtain intermediate 55-3 as a yellow solid (32 g).

Step (4) Preparation of Intermediate 55-4

Intermediate 55-3 (11.5 g), $BocNH_2$ (3.6 g) and $Cs_2CO_3$ (10.03 g) were weighed, and DMF (100 mL) was added, and the mixture was stirred to dissolve, then $PaCl_2$ (dppf) (1.5 g) and Xantphos (1.18 g) were added; the reaction system was replaced with $N_2$ for three times, then the mixture was stirred at 85° C. for 2 hours. The sample was taken, and the reaction solution was quenched with water and extracted with EA; TLC (PE:EA=2:1) showed that about 30% of raw material remained, and the mixture was added with water (100 mL) and EA (300 mL) after cooling, stirred then the phases were separated; the aqueous phase was extracted with EA (100 mL) for three times, and the organic phases were combined, washed with brine (300 mL), dried over anhydrous sodium sulfate, filtered, and the filtrate was concentrated under reduced pressure, then silica gel was added to mix with the sample and purified by column chromatography with PE:EA=4:1 to 1:1, and concentrated under reduced pressure at 45° C. to obtain intermediate 55-4 as a yellow solid (2.5 g).

Step (5) Preparation of Intermediate 55-5

Intermediate 55-4 (2.5 g) was dissolved in EA (10 mL), then 3M HCl/EA (40 mL) was added, and the mixture was stirred at room temperature for 3 hours, and sample was taken; TLC (PE:EA=1:1) showed that the reaction was completed, and $H_2O$ (50 mL) and EA (50 mL) were added, and the pH was adjusted to 8 to 9 with saturated $NaHCO_3$ solution; the phases were separated, and the organic phase was washed with brine, dried over anhydrous sodium sulfate, filtered and concentrated to obtain intermediate 55-5 as a yellow solid (1.5 g).

Step (6) Preparation of Intermediate 55-6

Intermediate 1-7 (2-chlorophenylacetic acid) (0.57 g) and HATU (1.28 g) were dissolved in DMF (20 mL), and the mixture was stirred at room temperature for 1 hour, and then intermediate 55-5 (1.4 g) and DIPEA (0.76 g) were added and the mixture was continued to stir for 16 hours. The sample was taken, and TLC (PE:EA=3:1) showed raw material:product=1:1, and then the mixture was added with EA (100 mL) and $H_2O$ (50 mL); the mixture was stirred then the phases were separated, and the aqueous phase was extracted with EA (50 mL) for three times, and the organic phases were combined, washed with brine, dried over anhydrous sodium sulfate, filtered, and the filtrate was concentrated under reduced pressure; silica gel was added to mix with the sample, and the mixture was purified by column chromatography with PE:EA=5:1 to 1:1, and concentrated under reduced pressure at 45° C. to obtain intermediate 55-6 as a yellow solid (800 mg).

Step (7) Preparation of Intermediate 55-7

Intermediate 55-6 (750 mg), trimethylboroxine (290 mg), cesium carbonate (750 mg) and tetrakistriphenylphosphine palladium (130 mg) were weighed and dissolved in DMF (10 mL), and the reaction system was replaced with $N_2$ for three times; the mixture was stirred at 85° C. for 40 hours, and the sample was taken, then TLC (PE:EA=2:1) showed that a small amount of raw material remained; EA (50 mL) and $H_2O$ (20 mL) were added to the reaction solution, then the mixture was stirred and the phases were separated; the aqueous phase was extracted with EA (20 mL) for three times, and the organic phases were combined, washed with brine, dried over anhydrous sodium sulfate, filtered, and the filtrate was concentrated under reduced pressure, then and silica gel was added to mix with the sample, and the mixture was purified by column chromatography with PE:EA=3:1 to 1:1, and concentrated under reduced pressure at 45° C. to obtain intermediate 55-7 as a yellow oil (250 mg).

Step (8) Preparation of Compound 55

Intermediate 55-7 (250 mg) was dissolved in DCM (10 mL), then TFA (30 mL) was added, and the mixture was stirred at 40 for 16 hours; the sample was taken, and TLC (PE:EA=2:1) showed that the raw materials were reacted completely; DCM (50 mL) and $H_2O$ (20 mL) were added to the reaction solution, and the reaction solution was stirred and the phases were separated; the aqueous phase was extracted with DCM (20 mL) for three times, and the organic phases were combined, washed with saturated sodium carbonate solution and brine, and dried over anhydrous sodium sulfate, filtered, and the filtrate was concentrated to obtain a crude product. The crude product was purified by prep-HPLC with $H_2O/CH_3CN$ system, and then lyophilized to obtain compound 55 as a white solid (51 mg) with a purity of 96.46%, $[M+H]^+$=390.06.

$^1$H NMR (400 MHz, DMSO) δ 10.93 (s, 1H), 8.84 (s, 1H), 8.59 (s, 1H), 8.40 (d, J=6.1 Hz, 1H), 8.23 (d, J=5.5 Hz, 1H), 7.79 (s, 2H), 7.49-7.45 (m, 2H), 7.36-7.32 (m, 2H), 3.95 (s, 2H), 2.87 (s, 3H).

Embodiment 56

Compound 56: Preparation of 2-(2-chlorophenyl)-N-(1-fluoromethyl)-5-sulfamoylisoquinolin-7-yl) acetamide

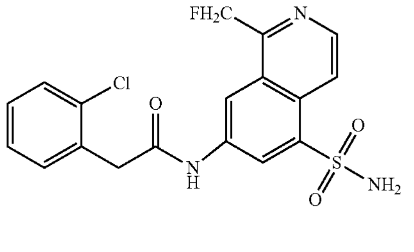
56

The compound was prepared by reference to the preparation method of embodiment 24. LC-MS: $[M+H]^+$=408.0.

Embodiment 57

Compound 57: Preparation of N-(5-(N,N-bis(4-methoxybenzyl)sulfamoyl)-2-chloroquinolin-7-yl)-2-(2-chlorophenyl)acetamide

57

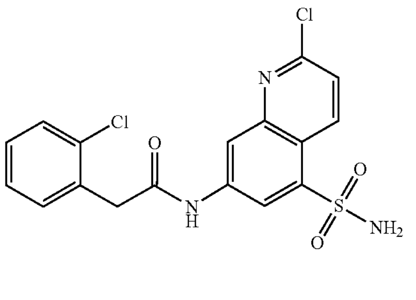

Synthetic Route:

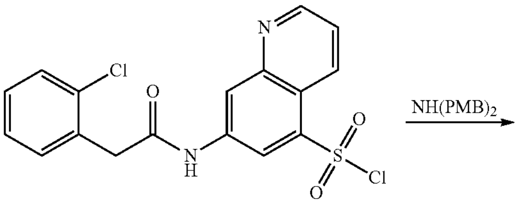

4-9

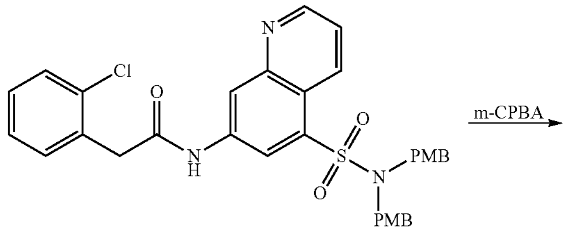

57-1

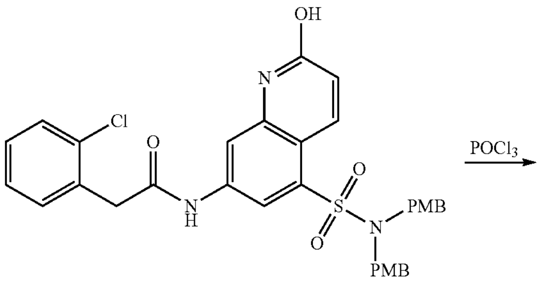

57-2

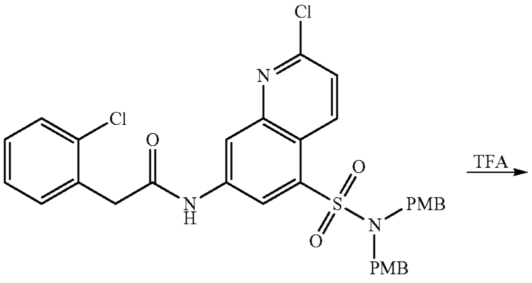

57-3

-continued

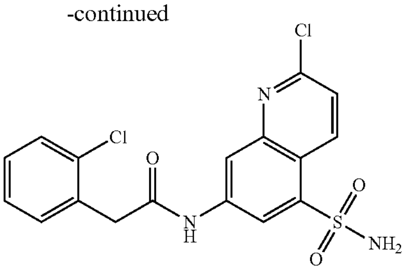

57

Step (1) Preparation of Intermediate 57-1

Intermediate 4-9 (500 mg) was added to DCM (10 mL), and triethylamine (260 mg) was added, and then NH(PMB)$_2$ (390 mg) was added to the solution in batches at 0° C., and the mixture stirred at room temperature 1 hour. TLC showed that the reaction was completed, and the reaction solution was concentrated under reduced pressure and purified by column chromatography to obtain intermediate 57-1 as a pale-yellow solid (580 mg, the purity was 97%, the yield was 75.3%). LC-MS: $[M]^+$=616.

Step (2) Preparation of Intermediate 57-2

Intermediate 57-1 (200 mg) was added to DCM (5 mL), and m-CPBA (150 mg) was added to the solution at 0° C., and the mixture stirred at room temperature 2 hours. TLC showed that the reaction was completed, and the pH of the reaction solution was adjusted to 8 with saturated sodium bicarbonate; the mixture was extracted with DCM, and the phases were separated, then the organic phase was concentrated under reduced pressure to obtain intermediate 57-2 as a pale-yellow oil (200 mg, the purity was 90%, the yield was 100%). LC-MS: $[M]^+$=632.

Step (3) Preparation of Intermediate 57-3

Intermediate 57-2 (200 mg) was added to DCM (2 mL), then $POCl_3$ (100 mg) was added to the solution, and the solution was stirred at 50° C. for 4 hours. LCMS showed that the reaction was completed, and the pH of the reaction solution was adjusted to 8 with saturated sodium bicarbonate; the mixture was extracted with DCM, and the phases were separated, then the organic phase was concentrated under reduced pressure to obtain intermediate 57-3 as a pale-yellow oil (230 mg of crude product), and the product was directly used in the next step without purification.

Step (4) Preparation of Compound 57

Intermediate 57-3 (230 mg of crude product) was dissolved in DCM (5 mL), then TFA (10 mL) was added, and the mixture was stirred at 50° C. for 2 hours. TLC showed that the reaction was completed, and the reaction solution was concentrated under reduced pressure to obtain a crude product. The crude product was purified by prep-HPLC with $H_2O$/CAN system, and lyophilized to obtain compound 57 as a white solid (51.2 mg, the purity was 98.31%, the yield was 39.2%). LC-MS: $[M]^+$=410.

$^1H$ NMR (400 MHz, DMSO) δ 10.96 (s, 1H), 8.90 (d, J=9.1 Hz, 1H), 8.47 (dd, J=17.4, 2.0 Hz, 2H), 7.85 (s, 2H), 7.65 (d, J=9.0 Hz, 1H), 7.45 (dd, J=5.3, 4.0 Hz, 2H), 7.37-7.24 (m, 2H), 3.94 (s, 2H).

Embodiment 58

Compound 58: Preparation of 2-(2-chlorophenyl)-N-(2-methoxy-5-sulfamoylquinolin-7-yl)acetamide

58

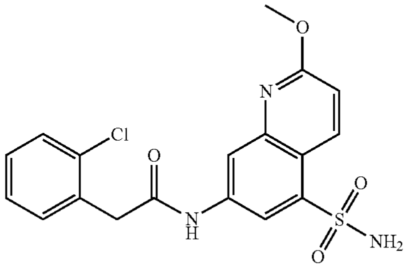

The compound was prepared by reference to the preparation method of embodiment 5. LC-MS: $[M+H]^+$=406.1

Embodiment 59

Compound 59: Preparation of N-(3-chloro-8-sulfamoylisoquinolin-6-yl)-2-(2-chlorophenyl)acetamide

59

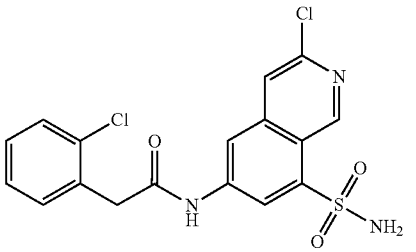

The compound was prepared by reference to the preparation method of embodiment 5. LC-MS: $[M+H]^+$=410.0.

Embodiment 60

Compound 60: Preparation of 2-(2-chlorophenyl)-N-(5-sulfamoyl-1-(trifluoromethoxy)isoquinolin-7-yl)acetamide

60

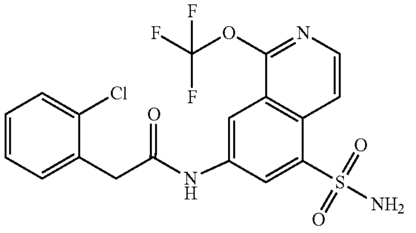

The compound was prepared by reference to the preparation method of embodiment 1. LC-MS: $[M+H]^+$=460.0.

Embodiment 61

Compound 61: Preparation of 2-(2-chlorophenyl)-N-(1-(fluoromethoxy)-5-sulfamoylisoquinolin-7-yl)acetamide

61

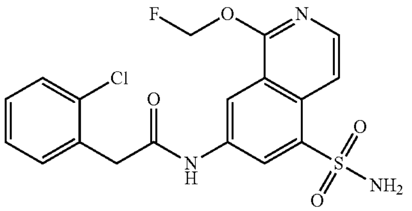

The compound was prepared by reference to the preparation method of embodiment 1. LC-MS: $[M+H]^+$=424.1.

Embodiment 62

Compound 62: Preparation of 2-(2-chloro-6-hydroxyphenyl)-N-(1-methoxy-5-sulfamoylisoquinolin-7-yl)acetamide

62

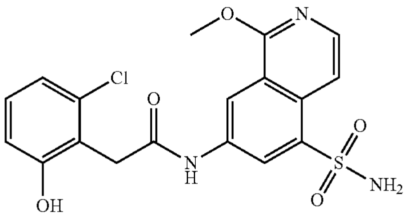

The compound was prepared by reference to the preparation method of embodiment 1. LC-MS: $[M+H]^+$=422.1.

Embodiment 63

Compound 63: Preparation of 2-(6-chloro-3-fluoro-2-hydroxyphenyl)-N-(1-methoxy-5-sulfamoylisoquinolin-7-yl)acetamide

63

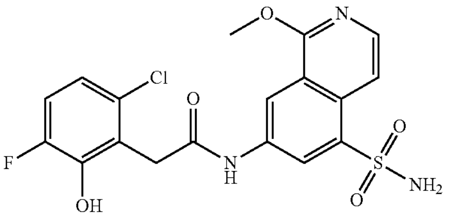

The compound was prepared by reference to the preparation method of embodiment 1. LC-MS: $[M+H]^+$=440.0.

Embodiment 64

Compound 64: Preparation of 2-(2-cyanophenyl)-N-(1-methoxy-5-sulfamoylisoquinolin-7-yl)acetamide

64

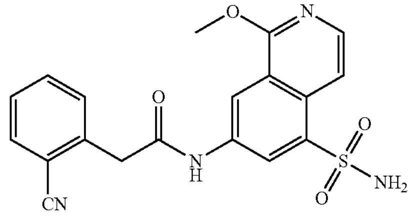

The compound was prepared by reference to the preparation method of embodiment 1. LC-MS: $[M+H]^+$=397.1.

Embodiment 65

Compound 65: Preparation of 2-(2-chlorophenyl)-N-(2-methoxy-5-sulfamoylquinolin-7-yl)acetamide

65

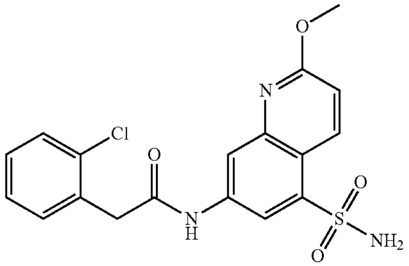

Synthetic Route

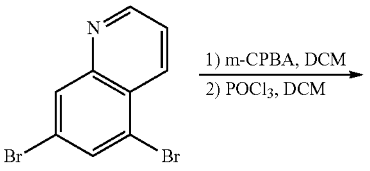

4-3

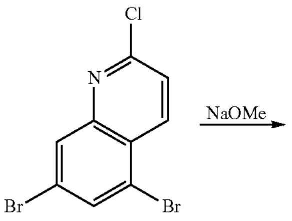

65-1

-continued

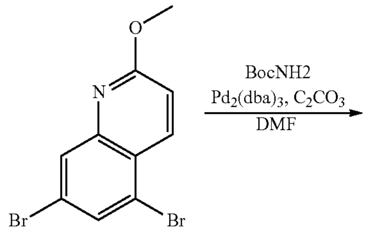

65-2

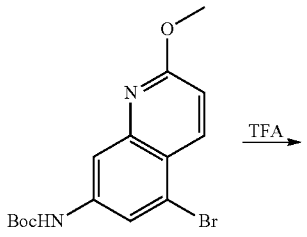

65-3

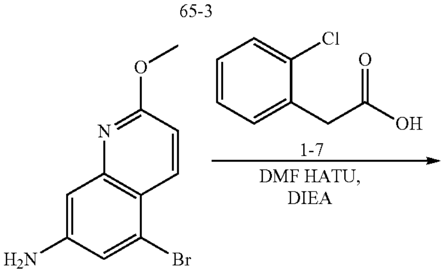

65-4

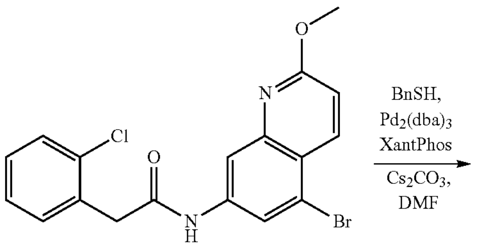

65-5

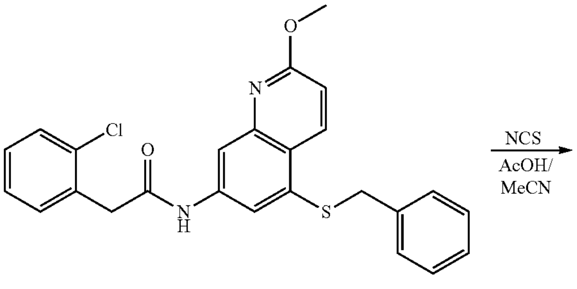

65-6

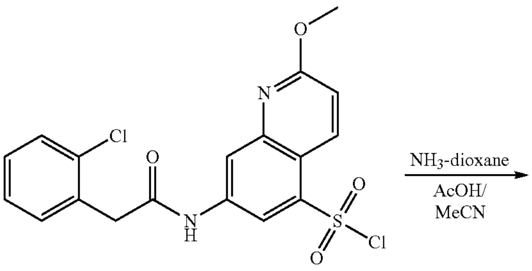

65-7

-continued

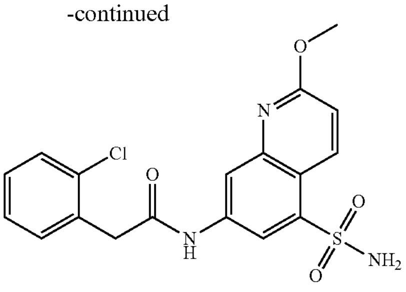

65

Step (1) Preparation of Intermediate 65-1

Intermediate 4-3 (2.6 g) was dissolved in DCM (20 mL), and the mixture was stirred for 5 min, then m-CPBA (3.1 g) was added in batches at 0° C., and the mixture was stirred at room temperature for 2 hours. TLC showed that the reaction was completed. The reaction solution was quenched with sodium thiosulfate solution, and the pH was adjusted to 10 with 1N NaOH, and then the mixture was extracted with dichloromethane (50 mL) for two times, and the organic phases were combined, washed sequentially with saturated brine, and dried over anhydrous sodium sulfate, filtered and concentrated to obtain 2.5 g of a crude product as a yellow solid. DCM (10 mL) and $POCl_3$ (2.5 g) were added to the crude product, and the tube was sealed and the reaction was carried out at 55° C. for 4 hours, and TLC showed that the reaction was completed. The reaction solution was quenched with sodium bicarbonate solution, extracted with dichloromethane (50 mL) for two times; the organic phases were combined, washed sequentially with saturated brine, dried over anhydrous sodium sulfate, filtered and concentrated, and subjected to column chromatography to obtain intermediate 65-1 as a brown solid (1.4 g, the purity was 95%, the yield was 56%). LC-MS: $[M]^+$=322.

Step (2) Preparation of Intermediate 65-2

Intermediate 65-1 (1.3 g) was dissolved in DMF (15 mL), then methanol solution (4 mL) of sodium methoxide was added, and the mixture was stirred at room temperature for 1 hour. TLC showed that the reaction was completed, then the reaction solution was added with water (50 mL), then extracted with ethyl acetate (30 mL) for two times; the organic phases were combined, washed with saturated brine, dried over anhydrous sodium sulfate, and filtered, and the filtrate was concentrated under reduced pressure and subjected to column chromatography to obtain intermediate 65-2 as a yellow solid (1.0 g, the purity was 98%, the yield was 74%). LC-MS: $[M]^+$=317.

Step (3) Preparation of Intermediate 65-3

Intermediate 65-2 (500 mg), $NH_2Boc$ (186 mg), $Pd_2(dba)_3$ (72 mg), cesium carbonate (760 mg) and Xantphos (45 mg) were dissolved in DMF (40 mL), and the mixture was stirred at 80° C. for 16 hours under the protection of $N_2$. TLC showed that the reaction was completed, then the reaction solution was added with water (50 mL), then extracted with ethyl acetate (20 mL) for two times; the organic phases were combined, washed sequentially with saturated brine, dried over anhydrous sodium sulfate, and filtered, and the filtrate was concentrated under reduced pressure and subjected to column chromatography to obtain intermediate 65-3 as a yellow solid (480 mg, the purity was 93.7%, the yield was 83%). LC-MS: $[M]^+$=355.

Step (4) Preparation of Intermediate 65-4

Intermediate 65-3 (480 mg) was dissolved in DCM (5 mL), then TFA (5 mL) was added, and the mixture was stirred at room temperature for 2 hours. TLC showed that the reaction was completed, and the reaction solution was concentrated under reduced pressure to obtain 520 mg of a crude product of intermediate 65-4 as a yellow oil, and the crude product was directly used in the next step without purification.

Step (5) Preparation of Intermediate 65-5

Intermediate 65-4 (520 mg), intermediate 1-7 (2-chlorophenylacetic acid) (340 g), HATU (760 mg), DIEA (520 mg) were dissolved in DMF (5 mL), and the mixture was stirred at room temperature for 2 hours. TLC showed that the reaction was completed, then the reaction solution was added with water (30 mL) then extracted with ethyl acetate (10 mL) for two times; the organic phases were combined, dried, and concentrated under reduced pressure and purified by column chromatography to obtain intermediate 65-5 as a pale-yellow solid (400 mg, the purity was 84.5%, the yield was 80%). LC-MS: $[M]^+$=406.

Step (6) Preparation of Intermediate 65-6

Intermediate 65-5 (400 mg), intermediate 4-7 (benzylthiol) (150 mg), $Pd_2(dba)_3$ (50 mg), cesium carbonate (488 mg), Xantphos (30 mg) were dissolved in DMF (5 mL), and the mixture was stirred at 85° C. for 4 hours. TLC showed that the reaction was completed, then the reaction solution was added with water (50 mL) then extracted with ethyl acetate (10 mL) for two times; the organic phases were combined, dried, and concentrated under reduced pressure and purified by column chromatography to obtain intermediate 65-6 as a pale-yellow solid (350 mg, the purity was 92.6%, the yield was 78%). LC-MS: $[M]^+$=449.

Step (7) Preparation of Intermediate 65-7

Intermediate 65-6 (160 mg) was added to $HOAc/H_2O$ (2/0.7 mL), and NCS (236 mg) was added to the turbid solution in batches, and the mixture was stirred at room temperature for 5 hours; TLC showed that the reaction was completed, and water (20 mL) was added to the reaction solution, and the mixture was extracted with ethyl acetate (10 mL) for two times; the organic phases were combined, and the pH was adjusted to 8 with saturated sodium bicarbonate, then the phases were separated, and the organic phase was concentrated under reduced pressure to obtain 160 mg of a crude product of intermediate 65-7 as a pale-yellow solid with a yield of 110%, and the crude product was directly used in the next step without purification.

Step (8) Preparation of Compound 65

Intermediate 65-7 (160 mg) was added to DCM (0.1 mL), and $NH_3$-dioxane (2.5 mL) was added to the solution, and the mixture was stirred at room temperature overnight. TLC showed that the reaction was completed, and the reaction solution was concentrated under reduced pressure to obtain a crude product. The crude product was purified by prep-HPLC with $H_2O$/CAN system, and lyophilized to obtain compound 65 as a white solid (55.2 mg, the purity was 99.7%, the yield was 32.6%). LC-MS: $[M]^+$=406.

$^1H$ NMR (400 MHz, DMSO) δ 10.77 (s, 1H), 8.75 (d, J=9.3 Hz, 1H), 8.42 (d, J=1.9 Hz, 1H), 8.18 (d, J=2.1 Hz, 1H), 7.71 (s, 2H), 7.48-7.41 (m, 2H), 7.36-7.26 (m, 2H), 7.05 (d, J=9.2 Hz, 1H), 3.97 (s, 3H), 3.91 (s, 2H).

Embodiment 66

Compound 66: Preparation of 2-(2-chlorophenyl)-N-(2-(2-hydroxyethoxy)-5-sulfamoylquinolin-7-yl) acetamide

66

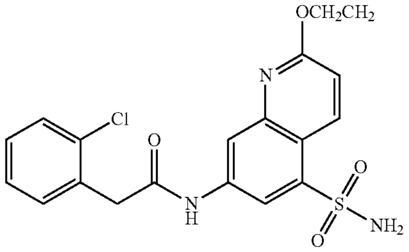

The compound was prepared by reference to the preparation method of embodiment 5. LC-MS: $[M+H]^+$=436.1

Embodiment 67

Compound 67: Preparation of 2-(2-chlorophenyl)-N-(2-(piperidin-1-yl)-5-sulfamoylquinolin-7-yl)acetamide

67

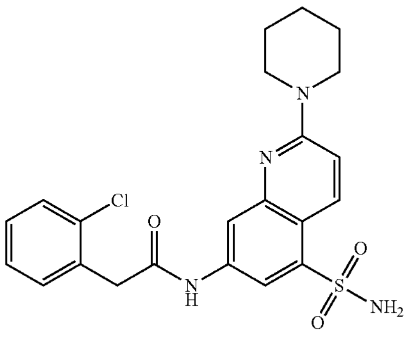

The compound was prepared by reference to the preparation method of embodiment 4. LC-MS: $[M+H]^+$=459.1.

Embodiment 68

Compound 68: Preparation of 2-(2-chlorophenyl)-N-(2-morpholino-5-sulfamoylquinolin-7-yl)acetamide

68

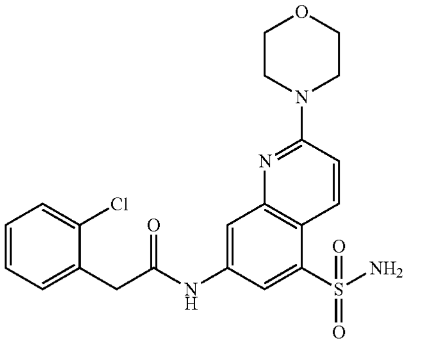

Synthetic Route:

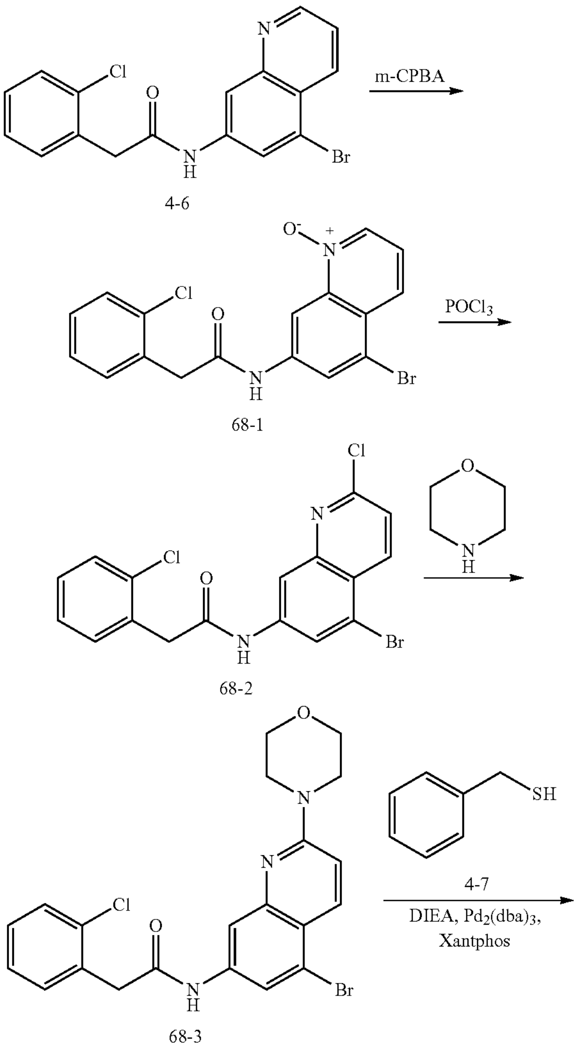

-continued

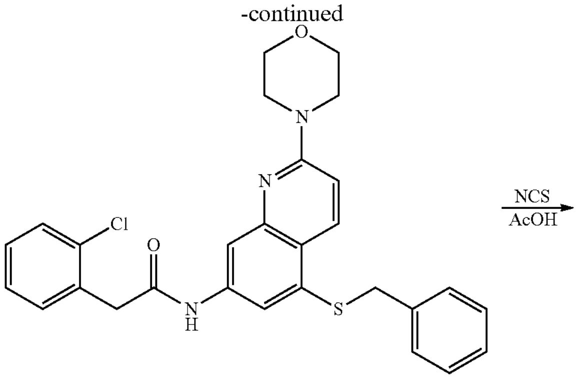

68-4

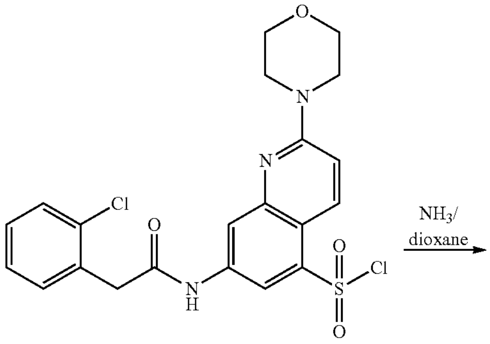

68-5

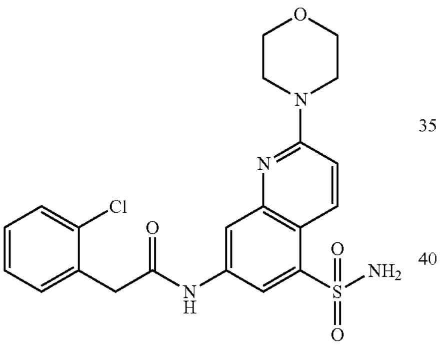

68

Step (1) Preparation of Intermediate 68-1

Intermediate 4-6 (8.2 g) was added to DCM (150 mL), and m-CPBA (9.3 g) was added to the solution at 0° C., and the mixture stirred at room temperature for 48 hours. TLC showed that the reaction was completed, and the pH of reaction solution was adjusted to 10 with 1M sodium hydroxide; the mixture was extracted with DCM, the organic phases were combined, dried, concentrated and purified by column chromatography (PE/EA=3/1 to 0/1) to obtain intermediate 68-1 as a yellow solid (5.2 g, the yield was 62.1%). LC-MS: $[M]^+$=391.

Step (2) Preparation of Intermediate 68-2

Intermediate 68-1 (5.2 g) was added to DCM (100 mL), then $POCl_3$ (6.0 g) was added to the solution, and the solution was stirred at 55° C. for 16 hours. LCMS showed that the reaction was completed, and the reaction solution was quenched with water in an ice-water bath, and the pH of reaction solution was adjusted to 9 with saturated sodium carbonate; the mixture was extracted with DCM, the organic phases were combined, dried, concentrated and purified by column chromatography (PE/EA=8/1 to 3/1) to obtain intermediate 68-2 as a yellow solid (2.9 g, the yield was 53.7%). LC-MS: $[M]^+$=410.

Step (3) Preparation of Intermediate 68-3

Intermediate 68-2 (250 mg), morpholine (160 mg), DIEA (390 mg) were dissolved in DMF (5 mL), and the mixture was stirred at 60° C. overnight. TLC showed that the reaction was completed, then the reaction solution was diluted with water (50 mL), then extracted with ethyl acetate (20 mL) for two times; the organic phases were combined, washed sequentially with saturated brine, dried over anhydrous sodium sulfate, and filtered, and the filtrate was concentrated under reduced pressure and purified by column chromatography to obtain intermediate 68-3 as a yellow solid (200 mg, the purity was 97.1%, the yield was 72%). LC-MS: $[M]^+$=461.

Step (4) Preparation of Intermediate 68-4

Intermediate 68-3 (200 mg), intermediate 4-7 (benzylthiol) (80.8 mg), $Pd_2(dba)_3$ (20 mg), DIEA (138 mg), Xantphos (15 mg) were dissolved in DMF (2 mL), and the mixture was stirred at 90° C. for 5 hours. TLC showed that the reaction was completed, then the reaction solution was added with water (50 mL) then extracted with ethyl acetate (10 mL) for two times; the organic phases were combined, dried, and concentrated under reduced pressure and purified by column chromatography to obtain intermediate 68-4 as a pale-yellow solid (250 mg, the purity was 99%, the yield was 98%). LC-MS: $[M]^+$=504.

Step (5) Preparation of Intermediate 68-5

Intermediate 68-4 (200 mg) was added to $HOAc/H_2O$ (4/1.2 mL), and NCS (260 mg) was added to the turbid solution in batches, and the mixture was stirred at room temperature for 3 hours; TLC showed that the reaction was completed, and water (20 mL) was added to the reaction solution, then the mixture was extracted with ethyl acetate (10 mL) for two times; the organic phases were combined, and the pH was adjusted to 8 with saturated sodium bicarbonate; the phases were separated, and the organic phase was concentrated under reduced pressure to obtain 190 mg of a crude product of intermediate 68-5 as a pale-yellow solid with a yield of 81%, and the crude product was directly used in the next step without purification.

Step (6) Preparation of Compound 68

Intermediate 68-5 (190 mg) was added to DCM (0.1 mL), and $NH_3$-dioxane (10 mL) was added to the solution, and the mixture was stirred at room temperature overnight. TLC showed that the reaction was completed, and the reaction solution was concentrated under reduced pressure to obtain a crude product. The crude product was purified by prep-HPLC with $H_2O$/CAN system, and lyophilized to obtain compound 68 as a white solid (88.3 mg, the purity was 99.58%, the yield was 42.1%). LC-MS: $[M]^+$=461.

$^1$H NMR (400 MHz, DMSO) δ 10.62 (s, 1H), 8.59 (d, J=9.5 Hz, 1H), 8.19 (d, J=1.5 Hz, 1H), 8.00 (d, J=2.0 Hz,

1H), 7.61 (s, 2H), 7.48-7.40 (m, 2H), 7.33-7.27 (m, 2H), 7.23 (d, J=9.6 Hz, 1H), 3.88 (s, 2H), 3.67 (dd, J=16.7, 4.8 Hz, 8H).

Embodiment 69

Compound 69: Preparation of 2-(2-chlorophenyl)-N-(2-(4-methylpiperazin-1-yl)-5-sulfamoylquinolin-7-yl)acetamide

69

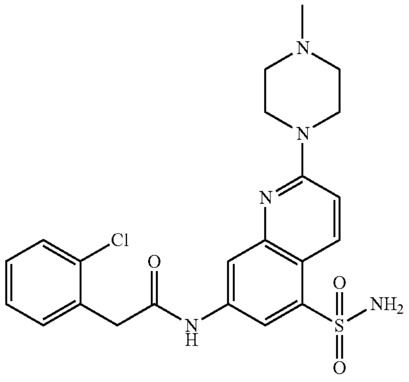

Synthetic Route

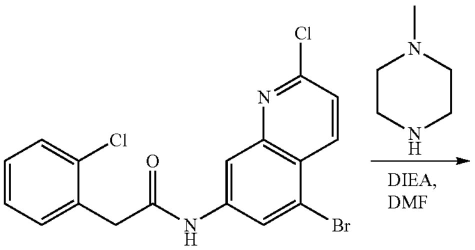

68-2

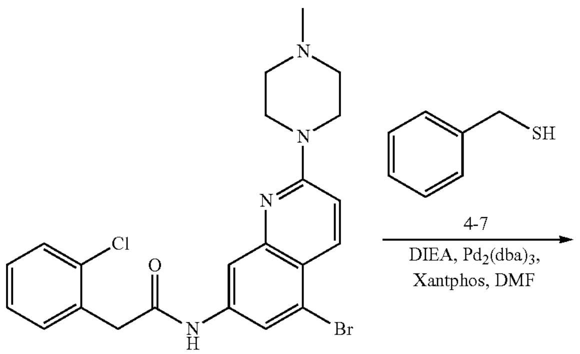

69-1

-continued

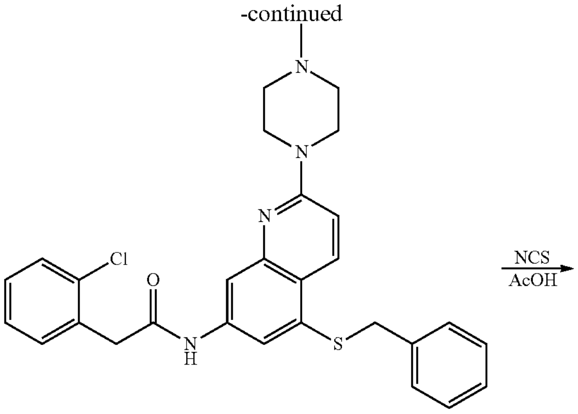

69-2

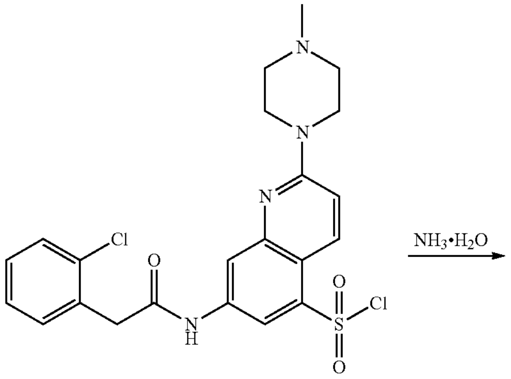

69-3

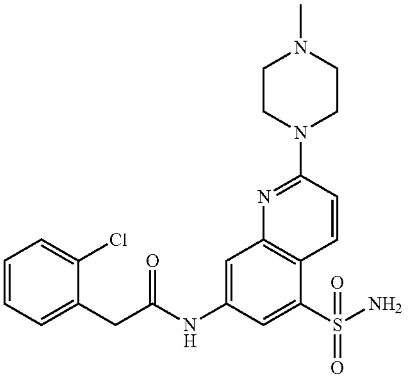

69

Step (1) Preparation of Intermediate 69-1

Intermediate 68-2 (400 mg), 1-methylpiperazine (489 mg), DIEA (630 mg), DMF (5 mL) were added to a reaction flask, and the reaction was stirred at 80° C. overnight. The reaction solution was poured into water, extracted with ethyl acetate; the organic phases were concentrated, and the sample was mixed with silica gel and purified by column chromatography to obtain 270 mg of a product of intermediate 69-1 as a yellow solid. LC-MS: ESI(+) m/z=475[M+1].

Step (2) Preparation of Intermediate 69-2

Intermediate 69-1 (250 mg), BnSH (327.7 mg), DIEA (341 mg) were dissolved in DMF (5 mL), then Xantphos (31 mg) and $Pd_2(dba)_3$ were added to the reaction flask; after the reaction system was replaced with $N_2$ for three times, the reaction was stirred at 100° C. for 36 hours. The reaction solution was poured into water, extracted with ethyl acetate; the organic phase was concentrated and the sample was mixed with silica gel and purified by column chromatography to obtain 220 mg of a product of intermediate 69-2 as a brown solid. LC-MS: ESI(+) m/z=517[M+1].

Step (3) Preparation of Intermediate 69-3

Intermediate 69-2 (210 mg) was dissolved in AcOH (6 mL) and $H_2O$ (2 mL), then NCS (271 mg) was added to the reaction flask in batches, and the reaction was stirred at room temperature for 1 hour. The reaction solution was directly used for the next reaction without post-treatment. LC-MS: ESI(+) m/z=493[M+1].

Step (4) Preparation of Compound 69

The reaction solution (8 mL) of intermediate 69-3 was added to a reaction flask containing $NH_3 \cdot H_2O$ (20 mL); after the dropwise addition was completed, the reaction solution was poured into water, extracted with EA; the organic phase was concentrated by rotary evaporation to obtain 150 mg of a crude product; after preparation, compound 69 was obtained as a white solid (32.6 mg, the purity was 99.993%). LC-MS: ESI(+) m/z=474[M+1].

$^1$H NMR (400 MHz, dmso) δ 10.69 (s, 1H), 9.88 (s, 1H), 8.64 (d, J=9.2 Hz, 1H), 8.30 (d, J=2.0 Hz, 1H), 8.00 (d, J=2.0 Hz, 1H), 7.68 (s, 2H), 7.49-7.40 (m, 2H), 7.36-7.22 (m, 3H), 4.65 (d, J=14.0 Hz, 2H), 3.89 (s, 2H), 3.53 (d, J=11.6 Hz, 2H), 3.25 (s, 2H), 3.09 (s, 2H), 2.83 (s, 3H).

Embodiment 70

Compound 70: Preparation of 2-(2-chlorophenyl)-N-(2-(4-methyl-3-carbonylpiperazin-1-yl)-5-sulfamoylquinolin-7-yl)acetamide

70

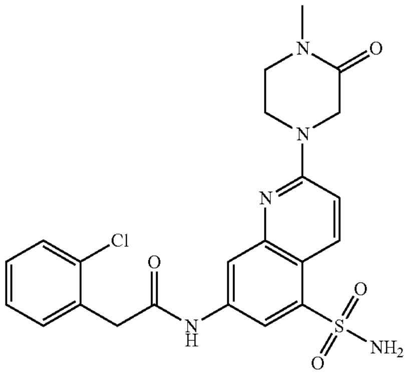

The compound was prepared by reference to the preparation method of embodiment 4. LC-MS: $[M+H]^+$=488.1

Embodiment 71

Compound 71: Preparation of 2-(2-chlorophenyl)-N-(2-((4-methoxyphenyl)amino)-5-sulfamoylquinolin-7-yl)acetamide

71

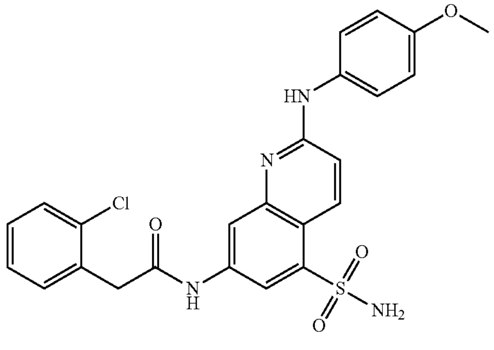

Synthetic Route:

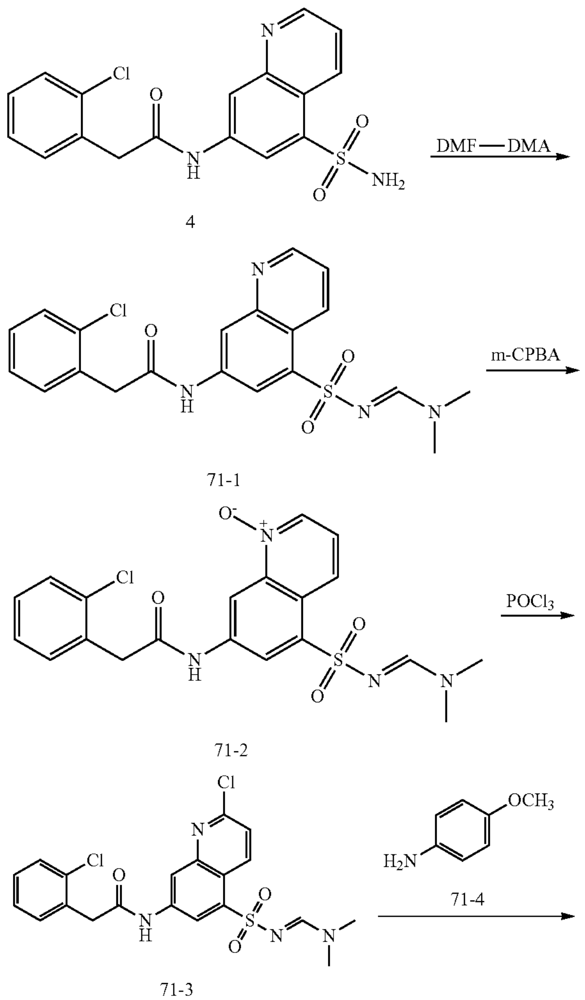

4
71-1
71-2
71-3

-continued

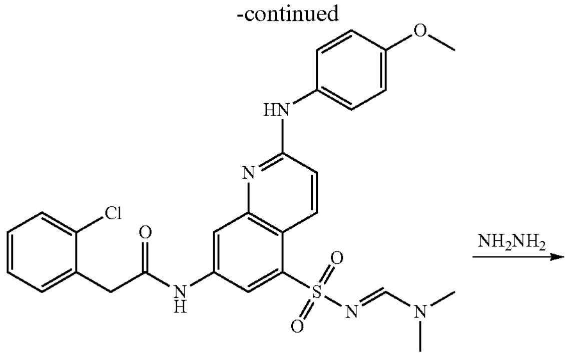

71-5

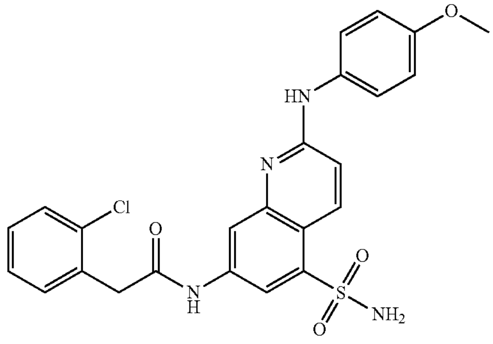

71

Step (1) Preparation of Intermediate 71-1

Compound 4 (600 mg) was dissolved in DMF (5 mL), then DMF-DMA (380 mg) was added, and the mixture was stirred at 60° C. for 3 hours. TLC showed that the reaction was completed, then the reaction solution was added with water (50 mL) then extracted with ethyl acetate (10 mL) for two times; the organic phases were combined, dried, and concentrated under reduced pressure and purified by column chromatography to obtain intermediate 71-1 as a pale-yellow solid (660 mg, the yield was 92%).

Step (2) Preparation of Intermediate 71-2

Intermediate 71-1 (560 mg) was dissolved in DCM (30 mL), and the mixture was stirred for 5 min, then m-CPBA (600 mg) was added in batches at 0° C., and the mixture was stirred at room temperature overnight. TLC showed that the reaction was completed. The reaction solution was added with water, and the pH was adjusted to 10 with 1N NaOH, and then the mixture was extracted with dichloromethane (20 mL) for two times; the organic phases were combined, washed sequentially with saturated brine, and dried over anhydrous sodium sulfate, filtered and concentrated to obtain intermediate 71-2 as a pale-yellow solid (600 mg, the yield was 92%)

Step (3) Preparation of Intermediate 71-3

Intermediate 71-2 (600 mg) was dissolved in DCM (5 mL) and $POCl_3$ (610 mg), and the tube was sealed at 55° C. and the reaction was carried out for 4 hours, and TLC showed that the reaction was completed. The reaction solution was quenched with sodium bicarbonate solution, extracted with dichloromethane (10 mL) for two times; the organic phases were combined, washed sequentially with saturated brine, dried over anhydrous sodium sulfate, filtered and concentrated, and subjected to column chromatography to obtain intermediate 71-3 as a pale-yellow solid (300 mg, the yield was 48.2%).

Step (4) Preparation of Intermediate 71-5

Intermediate 71-3 (100 mg), intermediate 71-4 (p-methoxyaniline) (50 mg), $Pd_2(dba)_3$ (9 mg), DIEA (77.4 mg), Xantphos (6 mg) were dissolved in DMF (4 mL), and the mixture was stirred at 100° C. for 16 hours. TLC showed that the reaction was completed, then the reaction solution was added with water (20 mL) then extracted with ethyl acetate (10 mL) for two times; the organic phases were combined, dried, and concentrated under reduced pressure and purified by column chromatography to obtain intermediate 71-5 as a yellow solid (42.6 mg, the yield was 41.8%).

Step (5) Preparation of Compound 71

Intermediate 71-5 (42 mg) was dissolved in methanol (2 mL), then hydrazine hydrate solution (12.7 mg, 85%) was added dropwise, and the mixture was stirred at room temperature for 30 min. TLC showed that the reaction was completed, and the reaction solution was concentrated under reduced pressure to obtain a crude product. The crude product was purified by prep-HPLC with $H_2O$/CAN system, and lyophilized to obtain compound 71 as a yellow solid (17.2 mg, the purity was 98.86%, the yield was 31.8%). LC-MS: $[M]^+$=497.

$^1$H NMR (400 MHz, DMSO) δ 10.70 (s, 1H), 9.54 (s, 2H), 8.56 (d, J=9.3 Hz, 1H), 8.32 (s, 1H), 7.99 (d, J=1.9 Hz, 1H), 7.77 (d, J=8.0 Hz, 2H), 7.63 (s, 2H), 7.50-7.40 (m, 2H), 7.37-7.25 (m, 2H), 7.00 (d, J=9.4 Hz, 1H), 6.93 (d, J=8.9 Hz, 2H), 3.90 (s, 3H), 3.72 (s, 3H).

Embodiment 72

Compound 72: Preparation of 2-(2-chlorophenyl)-N-(2-(4-methoxyphenoxy)-5-sulfamoylquinolin-7-yl)acetamide

72

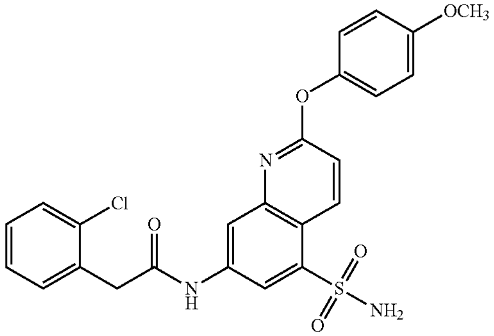

The compound was prepared by reference to the preparation method of embodiment 5. LC-MS: $[M+H]^+$=498.1.

Embodiment 73

Compound 73: Preparation of 2-(2-chlorophenyl)-N-(2-(isopropylamino)-5-sulfamoylquinolin-7-yl)acetamide

73

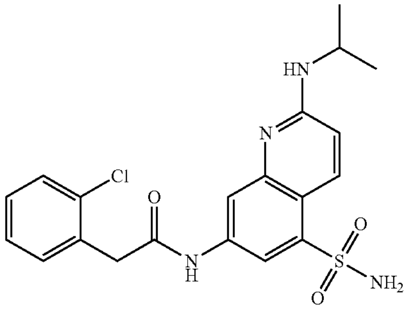

The compound was prepared by reference to the preparation method of embodiment 6. LC-MS: $[M+H]^+$=433.1.

Embodiment 74

Compound 74: Preparation of 2-(2-chlorophenyl)-N-(2-(2-methoxyethoxy)-5-sulfamoylquinolin-7-yl)acetamide

74

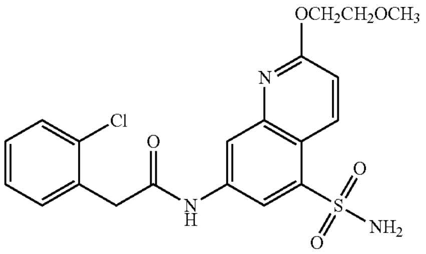

The compound was prepared by reference to the preparation method of embodiment 5. LC-MS: $[M+H]^+$=450.1.

Embodiment 75

Compound 75: Preparation of 2-(2-chlorophenyl)-N-(3-methoxy-5-sulfamoylisoquinolin-7-yl)acetamide

75

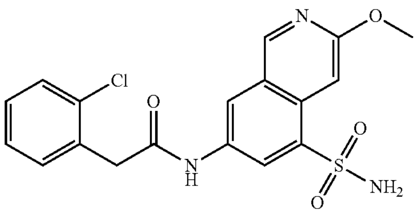

The compound was prepared by reference to the preparation method of embodiment 5. LC-MS: $[M+H]^+$=406.1.

Embodiment 76

Compound 76: Preparation of 2-(2-chlorophenyl)-N-(3-(2-hydroxyethoxy)-5-sulfamoylisoquinolin-7-yl)acetamide

76

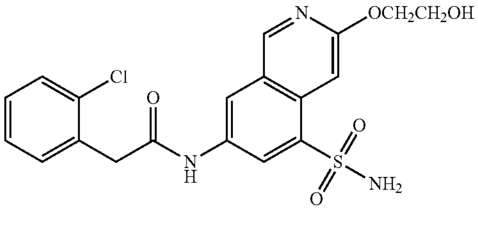

The compound was prepared by reference to the preparation method of embodiment 5. LC-MS: $[M+H]^+$=436.1.

Embodiment 77

Compound 77: Preparation of 2-(2-chlorophenyl)-N-(3-(piperidin-1-yl)-5-sulfamoylisoquinolin-7-yl)acetamide

77

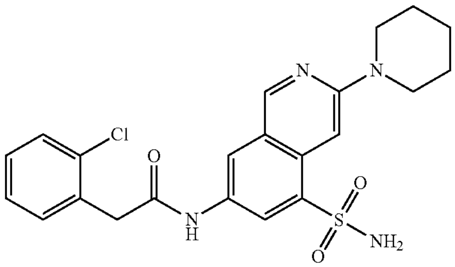

The compound was prepared by reference to the preparation method of embodiment 5. LC-MS: $[M+H]^+$=459.1.

Embodiment 78

Compound 78: Preparation of 2-(2-chlorophenyl)-N-(3-morpholino-5-sulfamoylisoquinolin-7-yl)acetamide

78

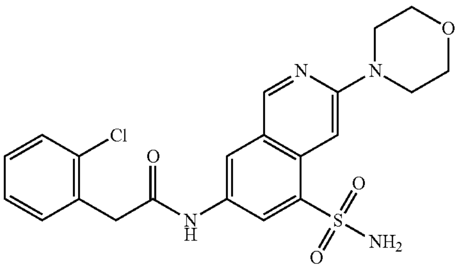

Synthetic Route:

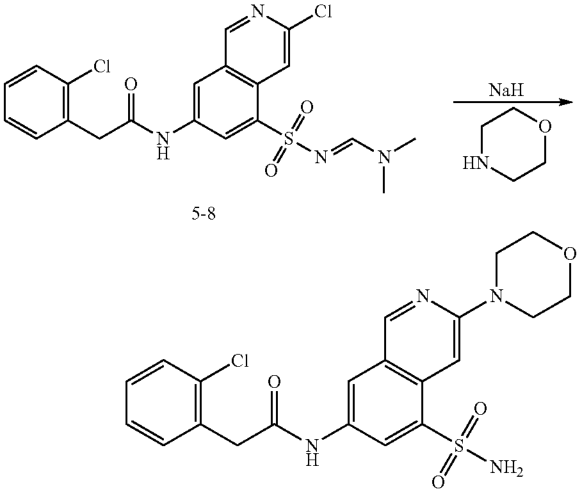

5-8

78

Step (1) Preparation of Compound 78

NaH (211 mg) was added to morpholine (3.0 mL) first, and the reaction was stirred at 80° C. for 1 hour; after cooling to room temperature, intermediate 5-8 (0.5 g) was added to the reaction system and then the reaction solution was warmed to 80° C. and reacted overnight; the sample was taken, and TLC showed that most of the raw materials were reacted completely; after adding water to quench the reaction, the aqueous phase was extracted with EA for three times, and the combined EA phase was separated and purified by column chromatography and sent to the preparation for further purification, and the preparation solution was lyophilized to obtain 10 mg of compound 78 as a yellow solid powder.

$^1$H NMR (400 MHz, dmso) δ 10.62 (s, 1H), 9.01 (s, 1H), 8.49 (s, 1H), 8.33 (d, J=2.0 Hz, 1H), 7.62 (s, 2H), 7.46-7.41 (m, 2H), 7.34-7.28 (m, 3H), 3.87 (s, 2H), 3.79-3.71 (m, 4H), 3.56-3.48 (m, 4H).

Embodiment 79

Compound 79: Preparation of 2-(2-chlorophenyl)-N-(3-(4-methylpiperazin-1-yl)-5-sulfamoylisoquinolin-7-yl)acetamide

79

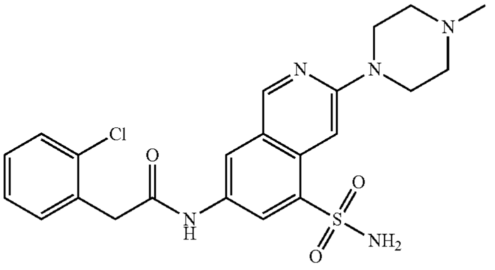

The compound was prepared by reference to the preparation method of embodiment 5. LC-MS: $[M+H]^+$=474.1.

Embodiment 80

Compound 80: Preparation of 2-(2-chlorophenyl)-N-(3-(4-methyl-3-carbonylpiperazin-1-yl)-5-sulfamoylisoquinolin-7-yl)acetamide

80

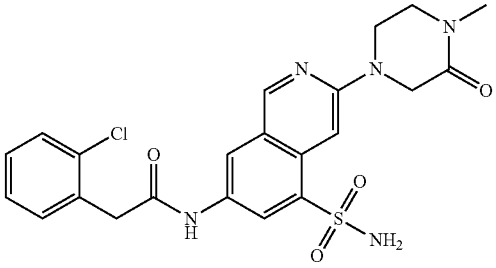

The compound was prepared by reference to the preparation method of embodiment 5. LC-MS: $[M+H]^+$=488.1.

Embodiment 81

Compound 81: Preparation of 2-(2-chlorophenyl)-N-(3-((4-methoxyphenyl)amino)-5-sulfamoylisoquinolin-7-yl)acetamide

81

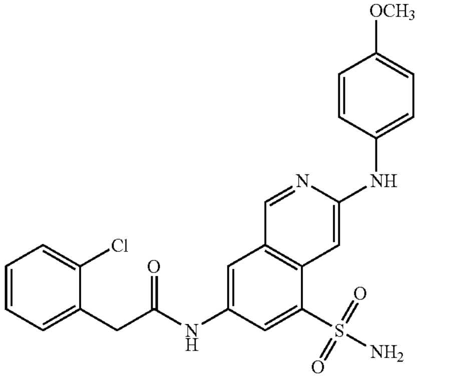

The compound was prepared by reference to the preparation method of embodiment 5. LC-MS: $[M+H]^+$=497.1.

Embodiment 82

Compound 82: Preparation of 2-(2-chlorophenyl)-N-(3-(4-methoxyphenoxy)-5-sulfamoylisoquinolin-7-yl)acetamide

82

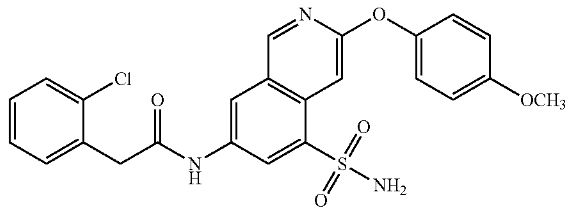

The compound was prepared by reference to the preparation method of embodiment 5. LC-MS: $[M+H]^+$=498.1.

Embodiment 83

Compound 83: Preparation of 2-(2-chlorophenyl)-N-(3-(isopropylamino)-5-sulfamoylisoquinolin-7-yl) acetamide

83

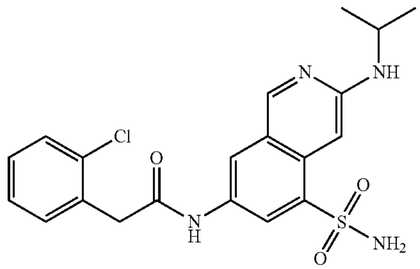

The compound was prepared by reference to the preparation method of embodiment 5. LC-MS: $[M+H]^+$=433.1.

Embodiment 84

Compound 84: Preparation of 2-(2-chlorophenyl)-N-(3-(2-methoxyethoxy)-5-sulfamoylisoquinolin-7-yl)acetamide

84

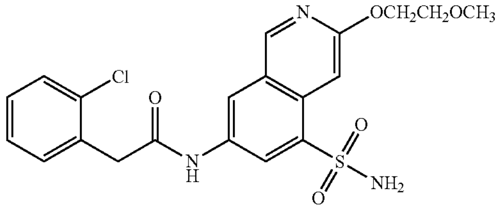

The compound was prepared by reference to the preparation method of embodiment 5. LC-MS: $[M+H]^+$=450.1.

Embodiment 85

Compound 85: Preparation of 2-(2-chlorophenyl)-N-(2-cyclopropyl-5-sulfamoylquinolin-7-yl)acetamide

85

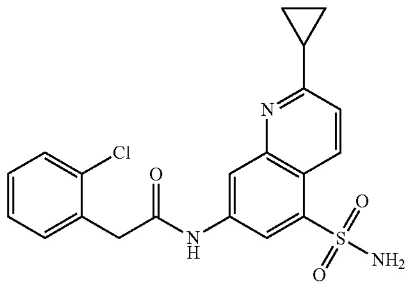

Synthetic Route:

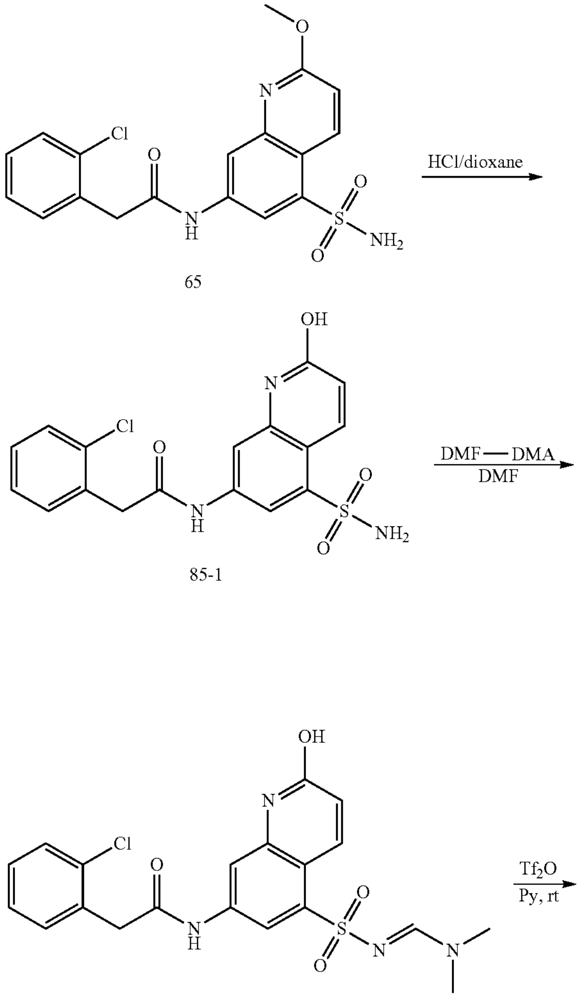

65

85-1

85-2

-continued

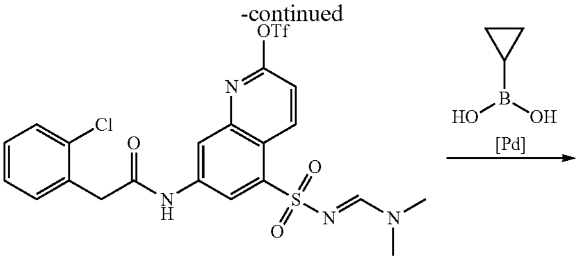

85-3

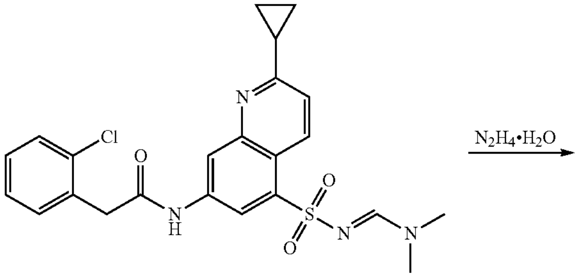

85-4

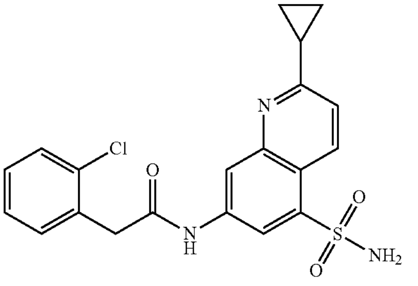

85

Step (1) Preparation of Intermediate 85-1

Compound 65 (2.0 g) was added to HCl/dioxane (dioxane hydrochloride) (40 mL) in a sealed flask, and the reaction was carried out at 80° C. overnight. LCMS showed that the reaction was completed, and the reaction solution was cooled to room temperature, filtered, and the filter cake was washed with ethyl acetate, and dried to obtain 1.2 g of intermediate 85-1 as a white solid with a yield of 62.12%. LCMS: ESI(+) m/z=392.05[M+1]$^+$.

Step (2) Preparation of Intermediate 85-2

Intermediate 85-1 (600 mg) was dissolved in DMF (6 mL), then DMF-DMA (548 mg) was added dropwise to the reaction with stirring, and after the addition was completed, the reaction was carried out at room temperature for 1 hour. LCMS showed that the reaction was completed, and the reaction solution was quenched by adding water (20 mL), and solid was precipitated; the mixture was filtered, and the filter cake was washed with water for two times and dried to obtain 535 mg of intermediate 85-2 as a white solid. LCMS: ESI(+) m/z=447.05[M+1]$^+$.

Step (3) Preparation of Intermediate 85-3

Intermediate 85-2 (535 mg) was dissolved in pyridine (5 mL). $Tf_2O$ (1.7 g) was added dropwise to the reaction, and the reaction was stirred at room temperature for 1 hour. LCMS showed that the reaction was completed. The reaction solution was stirred and dissolved with EtOAc (30 mL), and the organic phase was washed with 1M HCl solution for two times until the system became weakly acidic, and then washed with saturated $NaHCO_3$ solution for one time; the organic phase was dried over anhydrous sodium sulfate, filtered, and the filtrate was concentrated under reduced pressure to obtain 700 mg of intermediate 85-3 as a pale-yellow solid. LCMS: ESI(+) m/z=579.05[M+1]$^+$.

Step (4) Preparation of Intermediate 85-4

Intermediate 85-3 (150 mg), cyclopropylboronic acid (45 mg), $Na_2CO_3$, (85 mg), toluene/water (10/1, 3.0 mL) were sequentially added to a sealed reaction flask, and the reaction system was replaced with $N_2$ for three times, and the mixture was warmed to 110° C. and reacted overnight. LCMS showed that the reaction was completed, and the mixture was quenched with water, extracted with ethyl acetate for three times; the EtOAc phases were combined, washed with water for two times and saturated brine for one time, dried over anhydrous sodium sulfate, filtered, and the filtrate was concentrated under reduced pressure to obtain 80 mg of crude product and directly used in the next step. LCMS: ESI(+) m/z=471.05[M+1]$^+$.

Step (5) Preparation of Compound 85

Intermediate 85-4 (80 mg) was dissolved in MeOH (0.8 mL). Then hydrazine hydrate (0.4 mL) was added, and the mixture was reacted at room temperature for 1 hour. LCMS showed that the reaction was completed. The reaction solution was quenched with water, extracted three times with EtOAc (5 mL); the EtOAc phases were combined, washed with water for two times and saturated brine for one time, dried over anhydrous sodium sulfate, filtered, and the filtrate was concentrated under reduced pressure to obtain a crude product. The crude product was purified by perp-HPLC to obtain compound 85 as a white solid (2.4 mg, the purity was 99.316%). LCMS: ESI(+) m/z=416.10[M+1]$^+$.

$^1$H NMR (400 MHz, dmso) δ 10.77 (s, 1H), 8.70 (d, J=8.8 Hz, 1H), 8.42 (d, J=1.6 Hz, 1H), 8.24 (d, J=2.2 Hz, 1H), 7.70 (s, 2H), 7.47-7.41 (m, 3H), 7.32-7.28 (m, 2H), 3.90 (s, 2H), 2.28-2.24 (m, 1H), 1.05 (d, J=6.4 Hz, 4H).

Embodiment 86

Compound 86: Preparation of 2-(2-chlorophenyl)-N-(2-ethynyl-5-sulfamoylquinolin-7-yl)acetamide

86

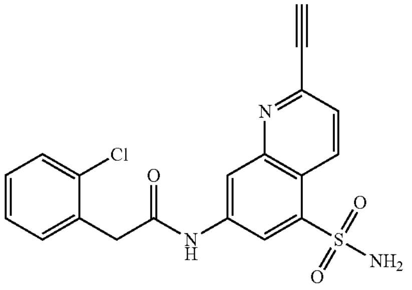

Synthetic Route:

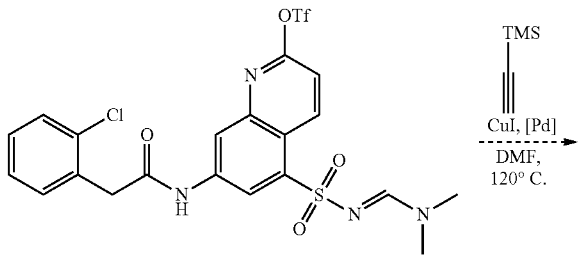

85-3

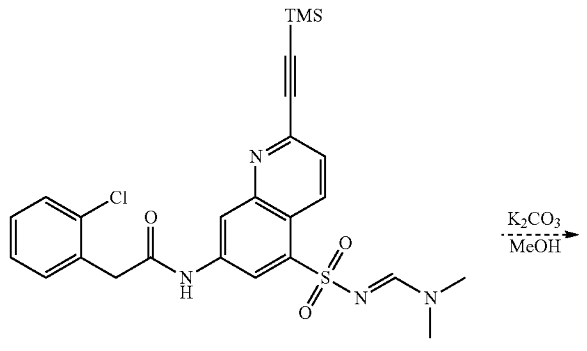

86-1

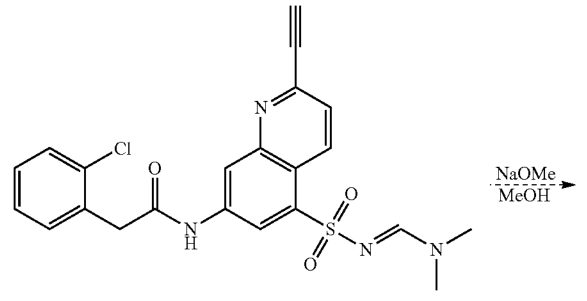

86-2

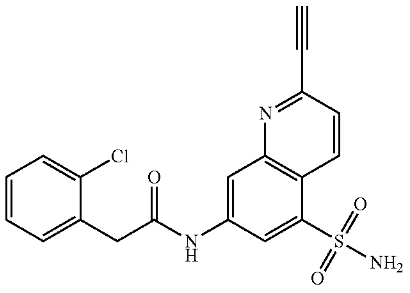

86

Step (1) Preparation of Intermediate 86-1

Intermediate 85-3 (200 mg), trimethylsilyl acetylene (42 mg), CuI (34 mg), DIEA (135 mg), bis(triphenylphosphine) palladium dichloride (70.1 mg), DMF (4 mL) were sequentially added to a sealed flask, and the reaction system was replaced with $N_2$ for three times, and the mixture was reacted at 120° C. for 2 hours. LCMS showed that the reaction was completed, and the reaction solution was cooled to room temperature, quenched with water, extracted with EtOAc (8 mL) for three times; the EtOAc phases were combined, washed with water for two times and saturated brine for one time, dried over anhydrous sodium sulfate, filtered, and the filtrate was concentrated under pressure to obtain a crude product. The crude product was purified by silica gel column to obtain intermediate 86-1 as a white solid (120 mg, the purity was 87%). LCMS: ESI(+) m/z=527.10 $[M+1]^+$.

Step (2) Preparation of Intermediate 86-2

Intermediate 86-1 (120 mg) was dissolved in MeOH (2 mL), then $K_2CO_3$ (94 mg) was added to the reaction with stirring, and after the addition was completed, the reaction was carried out at room temperature for 1 hour. LCMS showed that the reaction was completed, and the reaction solution was filtered and concentrated to obtain 200 mg of a crude product, and directly used in the next reaction. LCMS: ESI(+) m/z=455.05$[M+1]^+$.

Step (3) Preparation of Compound 86

Intermediate 86-2 (80 mg) was dissolved in MeOH (0.8 mL). Methanol (0.4 mL) solution of sodium methoxide was added, and the mixture was reacted at room temperature for 1 hour. LCMS showed that the reaction was completed. The reaction solution was quenched with water, extracted three times with EtOAc (5 mL); the EtOAc phases were combined, washed with water for two times and saturated brine for one time, dried over anhydrous sodium sulfate, filtered, and the filtrate was concentrated under reduced pressure to obtain a crude product. The crude product was purified by perp-HPLC to obtain compound 86 as a brown solid (2.5 mg, the purity was 98.174%). LCMS: ESI(+) m/z=400.00 $[M+1]^+$.

$^1$H NMR (400 MHz, dmso) δ 10.92 (s, 1H), 8.88 (d, J=8.8 Hz, 1H), 8.51 (d, J=1.6 Hz, 1H), 8.45 (d, J=2.2 Hz, 1H), 7.81 (s, 2H), 7.67 (d, J=8.8 Hz, 1H), 7.47-7.42 (m, 2H), 7.34-7.29 (m, 2H), 4.55 (s, 1H), 3.93 (s, 2H).

Embodiment 87

Compound 87: Preparation of 2-(2-chlorophenyl)-N-(2-(prop-1-yn-1-yl)-5-sulfamoylquinolin-7-yl) acetamide

87

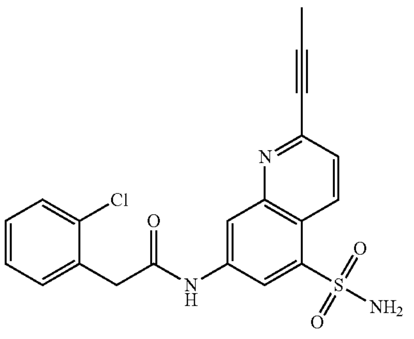

Synthetic Route:

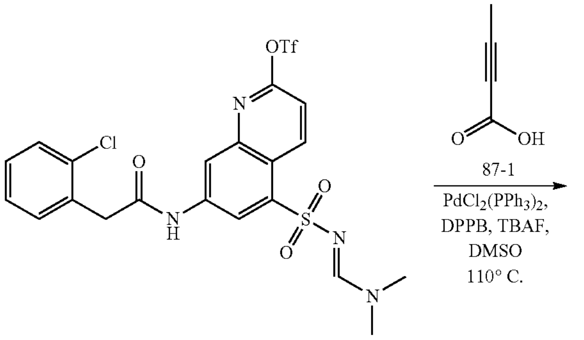

85-3

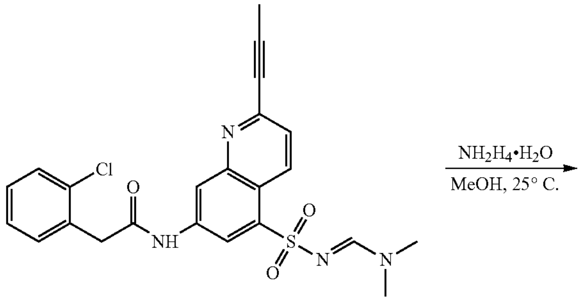

87-2

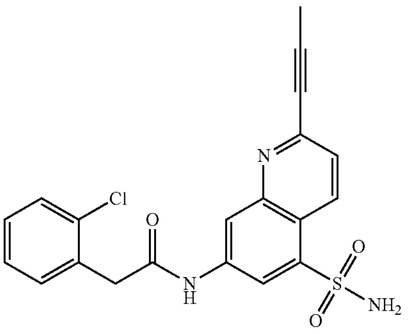

87

Step (1) Preparation of Intermediate 87-2

Intermediate 85-3 (150 mg), intermediate 87-1 (2-butynoic acid) (54 mg), DPPB (22.0 mg), TBAF (168 mg), $PdCl_2(PPh_3)_2$ (18.0 mg) were dissolved in DMF (2 mL), and after the reaction system was replaced with $N_2$ for four times, the temperature was warmed to 100° C., and the reaction was heated and reacted for 1 hour. TLC (PE/EA=0/1) showed that the reaction was completed, and the heating was turned off, then the mixture was cooled down naturally. After the reaction solution was diluted with EA (5 mL), water (10 mL) was added, and the aqueous phase was extracted with EA (5 mL) for three times. The organic phases were combined, washed with saturated brine (10 mL) for two times, dried over anhydrous sodium sulfate, filtered, and the filtrate was concentrated under reduced pressure to obtain a crude product. The crude product was purified by thin layer chromatography (PE/EA=0/1) to obtain intermediate 87-2 as a yellow solid (40.0 mg, the purity was 59%). LC-MS: $[M+H]^+$=469.10.

Step (2) Preparation of Compound 87

Intermediate 87-2 (1.30 g) was dissolved in THF (1 mL) and MeOH (1 mL), then hydrazine hydrate was added, and the reaction was carried out at room temperature of 25° C. for 0.5 hours. LCMS showed that the reaction was completed. The reaction solution was concentrated by rotary evaporation, purified by prep-HPLC, and lyophilized to obtain compound 87 (5.50 mg, the purity was 96.4%) as a yellow solid powder. LC-MS: $[M+H]^+$=416.05.

$^1H$ NMR (400 MHz, DMSO-d) δ 10.90 (s, 1H), 8.84 (d, J=8.8 Hz, 1H), 8.49 (d, J=1.6 Hz, 1H), 8.43 (d, J=2.0 Hz, 1H), 7.81 (s, 2H), 7.59 (d, J=8.8 Hz, 1H), 7.49-7.44 (m, 2H), 7.36-7.32 (m, 2H), 3.94 (s, 2H), 2.15 (s, 3H).

Embodiment 88

Compound 88: Preparation of 2-(2-chlorophenyl)-N-(2-(dimethylamino)-5-sulfamoylquinolin-7-yl) acetamide

88

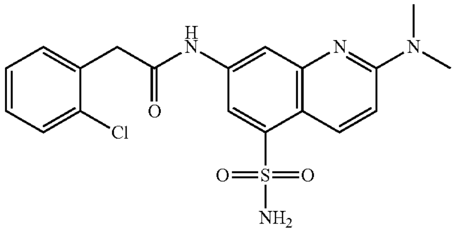

Synthetic Route

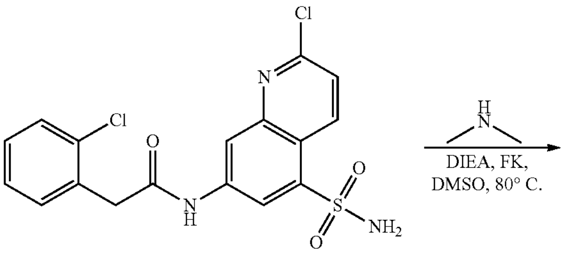

57

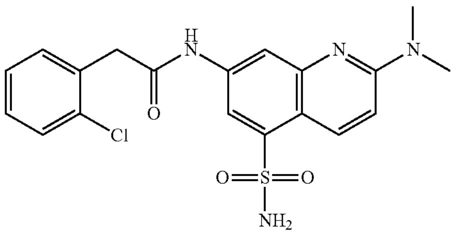

88

Step (1) Preparation of Compound 88

Compound 57 (62.0 mg) was dissolved in DMSO (1.30 mL), and dimethylamine hydrochloride (37.0 mg), DIEA (58.0 mg), and KF (26.0 mg) were added, and the mixture was reacted at 80° C. for 12 hours. LCMS showed that the reaction was completed. The reaction solution was cooled to room temperature, diluted with water (5 mL), filtered, and the filter cake was recovered, concentrated by rotary evaporation, purified by prep-HPLC, and lyophilized to obtain compound 88 (6.8 mg, the purity was 99.3%) as a yellow powder. LC-MS: $[M+H]^+$=419.05.

$^1$H NMR (400 MHz, DMSO-d) δ 10.62 (s, 1H), 8.55 (d, J=9.6 Hz, 1H), 8.18 (s, 1H), 7.95 (d, J=1.6 Hz, 1H), 7.60 (s, 2H), 7.46 (dd, J=8.8, 3.6 Hz, 2H), 7.37-7.28 (m, 2H), 7.08 (d, J=9.6 Hz, 1H), 3.90 (s, 2H), 3.16 (s, 6H).

Embodiment 89

Compound 89: Preparation of (2-chlorophenyl)-N-(2-(pyrrolidin-1-yl)-5-sulfamoylquinolin-7-yl)acetamide

89

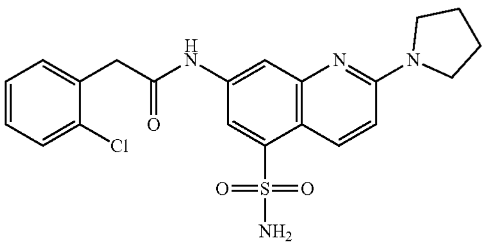

Synthetic Route:

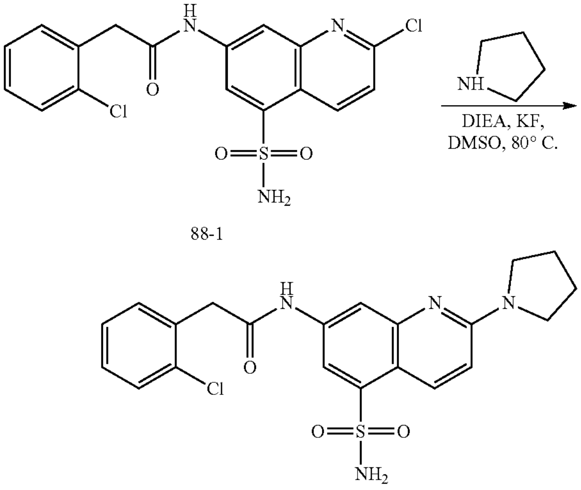

88-1

89

Intermediate 88-1 (62.0 mg) was dissolved in DMSO (1.50 mL), then pyrrolidine (32.0 mg), DIEA (58.0 mg), KF (26.0 mg) were added, and the mixture was reacted at 80° C. for 2 hours. LCMS showed that the reaction was completed. After the reaction solution was cooled to room temperature, the mixture was diluted with water (5 mL) and EA (3 mL); the aqueous phase was extracted with EA (3 mL) for three times. The EA phases were combined, washed with saturated brine, dried over anhydrous sodium sulfate, filtered, and the filtrate was concentrated under reduced pressure to obtain a crude product, then the crude product was dried by rotary evaporation, purified by prep-HPLC, and lyophilized to obtain compound 89 (8.30 mg, the purity was 98.3%) as a light green powder. LC-MS: $[M+H]^+$=445.10.

$^1$H NMR (400 MHz, DMSO-d) δ 10.58 (s, 1H), 8.54 (d, J=9.2 Hz, 1H), 8.16 (s, 1H), 7.93 (d, J=2.0 Hz, 1H), 7.59 (s, 2H), 7.48-7.41 (m, 2H), 7.35-7.28 (m, 2H), 6.87 (d, J=9.6 Hz, 1H), 3.89 (s, 2H), 3.53 (s, 4H), 1.97 (d, J=5.6 Hz, 4H).

Embodiment 90

Compound 90: 2-(2-chlorophenyl)-N-(1-isocyano-5-sulfamoylisoquinolin-7-yl)acetamide

90

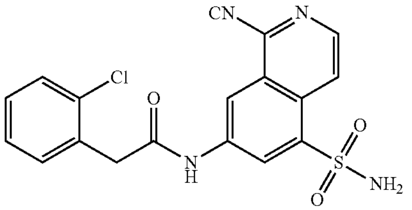

Synthetic Route:

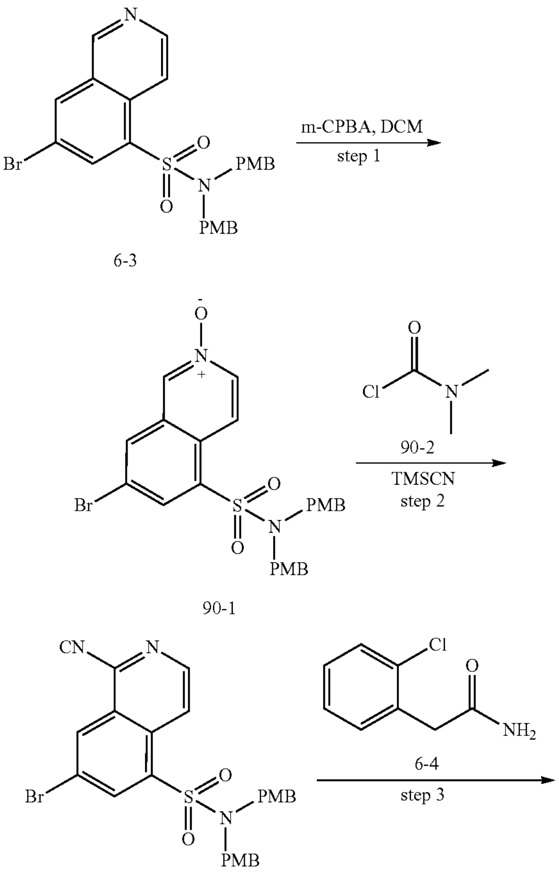

6-3

90-1

90-3

-continued

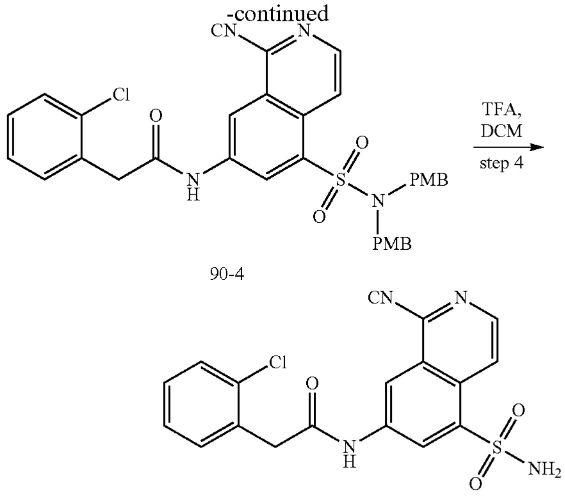

90-4

90

Step (1) Preparation of Intermediate 90-1

Intermediate 6-3 (7-bromo-N,N-bis(4-methoxybenzyl) isoquinoline-5-sulfonamide) (260 mg, 75%, 0.37 mmol) was dissolved in dichloromethane (10 mL), then m-chloroperoxybenzoic acid (100 mg, 85%, 0.49 mmol) was added at room temperature, and the mixture was stirred at room temperature for 2 hours. The reaction was monitored by TLC that the raw materials were disappeared, and the reaction mixture was diluted with dichloromethane (40 mL), washed sequentially with saturated sodium thiosulfate solution (10 mL), sodium bicarbonate solution (20 mL), saturated brine (20 mL), dried and concentrated to obtain a crude product and directly used in the next reaction. 150 mg of intermediate 90-1 was obtained as a yellow solid with a yield of 75%. MS: $[M+H]^+$: =543.1.

Step (2) Preparation of Intermediate 90-3

Intermediate 90-1 (150 mg) was dissolved in dichloromethane (10 mL), then intermediate 90-2 (dimethylcarbamoyl chloride) (297 mg) and trimethylcyanosilane (137 mg) were added sequentially. The mixture was reflux for 6 hours. The mixture was diluted with dichloromethane (40 mL), washed with saturated brine (30 mL), dried over anhydrous sodium sulfate, filtered and concentrated. The crude product was purified by silica gel column chromatography (petroleum ether:ethyl acetate=2:1) to obtain 140 mg of intermediate 90-3 as a white solid with a yield of 87%. MS: $[M+H]^+$: =551.5.

Step (3) Preparation of Intermediate 90-4

Under the protection of nitrogen, a dioxane (10 mL) solution of intermediate 90-3 (120 mg), intermediate 6-4 (2-(2-chlorophenyl)acetamide) (55 mg), cesium carbonate (212 mg) and tris(dibenzylidene-BASE acetone) dipalladium (14 mg) and 4,5-bis(diphenylphosphino)-9,9-dimethylxanthene (25 mg) was stirred at 90° C. for 11 hours. The mixture was directly concentrated by rotary evaporation, and purified by silica gel column chromatography to obtain intermediate 90-4 as a yellow solid with a total of 120 mg with a purity of 70% and a yield of 91%. MS: $[M+H]^+$: =640.6.

Step (4) Preparation of Compound 90

Intermediate 90-4 (60 mg) was dissolved in dichloromethane (2 mL), then trifluoroacetic acid (10 mL) was added, and the mixture was stirred at room temperature for 24 hours. After the mixture was concentrated under reduced pressure, the residue was dissolved in dichloromethane (40 mL), washed sequentially with saturated sodium bicarbonate solution (20 mL) and saturated brine (20 mL), dried over anhydrous sodium sulfate, filtered and concentrated, and purified by high performance liquid chromatography. Compound 90 was obtained as a white solid with a total of 15 mg and a yield of 38%. MS: $[M+H]^+$: =400.6.

$^1$H NMR (400 MHz, $d_6$-DMSO) δ 11.23 (s, 1H), 9.02 (d, J=1.2 Hz, 1H), 8.77 (d, J=5.9 Hz, 1H), 8.71 (d, J=2.0 Hz, 1H), 8.67 (d, J=5.9 Hz, 1H), 8.02 (s, 2H), 7.54-7.46 (m, 2H), 7.40-7.30 (m, 2H), 3.99 (s, 2H).

Embodiment 91

Compound 91: Preparation of 2-(2,6-dichlorophenyl)-N-(1-methoxy-5-sulfamoylisoquinolin-7-yl) acetamide

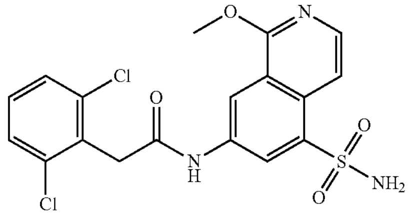 [SMILES: COc1nccc2c(S(N)(=O)=O)cc(NC(=O)Cc3c(Cl)cccc3Cl)cc12]

The compound was prepared by reference to the preparation method of embodiment 1. LC-MS: $[M+H]^+$=440.0.

Embodiment 92

Compound 92: Preparation of 2-(2,4-dichlorophenyl)-N-(1-methoxy-5-sulfamoylisoquinolin-7-yl) acetamide

92

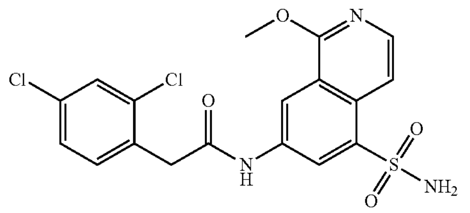

Synthetic Route:

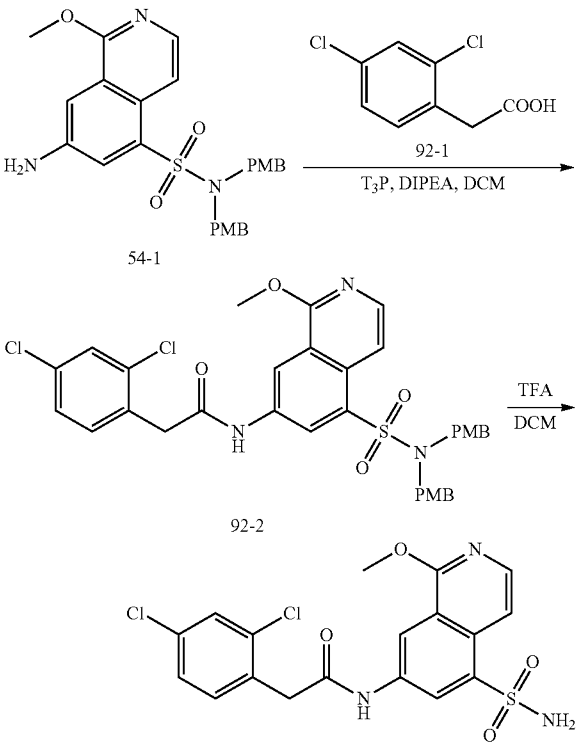

54-1

92-2

92

Step (1) Preparation of Intermediate 92-2

Intermediate 54-1 (50 mg) was weighed and dissolved in DCM (2 mL), then intermediate 92-1 (2,4-dichloropheny-lacetic acid) (24.8 mg), T3P (64.5 mg) and DIPEA (40 mg) were added, and the mixture was stirred at room temperature for 2 hours; the sample was taken, TLC (PE:EA=2:1) showed that the raw materials were reacted completely; DCM (10 mL) and $H_2O$ (5 mL) were added to the reaction solution, and the reaction solution was stirred then the phases were separated; the aqueous was extracted with DCM (5 mL) for two times, and the organic phases were combined, washed with brine, dried over anhydrous sodium sulfate, filtered, concentrated by rotary evaporation to obtain a crude product of intermediate 92-2 as a yellow oil (70 mg).

Step (2) Preparation of Compound 92

Compound 92-2 (70 mg) was weighed and dissolved in DCM (2 mL), then TFA (4 mL) was added dropwise, and the mixture was stirred at room temperature for 16 hours; the sample was taken, and sent to LCMS showed that 10% of the raw material remained; the reaction solution was diluted with DCM (20 mL), and the pH was adjusted to 7-8 with Sat. $NaHCO_3$, and the reaction solution was stirred and the phases were separated; the aqueous phase was extracted with DCM (10 mL) for two times, and the organic phases were combined, washed with brine, and dried over anhydrous sodium sulfate, filtered, and concentrated under reduced pressure to obtain a crude product; the crude product was purified by prep-HPLC with $H_2O/CH_3CN$ system, after lyophilization, compound 92 was obtained as a white solid (13.4 mg) with a purity of 99.05%, $[M+H]^+$=440.00.

$^1$H NMR (400 MHz, DMSO) δ 10.88 (s, 1H), 8.84 (s, 1H), 8.53 (d, J=2.4 Hz, 1H), 8.06 (d, J=6.4 Hz, 1H), 7.90 (d, J=6.0 Hz, 1H), 7.75 (s, 2H), 7.64 (d, J=2.0 Hz, 1H), 7.50 (d, J=8.4 Hz, 1H), 7.44 (dd, J=8.4, 2.0 Hz, 1H), 4.06 (s, 3H), 3.92 (s, 2H).

Embodiment 93

Compound 93: 2-(2-Chloro-5-fluorophenyl)-N-(1-methoxy-5-sulfamoylisoquinolin-7-yl)acetamide

93

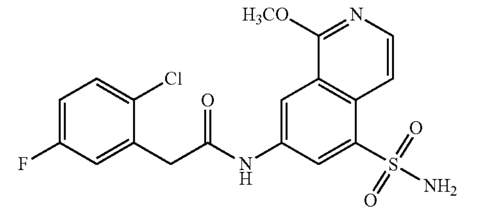

Synthetic Route:

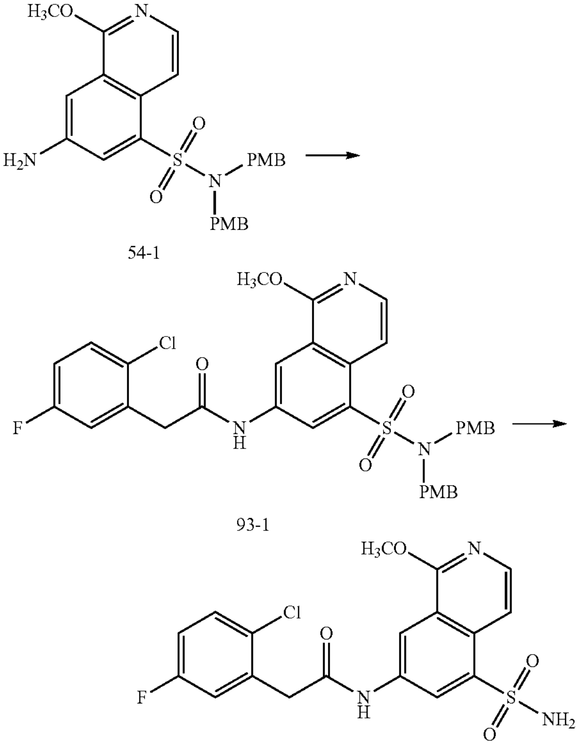

54-1

93-1

93

Step (1) Preparation of Intermediate 93-1

Intermediate 54-1 (110 mg) was weighed and dissolved in 2 mL of DCM, then 2-chloro-5-fluorophenylacetic acid, T3P and TEA were added; after the addition was completed, the reaction was carried out at room temperature for 1 hour, and LCMS showed that the reaction of the raw materials was completed, and the reaction solution was directly concentrated by rotary evaporation and mixed with silica gel, and subjected to column chromatography (PE/EA=4/1) to obtain 120 mg of intermediate 93-1 as a yellow oily liquid.

Step (2) Preparation of Compound 93

Intermediate 93-1 (120 mg) was weighed and dissolved in 10 mL of DCM, then 10 mL of TFA was added; after the addition was completed, the reaction was carried out at 40° C. overnight; LCMS showed that the product was formed and the reaction solution was concentrated by rotary evaporation, purified by Prep-HPLC to obtain 22.6 mg of compound 93 as a white solid. LC-MS: $[M+H]^+$=424.05.

$^1H$ NMR (400 MHz, dmso) δ 10.89 (s, 1H), 8.85 (d, J=1.9 Hz, 1H), 8.53 (d, J=2.2 Hz, 1H), 8.06 (d, J=6.2 Hz, 1H), 7.91 (d, J=6.2 Hz, 1H), 7.76 (s, 2H), 7.52 (dd, J=8.8, 5.3 Hz, 1H), 7.38 (dd, J=9.4, 3.1 Hz, 1H), 7.21 (td, J=8.5, 3.1 Hz, 1H), 4.06 (s, 3H), 3.94 (s, 2H).

Embodiment 94

Compound 94: Preparation of 2-(2-chloro-4-fluorophenyl)-N-(1-methoxy-5-sulfamoylisoquinolin-7-yl) acetamide

94

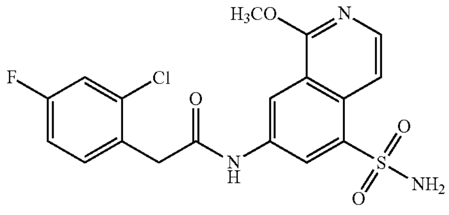

Synthetic Route:

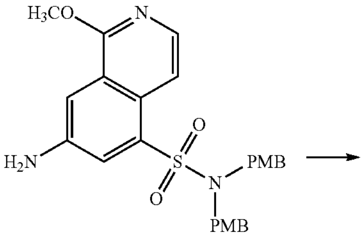

54-1

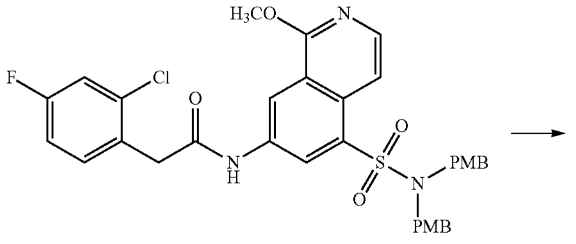

94-1

-continued

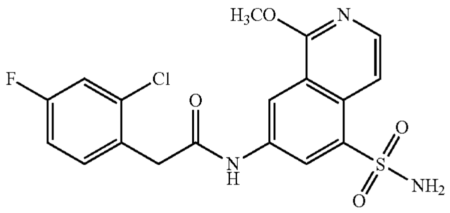

94

Step (1) Preparation of Intermediate 94-1

Intermediate 54-1 (110 mg) was weighed and dissolved in 2 mL of DCM, then 2-chloro-4-fluorophenylacetic acid, T3P and TEA were added; after the addition was completed, the reaction was carried out at room temperature for 1 hour. LCMS showed that the raw materials were reacted completely, and the reaction solution was directly concentrated by rotary evaporation and mixed with silica gel, and purified by column chromatography (PE/EA=4/1) to obtain 120 mg of intermediate 94-1 as a yellow oily liquid.

Step (2) Preparation of Compound 94

Intermediate 94-1 (120 mg) was weighed and dissolved in 10 mL of DCM, then 10 mL of TFA was added, and the reaction was carried out at 40° C. overnight; LCMS showed that the product was formed and the reaction solution was concentrated by rotary evaporation, purified by Prep-HPLC to obtain 22.7 mg of compound 94 as a white solid. LC-MS: $[M+H]^+$=424.00.

$^1H$ NMR (400 MHz, dmso) δ 10.86 (s, 1H), 8.85 (d, J=1.9 Hz, 1H), 8.54 (d, J=2.2 Hz, 1H), 8.06 (d, J=6.2 Hz, 1H), 7.93-7.88 (m, 1H), 7.76 (s, 2H), 7.49 (ddd, J=11.5, 8.7, 4.5 Hz, 2H), 7.23 (td, J=8.5, 2.7 Hz, 1H), 4.06 (s, 3H), 3.91 (s, 2H).

Embodiment 95

Compound 95: Preparation of 2-(5-fluoro-2-methoxyphenyl)-N-(1-methoxy-5-sulfamoylisoquinolin-7-yl)acetamide

95

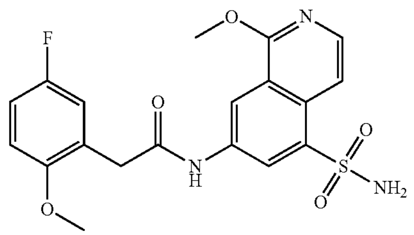

Synthetic Route:

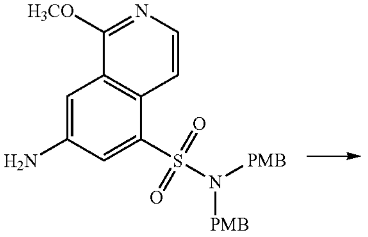

54-1

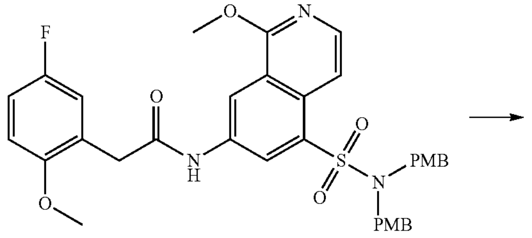

95-1

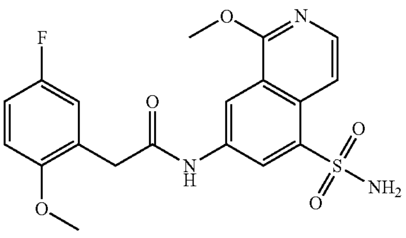

95

Step (1) Preparation of Intermediate 95-1

Intermediate 54-1 (110 mg) was weighed and dissolved in 2 mL of DCM, then 5-fluoro-2-methoxyphenylacetic acid, T3P and TEA were added; after the addition was completed, the reaction was carried out at room temperature for 1 hour. LCMS monitoring showed that the reaction of the raw materials was completed, and the reaction solution was directly concentrated by rotary evaporation and mixed with silica gel, and purified by column chromatography (PE/EA=4/1) to obtain 120 mg of intermediate 95-1 as a yellow oily liquid.

Step (2) Preparation of Compound 95

Intermediate 95-1 (120 mg) was weighed and dissolved in 10 mL of DCM, then 10 mL of TFA was added; after the addition was completed, the reaction was carried out at 40° C. overnight. LCMS showed that the product was formed and the reaction solution was concentrated by rotary evaporation, purified by Prep-HPLC to obtain 22.1 mg of a product of compound 95 as a white solid. LC-MS: $[M+H]^+$ =420.05.

$^1$H NMR (400 MHz, dmso) δ 10.73 (s, 1H), 8.85 (d, J=1.8 Hz, 1H), 8.54 (d, J=2.2 Hz, 1H), 8.05 (d, J=6.2 Hz, 1H), 7.90 (d, J=6.2 Hz, 1H), 7.75 (s, 2H), 7.16-7.06 (m, 2H), 6.99 (dd, J=9.0, 4.7 Hz, 1H), 4.06 (s, 3H), 3.75 (s, 3H), 3.72 (s, 2H).

Embodiment 96

COMPOUND 96: Preparation of N-(1-methoxy-5-sulfamoylisoquinolin-7-yl)-2-(2-(trifluoromethoxy)phenyl)acetamide

96

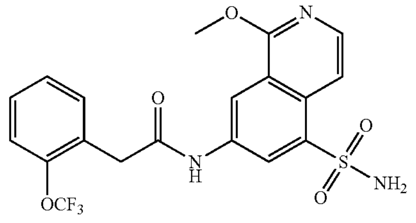

Synthetic Route:

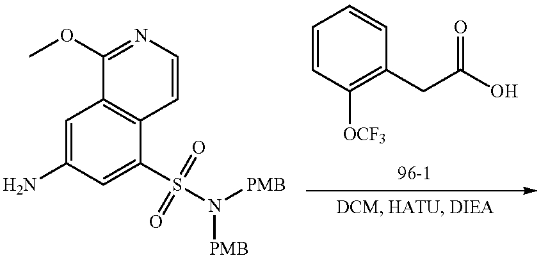

54-1

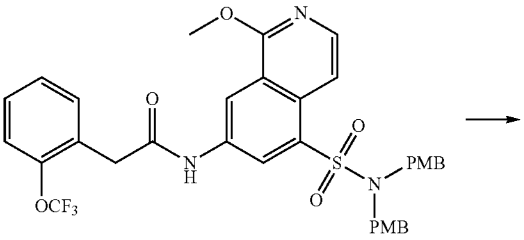

96-2

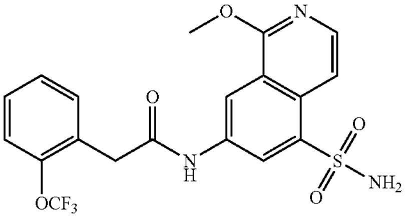

96

Step (1) Preparation of Intermediate 96-2

Intermediate 54-1 (90 mg), intermediate 96-1 (2-(2-(trifluoromethoxy)phenyl)acetic acid) (60 mg), DIEA (47 mg) were sequentially dissolved in DCM (1 mL), and HATU (103 mg) was added. LCMS showed that the reaction was completed, then the reaction solution was added with water (5 mL) then extracted with ethyl acetate (3 mL) for three times; the organic phases were combined, washed sequentially with saturated brine, dried over anhydrous sodium sulfate, and filtered, and the filtrate was concentrated under reduced pressure to obtain a crude product. The crude product was purified by perp-TLC to obtain intermediate 96-2 as a white solid (60 mg, the purity was 95%). LCMS: ESI(+) m/z=696.15[M+1]$^+$.

Step (2) Preparation of Compound 96

Intermediate 96-2 (60 mg) was dissolved in DCM (0.1 mL). TFA (0.1 mL) was added and the reaction was carried out at 60° C. for 12 hours. LCMS showed that the reaction was completed. The pH of the reaction solution was adjusted with saturated $NaHCO_3$ solution to weakly alkaline, and the mixture was extracted with EtOAc (20 mL) for three times; the EtOAc phases were combined, washed with water for two times and saturated brine for one time, dried over anhydrous sodium sulfate, filtered, and the filtrate was concentrated under reduced pressure to obtain a crude product. The crude product was purified by perp-HPLC to obtain compound 96 as a white solid (6.8 mg, the purity was 99.807%). LCMS: ESI(+) m/z=456.05[M+1]$^+$.

$^1$H NMR (400 MHz, dmso) δ 10.871 (s, 1H), 8.849 (d, J=1.6 Hz, 1H), 8.528 (d, J=2.0 Hz, 1H), 8.065 (d, J=6.4 Hz, 1H), 7.907 (d, J=6.4 Hz, 1H), 7.764 (s, 2H), 7.529 (dd, J=7.2, 2.0 Hz, 1H), 7.463-7.361 (m, 3H), 4.061 (s, 3H), 3.865 (s, 2H).

Embodiment 97

Compound 97: Preparation of 2-(2-chloro-3-fluorophenyl)-N-(1-methoxy-5-sulfamoylisoquinolin-7-yl) acetamide

97

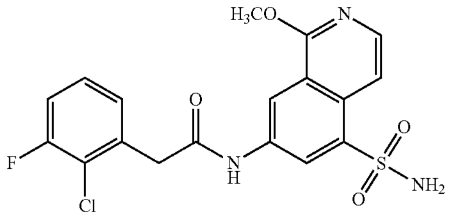

Synthetic Route:

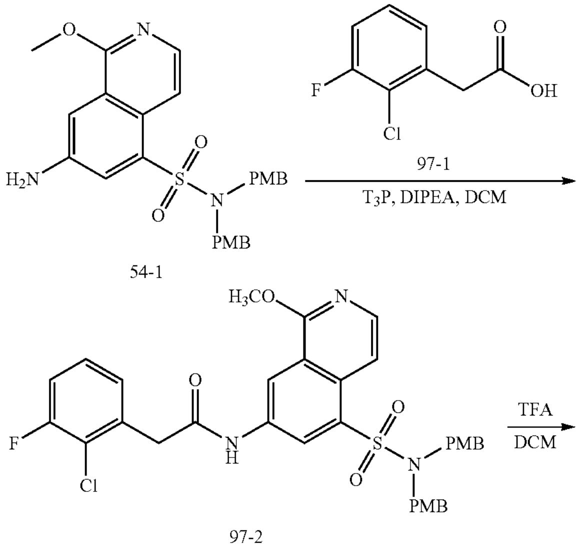

-continued

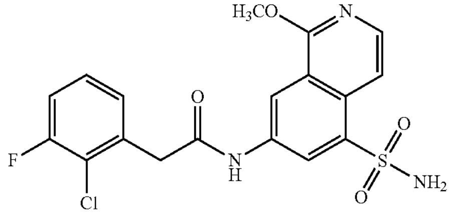

97

Step (1) Preparation of Intermediate 97-2

Intermediate 54-1 (80 mg), intermediate 97-1 (2-(2-chloro-3-fluorophenyl)acetic acid) (37 mg), T3P (206 mg), $Et_3N$ (49 mg) and DCM (2 mL) were added to the reaction flask, and the reaction solution was stirred at room temperature overnight. The reaction solution was poured into water, extracted with DCM; the organic phase was concentrated, and the mixed with silica gel, and then purified by column chromatography to obtain intermediate 97-2 as a pale-yellow solid (60 mg). The product was confirmed by TLC (PE/EA=2/1).

Step (2) Preparation of Compound 97

Intermediate 97-2 (60 mg) was dissolved in DCM (2 mL), then TFA (2 mL) was added to the reaction flask, and the reaction was stirred at 50° C. for 2 hours. The pH of the reaction solution was adjusted to about 8 with an aqueous sodium bicarbonate solution, and the mixture was extracted with EA; the organic phase was concentrated by rotary evaporation, and purified by column chromatography to give compound 97 as a white solid (10.1 mg, the purity was 98.635%). LC-MS: ESI(+) m/z=424[M+1].

$^1$H NMR (400 MHz, dmso) δ 10.89 (s, 1H), 8.83 (d, J=2.0 Hz, 1H), 8.52 (d, J=2.4 Hz, 1H), 8.04 (d, J=6.4 Hz, 1H), 7.90-7.87 (m, 1H), 7.74 (s, 1H), 7.39-7.28 (m, 4H), 4.04 (s, 3H), 3.96 (s, 2H).

Embodiment 98

Compound 98: Preparation of 2-(2-chlorophenyl)-N-(5-sulfamoyl-1,2,3,4-tetrahydroisoquinolin-7-yl) acetamide

98

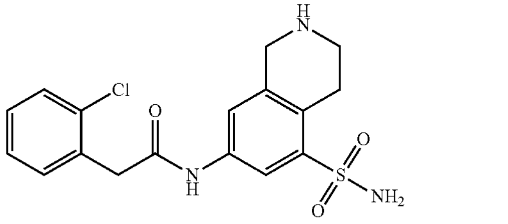

Synthetic Route:

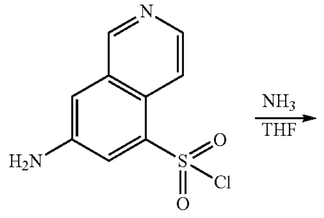

6-2

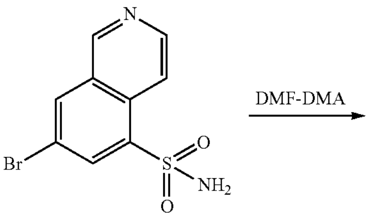

98-1

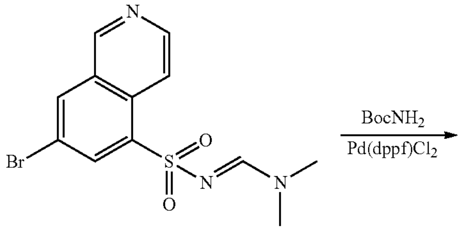

98-2

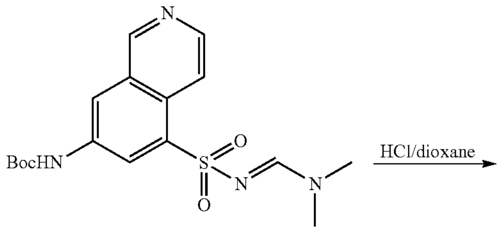

98-3

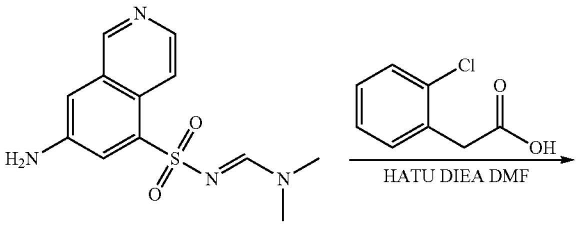

98-4

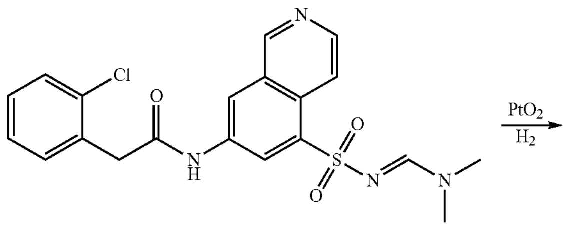

98-5

-continued

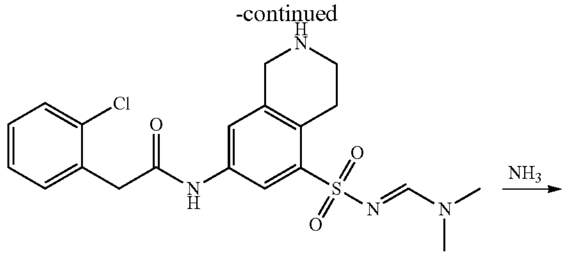

98-6

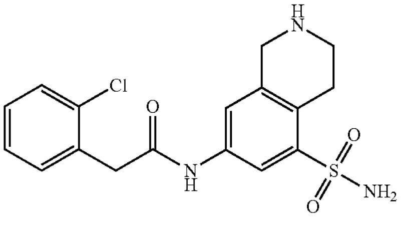

98

Step (1) Preparation of Intermediate 98-1

Intermediate 6-2 (1.0 g) was dissolved in tetrahydrofuran solution (7 mol/L, 15 mL) of ammonia, and the reaction was stirred at room temperature for 3 hours. The sample was taken, and TLC showed that the raw materials were reacted completely. The reaction solution was added to water, and the mixture was extracted with EA for three times; the EA phases were combined, washed sequentially with saturated brine, dried over anhydrous sodium sulfate, filtered, and the filtrate was concentrated under reduced pressure to obtain a crude product of intermediate 98-1 with a total of 800 mg.

Step (2) Preparation of Intermediate 98-2

Intermediate 98-1 (800 mg) was dissolved in DMF-DMA (10 mL), and the reaction was stirred at room temperature for 3 hours to obtain 650 mg of crude product, which was directly used in the next reaction.

Step (3) Preparation of Intermediate 98-3

Intermediate 98-2 (600 mg), $NH_2Boc$ (310 mg), cesium carbonate (860 mg), XantPhos (100 mg), $Pd(dppf)Cl_2$ were sequentially dissolved in dioxane, and the reaction system was replaced with nitrogen; and the temperature was warmed to 85° C. under the protection of $N_2$, the reaction solution was stirred overnight, then the reaction was completed; water and EA were added to the reaction solution, and the EA phase was separated and the aqueous phase was quenched with EA for three times; the EA phases were combined, and washed sequentially with saturated brine, dried over anhydrous sodium sulfate and concentrated to obtain 510 mg of the product.

Step (4) Preparation of Intermediate 98-4

Intermediate 98-3 (500 mg) was dissolved in an ethyl acetate solution of hydrogen chloride (20 mL), and the reaction was stirred at room temperature for 3 hours; the sample was taken, and TLC showed that raw materials were reacted completely. Water and EA were added to the reaction solution, after fully shaking, the EA phase was separate, and the aqueous phase was added with $K_2CO_3$ to adjust the pH to 9 to 10, then the aqueous phase was extracted with EA for three times; the EA phases were combined, and then washed with saturated brine, dried over anhydrous sodium sulfate, filtered, and the filtrate was concentrated under reduced pressure to obtain a product of intermediate 98-4 (380 mg, the purity was 82.2%).

Step (5) Preparation of Intermediate 98-5

Intermediate 98-4 (350 mg), intermediate 1-7 (246.5 mg), HATU (684 mg), DIEA (490 mg) were sequentially dissolved in DMF (5 mL), and the reaction was stirred at room temperature overnight; after the reaction was completed, water was added to the reaction, then the mixture was extracted with EA for three times; the EA phases were combined, washed with saturated brine, dried over anhydrous sodium sulfate, filtered, and the filtrate was concentrated under reduced pressure to obtain a product of intermediate 98-5 (210 mg).

Step (6) Preparation of Intermediate 98-6

Intermediate 98-5 (200 mg) was dissolved in methanol, then $PtO_2$ (50 mg) was added thereto; after the reaction system was replaced with hydrogen, the reaction was stirred at 50° C. overnight under the protection of hydrogen. The sample was taken, and TLC showed that the raw materials were reacted completely, and the reaction solution was filtered and then concentrated by rotary evaporation to obtain a product of intermediate 98-6 (160 mg).

Step (7) Preparation of Compound 98

Intermediate 98-6 (75 mg) was dissolved in a methanol solution (4 mol/L, 0.4 mL) of ammonia, and the mixture was reacted overnight at room temperature, then the reaction was completed; the reaction solution was concentrated by rotary evaporation and sent to preparation, and the preparation solution was lyophilized to obtain compound 98 (15 mg) as a white solid.

Embodiment 99

Compound 99: Preparation of methyl 7-(2-(2-chlorophenyl)acetamido)-5-sulfamoyl-3,4-dihydroisoquinoline-2(1H)-carboxylate

99

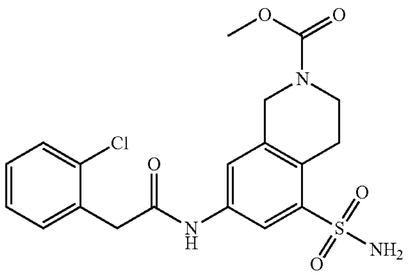

Synthetic Route:

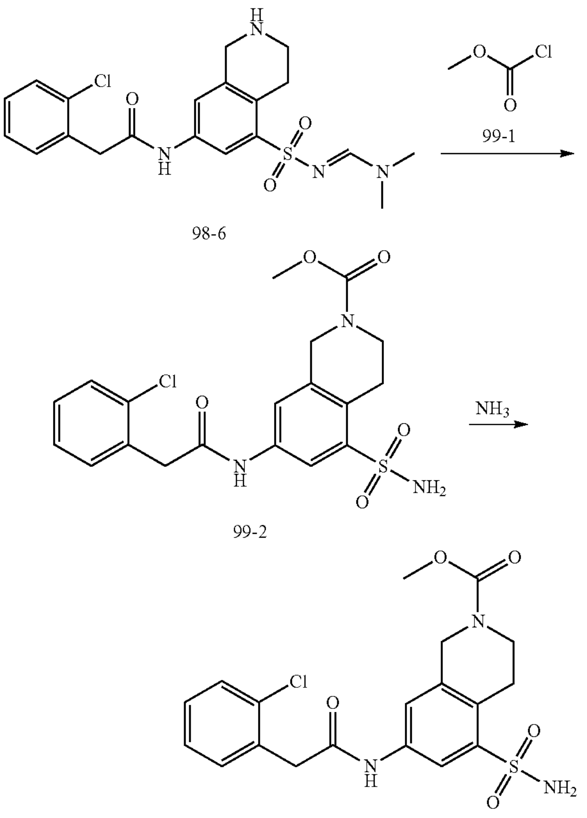

Step (1) Preparation of Intermediate 99-2

Intermediate 98-6 (75 mg) was dissolved in DCM (3 mL), then DIEA (45 mg) was added, then intermediate 99-1 (methyl chloroformate) (19.5 mg) was added dropwise thereto in an ice bath and the mixture was stirred for 0.5 hours at room temperature; the sample was taken, and TLC showed that the raw materials were reacted completely. The reaction was quenched with water, and the aqueous phase was extracted with EA for three times; the EA phases were combined, washed with saturated brine, dried over anhydrous sodium sulfate, filtered, and the filtrate was concentrated under reduced pressure to obtain a product of intermediate 99-2 (50 mg).

Step (2) Preparation of Compound 99

Intermediate 99-2 (40 mg) was dissolved in a methanol solution (4 mol/L, 0.4 mL) of ammonia, and the mixture was reacted overnight at room temperature, then the reaction was completed; the reaction solution was concentrated by rotary evaporation and sent to preparation, and the preparation solution was lyophilized to obtain 12 mg of compound 99 as a white solid.

$^1$H NMR (400 MHz, dmso) δ 10.50 (s, 1H), 8.0 (s. 1H), 7.6 (s. 1H), 7.41-743 (m, 2H), 7.25-7.30 (m. 2H), 4.5 (s, 2H), 3.8 (s, 2H), 3.7 (s, 2H), 3.6-3.7 (m, 2H), 3.1-3.2 (m, 2H).

Embodiment 100

Compound 100: Preparation of isopropyl-7-(2-(2-chlorophenyl)acetamido)-5-sulfamoyl-3,4-dihydroisoquinoline-2(1H)-carboxylate

100

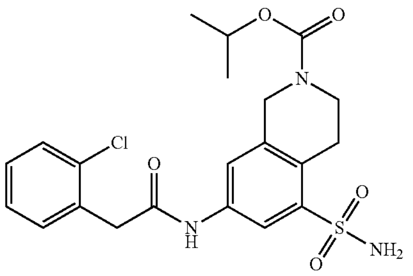

The compound was prepared by reference to the preparation method of embodiment 99. LC-MS: $[M+H]^+=466.1$, Embodiment 101

Compound 101: Preparation of cyclopropyl-7-(2-(2-chlorophenyl)acetamido)-5-sulfamoyl-3,4-dihydroisoquinoline-2(1H)-carboxylate

101

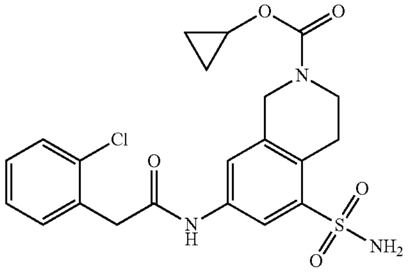

The compound was prepared by reference to the preparation method of embodiment 99. LC-MS: $[M+H]^+=464.1$.

Embodiment 102

Compound 102: Preparation of N-(2-acetyl-5-sulfamoyl-1,2,3,4-tetrahydroisoquinolin-7-yl)-2-(2-chlorophenyl)acetamide

102

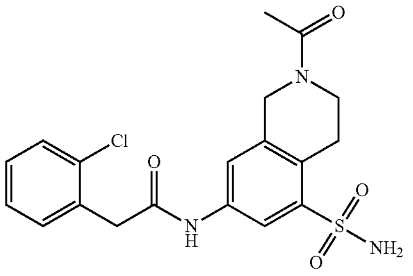

The compound was prepared by reference to the preparation method of embodiment 99. LC-MS: $[M+H]^+=422.1$.

Embodiment 103

Compound 103: Preparation of 2-(2-chlorophenyl)-N-(2-cyclopropyl-5-sulfamoyl-1,2,3,4-tetrahydroisoquinolin-7-yl)acetamide

103

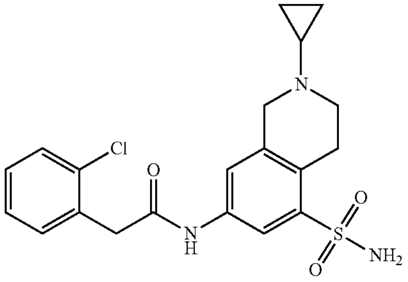

Synthetic Route:

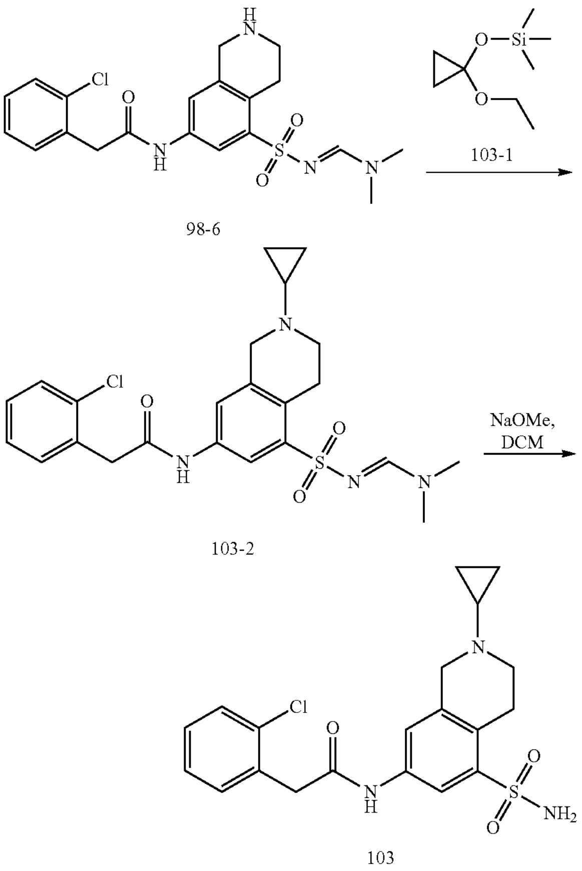

Step (1) Preparation of Intermediate 103-2

Intermediate 98-6 (140 mg), and intermediate 103-1 (1-ethoxycyclopropoxy)trimethylsilane (112 mg), $NaBH_3CN$ (61 mg) and MeOH (2 mL) were added to the reaction flask, and the reaction was stirred at 60° C. overnight. The reaction solution was poured into water, extracted with EA, and the organic phase was concentrated, mixed with silica gel and purified by column chromatography to obtain intermediate 103-2 as a white solid (80 mg), LC-MS: ESI(+) m/z=475[M+1].

Step (2) Preparation of Compound 103

Intermediate 103-2 (60 mg) was dissolved in DCM (1 mL), then NaOMe (34 mg) was added to a reaction flask, and the reaction was stirred at room temperature for 30 min. The reaction solution was poured into water, extracted with EA, and the organic phase was concentrated by rotary evaporation to obtain compound 103 as a white solid (5.9 mg). LC-MS: ESI(+) m/z=420[M+1].

$^1$H NMR (400 MHz, dmso) δ 10.57 (s, 1H), 9.57 (s, 1H), 8.07 (s, 1H), 7.76 (s, 1H), 7.58 (s, 2H), 7.44-7.37 (m, 2H), 7.32-7.25 (m, 2H), 4.68-4.42 (m, 2H), 3.83 (s, 2H), 3.31-3.10 (m, 3H), 2.94 (s, 2H), 1.12-0.71 (m, 4H).

Embodiment 104

Compound 104: Preparation of 2-(2-chlorophenyl)-N-(2-phenyl-5-sulfamoyl-1,2,3,4-tetrahydroisoquinolin-7-yl)acetamide

104

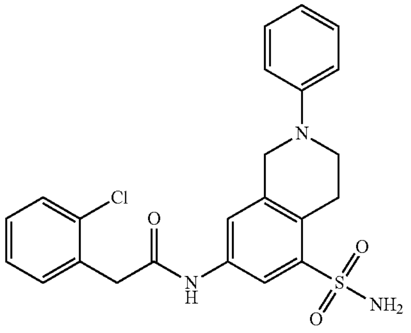

The compound was prepared by reference to the preparation method of embodiment 99. LC-MS: $[M+H]^+$=456.1.

Embodiment 105

Compound 105: Preparation of phenyl 7-(2-(2-chlorophenyl)acetamido)-5-sulfamoyl-3,4-dihydroisoquinoline-2(1H)-carboxylate

105

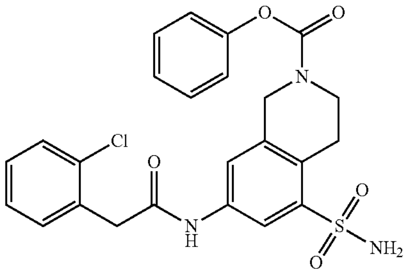

The compound was prepared by reference to the preparation method of embodiment 99. LC-MS: $[M+H]^+$=500.1.

Embodiment 106

Compound 106: Preparation of N-(2-benzoyl-5-sulfamoyl-1,2,3,4-tetrahydroisoquinolin-7-yl)-2-(2-chlorophenyl)acetamide

106

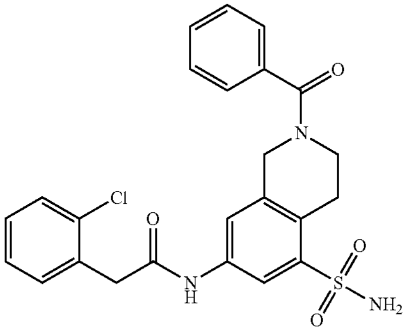

Synthetic Route:

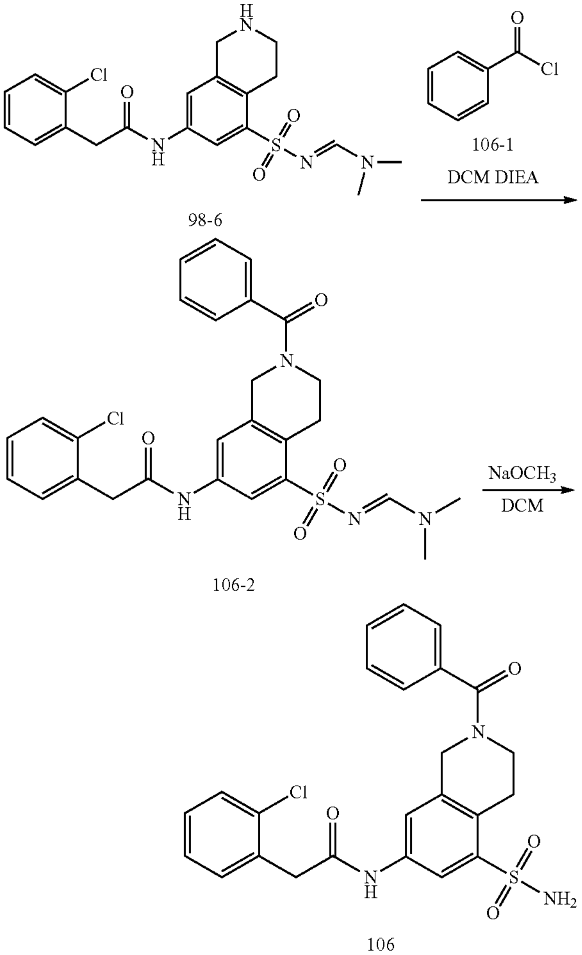

98-6 106-1 106-2 106

Step (1) Preparation of Intermediate 106-2

Intermediate 98-6 was weighed and dissolved in 5 mL of DMF, then DIEA and benzoyl chloride were added, and the reaction was carried out at room temperature for 1 hour; the completion of the reaction of the raw materials was monitored by TLC, and the reaction solution was directly concentrated by rotary evaporation and purified by Prep-TLC (DCM/MeOH=40/1) to obtain 90 mg of product as a yellow solid.

Step (2) Preparation of Compound 106

Intermediate 106-2 was weighed and dissolved in 3 mL of DCM, then sodium methoxide solution was added, and the reaction was carried out at room temperature for 1 hour; the completion of the reaction of the raw materials was monitored by TLC, and the reaction solution was added with water and extracted with EA, and the organic phase was concentrated and purified by Prep-TLC (DCM/MeOH=15/1) to obtain 19.4 mg of the product as a white solid. LC-MS: $[M+H]^+$=484.10.

$^1H$ NMR (400 MHz, dmso) δ 10.51 (s, 1H), 8.08 (s, 1H), 7.75 (s, 1H), 7.46 (dd, J=16.4, 7.5 Hz, 7H), 7.31 (d, J=3.8 Hz, 2H), 4.69 (d, J=76.8 Hz, 2H), 3.84 (s, 2H), 3.71-3.42 (m, 2H), 3.16 (s, 2H).

Embodiment 107

Compound 107: Preparation of 2-(2-chlorophenyl)-N-(2-cyclobutanecarbonyl)-5-sulfamoyl-1,2,3,4-tetrahydroisoquinolin-7-yl)acetamide

107

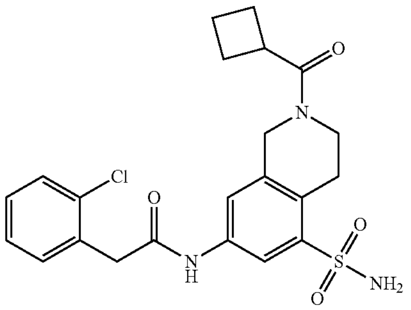

Synthetic Route:

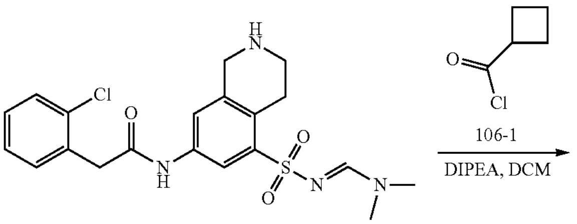

98-6

-continued

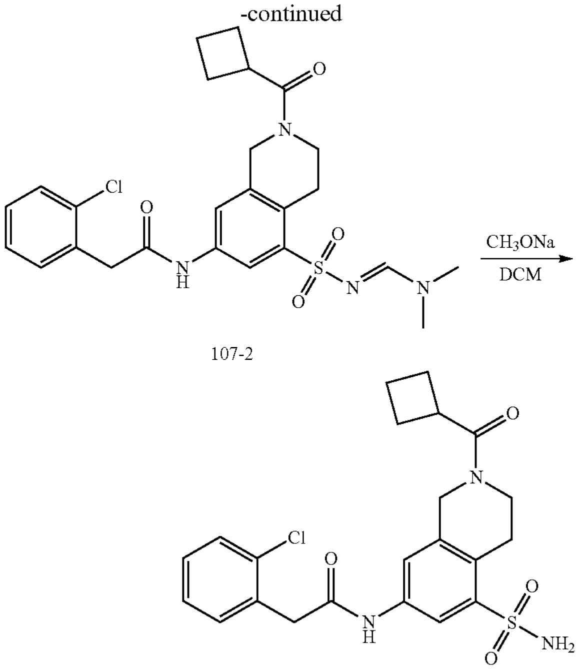

107-2

107

Step (1) Preparation of Intermediate 107-1

Intermediate 98-6 (100 mg) and DIPEA (82 mg) were sequentially dissolved in DCM (5 mL), and intermediate 107-1 (cyclobutylcarbonyl chloride) (36 mg) was slowly added dropwise in an ice-water bath; after the dropwise addition was completed, the reaction was stirred at room temperature for 1 hour; the sample was taken, and TLC (PE:EA=1:1) showed that the raw materials were reacted completely. The reaction solution was diluted with DCM (20 mL), washed with water (10 mL), stirred for 10 minutes, and then stood to separate the organic phase; and the organic phase was washed sequentially with saturated aqueous ammonium chloride solution and saturated brine, and dried over anhydrous sodium sulfate, filtered, and the filtrate was concentrated under reduced pressure to obtain a crude product of intermediate 107-2 as a red oil (160 mg).

Step (2) Preparation of Compound 107

The crude product of intermediate 107-2 (0.16 g) was dissolved in DCM (5 mL), then 30% $CH_3ONa$/MeOH solution (4 mL) was added, and the mixture was reacted at room temperature for 2 hours. The sample was taken, and TLC (PE:EA=2:1) showed that the raw materials were reacted completely. The reaction mixture was purified by prep-HPLC with $H_2O/CH_3CN$ system, and lyophilized to obtain compound 107 (34 mg, the purity was 99.6%) as a white solid. LC-MS: $[M+H]^+$=462.10.

$^1H$ NMR (400 MHz, DMSO) δ 10.48 (s, 1H), 8.02 (d, J=32.8 Hz, 1H), 7.77 (s, 1H), 7.66 (s, 1H), 7.46-7.41 (m, 3H), 7.31 (p, J=5.9 Hz, 2H), 4.61 (s, 1H), 4.54 (s, 1H), 3.84 (s, 2H), 3.64 (t, J=6.0 Hz, 1H), 3.56 (t, J=5.9 Hz, 1H), 3.47-3.41 (m, 1H), 3.11 (t, J=5.8 Hz, 1H), 3.06 (t, J=5.8 Hz, 1H), 2.13 (dt, J=17.3, 8.7 Hz, 4H), 1.96-1.87 (m, 1H), 1.74 (d, J=6.6 Hz, 1H).

Embodiment 108

Compound 108: Preparation of 2-(2-chlorophenyl)-N-(2-cyclopropylcarbonyl)-5-sulfamoyl-1,2,3,4-tetrahydroisoquinolin-7-yl)acetamide

108

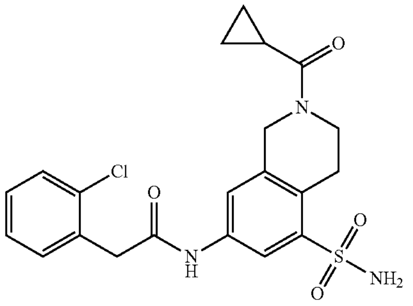

Synthetic Route:

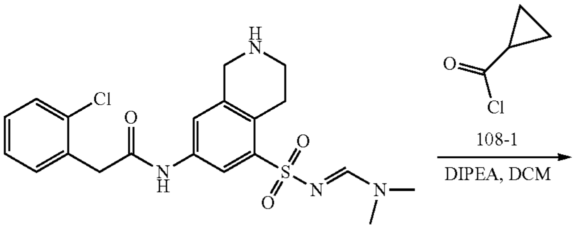

98-6

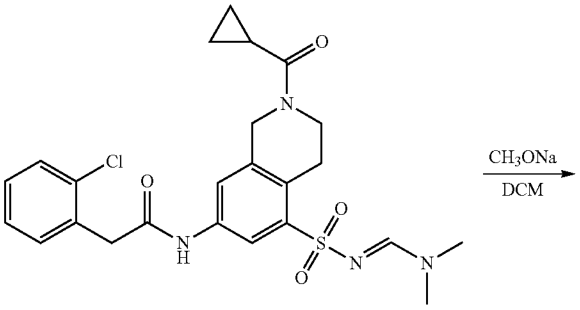

108-2

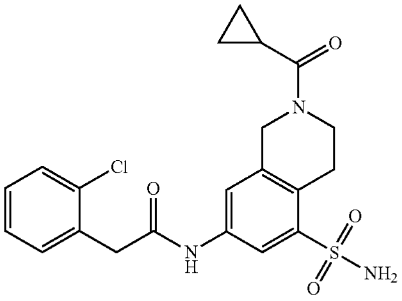

108

Step (1) Preparation of Intermediate 108-2

Intermediate 98-6 (100 mg) and DIPEA (82 mg) were sequentially dissolved in DCM (5 mL), and intermediate 108-1 (cyclopropylcarbonyl chloride) (32 mg) was slowly added dropwise in an ice-water bath; after the dropwise addition was completed, the reaction was stirred at room temperature for 1 hour; the sample was taken, and TLC (PE:EA=1:1) showed that the raw materials were reacted completely. The reaction solution was diluted with DCM (20 mL), washed with water (10 mL), stirred for 10 minutes, and then stood to separate the organic phase, and the organic phase was washed sequentially with saturated aqueous ammonium chloride solution and saturated brine, and dried over anhydrous sodium sulfate, filtered, and the filtrate was concentrated under reduced pressure to obtain a crude product of intermediate 108-2 (150 mg) as a red oil.

Step (2) Preparation of Compound 108

The crude product of intermediate 108-2 (0.16 g) was dissolved in DCM (5 mL), then 30% $CH_3ONa/MeOH$ solution (4 mL) was added, and the mixture was reacted at room temperature for 2 hours. The sample was taken, and TLC (PE:EA=2:1) showed that the raw materials were reacted completely. The reaction solution was purified by prep-HPLC with $H_2O/CH_3CN$ system, and lyophilized to obtain intermediate 108 (25 mg, the purity was 99.8%) as a white solid, LC-MS: $[M+H]^+$=448.10.

$^1H$ NMR (400 MHz, DMSO) δ 10.48 (s, 1H), 8.04 (d, J=20.8 Hz, 1H), 7.80 (s, 1H), 7.66 (s, 1H), 7.46-7.41 (m, 3H), 7.34-7.28 (m, 2H), 4.92 (s, 1H), 4.63 (s, 1H), 3.90 (s, 1H), 3.84 (s, 2H), 3.67 (s, 1H), 3.20 (s, 1H), 3.07 (s, 1H), 2.07 (s, 1H), 0.75 (d, J=4.4 Hz, 4H).

Embodiment 109

Compound 109: Preparation of 2-(2-chlorophenyl)-N-(2-ethyl-5-sulfamoyl-1,2,3,4-tetrahydroisoquinolin-7-yl)acetamide

109

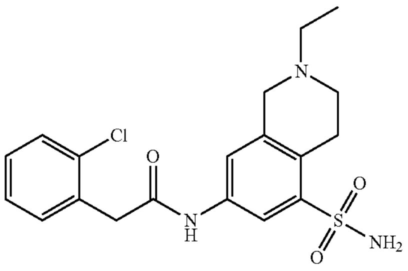

Synthetic Route:

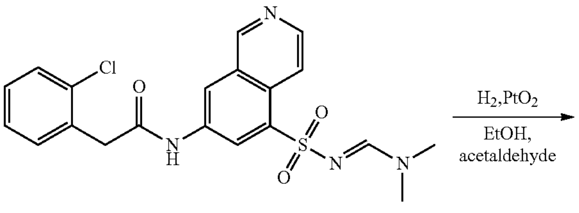

98-5

-continued

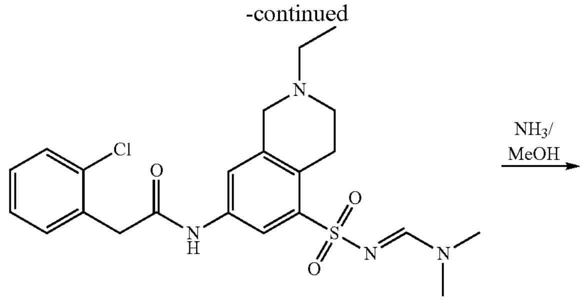

109-1

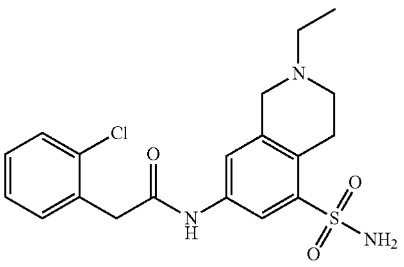

109

Step (1) Preparation of Intermediate 109-1

Intermediate 98-5 (150 mg), acetaldehyde (30.7 mg) and platinum dioxide (40 mg) were dissolved in EtOH (5 mL), and the reaction system was replaced with $H_2$ for three times and the reaction solution was stirred and reacted at 60° C. for 15 hours with hydrogen balloon (15 Psi). TLC (PE:EA=1:1) showed that the reaction of the raw materials was completed. The reaction solution was cooled to room temperature, and the reaction solution was stood overnight, and the filtrate was concentrated under reduced pressure to obtain a crude product of intermediate 109-1 (100 mg) as a yellow solid.

Step (2) Preparation of Compound 109

Intermediate 109-1 (100 mg) was dissolved in MeOH (2 mL), then $NH_3$/MeOH (20 mL) was slowly added to the reaction solution, and the reaction solution was warmed to 50° C. and reacted overnight. TLC (PE:EA=1:1) showed that the reaction of the reaction was completed. LCMS showed that the raw materials were reacted completely. The reaction solution was purified by prep-HPLC with $H_2O$/MeCN system, and then lyophilized to obtain target compound 109 as a white solid (26.5 mg, the purity was 98.823%). LC-MS: $[M+H]^+$=408.10.

$^1$H NMR (400 MHz, $CD_3OD$) 8.13 (d, J=2.2 Hz, 1H), 7.87 (d, J=2.2 Hz, 1H), 7.40 (s, 2H), 7.31-7.26 (m, 2H), 4.57 (s, 2H), 4.47-4.33 (m, 2H), 3.89 (s, 2H), 3.36 (d, J=7.2 Hz, 2H), 3.16 (s, 1H), 3.04 (s, 1H), 2.68 (s, 1H), 1.43 (t, J=7.2 Hz, 3H).

Embodiment 110

Compound 110: Preparation of N-(2-benzyl-5-sulfamoyl-1,2,3,4-tetrahydroisoquinolin-7-yl)-2-(2-chlorophenyl)acetamide

110

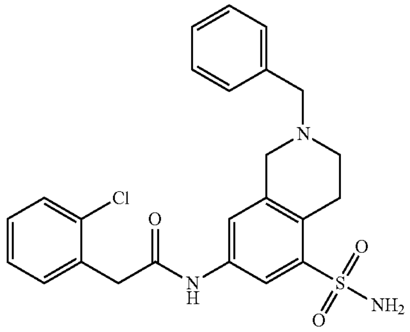

Synthetic Route:

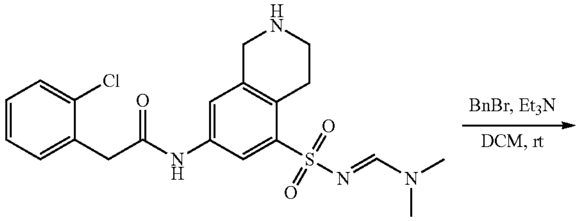

98-6

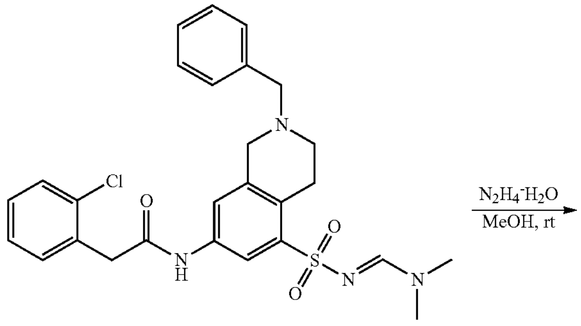

110-1

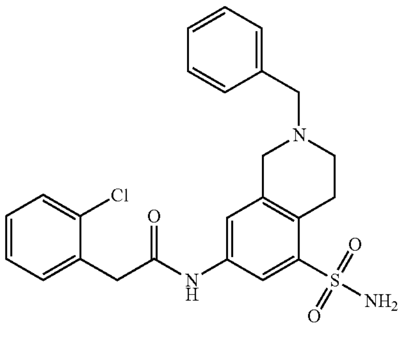

110

Step (1) Preparation of Intermediate 110-1

Intermediate 98-6 (100.0 mg) was dissolved in DCM (10 mL), then BnBr (39.3 mg) and $Et_3N$ (34.9 mg) were added. The reaction was stirred overnight at room temperature. TLC (MeOH:DCM=1:10) showed that the raw materials were reacted completely. The reaction solution was diluted with 30 mL of water and 30 mL of DCM, and the phases were separated; the organic phases were collected, and the solvent was removed by rotary evaporation to obtain intermediate 110-1 as a yellow solid (90.5 mg). LC-MS: $[M+H]^+$=525.

Step (2) Preparation of Compound 110

Intermediate 110-1 (80.5 mg) was dissolved in MeOH (10 mL), then hydrazine hydrate (180.6 mg) was added, and the reaction was stirred for 1 hour at room temperature. TLC (MeOH:DCM=1:10) showed that the reaction of the raw materials was completed, and the reaction was stopped. The solvent was removed by rotary evaporation to obtain a crude product. The crude product was purified by prep-HPLC with $H_2O$/ACN system, and lyophilized to obtain compound 110 as a beige solid (51.2 mg, the purity was 95.848%). LC-MS: $[M+H]^+$=470.05. $^1H$ NMR:

$^1H$ NMR (400 MHz, DMSO-$d_6$) δ 10.57 (s, 1H), 8.04 (s, 1H), 7.77 (s, 1H), 7.63-7.50 (m, 5H), 7.49 (s, 2H), 7.45-7.39 (m, 2H), 7.34-7.28 (m, 2H), 4.46 (s, 2H), 4.37 (s, 2H), 3.84 (s, 2H), 3.77-3.60 (m, 1H), 3.56-3.43 (m, 3H).

Embodiment 111

Compound 111: Preparation of 2-(2-chlorophenyl)-N-(2-cyclopropylmethyl)-5-sulfamoyl-1,2,3,4-tetrahydroisoquinolin-7-yl)acetamide

111

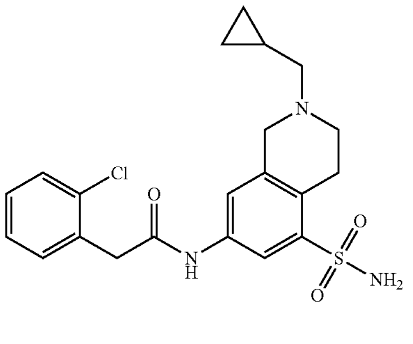

Synthetic Route:

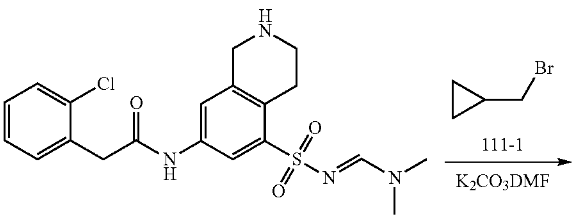

98-6

-continued

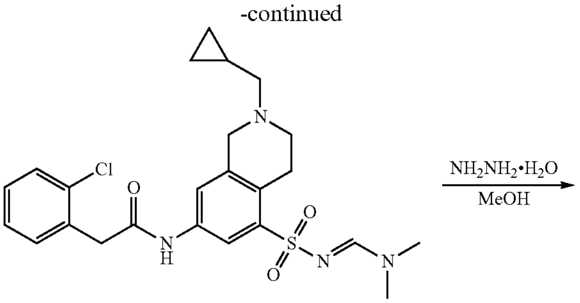

111-2

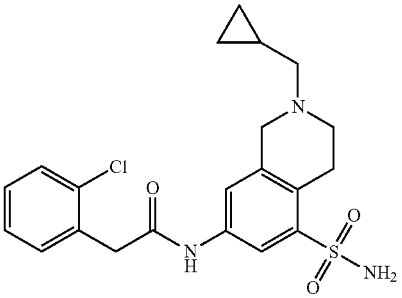

111

Step (1) Preparation of Intermediate 111-2

Intermediate 98-6 (150 mg), intermediate 111-1 (cyclopropylmethyl bromide) (45.9 mg) and potassium carbonate (145 mg) were sequentially dissolved in DMF (3 mL), and the reaction system was replaced with $N_2$ for one time, and the mixture was stirred at room temperature overnight. LCMS showed that the reaction was completed, and the reaction solution was diluted with water (10 mL), and then added with ethyl acetate (3 mL), stirred for 10 minutes, then stood to separate the ethyl acetate phase. The aqueous phase was extracted with ethyl acetate (3 mL) for one time, and the organic phases were combined, washed sequentially with saturated brine, dried over anhydrous sodium sulfate, filtered, and the filtrate was concentrated under reduced pressure to obtain a crude product of intermediate 111-2 as a pale-yellow oil (180 mg). LC-MS: $[M]^+$=489.1.

Step (2) Preparation of Compound 111

Intermediate 111-2 (180 mg) was dissolved in methanol (2 mL), then hydrazine hydrate solution (1.5 mL, 85%) was added dropwise, and the mixture was stirred at room temperature for 30 min. LCMS showed that the reaction was completed, and the reaction solution was concentrated under reduced pressure to obtain a crude product. The crude product was purified by prep-HPLC with $H_2O$/CAN system, and lyophilized to obtain compound 111 as a brown solid (22.1 mg, the purity was 98.29%, the yield was 11.7%, trifluoroacetate). LC-MS: $[M]^+$=434.

$^1H$ NMR (400 MHz, DMSO) δ 10.60 (s, 1H), 9.97 (s, 1H), 8.06 (d, J=2.1 Hz, 1H), 7.82 (d, J=1.7 Hz, 1H), 7.59 (s, 2H), 7.45-7.37 (m, 2H), 7.33-7.25 (m, 2H), 4.63 (d, J=16.0 Hz, 1H), 4.40-4.41 (m, 1H), 3.81 (d, J=24.1 Hz, 3H), 3.42 (s, 3H), 3.13 (s, 2H), 1.21-1.12 (m, 1H), 0.66 (d, J=7.5 Hz, 2H), 0.40 (d, J=4.6 Hz, 2H).

Embodiment 112

Compound 112: Preparation of 2-(2-chlorophenyl)-N-(2-methyl-5-sulfamoyl-1,2,3,4-tetrahydroisoquinolin-7-yl)acetamide

112

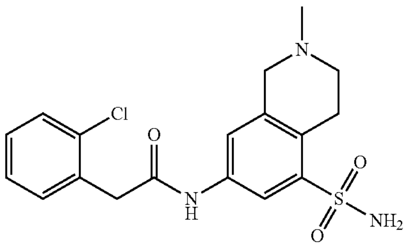

Synthetic Route:

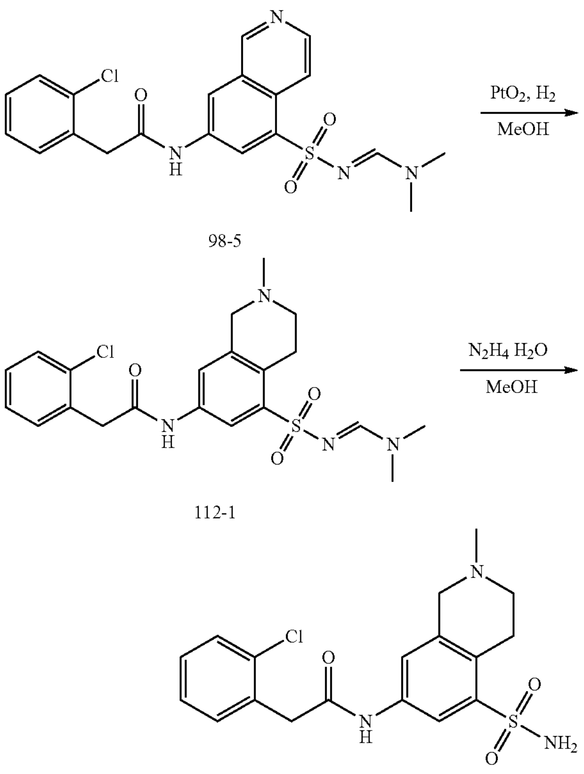

98-5

112-1

112

Step (1) Preparation of Intermediate 112-1

Intermediate 98-5 (1.2 g) was dissolved in MeOH (20 mL, chemically pure), then $PtO_2$ (63 mg) was added, and the reaction solution was stirred in $H_2$ at 40° C. for 72 hours. After the reaction was completed, the reaction solution was filtered through diatomite, and the filtrate was concentrated to obtain a crude product, and the crude product was purified by silica gel column to obtain intermediate 112-1 (580 mg of yellow solid). $[M+H]^+$=449.

Step (2) Preparation of Compound 112

Intermediate 112-1 (200 mg) was dissolved in MeOH (5 mL), then $N_2H_4 \cdot H_2O$ (529 mg, 85%) was added, and the reaction solution was stirred at room temperature for 20 min. After the reaction was completed, the reaction solution was concentrated under reduced pressure at room temperature to obtain a crude product, and the crude product was purified by prep-HPLC to obtain compound 112 (19 mg, white solid powder). LCMS: $[M+H]^+$=393.95.

$^1$H NMR (400 MHz, DMSO-$d_6$) δ 10.65 (s, 1H), 10.44 (br. s, 1H), 8.14 (d, J=1.6 Hz, 1H), 7.73 (d, J=1.3 Hz, 1H), 7.61 (s, 2H), 7.47-7.39 (m, 2H), 7.35-7.27 (m, 2H), 4.46 (d, J=63.2 Hz, 2H), 3.86 (s, 2H), 3.77-3.55 (m, 4H), 2.94 (s, 3H).

Embodiment 113

Compound 113: Preparation of 2-(2-chlorophenyl)-N-(2-isopropyl-5-sulfamoyl-1,2,3,4-tetrahydroisoquinolin-7-yl)acetamide

113

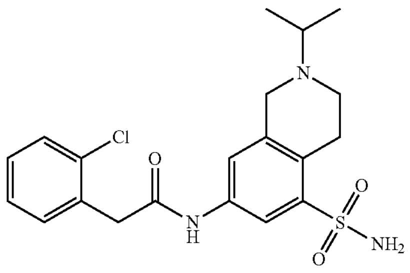

Synthetic Route:

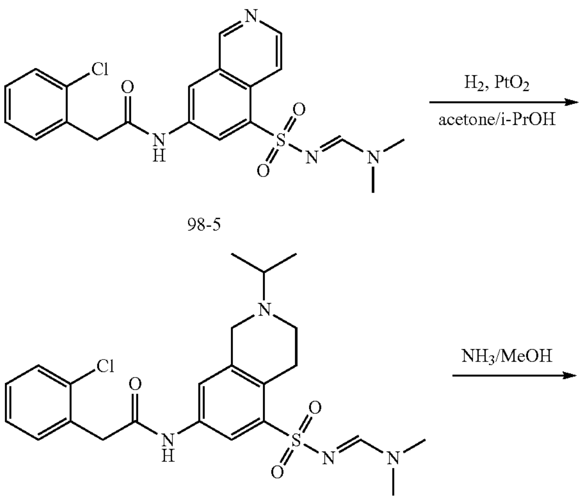

98-5

113-1

-continued

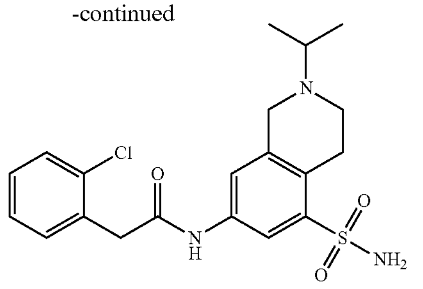

113

Step (1) Preparation of Intermediate 113-1

Intermediate 98-5 (150 mg), acetone (2 mL), isopropanol (2 mL), $PtO_2$ (40 mg) were added to a flask, and the reaction system was replaced with $H_2$ for three times and kept the pressure with $H_2$, and the mixture was stirred at 50° C. overnight (14 hours); LCMS showed that the raw materials was basically reacted, and the reaction solution was directly concentrated to obtain 135 mg of intermediate 113-1 as a yellow solid, which was directly used in the next reaction. LC-MS: $[M+H]^+$=477.02.

Step (2) Preparation of 2-(2-chlorophenyl)-N-(2-isopropyl-5-sulfamoyl-1,2,3,4-tetrahydroisoquinolin-7-yl)acetamide The intermediate 113-1 obtained in the first step was dissolved in 1.5 mL of methanol, then $NH_3/CH_3OH$ (10 mL) was added to the reaction solution, and the mixture was stirred at room temperature overnight (14 hours). LCMS showed that the reaction of the raw materials was completed. The reaction solution was concentrated under reduced pressure and purified by column chromatography to give a white solid (6.3 mg, the purity was 91.35%). LC-MS: $[M+H+2]^+$=421.94.

$^1$H NMR (400 MHz, dmso) δ 10.62 (s, 1H), 9.84 (s, 1H), 8.08 (d, J=1.4 Hz, 1H), 7.82 (d, J=1.7 Hz, 1H), 7.62 (s, 2H), 7.50-7.36 (m, 2H), 7.36-7.20 (m, 2H), 4.44 (d, J=5.0 Hz, 2H), 3.86 (s, 2H), 3.73-3.56 (m, 2H), 3.31-3.22 (m, 2H), 3.18-3.08 (m, 1H), 1.33 (d, J=5.7 Hz, 4H), 1.25 (dd, J=12.9, 6.4 Hz, 3H).

Embodiment 114

Compound 114: Preparation of 2-(2-chlorophenyl)-N-(5-sulfamoyl-2-(2,2,2-trifluoroacetyl)-1,2,3,4-tetrahydroisoquinolin-7-yl) acetamide

114

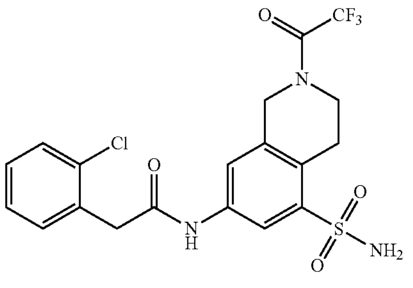

Synthetic Route:

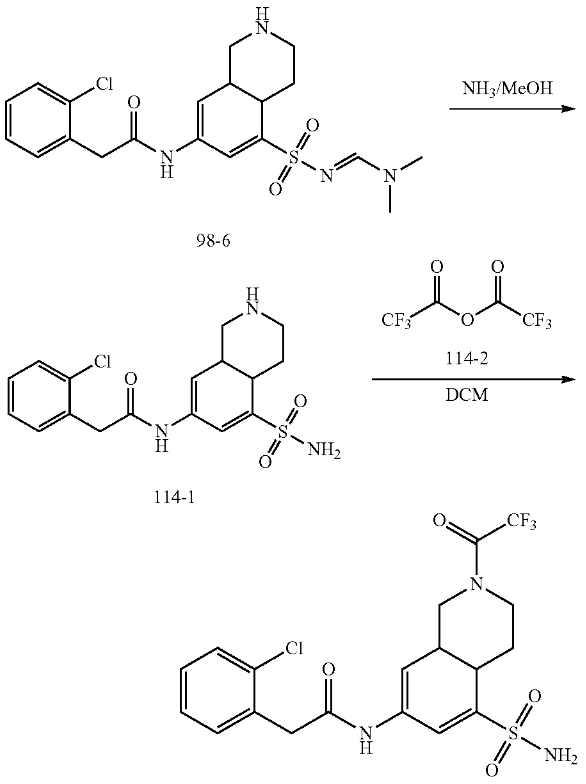

98-6
114-1
114

Step (1) Preparation of Intermediate 114-1

Intermediate 98-6 (100 mg) was dissolved in methanol solution (5.0 mL) of ammonia, and the reaction was stirred at room temperature for 2 hours. The sample was taken, and TLC showed that raw materials were reacted completely. The reaction solution was directly concentrated by rotary evaporation to obtain 60 mg of a product of intermediate 114-1. LC-MS: $[M+H]^+$=382.

Step (2) Preparation of Compound 114

Intermediate 114-1 (60 mg) was dissolved in DCM (2 mL), and then an equal volume of trifluoroacetic anhydride was added thereto, and the reaction was stirred at room temperature for 3 hours. The sample was taken, and TLC showed that the raw materials were reacted completely. The reaction solution was concentrated by rotary evaporation and purified by preparative chromatography, and the preparation solution was lyophilized to obtain 11 mg of a product of compound 114 as a white solid.

$^1$H NMR (400 MHz, dmso) δ 10.50 (s, 1H), 8.07 (s, 1H), 8.03 (d, J=2.1 Hz, 1H), 7.79 (s, 1H), 7.71 (s, 1H), 7.45 (s, 2H), 7.44-7.35 (m, 2H), 7.32-7.25 (m, 2H), 4.76 (d, J=5.4 Hz, 2H), 3.86-3.72 (m, 4H), 3.21 (d, J=65 Hz, 2H).

Embodiment 115

Compound 115: Preparation of 2-(2-chlorophenyl)-N-(2-(dichloromethyl)-sulfamoyl-1,2,3,4-tetrahydroisoquinolin-7-yl)acetamide

115

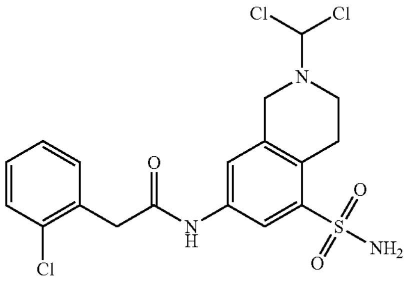

Synthetic Route:

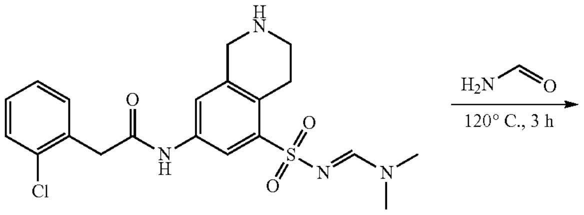

98-6

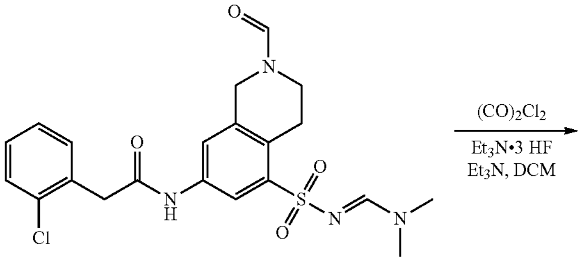

115-1

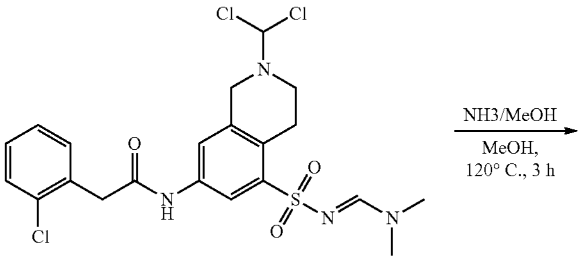

115-2

-continued

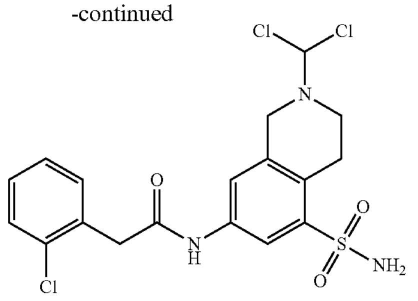

115

Step (1) Preparation of Intermediate 115-1

Intermediate 98-6 (300 mg) was dissolved in formamide (5 mL), and the mixture was stirred for 3 hours at 120° C.; water and EA were added to the reaction solution, and the EA phase was separated after fully stirring, and the aqueous phase was extracted for two times with EA and the EA phases were combined, washed with saturated brine, dried over anhydrous sodium sulfate, and concentrated by rotary evaporation to obtain 90 mg of yellow solid. LC-MS: $[M+H]^+=463.10$.

Step (2) Preparation of Intermediate 115-2 ((E)-2-(2-chlorophenyl)-N-(5-(N-((dimethylamino)methylene)aminosulfonyl)-2-formyl-1,2,3,4-tetrahydroisoquinolin-7-yl)acetamide)

Intermediate 115-1 (10 mg) was dissolved in DCM (0.5 mL), then $(CO)_2Cl_2$ (10 mg) was added and the reaction was stirred at room temperature for 0.5 hours, and the temperature was warmed to 47° C., and the mixture was refluxed for 1.5 hours. After cooling to room temperature, $Et_3N{\cdot}3HF$ (16 mg) and $Et_3N$ (10 mg) were sequentially added, and the reaction was stirred at room temperature overnight; water and DCM were added to the reaction solution, after fully stirring, the DCM phase was separated; the aqueous phase was extracted with DCM for two times, and the DCM phases were combined, and washed with saturated brine, dried over anhydrous sodium sulfate, and concentrated by rotary evaporation to obtain 16 mg of intermediate 115-2 as a yellow solid. LC-MS: $[M+H]^+=517.10$.

Step (3) Preparation of Compound 115

Intermediate 115 (6 mg) was dissolved in MeOH (2.0 mL), then $NH_3$/MeOH (2.0 mL) was added, and the reaction was stirred at room temperature at 120° C. for 3 hours, and the reaction solution was concentrated to obtain 5 mg of crude product, and prepared to obtain 1.1 mg of yellow solid. LC-MS: $[M+H]^+=462.00$.

$^1H$ NMR (400 MHz, dmso) δ 8.21 (d, J=14.6 Hz, 1H), 8.13 (s, 1H), 7.81 (dd, J=9.6, 2.0 Hz, 1H), 7.53 (d, J=4.4 Hz, 2H), 7.39 (ddd, J=9.8, 9.2, 5.8 Hz, 2H), 7.27-7.14 (m, 2H), 7.08 (s, 1H), 6.95 (s, 1H), 4.67 (d, J=19.6 Hz, 2H), 3.72-3.61 (m, 2H), 3.41 (s, 2H), 3.23-3.13 (m, 2H).

Embodiment 116

Compound 116: Preparation of 2-(2-chlorophenyl)-N-(2-(5-chloropyridin-2-yl)-5-sulfamoyl-1,2,3,4-tetrahydroisoquinolin-7-yl)acetamide

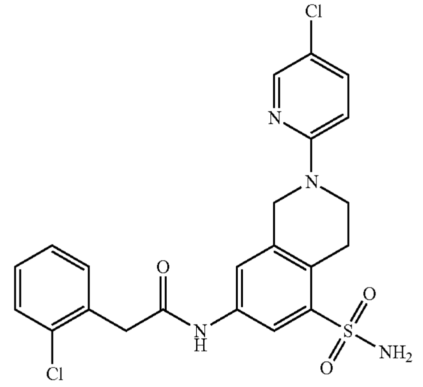 [SMILES: NS(=O)(=O)c1cc(NC(=O)Cc2ccccc2Cl)cc2c1CCN(c1ccc(Cl)cn1)C2]

Synthetic Route:

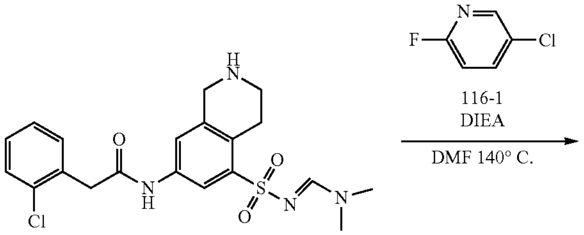

98-6

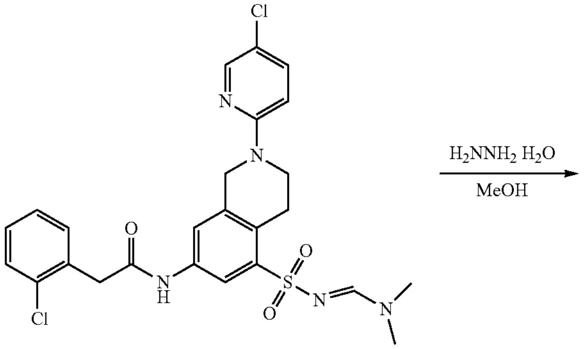

116-2

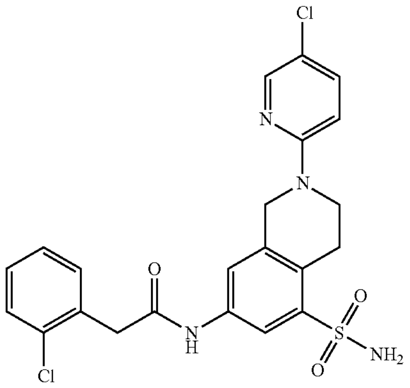

116

Step (1) Preparation of Intermediate 116-2

Intermediate 98-6 (130 mg) was weighed and dissolved in 6 mL of DMF, then intermediate 116-15-chloro-2-fluoro-pyridine (130 mg) and DIEA (195 mg) were added; after the addition was completed, the reaction was carried out at 140° C. 1.5 hours. LCMS showed that the product was formed, and the reaction solution was cooled to room temperature, and water was added; the mixture was extracted with EA, and the organic phase was washed with saturated brine, dried over sodium sulfate, and subjected to Prep-TLC (DCM/MeOH=20/1) to obtain 90 mg of a product as a yellow oily liquid.

Step (2) Preparation of Compound 116

Intermediate 116-2 (100 mg) was weighed and dissolved in 5 mL of methanol, then 2 mL of hydrazine hydrate was added; after the addition was completed, the reaction was carried out at room temperature for 0.5 hours. LCMS showed that the product was formed, and the reaction solution was directly concentrated by rotary evaporation, purified by Prep-HPLC to obtain 19.8 mg of a crude product of compound 116 as a white solid. LC-MS: $[M+H]^+$=491.05.

$^1H$ NMR (400 MHz, dmso) δ 10.48 (s, 1H), 8.13 (d, J=2.6 Hz, 1H), 8.03 (d, J=1.9 Hz, 1H), 7.77 (s, 1H), 7.63 (dd, J=9.1, 2.7 Hz, 1H), 7.53-7.38 (m, 4H), 7.31 (p, J=6.3 Hz, 2H), 6.96 (d, J=9.2 Hz, 1H), 4.71 (s, 2H), 3.85 (s, 2H), 3.79 (t, J=5.9 Hz, 2H), 3.18 (t, J=5.7 Hz, 2H).

Embodiment 117

Compound 117: Preparation of 2-(2-chlorophenyl)-N-(5-sulfamoyl-2-(5-(trifluoromethyl)pyridin-2-yl)-1,2,3,4-tetrahydroisoquinolin-7-yl)acetamide

117

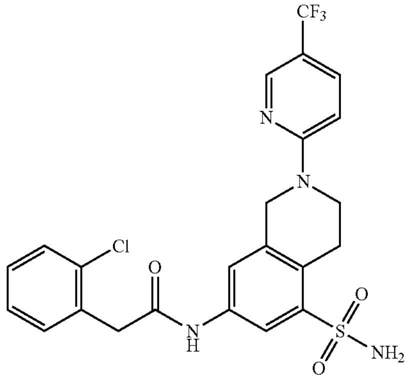

Synthetic Route

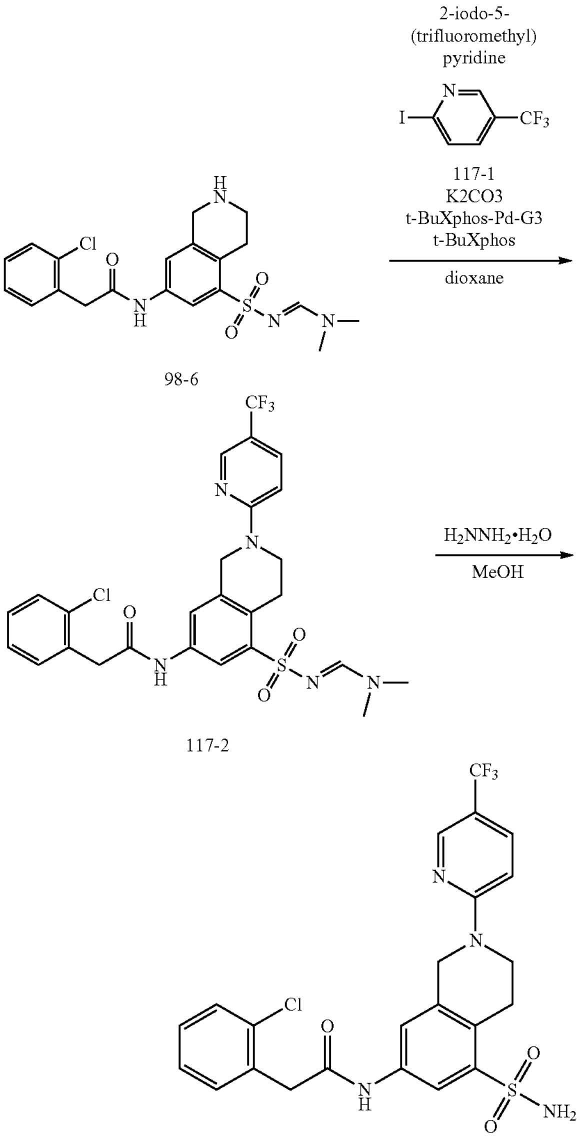

98-6

117-2

117

Step (1) Preparation of Intermediate 117-2

Intermediate 98-6 (100 mg) was weighed and dissolved in 5 mL of dioxane, and intermediate 117-1 (2-iodo-5-(trifluoromethyl)pyridine) (76 mg), t-BuXphos-Pd-G3 (19 mg), t-BuXphos (10 mg) and $K_2CO_3$ (96 mg) were added; after the addition was completed, the reaction was carried out at 110° C. overnight under the protection of $N_2$. LCMS showed that the product was formed, and the reaction solution was cooled to room temperature, water was added; the mixture was extracted with EA, and the organic phase was washed with saturated brine, dried over sodium sulfate, and subjected to Prep-TLC (DCM/MeOH=10/1) to obtain 90 mg of a crude product of intermediate 117-2 as a yellow solid.

Step (2) Preparation of Compound 117

Intermediate 117-2 (90 mg) was weighed and dissolved in 5 mL of methanol, then 2 mL of hydrazine hydrate was added; after the addition was completed, the reaction was carried out at room temperature for 0.5 hours. LCMS showed that the product was formed, and the reaction solution was directly concentrated by rotary evaporation, purified by Prep-HPLC to obtain 5.8 mg of a crude product as a white solid. LC-MS: $[M+H]^+$=525.10.

$^1H$ NMR (400 MHz, dmso) δ 10.50 (s, 1H), 8.45 (s, 1H), 8.04 (d, J=2.1 Hz, 1H), 7.85-7.79 (m, 2H), 7.44 (dt, J=11.5, 5.5 Hz, 4H), 7.34-7.28 (m, 2H), 7.03 (d, J=9.0 Hz, 1H), 4.83 (s, 2H), 3.88 (t, J=6.0 Hz, 2H), 3.85 (s, 2H), 3.22 (t, J=5.9 Hz, 2H).

Embodiment 118

Compound 118: Preparation of N-(2-(4-chloro-5-fluoropyridin-2-yl)-5-sulfamoyl-1,2,3,4-tetrahydroisoquinolin-7-yl)-2-(2-chlorophenyl)acetamide

118

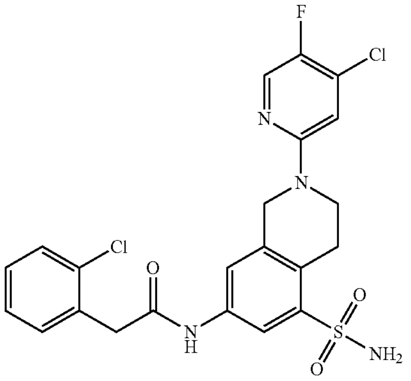

Synthetic Route:

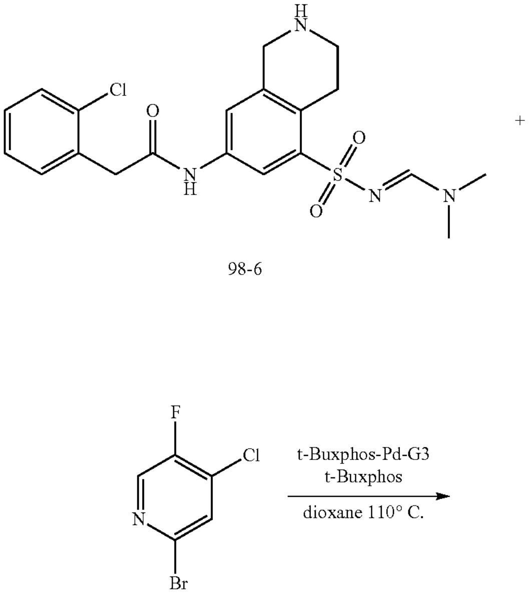

98-6

118-1

-continued

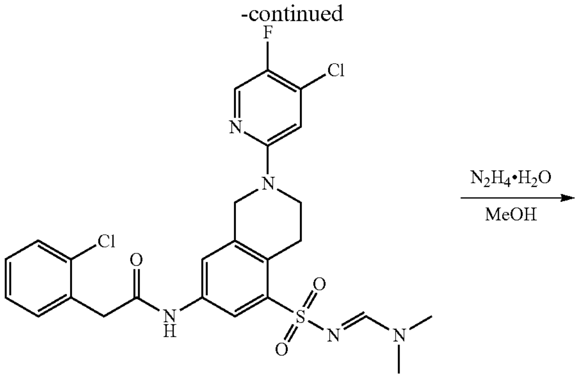

118-2

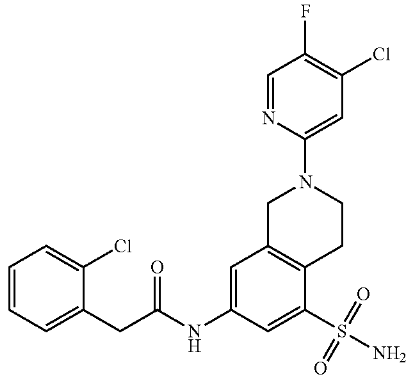

118

Step (1) Preparation of Intermediate 118-2

Intermediate 98-6 (150 mg), intermediate 118-1 (2-bromo-4-chloro-5-fluoropyridine) (147 mg), t-Buxphos-Pd-G3 (28 mg), t-Buxphos (15 mg) and $K_2CO_3$ (145 mg) were accurately weighed and dissolved in dioxane, and the temperature was warmed to 110° C. and the mixture was stirred and reacted overnight. The sample was taken, and TLC showed that the raw materials were basically reacted completely. In post treatment, water and EA were added to the reaction solution, and the EA phase was separated, then the aqueous phase was extracted with EA for three times; the EA phases were combined, washed with saturated brine, dried over sodium sulfate, and then evaporated by rotary evaporation to about 3 mL, and purified by thin layer chromatography, and the silica gel with product in the thin layer chromatography was scraped and soaked in the solvent, and concentrated by rotary evaporation to obtain the product. The reaction was successful, and 60 mg of intermediate 118-2 was obtained as a white solid. LCMS: $[M+H]^+$=564.

Step (2) Preparation of Compound 118

Intermediate 118-2 (60 mg) was accurately weighed and dissolved in methanol, then hydrazine hydrate (20 mg) was added to the reaction system, and the reaction was stirred at room temperature for 2 hours. The sample was taken, and TLC showed that the raw materials were reacted completely. In post treatment, the reaction solution was concentrated by rotary evaporation, purified by preparative chromatography, and the preparation solution was lyophilized to obtain compound 118. The reaction was successful, and 2 mg of white foamy solid was obtained. LCMS: $[M+H]^+$=509.

$^1H$ NMR (400 MHz, dmso) δ 10.46 (s, 1H), 8.22 (s, 1H), 8.00 (d, J=2.0 Hz, 1H), 7.75 (s, 1H), 7.42 (dd, J=10.2, 7.6 Hz, 4H), 7.32-7.26 (m, 2H), 7.18 (d, J=4.7 Hz, 1H), 4.68 (s, 2H), 3.82 (s, 2H), 3.77 (t, J=5.8 Hz, 2H), 3.15 (t, J=5.7 Hz, 2H).

Embodiment 119

Compound 119: Preparation of 2-(2-chlorophenyl)-N-(2-(1,1-difluoroallyl)-5-sulfamoyl-1,2,3,4-tetrahydroisoquinolin-7-yl)acetamide

119

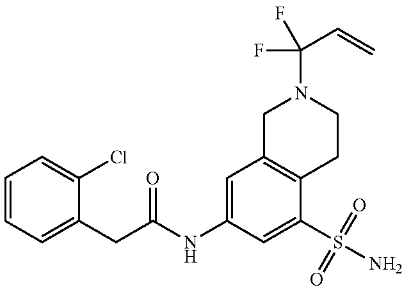

Synthetic Route:

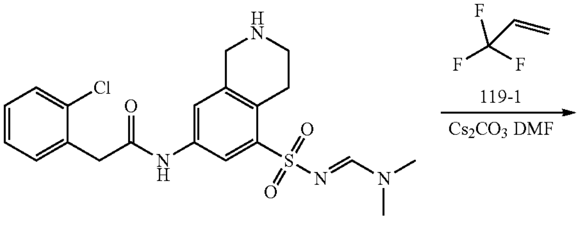

98-6

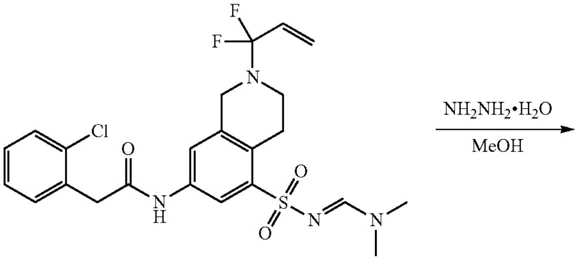

119-2

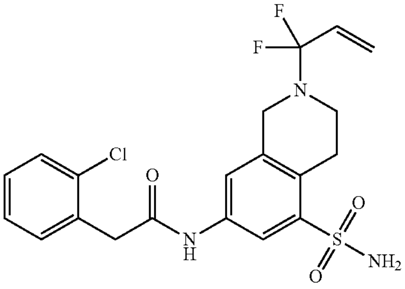

119

Step (1) Preparation of Intermediate 119-2

Intermediate 98-6 (150 mg) was dissolved in DMF (3 mL), then $CS_2CO_3$ (225 mg) and intermediate 119-1 (3-bromo-3,3-difluoropropene) (60 mg) were added, and the reaction was stirred at room temperature for 2 hours; water and EA were added to the reaction solution, and the EA phase was separated after full stirring. The aqueous phase was extracted with EA for two times, and the EA phases were combined, washed with saturated brine, dried over saturated sodium sulfate, and concentrated by rotary evaporation to obtain 100 mg of yellow solid. LC-MS: $[M+H]^+$ =511.10.

Step (2) Preparation of Compound 119

Intermediate 119-2 (100 mg) was dissolved in MeOH (4 mL), then hydrazine hydrate (2 mL) was added and the reaction was stirred at room temperature for 2 hours; the reaction solution was concentrated to obtain 40 mg of crude product, and the crude product was purified by prep-HPLC with $H_2O$/CAN system, and lyophilized to obtain compound 119 as a white solid (4.3 mg, the purity was 99.714%, the yield was 11.8%). LC-MS: $[M]^+$=456.

$^1H$ NMR (400 MHz, dmso) δ 10.57 (s, 1H), 10.19 (s, 3H), 8.03 (s, 1H), 7.79 (s, 1H), 7.58 (s, 2H), 7.41 (ddd, J=10.7, 4.9, 2.4 Hz, 2H), 7.35-7.23 (m, 2H), 7.20 (s, 1H), 7.07 (s, 1H), 6.94 (s, 1H), 4.91 (d, J=24.8 Hz, 2H), 4.57 (s, 2H), 4.34 (s, 2H), 3.83 (s, 4H).

Embodiment 120

Compound 120: Preparation of 2-(2-chlorophenyl)-N-(2-(4-fluorophenyl)-5-sulfamoyl-1,2,3,4-tetrahydroisoquinolin-7-yl)acetamide

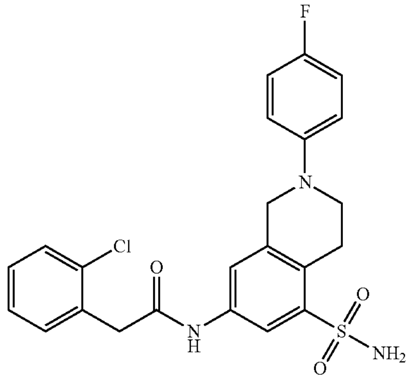 [SMILES: NS(=O)(=O)c1cc(NC(=O)Cc2ccccc2Cl)cc2c1CCN(c1ccc(F)cc1)C2]

Synthetic Route:

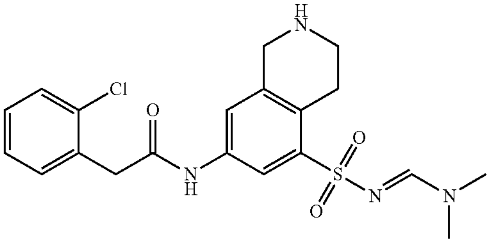

98-6

+

-continued

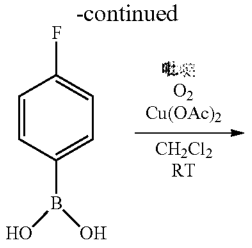

120-1

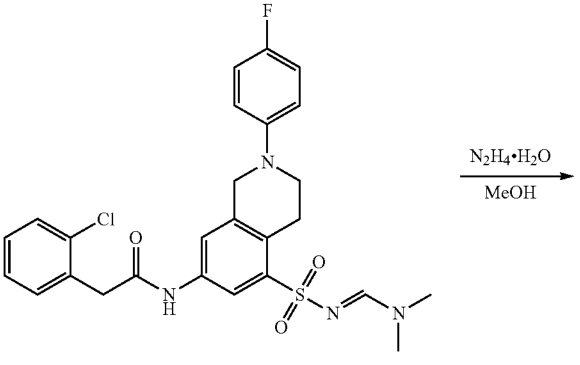

120-2

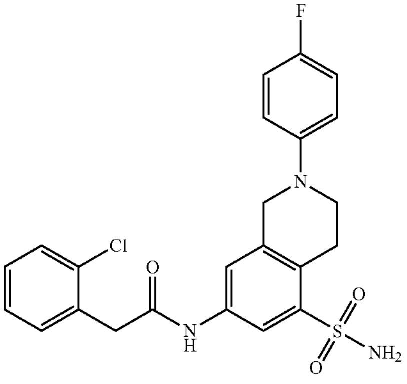

120

Step (1) Preparation of Intermediate 120-2

Intermediate 98-6 (80 mg), intermediate 120-1 (4-fluorophenyl)boronic acid) (130 mg), $Cu(OAc)_2$, pyridine were accurately weighed and dissolved in $CH_2Cl_2$, and the reaction was stirred at room temperature under the atmosphere of $O_2$ overnight. The sample was taken, TLC showed that the raw materials were basically reacted completely. In post treatment, water and EA were added to the reaction solution, and the EA phase was separated, then the aqueous phase was extracted with EA for three times; the EA phases were combined, and the EA phases were washed with saturated brine, dried over sodium sulfate, and then concentrated by rotary evaporation to about 3 mL and purified by thin layer chromatography, and the silica gel with product in the thin layer chromatography was scraped and soaked in the solvent, and concentrated by rotary evaporation to obtain the product. The reaction was successful, and 60 mg of intermediate 120-2 was obtained as a white solid. LCMS: $[M+H]^+$=529.

Step (2) Preparation of Compound 120

Intermediate 120-2 (60 mg) was accurately weighed and dissolved in methanol, then hydrazine hydrate (20 mg) was added to the reaction system, and the reaction was stirred at room temperature for 2 hours. The sample was taken, and TLC showed that the raw materials were reacted completely. In post treatment, the reaction solution was concentrated by rotary evaporation and purified by preparative chromatography, and the preparation solution was lyophilized to obtain the product. The reaction was successful to obtain 2 mg of compound 120 as a white foamy solid. LCMS: $[M+H]^+$=474.

$^1$H NMR (400 MHz, dmso) δ 10.45 (s, 1H), 8.00 (s, 1H), 7.74 (s, 1H), 7.46-7.35 (m, 4H), 7.32-7.25 (m, 2H), 7.05 (dd, J=11.1, 6.6 Hz, 4H), 4.36-4.30 (m, 2H), 3.83 (s, 2H), 3.46 (dd, J=12.6, 6.5 Hz, 2H), 3.18 (t, J=5.7 Hz, 2H).

Embodiment 121

Compound 121: Preparation of 2-(2-chlorophenyl)-N-(2-(5-methylpyridin-2-yl)-5-sulfamoyl-1,2,3,4-tetrahydroisoquinoline-7-yl)acetamide

121

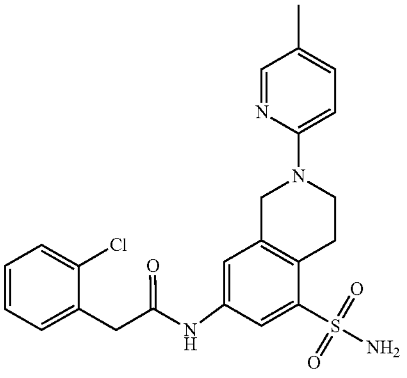

Synthetic Route:

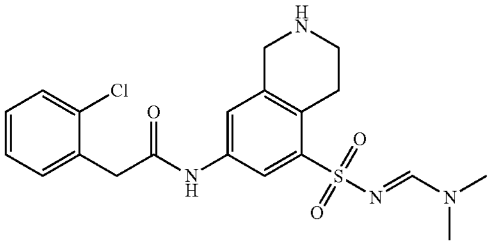

98-6

+

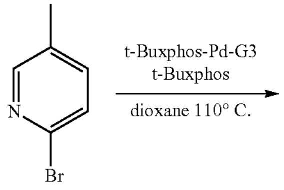

121-1

-continued

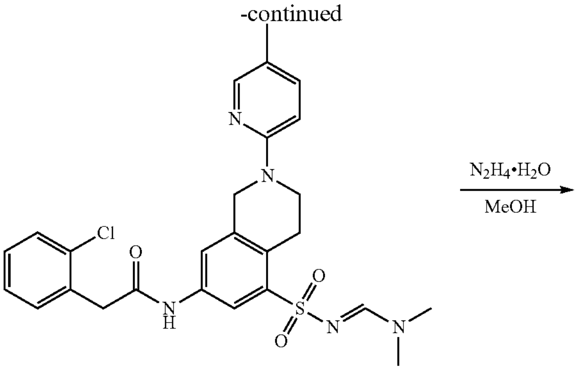

121-2

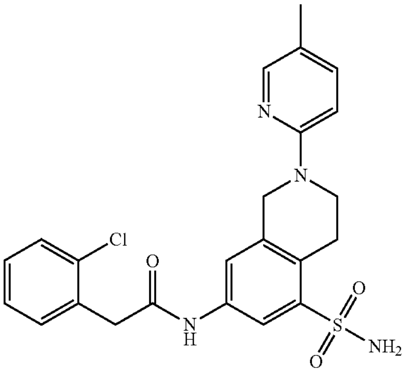

121

Step (1) Preparation of Intermediate 121-2

Intermediate 98-6 (150 mg), intermediate 121-1 (2-bromo-5-methylpyridine) (147 mg), t-Buxphos-Pd-G3 (28 mg), t-Buxphos (15 mg) and $K_2CO_3$ (145 mg) were accurately weighed and dissolved in dioxane, and the temperature was warmed to 110° C., and the mixture was stirred overnight. Sample was taken, and TLC showed that raw materials were basically reacted completely. In post treatment, water and EA were added to the reaction solution, and the EA phase was separated, then the aqueous phase was extracted with EA for three times; the EA phases were combined, and the EA phases were washed with saturated brine, dried over sodium sulfate, and then evaporated by rotary evaporation to about 3 mL and purified by thin layer chromatography, and the silica gel with product in the thin layer chromatography was scraped and soaked in the solvent, and concentrated by rotary evaporation to obtain the product. The reaction was successful, and 60 mg of intermediate 121-2 was obtained as a white solid. LCMS: $[M+H]^+$=526.

Step (2) Preparation of Compound 121

Intermediate 121-2 (60 mg) was accurately weighed and dissolved in methanol, then hydrazine hydrate (20 mg) was added to the reaction system, and the reaction was stirred at room temperature for 2 hours. Sample was taken, and TLC showed that the raw materials were reacted completely. In post treatment, the reaction solution was concentrated by rotary evaporation and purified by preparative chromatography, and the preparation solution was lyophilized to obtain the product. The reaction was successful to obtain 2 mg of compound 121 as a white foamy solid. LCMS: $[M+H]^+$=471.

$^1$H NMR (400 MHz, dmso) δ 10.44 (s, 1H), 8.00 (s, 1H), 7.95 (s, 1H), 7.74 (s, 1H), 7.38 (dd, J=26.4, 17.4 Hz, 5H), 7.31 (s, 2H), 6.84 (d, J=8.6 Hz, 1H), 4.65 (s, 2H), 3.83 (s, 2H), 3.75 (s, 2H), 3.14 (s, 2H), 2.12 (s, 3H).

Embodiment 122

Compound 122: Preparation of 2-(2-chloro-4-fluorophenyl)-N-(2-(5-methylpyridin-2-yl)-5-sulfamoyl-1,2,3,4-tetrahydroisoquinolin-7-yl)acetamide

122

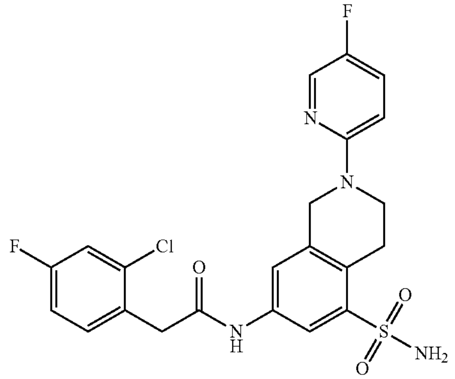

The compound was prepared by reference to the preparation method of embodiment 99. LC-MS: $[M+H]^+$=493.1.

Embodiment 123

Compound 123: Preparation of 2-(2-chlorophenyl)-N-(2-(oxetan-3-yl)-5-sulfamoyl-1,2,3,4-tetrahydroisoquinolin-7-yl)acetamide

123

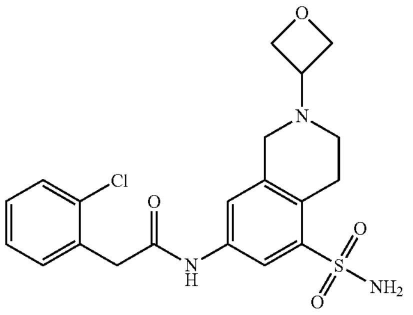

Synthetic Route:

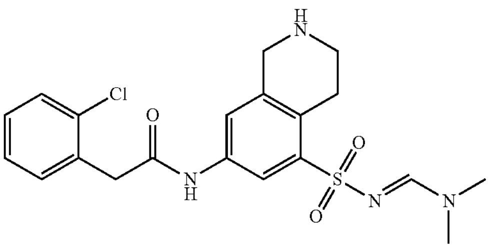

98-6

+

-continued

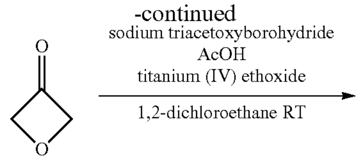

123-1

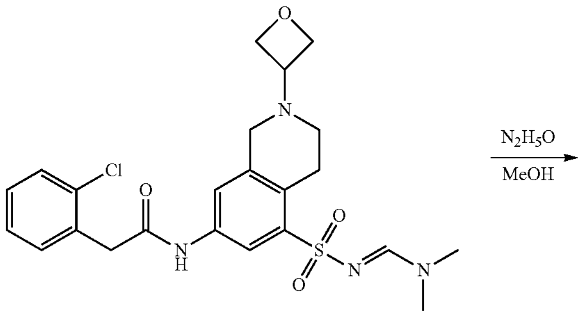

123-2

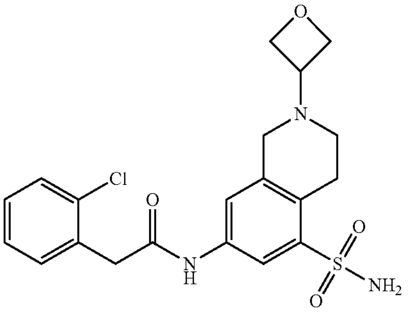

123

Step (1) Preparation of Intermediate 123-2

Intermediate 98-6 (200 mg), sodium triacetoxyborohydride (340 mg), acetic acid (83 mg), titanium (IV) ethoxide (315 mg) and intermediate 123-1-oxetane-3-one (66 mg) were accurately weighed and dissolved in 1,2-dichloroethane, and the mixture was stirred and reacted at room temperature overnight. The reaction system was replaced with $N_2$ and the mixture was stirred and reacted at room temperature overnight. Sample was taken, and TLC showed that raw materials were reacted completely. In post treatment, water and EA were added to the reaction solution, and the mixture was fully stirred and separated the EA phase; the aqueous phase was extracted with EA for two times, and the EA phases were combined, dried, concentrated by rotary evaporation, and purified by thin layer chromatography to obtain the product. The reaction was successful, and 50 mg of yellow oily liquid was obtained. LCMS. $[M+H]^+$=491.

Step (2) Preparation of Compound 123

Intermediate 123-2 (50 mg) was accurately weighed and dissolved in methanol, and a few drops of hydrazine hydrate were added dropwise, and the reaction was stirred at room temperature for 1 hour; sample was taken, and TLC showed that the raw materials were reacted completely. The reaction solution was concentrated by rotary evaporation, purified by preparative chromatography, and the preparation solution was lyophilized to obtain the product. The reaction was successful, and 11 mg of white foamy solid was obtained. LCMS: $[M+H]^+$=436.

$^1$H NMR (400 MHz, dmso) δ 10.40 (s, 1H), 7.99 (s, 2H), 7.58 (s, 1H), 7.44-7.38 (m, 2H), 7.34 (s, 1H), 7.31-7.26 (m, 2H), 4.55 (d, J=38.5 Hz, 6H), 3.82 (s, 2H), 3.58-3.53 (m, 1H), 3.46 (s, 2H), 3.11 (s, 2H).

Biological Test

Embodiment A In Vitro Evaluation of Biological Activity

The antagonistic properties of the compounds of the present disclosure were determined by the FLIPR (fluorescence imaging plate reader) method, and the compounds were inhibitors of intracellular calcium elevation induced by activation of hP2X4 (human purinergic P2X receptor subtype 4, accession number NM_001256796.2) expressed in HEK293 cells (human renal epithelial cell line, ATCC).

HEK293 cells stably expressing hP2X4 were cultured in DMEM high glucose medium containing 10% FBS (fetal bovine serum, Biosera, FB-1058/500), 1% penicillin-streptomycin (Gibco, 15140-122) and 1 mg/mL G418 (CABIOCHE, 345810) in a cell incubator (37° C., 5% humidity). Cells at 400,000 cells/mL were seeded into a 384-well plate (10,000 cells/well) 18-24 h prior to the FLIPR experiment and then incubated overnight in a cell incubator. On the day of the experiment, the medium was discarded and the cells were washed in an FLIPR buffer (0.3 mL of probenecid (Thermo, P36400), 0.6 mL of 1 M HEPES (Invitrogen, 15630080) and 29.1 mL of HBSS (Invitrogen, 14065056) per 30 mL of the buffer). Each well was added with 20 μL of 0.5×Calcium 6 fluorescent dye (Molecular Devices, R8190) and then the cells were subjected to dye-loading incubation at 37° C. for 1.5 h. Each well was added with 10 μL of respective test compound (dissolved in DMSO at a concentration of 10 mM and serially diluted with buffer) or vehicle and the mixture was equilibrated for 30 min at room temperature. The cell plate was then placed in the FLIPR for baseline fluorescence measurements (excitation at 485 nm and emission at 525-535 nm). An agonist (BZ-ATP (Sigma, B6396) at a final concentration of 2.5 μM) or a vehicle (ultrapure water) was then added at 10 μL/well, fluorescence values were measured for 2 min at 1-second intervals, and finally the output fluorescence counts were analyzed.

IC50 values obtained using the above method was shown in Table 1.

TABLE 1

$IC_{50}$ values of compounds of embodiments 1-43 for P2X4 receptor

| Compound | P2X4 $IC_{50}$ (nM) |
|---|---|
| Compound 1 | A |
| Compound 2 | B |
| Compound 3 | D |
| Compound 4 | B |
| Compound 5 | C |
| Compound 6 | B |
| Compound 7 | C |
| Compound 8 | B |
| Compound 9 | B |
| Compound 10 | B |
| Compound 11 | B |
| Compound 12 | B |
| Compound 13 | B |
| Compound 14 | B |
| Compound 15 | C |
| Compound 16 | B |
| Compound 17 | C |
| Compound 18 | C |
| Compound 19 | A |
| Compound 20 | B |
| Compound 21 | A |
| Compound 22 | B |
| Compound 23 | A |
| Compound 24 | A |
| Compound 25 | A |
| Compound 26 | A |
| Compound 27 | A |
| Compound 28 | A |
| Compound 29 | B |
| Compound 30 | B |
| Compound 31 | B |
| Compound 32 | B |
| Compound 33 | B |
| Compound 34 | B |
| Compound 35 | B |
| Compound 36 | A |
| Compound 37 | B |
| Compound 38 | C |
| Compound 39 | D |
| Compound 40 | C |
| Compound 41 | C |
| Compound 42 | B |
| Compound 43 | D |
| Compound 44 | D |
| Compound 45 | C |
| Compound 46 | D |
| Compound 47 | C |
| Compound 48 | D |
| Compound 49 | C |
| Compound 50 | D |
| Compound 51 | D |
| Compound 52 | D |
| Compound 53 | D |
| Compound 54 | D |
| Compound 55 | C |
| Compound 56 | C |
| Compound 57 | C |
| Compound 58 | C |
| Compound 59 | C |
| Compound 60 | C |
| Compound 61 | C |
| Compound 62 | D |
| Compound 63 | D |
| Compound 64 | D |
| Compound 65 | B |
| Compound 66 | C |
| Compound 67 | D |
| Compound 68 | C |
| Compound 69 | D |
| Compound 70 | C |
| Trifluoroacetate of compound 71 | D |
| Compound 72 | C |
| Compound 73 | D |
| Compound 74 | C |
| Compound 75 | C |
| Compound 76 | C |
| Compound 77 | C |
| Compound 78 | C |
| Compound 79 | C |
| Compound 80 | C |
| Compound 81 | D |
| Compound 82 | D |
| Compound 83 | C |
| Compound 84 | C |
| Compound 85 | D |
| Compound 86 | D |
| Compound 87 | B |
| Compound 88 | C |
| Compound 89 | D |
| Compound 90 | C |

TABLE 1-continued

| IC$_{50}$ values of compounds of embodiments 1-43 for P2X4 receptor | |
|---|---|
| Compound | P2X4 IC$_{50}$ (nM) |
| Compound 91 | D |
| Compound 92 | C |
| Compound 93 | C |
| Compound 94 | C |
| Compound 95 | D |
| Compound 96 | D |
| Compound 97 | C |
| Compound 98 | D |
| Compound 99 | B |
| Compound 100 | B |
| Compound 101 | B |
| Compound 102 | B |
| Compound 103 | B |
| Compound 104 | C |
| Compound 105 | C |
| Compound 106 | B |
| Compound 107 | B |
| Compound 108 | A |
| Compound 109 | D |
| Compound 110 | D |
| Compound 111 | D |
| Compound 112 | B |
| Compound 113 | C |
| Compound 114 | B |
| Compound 115 | D |
| Compound 116 | C |
| Compound 117 | B |
| Compound 118 | C |
| Compound 119 | D |
| Compound 120 | C |
| Compound 121 | C |
| Compound 122 | D |
| Compound 123 | D |
| — | — |

A: IC50 ≤ 10 nM,
B: 10 < IC50 ≤ 50 nM,
C: 50 < IC50 ≤ 200 nM,
D: 200 < IC50 ≤ 5000 nM

As can be seen from the data in Table 1, the compounds disclosure herein have good P2X4 inhibitory activity. Preferred are compounds with IC50<500 nM, and more preferred are compounds with IC50<100 nM.

Embodiment B Activity Test of Simple Citric Acid Cough Model

Male Dunkin Hartley guinea pigs (300-350 g) were placed in an animal atomization box, and then the door of the atomization box was closed while the ultrasonic atomizer (Guangdong Yuehua) was turned on. 17.5% citric acid gas was introduced into the atomization box at a maximum atomization rate (about 2 mL/min) for 20 s, and coughs of the animals within 10 min were continuously observed from the time of the start of atomization. During the 10-min observation, coughs of the animals needed to be counted manually, and the number of coughs were judged according to cough postures of the guinea pigs, such as abdominal twitching, mouth opening, and head inclining downward abruptly. The number of coughs during the first 5 min and that during 10 min were recorded, and the cough latency of the guinea pigs, namely the time from the initiation of citric acid induction to the appearance of the 1st cough, was also recorded.

Cough inhibition rate Vs vehicle indicates the percentage of reduction in cough times in the administration group compared with the vehicle group when stimulated with citric acid (cough inhibition rate Vs vehicle=(cough times in the vehicle group−cough times in each administration group)/cough times after administration in the vehicle group×1000); the cough inhibition rate Vs basic value indicates the percentage of reduction in the self-coughing times in the administration group before and after administration (cough suppression rate Vs basic value=(cough times before administration−cough times after administration)/cough times before administration×100%).

TABLE 2

| Cough inhibition rates obtained form some compounds in vivo | | | | |
|---|---|---|---|---|
| | | Average cough times | Cough inhibition rate Vs vehicle (%) | Cough inhibition rate Vs basic value (%) |
| Vehicle group | Before administration | 19.11 | / | / |
| | After administration | 18.22 | | |
| Dextromethorphan 60 mg/kg | Before administration | 19.70 | 38.54 | 43.15 |
| | After administration | 11.20 | | |
| Compound 1 20 mg/kg | Before administration | 19.00 | 38.41 | 40.94 |
| | After administration | 11.22 | | |
| Compound 1 60 mg/kg | Before administration | 19.40 | 42.38 | 45.88 |
| | After administration | 10.50 | | |
| Compound 1 100 mg/kg | Before administration | 19.90 | 52.80 | 56.78 |
| | After administration | 8.60 | | |

The above experiment was performed using compound 1 and the results in Table 2 show that, compared with a blank vehicle group or the administration group before administration, compound 1 at the dosage of 20 mg/kg and 60 mg/kg can reduce the number of coughs and prolong the cough latency in a dose-dependent manner, and the group at the dosage of 60 mg/kg has a significant improvement effect, and has no significant difference in the drug effect compared with the positive compound dextromethorphan at the same dosage, which indicates that compound 1 has the effects of reducing the number of coughs and improving the cough latency and is comparable to the positive compound.

Embodiment C In Vitro Cytotoxicity Assay

In vitro cytotoxicity assay for the compounds disclosed herein was performed in HepG2 cells using the CCK-8 method. HepG2 cells (Beina Bio) in the logarithmic growth phase were collected, the concentration of cell suspension was adjusted, and then the cells were plated on a 96-well cell culture plate at 50,000 cells/well. The cells were then incubated overnight in a cell incubator (5% humidity, 37° C.), and after 80-90% cell confluence was achieved, test compounds or vehicle (DMSO) at various concentration gradients were added after medium change. The resulting mixture was incubated in the cell incubator (5% humidity, 37° C.) for 48 h. After the treatment, the medium in the plate was discarded. The plate was washed twice with PBS, added with CCK-8 working solution (Beyotime) at 100 μL per well, and then incubated at 37° C. for 1.5 h away from the light. Absorbance at OD450 nm was measured for each well on a microplate reader, and CC50 value of each compound was analyzed and calculated.

The $CC_{50}$ obtained using the above method was shown in Table 3.

TABLE 3

$CC_{1/50}$ obtained from some compounds

| Compound | HepG2 $CC_{50}$ (M) |
|---|---|
| Compound 1 | >200 |
| Compound 2 | 103.4 |
| Compound 6 | >200 |
| Compound 57 | >200 |
| Compound 65 | >200 |
| Compound 99 | >200 |
| Compound 102 | >200 |
| Compound 103 | >200 |

As can be seen from the data in Table 3, most of the compounds disclosed herein exhibit relatively good safety, and the CC50 ranges are all more than 30 μM, which satisfies the requirement for in vitro cytotoxicity of general compounds. Preferred are compounds with CC50>30 μM, and more preferred are compounds with CC50>100 μM.

Embodiment D Test of In Vitro Metabolic Stability

The in vitro metabolic stability of the compounds disclosed herein was determined through incubation of liver microsomes of various species. A proper amount of test compound was added into a liver microsome reaction system (1 mg/mL liver microsome protein, 25 U/mL glucose-6 phosphate dehydrogenase, 1 mM NADP, 6 mM D-glucose 6-phosphate and 5 mM MgCl2), and then the mixture was incubated in a water bath kettle at 37° C. to start the reaction. At each time point, 100 μL of the reaction system was added into a centrifuge tube containing 400 L of internal standard working solution (containing a 200 ng/mL solution of dexamethasone, diclofenac, tolbutamide and labetalol in acetonitrile) precooled at 0° C. so as to stop the reaction, and the mixture was then centrifuged at 10,000 g for 10 min at 4° C. The supernatant was collected for LC-MS assay so as to obtain the values of in vitro metabolic half-life of the test compounds in liver microsomes of various species.

T½ values obtained using the above method are shown in Table 4.

TABLE 4

T1/2 values obtained for some of the compounds

| Compound | T1/2 in human liver microsome min | T1/2 in rat liver microsome min | T1/2 in guinea pig liver microsome min |
|---|---|---|---|
| Compound 1 | 284.37 | 816.37 | 714.14 |
| Compound 2 | 719.76 | 1894.67 | 530.68 |
| Compound 6 | 262.92 | 54.69 | 10.87 |
| Compound 27 | 241.33 | 234.43 | / |
| Compound 57 | 613.20 | 136.81 | 82.54 |
| Compound 65 | 255.02 | 140.85 | / |
| Compound 92 | 989.07 | 100.57 | / |
| Compound 99 | 25.84 | 95.12 | 48.82 |
| Compound 102 | 651.11 | / | / |
| Compound 103 | 105.86 | 86.57 | 7.88 |
| Compound 106 | 16.03 | / | / |
| Compound 107 | 31.98 | / | / |
| Compound 108 | 62.79 | / | / |
| Compound 109 | 1896.04 | 94.90 | / |
| Compound 112 | 875.51 | 82.26 | / |
| Compound 113 | 284.67 | 93.33 | / |
| Compound 114 | 81.46 | 48.23 | / |

Note:
"/" means not measured.

As can be seen from the data in Table 4, the compounds disclosed herein have a relatively good metabolic stability in human, rat and guinea pig. Preferred are compounds with T1/2>30 min in human liver microsome, and more preferred are compounds with T1/2>90 min in human liver microsome.

Although the specific embodiments of the present disclosure have been described above, those skilled in the art should understand that these are only embodiments, and various changes or modifications can be made to these embodiments without departing from the principle and essence of the present disclosure. Accordingly, the scope of protection of the present disclosure is defined by the claims.

The invention claimed is:

1. A fused ring compound represented by formula I, a pharmaceutically acceptable salt thereof, a stereoisomer thereof, a tautomer thereof, an isotopic compound thereof, a crystal form thereof, a nitrogen oxide thereof, a solvate thereof or a solvate of the pharmaceutically acceptable salt thereof;

I

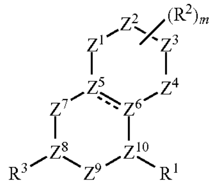

wherein,

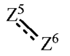

is a single bond or a double bond;

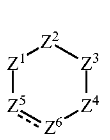

is benzene ring, 6-membered heteroaromatic ring having one or two heteroatoms N or 6-membered heterocycloalkene having one heteroatom N;

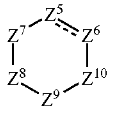

is benzene ring;

$R^1$ is

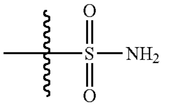

or

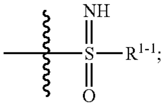

$R^{1-1}$ is halogen, hydroxyl, amino, $—NHR^{1-1-4}$, $—N(R^{1-1-5})(R^{1-1-6})$, $C_1$-$C_6$ alkyl, $C_3$-$C_6$ cycloalkyl, $C_1$-$C_6$ alkyl substituted by one or more $R^{1-1-1}$, $C_3$-$C_6$ cycloalkyl substituted by one or more $R^{1-1-2}$, or, "4- to 7-membered heterocycloalkyl with 1, 2 or 3 heteroatoms selected from one or more of N, O and S" substituted by one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4- to 7-membered heterocycloalkyl with 1, 2 or 3 heteroatoms selected from one or more of N, O and S";

$R^3$ is

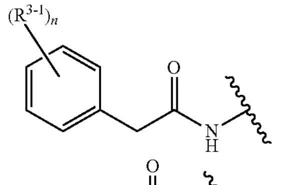

or

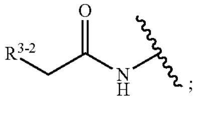

n is 0, 1, 2 or 3;

$R^{3-1}$ is independently halogen, cyano, hydroxyl, $C_1$-$C_6$ alkyl, $C_1$-$C_6$ alkoxy, $C_3$-$C_6$ cycloalkyl, $C_1$-$C_6$ alkyl substituted by one or more $R^{3-1-1}$, $C_1$-$C_6$ alkoxy substituted by one or more $R^{3-1-2}$, or $C_1$-$C_6$ alkoxy substituted by $C_1$-$C_6$ alkoxy; $R^{3-1-1}$ and $R^{3-1-2}$ are independently halogen;

$R^{3-2}$ is $C_3$-$C_6$ cycloalkyl substituted by one or more $R^{3-2-1}$, "5- to 6-membered heterocycloalkyl with 1, 2 or 3 heteroatoms selected from one or more of N, O and S" substituted by one or more $R^{3-2-2}$, "7- to 8-membered heterocycloalkyl with 1, 2 or 3 heteroatoms selected from one or more of N, O and S" substituted by one or more $R^{3-2-2}$ or "5- to 6-membered heteroaryl with 1, 2 or 3 heteroatoms selected from one or more of N, O and S" substituted by one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or, $C_1$-$C_6$ alkoxy substituted by $C_1$-$C_6$ alkoxy;

m is 0, 1, 2, 3 or 4;

$R^2$ is oxo, halogen, cyano, isocyano, amino, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted one or more $R^{2-26}$, $C_2$-$C_{10}$ alkynyl, $C_2$-$C_{10}$ alkynyl substituted by one or more $R^{2-27}$, $C_3$-$C_6$ cycloalkyl, $C_3$-$C_6$ cycloalkyl substituted by one or more $R^{2-3}$, "5- to 6-membered heterocycloalkyl with 1, 2 or 3 heteroatoms selected from one or more of N, O and S", "3- to 4-membered heterocycloalkyl with 1 or 2 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, $—(C{=}O)—R^{2-2}$, $—OR^{2-6}$, $—C({=}O)OR^{2-7}$, $—NR^{2-8}R^{2-9}$, "5- to 6-membered heterocycloalkyl with 1, 2 or 3 heteroatoms selected from one or more of N, O and S" substituted by one or more $R^{2-10}$, "3- to 4-membered heterocycloalkyl with 1 or 2 heteroatoms selected from one or more of N, O and S" substituted by one or more $R^{2-10}$, $—C({=}O)NHR^{2-11}$, $—C({=}O)NR^{2-12}R^{2-13}$, $—NR^{2}$-$^{14}C({=}O)R^{2-1}$, $—NR^{2-16}S({=}O)_2R^{2-17}$, $—NR^{2-18}S({=}O)R^{2-19}$, $—S({=}O)_2NHR^{2-20}$, $—S({=}O)NHR^{2-21}$, $—S({=}O)_2NR^{2-22}R^{2-23}$, $—S({=}O)_2R^{2-24}$ or $—S({=}O)R^{2-25}$;

$R^{2-1}$ is independently halogen, hydroxyl, $C_3$-$C_6$ cycloalkyl, $C_3$-$C_6$ cycloalkyl substituted by one or more $R^{2-1-8}$, "4- to 6-membered heterocycloalkyl with 1, 2 or 3 heteroatoms selected from one or more of N, O and S", "4- to 6-membered heterocycloalkyl with 1, 2 or 3 heteroatoms selected from one or more of N, O and S" substituted by one or more $R^{2-17}$, phenyl, phenyl substituted by one or more $R^{2-1-1}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-1-6}$, $—OR^{2-1-2}$, $—N(R^{2-1-3})(R^{2-1-4})$, or, $—S({=}O)_2R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted by one or more halogen, $—OR^{2-1-1}$, or, $—N(R^{2-1-1-2})(R^{2-1-1-3})$; $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, $C_1$-$C_6$ alkyl, $C_1$-$C_6$ alkyl substituted by one or more $R^{2-4-3}$, $—N(R^{2-4-1})(R^{2-4-2})$ or $C_1$-$C_6$ alkoxy; $R^{2-4-1}$ and $R^{2-4-2}$ are independently hydrogen, $C_1$-$C_6$ alkyl or $C_3$-$C_6$ cycloalkyl; $R^{2-4-3}$ is halogen;

$R^{2-2}$ is $C_1$-$C_6$ alkyl, $C_3$-$C_6$ cycloalkyl, phenyl, $C_1$-$C_6$ alkyl substituted by one or more $R^{2-2}$-2, or, phenyl substituted by one or more $R^{2-2-1}$; $R^{2-2-1}$ is independently halogen; $R^{2-2-2}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently oxo, halogen, hydroxyl, amino, carboxyl, —CN, $C_1$-$C_6$ alkyl, $C_1$-$C_6$ alkyl substituted by one or more halogen, $C_1$-$C_6$ alkoxy, $C_3$-$C_6$ cycloalkyl, $C_6$-$C_{10}$ aryl, $C_6$-$C_{10}$ aryl substituted by one or more $R^{2-6-1-1}$, —$OR^{2-6-1-2}$ or —$N(R^{2-6-1-3})(R^{2-6-1-4})$;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-1-2}$, $R^{2-6-1-3}$ and $R^{2-6-1-4}$ are independently $C_1$-$C_6$ alkyl;

$R^{2-7}$ is $C_1$-$C_6$ alkyl, $C_3$-$C_6$ cycloalkyl or phenyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{2-10}$ is independently $C_1$-$C_6$ alkyl or oxo;

$R^{2-26}$ and $R^{2-27}$ are independently halogen or $C_1$-$C_6$ alkyl;

$R^{2-11}$, $R^{2-12}$, $R^{2-13}$, $R^{2-14}$, $R^{2-15}$, $R^{2-16}$, $R^{2-17}$, $R^{2-18}$, $R^{2-19}$, $R^{2-20}$, $R^{2-21}$, $R^{2-22}$, $R^{2-23}$, $R^{2-24}$ and $R^{2-2}$ are independently $C_1$-$C_6$ alkyl, $C_1$-$C_6$ alkoxy, $C_3$-$C_6$ cycloalkyl, "5- to 6-membered heterocycloalkyl with 1, 2 or 3 heteroatoms selected from one or more of N, O and S", phenyl, phenyl substituted by one or more $R^{2-11-1}$, "5- to 6-membered heteroaryl with 1, 2 or 3 heteroatoms selected from one or more of N, O and S", or "5- to 6-membered heteroaryl with 1, 2 or 3 heteroatoms selected from one or more of N, O and S" substituted by one or more $R^{2-11-2}$;

$R^{2-11-1}$ and $R^{2-11-2}$ are independently halogen, cyano, hydroxyl, $C_1$-$C_6$ alkyl, $C_1$-$C_6$ alkoxy or $C_3$-$C_6$ cycloalkyl;

$R^2$ is located on

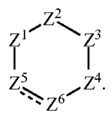

2. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 1, wherein,

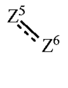

is a single bond or a double bond;

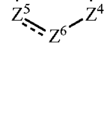

is benzene ring 6-membered heteroaromatic ring having one or two heteroatoms N or 6-membered heterocycloalkene having one heteroatom N;

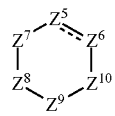

is benzene ring;

$R^1$ is

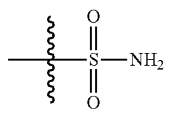

or

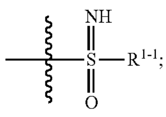

$R^{1-1}$ is halogen, hydroxyl, amino, —$NHR^{1-1-4}$, —$N(R^{1-1-5})(R^{1-1-6})$, $C_1$-$C_6$ alkyl, $C_3$-$C_6$ cycloalkyl, $C_1$-$C_6$ alkyl substituted by one or more $R^{1-1}$, $C_3$-$C_6$ cycloalkyl substituted by one or more $R^{1-1-2}$ or, "4- to 7-membered heterocycloalkyl with 1, 2 or 3 heteroatoms selected from one or more of N, O and S" substituted by one or more $R^{1-1-3}$;

$R^{1-1-1}$, $R^{1-1-2}$, $R^{1-1-3}$, $R^{1-1-4}$, $R^{1-1-5}$ and $R^{1-1-6}$ are independently halogen, hydroxyl, $C_1$-$C_6$ alkyl, $C_3$-$C_6$ cycloalkyl, $C_1$-$C_6$ alkoxy or "4- to 7-membered heterocycloalkyl with 1, 2 or 3 heteroatoms selected from one or more of N, O and S";

$R^3$ is

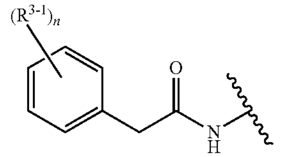

or

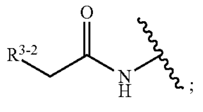

n is 0, 1, 2 or 3;

$R^{3-1}$ is independently halogen, cyano, hydroxyl, $C_1$-$C_6$ alkyl, $C_1$-$C_6$ alkoxy, $C_3$-$C_6$ cycloalkyl, or, $C_1$-$C_6$ alkoxy substituted by $C_1$-$C_6$ alkoxy;

$R^{3-2}$ is $C_3$-$C_6$ cycloalkyl substituted by one or more $R^{3-2-1}$, "5- to 6-membered heterocycloalkyl with 1, 2 or 3 heteroatoms selected from one or more of N, O and S" substituted by one or more $R^{3-2-2}$, "7- to 8-membered heterocycloalkyl with 1, 2 or 3 heteroatoms selected from one or more of N, O and S" substituted by one or more $R^{3-2-2}$ or "5- to 6-membered heteroaryl with 1, 2 or 3 heteroatoms selected from one or more of N, O and S" substituted by one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or, $C_1$-$C_6$ alkoxy substituted by $C_1$-$C_6$ alkoxy;

m is 0, 1, 2, 3 or 4;

$R^2$ is oxo, halogen, cyano, amino, $C_1$-$C_{10}$ alkyl, $C_1$-$C_{10}$ alkyl substituted by one or more $R^{2-}$, $C_3$-$C_6$ cycloalkyl, $C_3$-$C_6$ cycloalkyl substituted by one or more $R^{2-3}$, "5- to 6-membered heterocycloalkyl with 1, 2 or 3 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)—$R^{2-2}$, —$OR^{2-6}$, —C(═O)$OR^{2-7}$, —$NR^{2-8}R^{2-9}$, "5- to 6-membered heterocycloalkyl with 1, 2 or 3 heteroatoms selected from one or more of N, O and S" substituted by one or more $R^{2-10}$, —C(═O)$NHR^{2-11}$, —C(═O)$NR^{2-12}$ $R^{2-13}$, —$NR^{2-14}$C(═O)$R^{2-1}$, —$NR^{2-16}$S(═O)$_2R^{2-17}$, —$NR^{2-18}$S(═O)$R^{2-19}$, —S(═O)$_2NHR^{2-20}$, —S(═O)$NHR^{2-21}$, —S(═O)$_2$ $NR^{2-22}R^{2-23}$, —S(═O)$_2R^{2-24}$ or —S(═O)$R^{2-25}$;

$R^{2-1}$ is independently halogen, hydroxyl, $C_3$-$C_6$ cycloalkyl, $C_3$-$C_6$ cycloalkyl substituted by one or more $R^{2-1-8}$, "4- to 6-membered heterocycloalkyl with 1, 2 or 3 heteroatoms selected from one or more of N, O and S", "4- to 6-membered heterocycloalkyl with 1, 2 or 3 heteroatoms selected from one or more of N, O and S" substituted by one or more $R^{2-17}$, phenyl, phenyl substituted by one or more $R^{2-1-1}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-1-6}$, —$OR^{2-1-2}$, —N($R^{2-1-3}$)($R^{2-1-4}$), or, —S(═O)$_2R^{2-1-5}$;

$R^{2-1-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted by one or more halogen, —$OR^{2-1-1-1}$, or, —N($R^{2-1-1-2}$)($R^{2-1-1-3}$); $R^{2-1-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, —N($R^{2-4-1}$)($R^{2-4-2}$) or $C_1$-$C_6$ alkoxy; $R^{2-4-1}$ and $R^{2-4-2}$ are independently hydrogen, $C_1$-$C_6$ alkyl or $C_3$-$C_6$ cycloalkyl;

$R^{2-2}$ is $C_1$-$C_6$ alkyl, $C_3$-$C_6$ cycloalkyl, phenyl, or, phenyl substituted by one or more $R^{2-2-1}$; $R^{2-2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently oxo, halogen, hydroxyl, amino, carboxyl, —CN, $C_1$-$C_6$ alkyl, $C_1$-$C_6$ alkyl substituted by one or more halogen, $C_1$-$C_6$ alkoxy, $C_3$-$C_6$ cycloalkyl, $C_6$-$C_{10}$ aryl, $C_6$-$C_{10}$ aryl substituted by one or more $R^{2-6-1-1}$, —$OR^{2-6-1-2}$ or —N($R^{2-6-1-3}$)($R^{2-6-1-4}$);

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-1-2}$, $R^{2-6-1-3}$ and $R^{2-6-1-4}$ are independently $C_1$-$C_6$ alkyl;

$R^{2-7}$ is $C_1$-$C_6$ alkyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{2-10}$ is independently $C_1$-$C_6$ alkyl or oxo;

$R^{2-11}$, $R^{2-12}$, $R^{2-13}$, $R^{2-14}$, $R^{2-15}$, $R^{2-16}$, $R^{2-17}$, $R^{2-18}$, $R^{2-19}$, $R^{2-20}$, $R^{2-21}$, $R^{2-22}$, $R^{2-23}$, $R^{2-24}$ and $R^{2-25}$ are independently $C_1$-$C_6$ alkyl, $C_1$-$C_6$ alkoxy, $C_3$-$C_6$ cycloalkyl, "5- to 6-membered heterocycloalkyl with 1, 2 or 3 heteroatoms selected from one or more of N, O and S", phenyl, phenyl substituted by one or more $R^{2-11-1}$, "5- to 6-membered heteroaryl with 1, 2 or 3 heteroatoms selected from one or more of N, O and S", or "5- to 6-membered heteroaryl with 1, 2 or 3 heteroatoms selected from one or more of N, O and S" substituted by one or more $R^{2-11-2}$;

$R^{2-11-1}$ and $R^{2-11-2}$ are independently halogen, cyano, hydroxyl, $C_1$-$C_6$ alkyl, $C_1$-$C_6$ alkoxy or $C_3$-$C_6$ cycloalkyl;

$R^2$ is located on

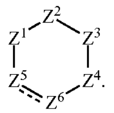

3. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 2, wherein, when $R^{1-1}$ is $C_1$-$C_6$ alkyl, the $C_1$-$C_6$ alkyl is $C_1$-$C_4$ alkyl;

or, when $R^{3-1}$ is independently halogen, the halogen is fluorine, chlorine, bromine or iodine;

or, when $R^2$ is halogen, the halogen is fluorine, chlorine, bromine or iodine;

or, when $R^2$ is $C_1$-$C_{10}$ alkyl, the $C_1$-$C_{10}$ alkyl is $C_1$-$C_4$ alkyl;

or, when $R^2$ is $C_1$-$C_{10}$ alkyl substituted by one or more $R^{2-1}$, the $C_1$-$C_{10}$ alkyl is $C_1$-$C_4$ alkyl;

or, when $R^2$ is $C_3$-$C_6$ cycloalkyl, the $C_3$-$C_6$ cycloalkyl is cyclopropyl, cyclobutyl, cyclopentyl or cyclohexyl;

or, when $R^2$ is "5- to 6-membered heterocycloalkyl with 1, 2 or 3 heteroatoms selected from one or more of N, O and S", in the 5- to 6-membered heterocycloalkyl, the heteroatoms are selected from one or more of N and O;

or, when $R^2$ is "5- to 6-membered heteroaryl with 1, 2 or 3 heteroatoms selected from one or more of N, O and S", in the 5- to 6-membered heteroaryl, the heteroatoms are N;

or, when $R^2$ is "5- to 6-membered heterocycloalkyl with 1, 2 or 3 heteroatoms selected from one or more of N, O and S" substituted by one or more $R^{2-10}$, in the 5- to 6-membered heterocycloalkyl, the heteroatoms are N;

or, when $R^{2-1}$ is independently halogen, the halogen is fluorine, chlorine, bromine or iodine;

or, when $R^{2-6}$ is $C_1$-$C_{10}$ alkyl, the $C_1$-$C_{10}$ alkyl is $C_1$-$C_6$ alkyl;

or, when $R^{2-6}$ is $C_1$-$C_{10}$ alkyl substituted by one or more $R^{2-6-1}$, the $C_1$-$C_{10}$ alkyl is $C_1$-$C_4$ alkyl;

or, when $R^{2-6}$ is $C_3$-$C_6$ cycloalkyl, the $C_3$-$C_6$ cycloalkyl is cyclopropyl, cyclobutyl, cyclopentyl or cyclohexyl;

or, when $R^{2-6}$ is $C_6$-$C_{10}$ aryl, the $C_6$-$C_{10}$ aryl is phenyl or naphthyl;

or, when $R^{2-6}$ is $C_6$-$C_{10}$ aryl substituted by one or more $R^{2-6-2}$, the $C_6$-$C_{10}$ aryl is phenyl or naphthyl;

or, when $R^{2-6}$ is "3- to 6-membered heterocycloalkyl with 1, 2 or 3 heteroatoms selected from one or more of N, O and S", the 3- to 6-membered heterocycloalkyl is 3- to 4-membered heterocycloalkyl;

or, when $R^{2-6}$ is "3- to 6-membered heterocycloalkyl with 1, 2 or 3 heteroatoms selected from one or more of N, O and S" substituted by one or more $R^{2-6-3}$, the 3- to 6-membered heterocycloalkyl is 3- to 4-membered heterocycloalkyl;

or, when $R^{2-6-1}$ is independently halogen, the halogen is fluorine, chlorine, bromine or iodine;

or, when $R^{2-6-1}$ is independently $C_1$-$C_6$ alkoxy, the $C_1$-$C_6$ alkoxy is $C_1$-$C_4$ alkoxy;

or, when $R^{2-6-1}$ is independently $C_3$-$C_6$ cycloalkyl, the $C_3$-$C_6$ cycloalkyl is cyclopropyl, cyclobutyl, cyclopentyl or cyclohexyl;

or, when $R^{2-6-1}$ is independently $C_6$-$C_{10}$ aryl, the $C_6$-$C_{10}$ aryl is phenyl or naphthyl;

or, when $R^{2-6-1}$ is independently $C_6$-Clo aryl substituted by one or more $R^{2-6-1-1}$, the $C_6$-$C_{10}$ aryl is phenyl or naphthyl;

or, when $R^{2-6-2}$ is independently halogen, the halogen is fluorine, chlorine, bromine or iodine;

or, when $R^{2-6-2}$ is independently $C_1$-$C_6$ alkyl, the $C_1$-$C_6$ alkyl is $C_1$-$C_4$ alkyl;

or, when $R^{2-6-2}$ is independently $C_1$-$C_6$ alkoxy, the $C_1$-$C_6$ alkoxy is $C_1$-$C_4$ alkoxy;

or, when $R^{2-6-3}$ is independently —C(═O)—$C_1$-$C_4$ alkyl, in the —C(═O)—$C_1$-$C_4$ alkyl, the $C_1$-$C_4$ alkyl is methyl, ethyl, n-propyl, isopropyl, n-butyl, isobutyl, sec-butyl or tert-butyl;

or, $R^{2-6-1-1}$ is independently fluorine, chlorine, bromine or iodine;

or, $R^{2-7}$ is $C_1$-$C_4$ alkyl;

or, when $R^{2-8}$ and $R^{2-9}$ are independently $C_1$-$C_6$ alkyl, the $C_1$-$C_6$ alkyl is $C_1$-$C_4$ alkyl;

or, when $R^{2-8}$ and $R^{2-9}$ are independently $C_6$-$C_{10}$ aryl, the $C_6$-$C_{10}$ aryl is phenyl or naphthyl;

or, when $R^{2-8}$ and $R^{2-9}$ are independently $C_6$-$C_{10}$ aryl substituted by one or more $R^{2-8-1}$, in the $C_6$-$C_{10}$ aryl substituted by one or more $R^{2-8-1}$, the $C_6$-$C_{10}$ aryl is phenyl or naphthyl;

or, when $R^{2-8-1}$ is halogen, the halogen is fluorine, chlorine, bromine or iodine;

or, when $R^{2-8-1}$ is $C_1$-$C_6$ alkoxy, the $C_1$-$C_6$ alkoxy is $C_1$-$C_4$ alkoxy;

or, when $R^{2-10}$ is independently $C_1$-$C_6$ alkyl, the $C_1$-$C_6$ alkyl is $C_1$-$C_4$ alkyl;

or, when $R^{1-1}$ is $C_3$-$C_6$ cycloalkyl, the $C_3$-$C_6$ cycloalkyl is cyclopropyl, cyclobutyl or cyclopentyl;

or, when $R^{1-1}$ is $C_1$-$C_6$ alky substituted by one or more $R^{1-1-1}$, in the $C_1$-$C_6$ alky substituted by one or more $R^{1-1-1}$, the $C_1$-$C_6$ alkyl is $C_1$-$C_4$ alkyl;

or, when $R^{1-1}$ is $C_3$-$C_6$ cycloalkyl substituted by one or more $R^{1-1-2}$, in the $C_3$-$C_6$ cycloalkyl substituted by one or more $R^{1-1-2}$, the $C_3$-$C_6$ cycloalkyl is cyclopropyl, cyclobutyl or cyclopentyl;

or, when $R^{1-1-1}$ and $R^{1-1-2}$ are independently halogen, the halogen is fluorine, chlorine, bromine or iodine;

or, when $R^{3-1}$ is independently $C_1$-$C_6$ alkoxy or $C_1$-$C_6$ alkoxy substituted by one or more $R^{3-1-2}$, in the $C_1$-$C_6$ alkoxy or $C_1$-$C_6$ alkoxy substituted by one or more $R^{3-1-2}$, the $C_1$-$C_6$ alkoxy is $C_1$-$C_4$alkoxy;

or, when $R^{3-1-1}$ and $R^{3-1-2}$ are independently halogen, the halogen is fluorine, chlorine, bromine or iodine;

or, when $R^2$ is $C_2$-$C_{10}$ alkenyl, $C_2$-$C_{10}$ alkenyl substituted by one or more $R^{2-26}$, in the $C_2$-$C_{10}$ alkenyl and $C_2$-$C_{10}$ alkenyl substituted by one or more $R^{2-26}$, the $C_2$-$C_{10}$ alkenyl is $C_2$-$C_4$ alkenyl;

or, when $R^2$ is $C_2$-$C_{10}$ alkynyl or $C_2$-$C_{10}$ alkynyl substituted by one or more $R^{2-27}$, in the $C_2$-$C_{10}$ alkynyl and $C_2$-$C_{10}$ alkynyl substituted by one or more $R^{2-27}$, the $C_2$-$C_{10}$ alkynyl is $C_2$-$C_4$ alkynyl;

or, when $R^{2-26}$ and $R^{2-27}$ are independently halogen, the halogen is fluorine, chlorine, bromine or iodine;

or, when $R^2$ is "3- to 4-membered heterocycloalkyl with 1 or 2 heteroatoms selected from one or more of N, O and S" or "3- to 4-membered heterocycloalkyl with 1 or 2 heteroatoms selected from one or more of N, O and S" substituted by one or more $R^{2-10}$, in the 3- to 4-membered heterocycloalkyl, the heteroatoms are selected from one or more of N and O;

or, when $R^2$ is "5- to 6-membered heteroaryl with 1, 2 or 3 heteroatoms selected from one or more of N, O and S" substituted by one or more $R^{2-5}$, in the 5- to 6-membered heteroaryl, the heteroatoms are N;

or, when $R^{2-1}$ is independently $C_3$-$C_6$ cycloalkyl, the $C_3$-$C_6$ cycloalkyl is cyclopropyl, cyclobutyl, cyclopentyl or cyclohexyl;

or, when $R^{2-2}$ is $C_1$-$C_6$ alkyl or $C_1$-$C_6$ alkyl substituted by one or more $R^{2-2-2}$, the $C_1$-$C_6$ alkyl is methyl, ethyl, n-propyl, isopropyl, n-butyl, isobutyl, sec-butyl, tert-butyl, n-pentyl or isopentyl or, when $R^{2-2}$ is $C_3$-$C_6$ cycloalkyl, the $C_3$-$C_6$ cycloalkyl is cyclopropyl, cyclobutyl, cyclopentyl or cyclohexyl;

or, when $R^{2-2-2}$ is independently halogen, the halogen is fluorine, chlorine, bromine or iodine;

or, when $R^{2-4}$ and $R^{2-5}$ are independently halogen, the halogen is fluorine, chlorine, bromine or iodine;

or, when $R^{2-4}$ and $R^{2-5}$ are independently $C_1$-$C_6$ alkyl or $C_1$-$C_6$ alkyl substituted by one or more $R^{2-4-3}$, in the $C_1$-$C_6$ alkyl and $C_1$-$C_6$ alkyl substituted by one or more $R^{2-4-3}$, the $C_1$-$C_6$ alkyl is methyl, ethyl, n-propyl, isopropyl, n-butyl, isobutyl, sec-butyl, tert-butyl, n-pentyl or isopentyl;

or, when $R^{2-4-3}$ is halogen, the halogen is fluorine, chlorine, bromine or iodine;

or, when $R^{2-7}$ is $C_3$-$C_6$ cycloalkyl, the $C_3$-$C_6$ cycloalkyl is cyclopropyl, cyclobutyl, cyclopentyl or cyclohexyl;

or, when $R^2$ is "5- to 6-membered heterocycloalkyl with 1, 2 or 3 heteroatoms selected from one or more of N, O and S", the 5- to 6-membered heterocycloalkyl is

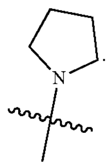 [SMILES: *N1CCCC1]

4. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 2, wherein,

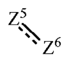

is a double bond;

or, $R^1$ is

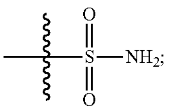 [SMILES: *S(N)(=O)=O]

or, $R^{1-1}$ is $C_1$-$C_6$ alkyl, $C_3$-$C_6$ cycloalkyl, $C_1$-$C_6$ alkyl substituted by one or more $R^{1-1-1}$ or $C_3$-$C_6$ cycloalkyl substituted by one or more $R^{1-1-2}$;

or, $R^3$ is

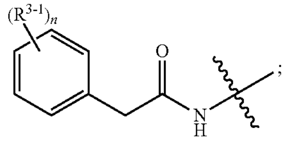

or, n is 1, 2 or 3;

or, $R^{3-1}$ is independently halogen, cyano, hydroxyl, $C_1$-$C_6$ alkoxy substituted by one or more $R^{3-1-2}$;

or, m is 0 or 1;

or, $R^2$ is oxo, halogen, cyano, isocyano, amino, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted by one or more $R^{2-26}$, $C_2$-$C_{10}$ alkynyl, $C_2$-$C_{10}$ alkynyl substituted by one or more $R^{2-27}$, $C_3$-$C_6$ cycloalkyl, “5- to 6-membered heterocycloalkyl with 1, 2 or 3 heteroatoms selected from one or more of N, O and S”, “3- to 4-membered heterocycloalkyl with 1 or 2 heteroatoms selected from one or more of N, O and S”, phenyl, phenyl substituted by one or more $R^{2-4}$, “5- to 6-membered heteroaryl with 1, 2 or 3 heteroatoms selected from one or more of N, O and S”, “5- to 6-membered heteroaryl with 1, 2 or 3 heteroatoms selected from one or more of N, O and S” substituted by one or more $R^{2-5}$, —(C═O)—$R^{2-2}$, —$OR^{2-6}$, —C(═O)$OR^{2-7}$, —$NR^{2-8}R^{2-9}$, or, “5- to 6-membered heterocycloalkyl with 1, 2 or 3 heteroatoms selected from one or more of N, O and S” substituted by one or more $R^{2-10}$;

or, $R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, “5- to 6-membered heteroaryl with 1, 2 or 3 heteroatoms selected from one or more of N, O and S”, or, —$OR^{2-6}$;

or, $R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, “3- to 6-membered heterocycloalkyl with 1, 2 or 3 heteroatoms selected from one or more of N, O and S” or, “3- to 6-membered heterocycloalkyl with 1, 2 or 3 heteroatoms selected from one or more of N, O and S” substituted by one or more $R^{2-6-3}$;

or, $R^{2-6-1}$ is independently halogen, hydroxyl, $C_1$-$C_6$ alkoxy, $C_3$-$C_6$ cycloalkyl, or, $C_6$-$C_{10}$ aryl substituted by one or more $R^{2-6-1-1}$;

or, $R^{1-1}$ is $C_1$-$C_6$ alkyl;

or, $R^{1-1-1}$ and $R^{1-1-2}$ are independently halogen;

or, $R^{2-1}$ is independently halogen, $C_3$-$C_6$ cycloalkyl or phenyl;

or, $R^{2-1}$ is independently halogen;

or, $R^{2-2}$ is $C_1$-$C_6$ alkyl, $C_3$-$C_6$ cycloalkyl, phenyl, $C_1$-$C_6$ alkyl substituted by one or more $R^{2-2-2}$;

or, $R^{2-4}$ and $R^{2-5}$ are independently halogen, $C_1$-$C_6$ alkyl, $C_1$-$C_6$ alkyl substituted by one or more $R^{2-4-3}$;

or, $R^{2-7}$ is $C_3$-$C_6$ cycloalkyl or phenyl.

5. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 1, wherein, when $R^3$ is

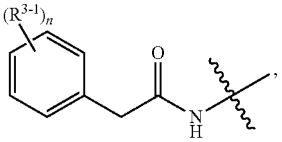

the $R^3$ is

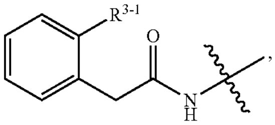
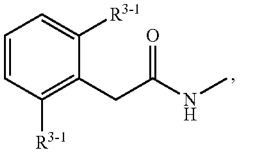
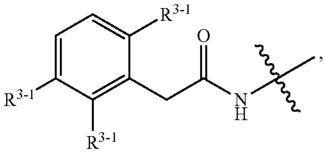
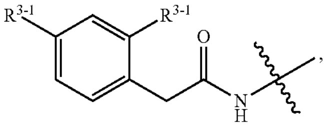
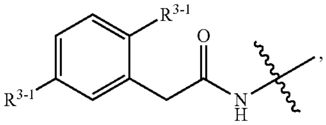
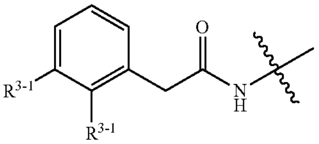
or
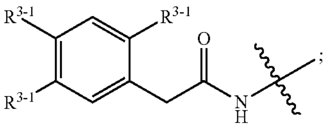

or, when $R^3$ is

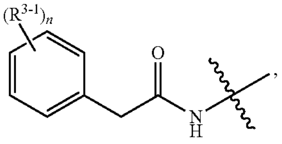

the $R^3$ is
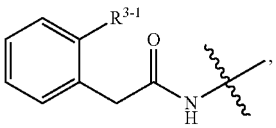
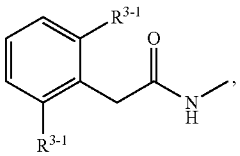
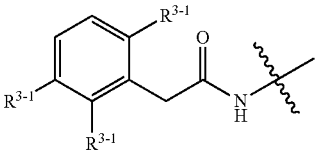
or
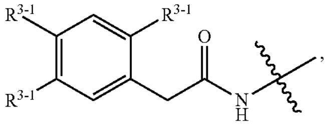
or, when $R^3$ is
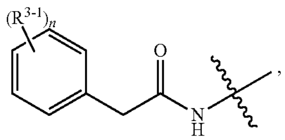
the $R^3$ is
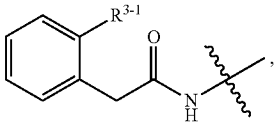
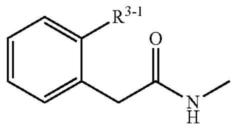
or
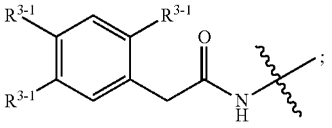
; or
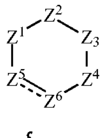
is
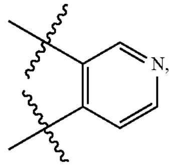
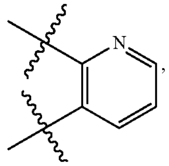
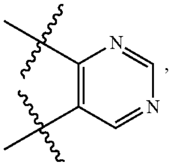
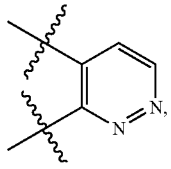
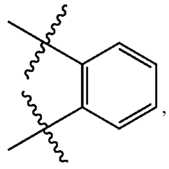
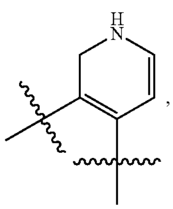
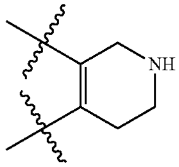
or
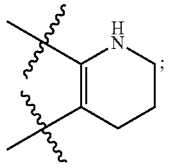
; or
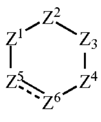
is
-continued
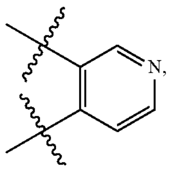
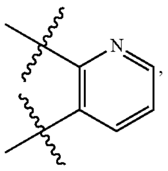
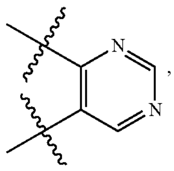
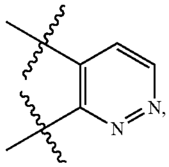
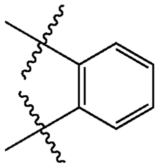
or
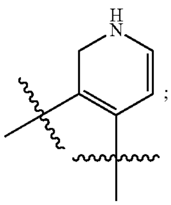
; or
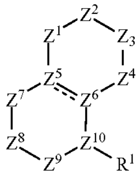
is
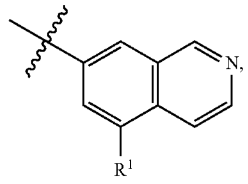
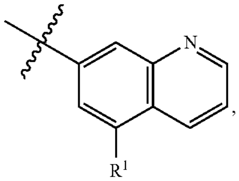
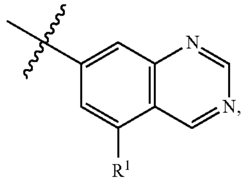
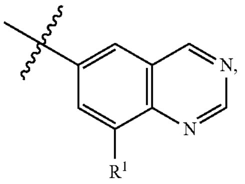
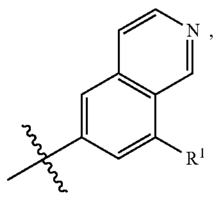
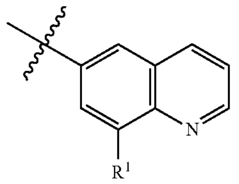
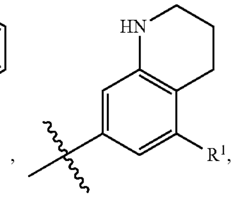
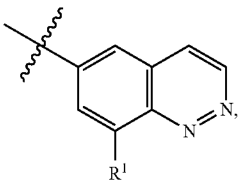
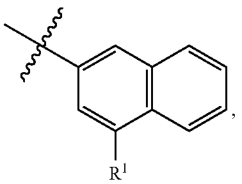
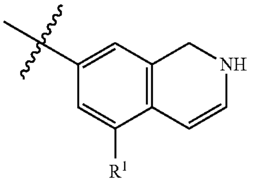
or -continued
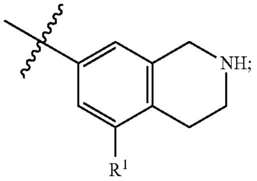 or,
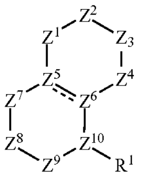 is 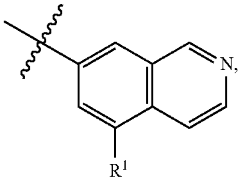
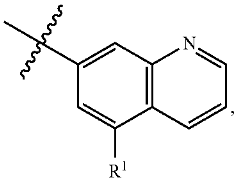, 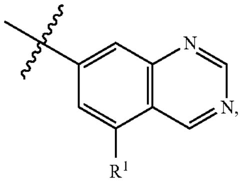
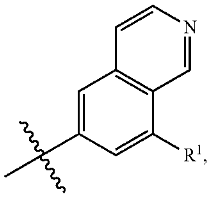 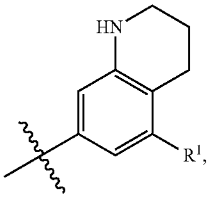
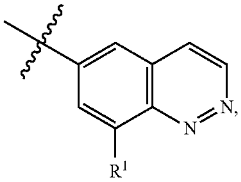 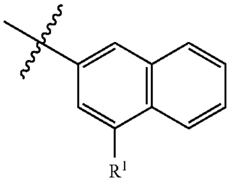 or
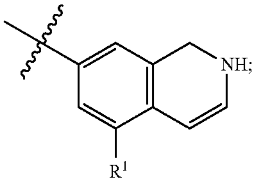 or,
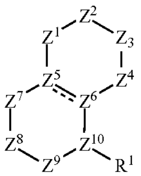 is 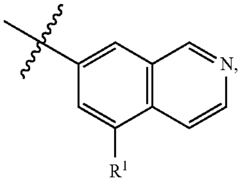
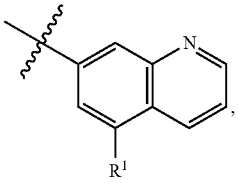, 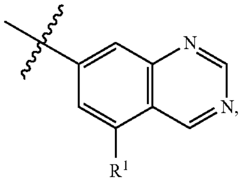
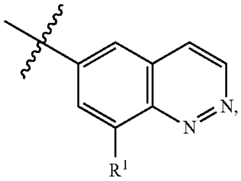 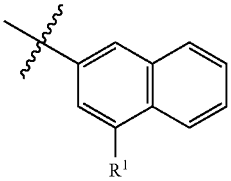 or
-continued
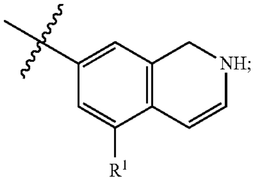
or, $R^2$ is oxo, methoxy, fluorine, chlorine, hydroxyl, amino, —$CH_2F$, difluoromethyl, trifluoromethyl, methyl, isopropyl, cyclopropyl, cyano, ethoxy, isopropoxy, monofluoromethoxy, difluoromethoxy, trifluoromethoxy,
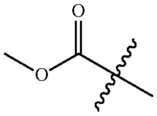, 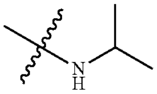, 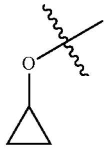,
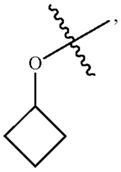, 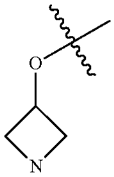, 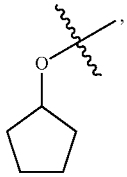, 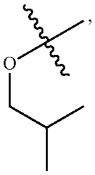,
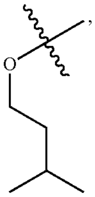, 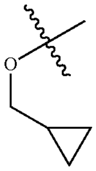, 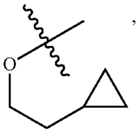, 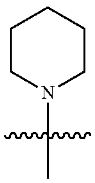, 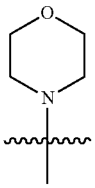
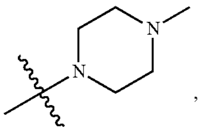, 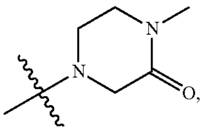
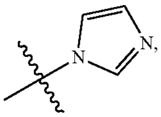 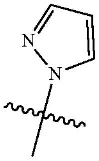, 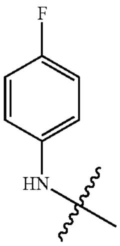,
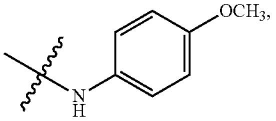 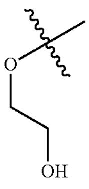, 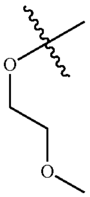, -continued
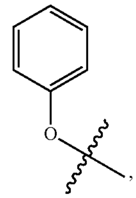, 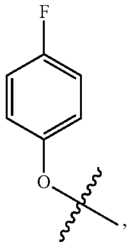, 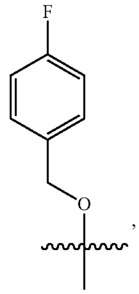, 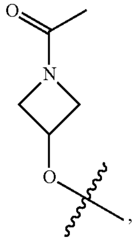, 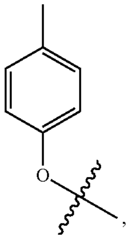, 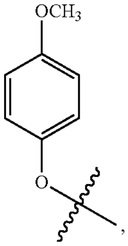, ethyl, dichloromethyl, 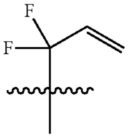, ethynyl, propynyl, 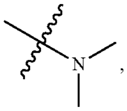, 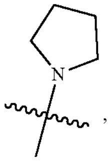, 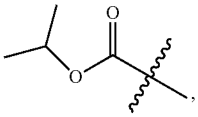, 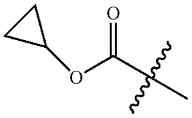, 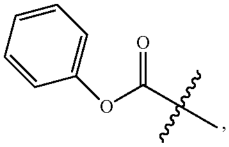, 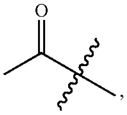, 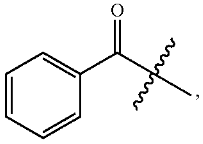, 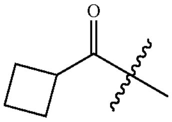, 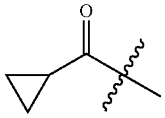, 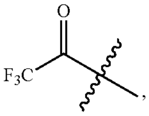, benzyl, 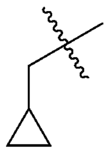, phenyl, 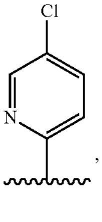, 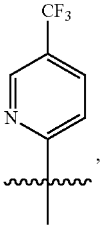, 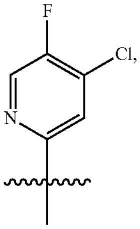, 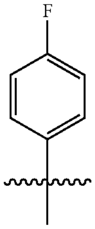, 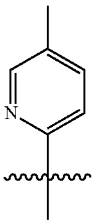, 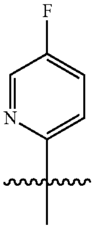 or
-continued
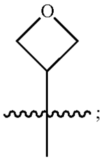;
or, $R^2$ is oxo, methoxy, fluorine, chlorine, hydroxyl, amino, —$CH_2F$, difluoromethyl, trifluoromethyl, methyl, isopropyl, cyclopropyl, cyano, ethoxy, isopropoxy, monofluoromethoxy, difluoromethoxy, trifluoromethoxy,
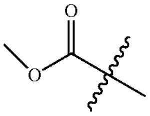, 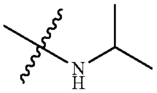, 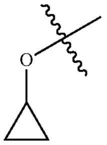, 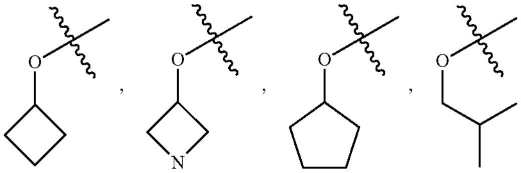, 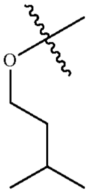, 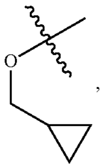, 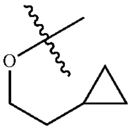, 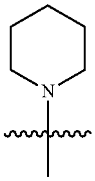, 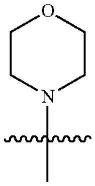, 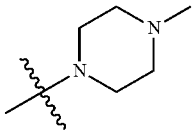, 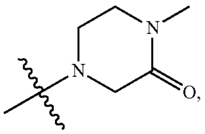, 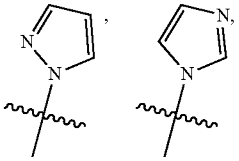, 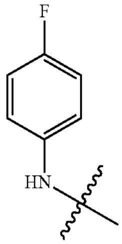, 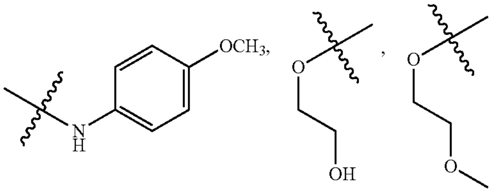, -continued
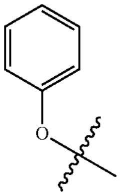,
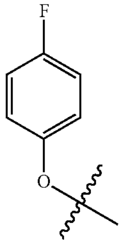,
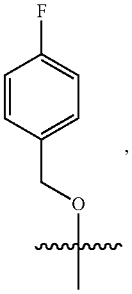,
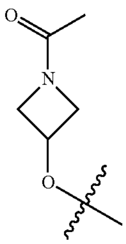,
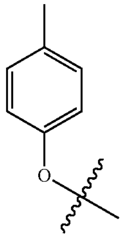 or 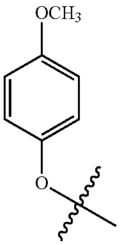;
or, $R^2$ is oxo, methoxy, fluorine, chlorine, hydroxyl, amino, difluoromethyl, trifluoromethyl, isopropyl, cyclopropyl, cyano, ethoxy, isopropoxy, difluoromethoxy,
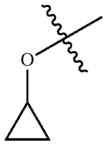,
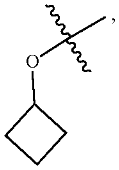,
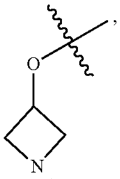,
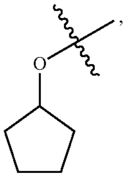,
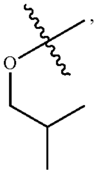
-continued
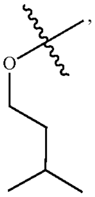,
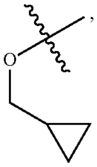,
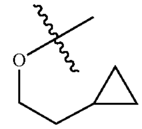,
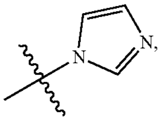,
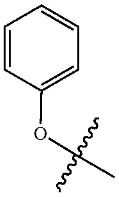,
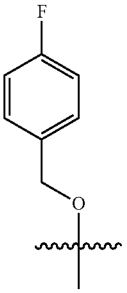,
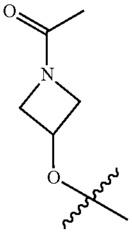,
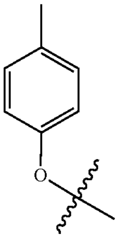, and -continued
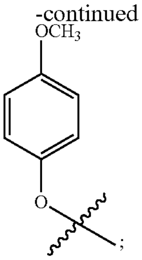
; or,
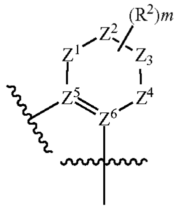
is
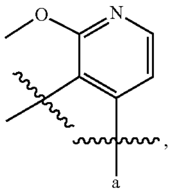
,
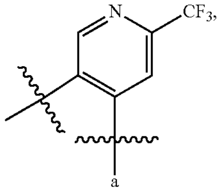
,
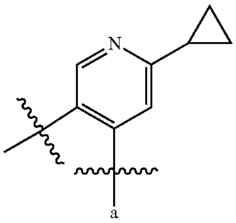
,
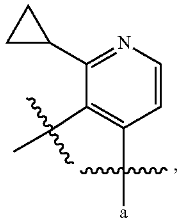
,
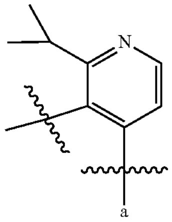
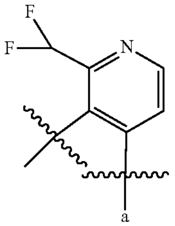
,
-continued
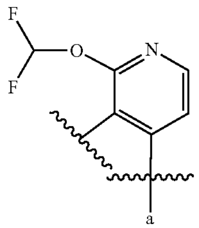
,
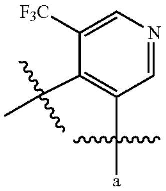
,
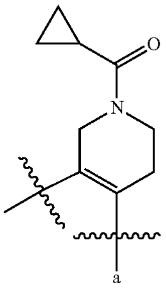
,
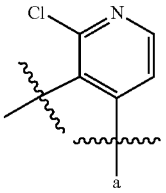
,
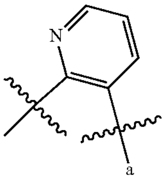
,
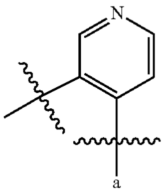
,
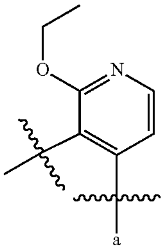
, -continued
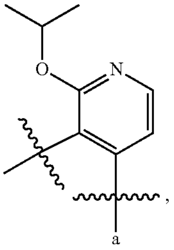
,
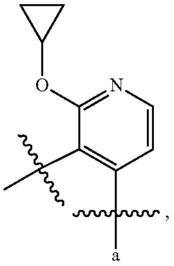
,
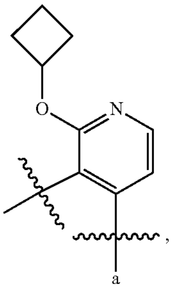
,
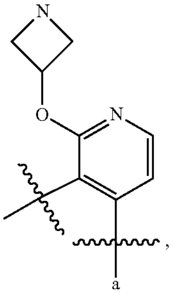
,
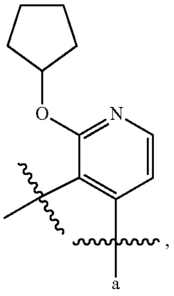
,
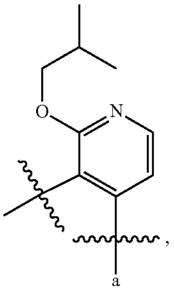
,
-continued
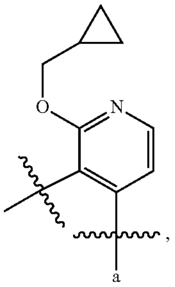
,
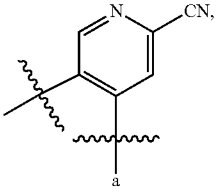
,
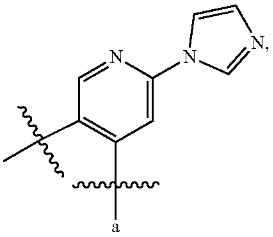
,
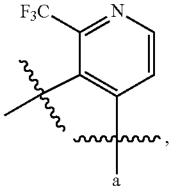
,
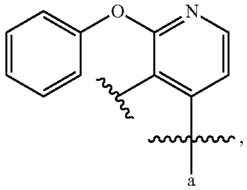
,
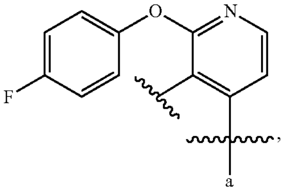
,
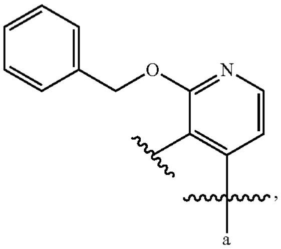
, -continued
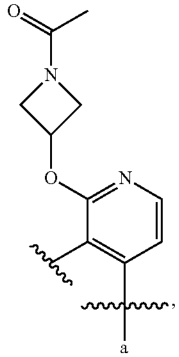
,
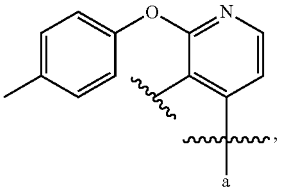
,
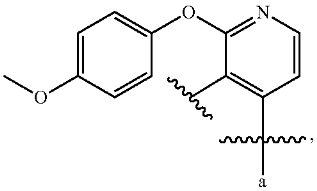
,
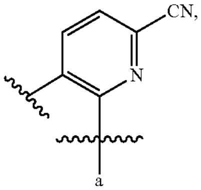
,
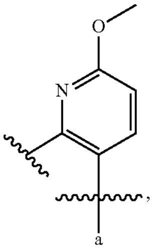
,
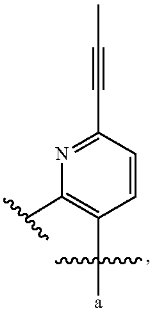
,
-continued
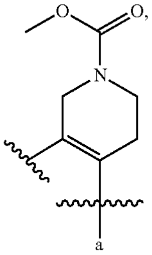
,
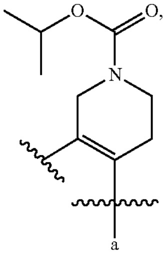
,
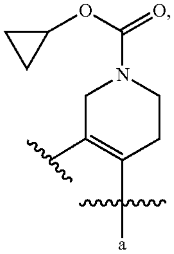
,
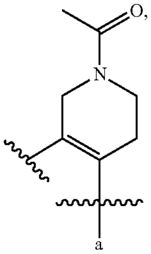
,
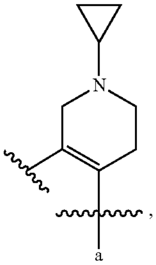
,
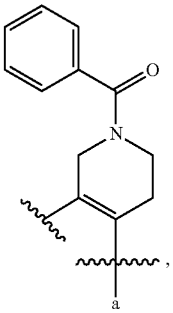
, -continued
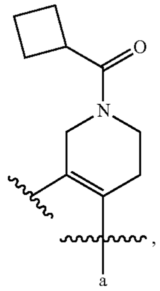
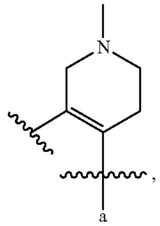
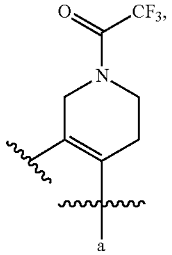
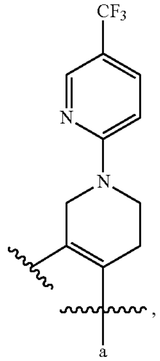
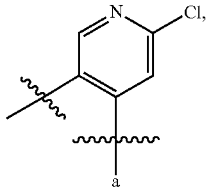
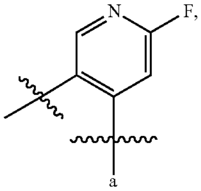
-continued
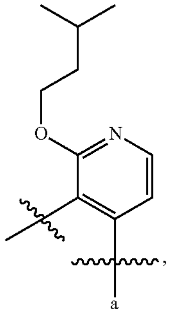
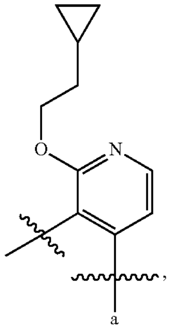
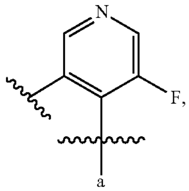
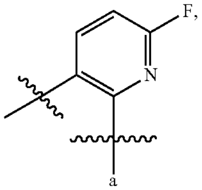
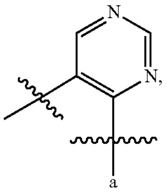
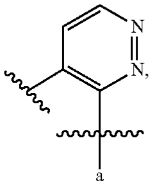
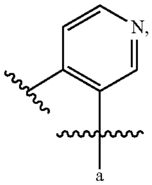

-continued
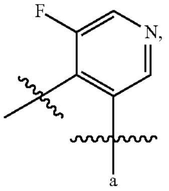
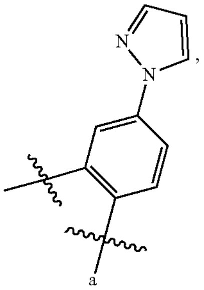
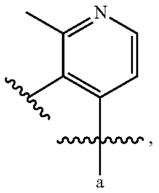
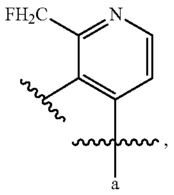
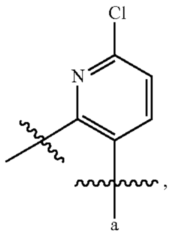
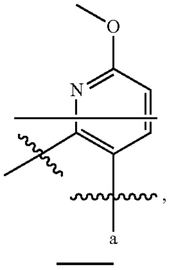
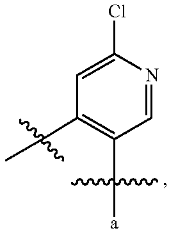
-continued
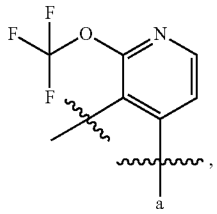
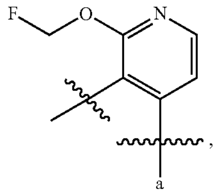
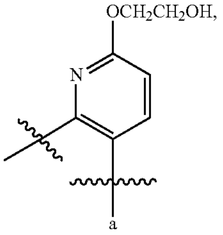
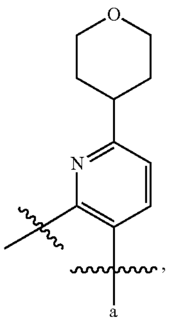
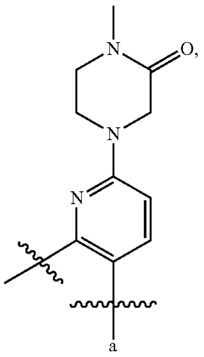
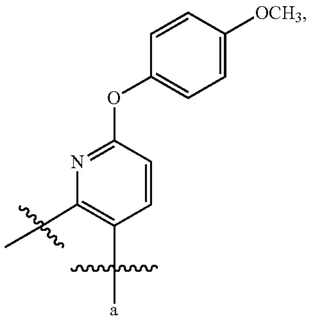

-continued
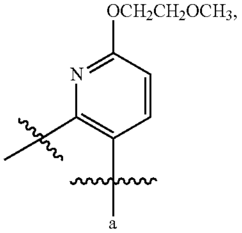
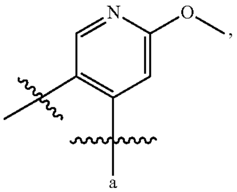
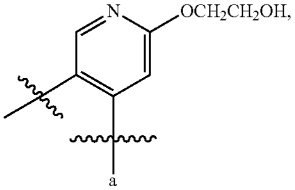
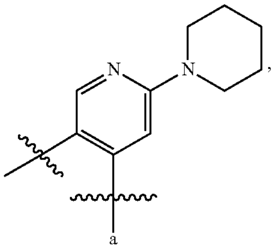
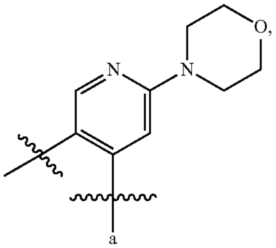
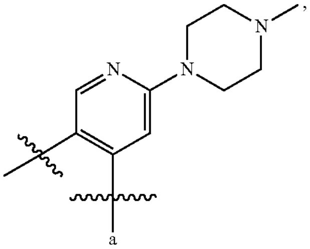
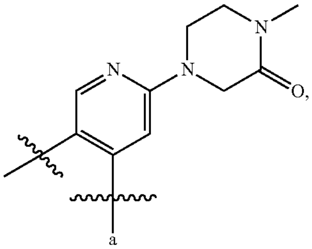
-continued
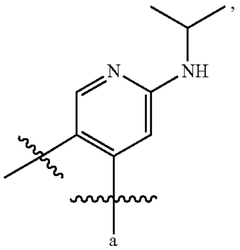
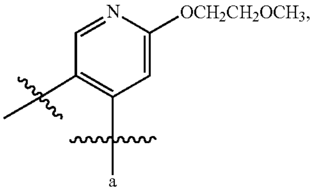
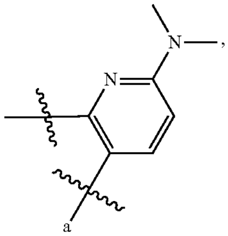
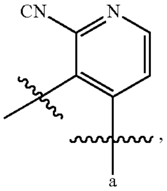
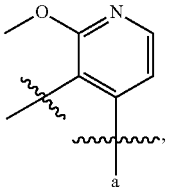
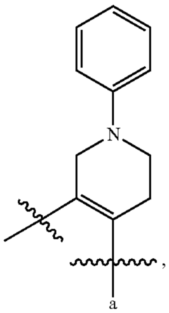
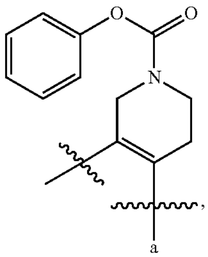

-continued
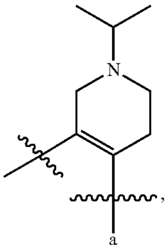,
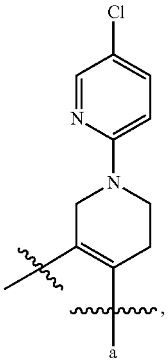,
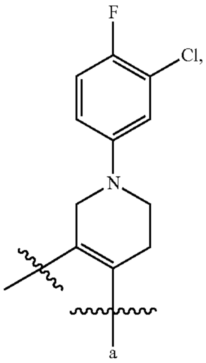,
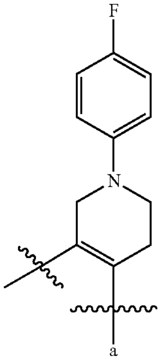,
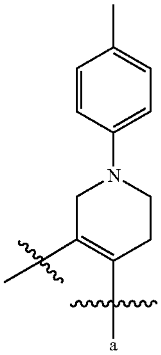,
-continued
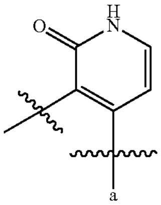,
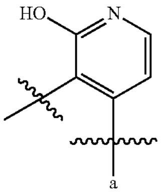,
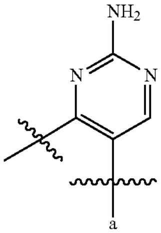,
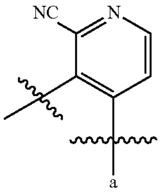,
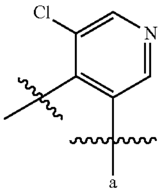,
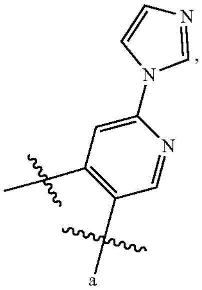,
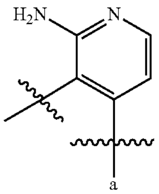, -continued
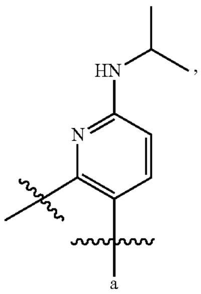
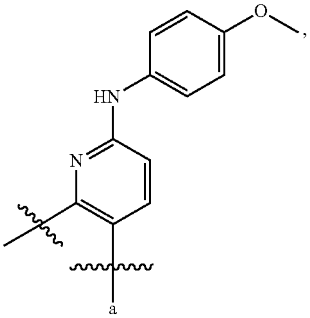
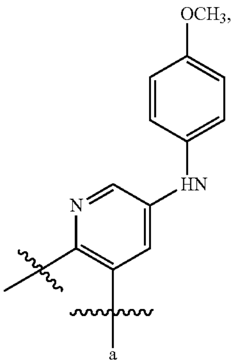
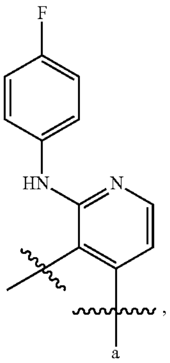
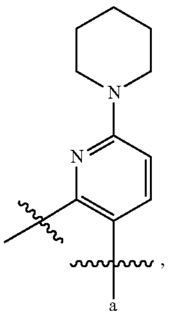
-continued
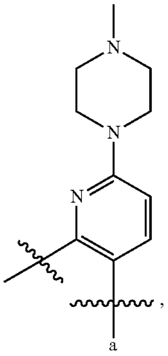
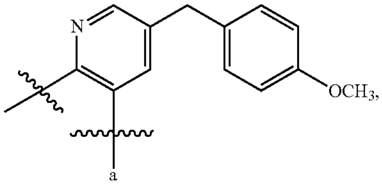
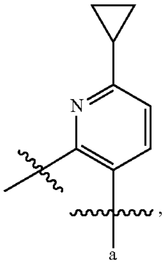
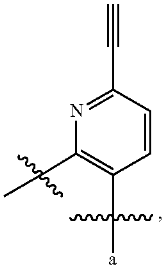
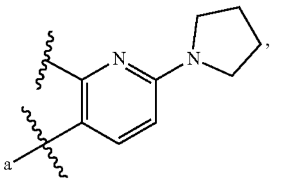
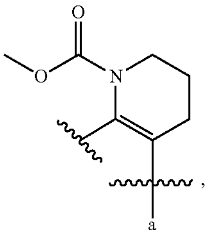
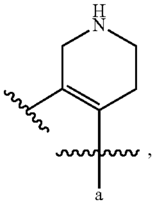

-continued
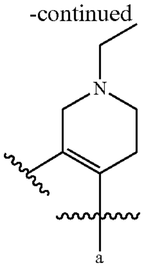
,
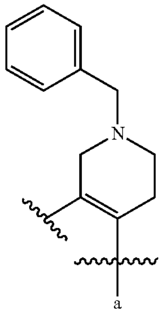
,
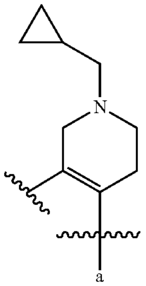
,
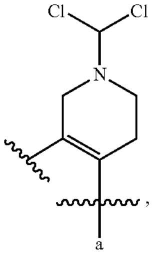
,
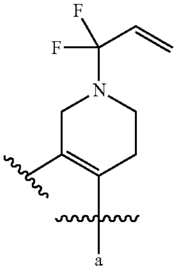
,
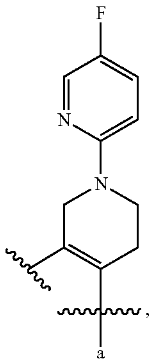
, or
-continued
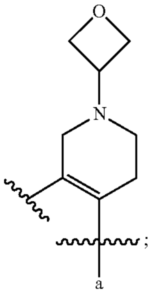
; or
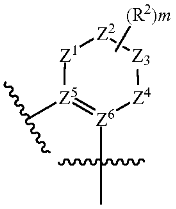
is
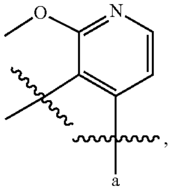
,
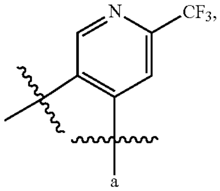
,
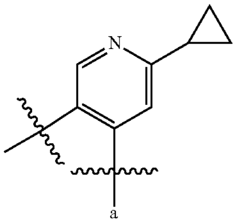
,
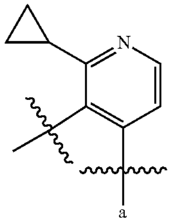
,
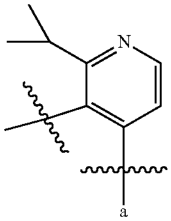

-continued
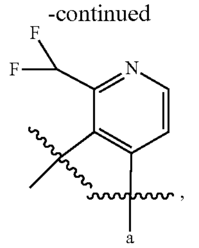
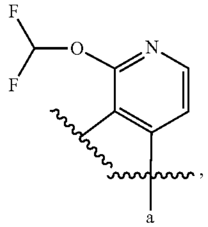
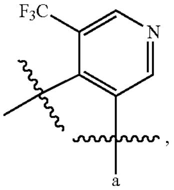
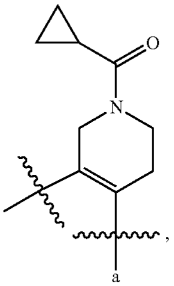
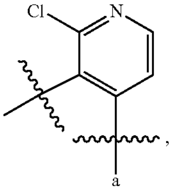
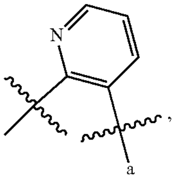
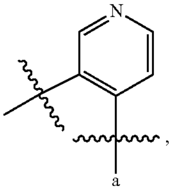
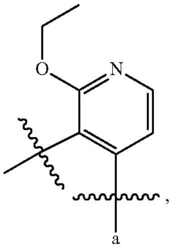
-continued
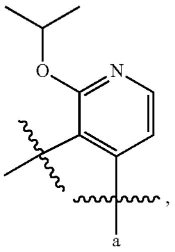
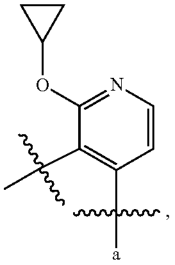
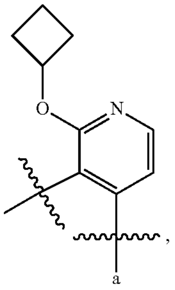
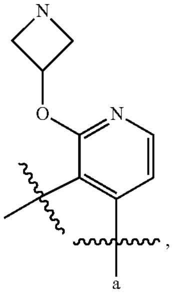
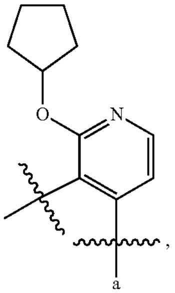
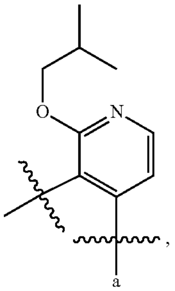

-continued
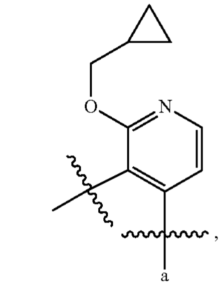
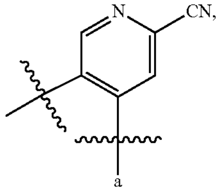
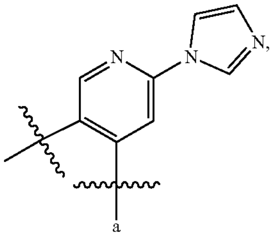
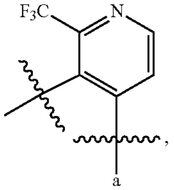
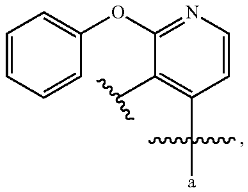
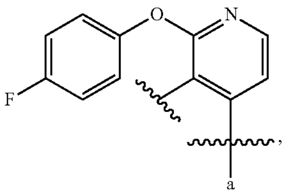
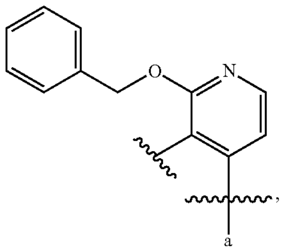
-continued
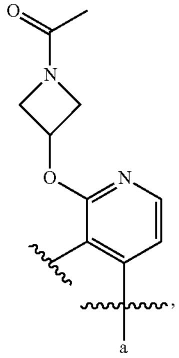
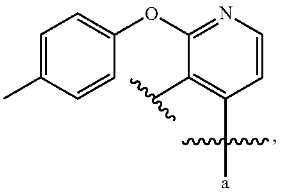
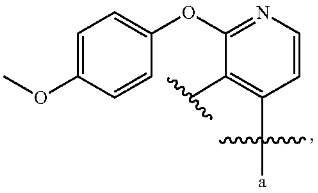
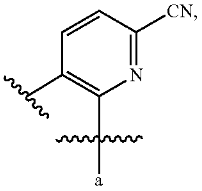
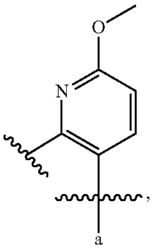
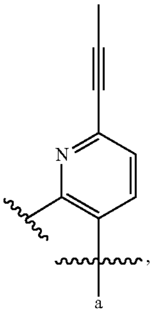

-continued
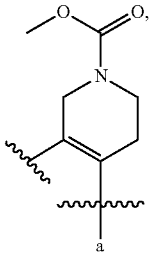
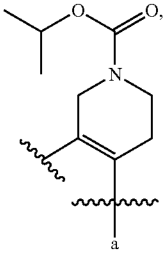
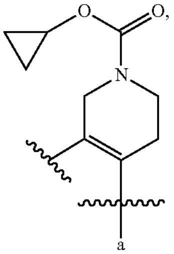
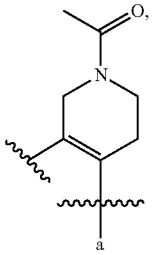
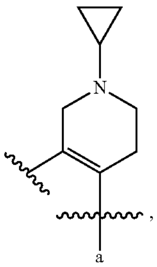
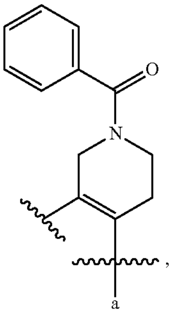
-continued
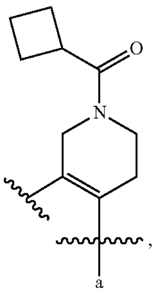
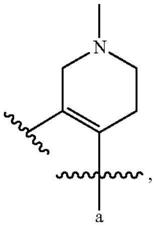
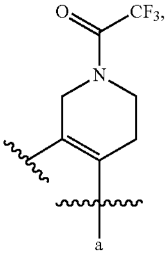
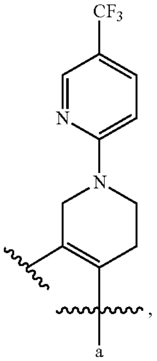
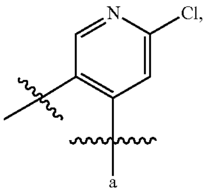
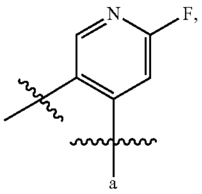

-continued
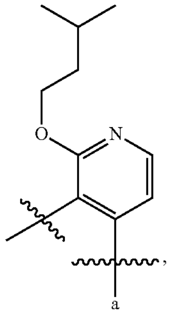
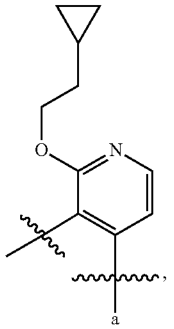
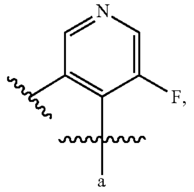
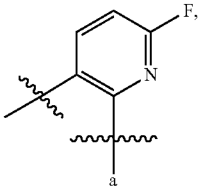
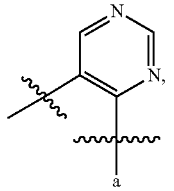
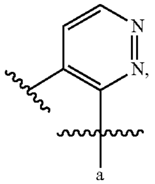
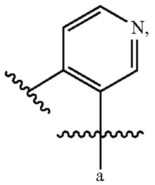
-continued
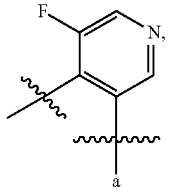
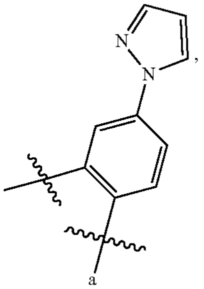
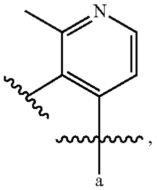
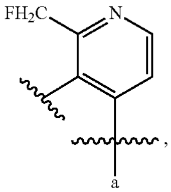
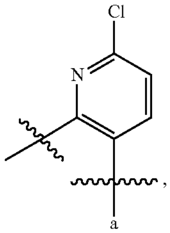
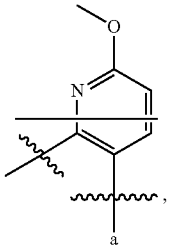
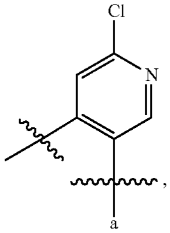

-continued
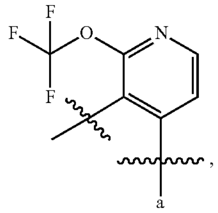
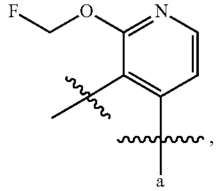
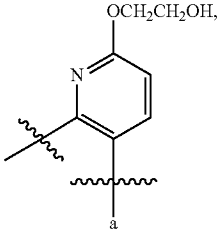
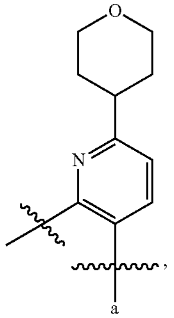
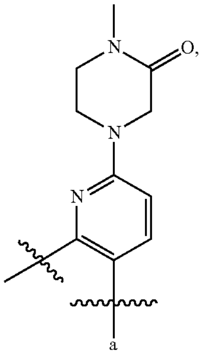
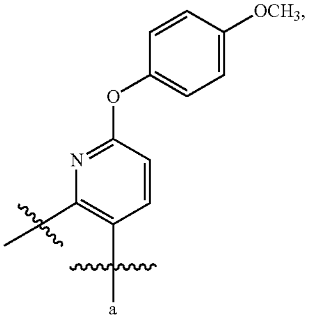
-continued
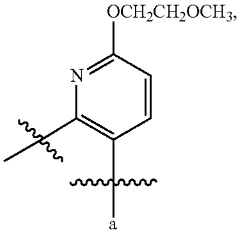
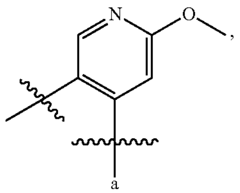
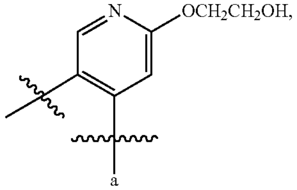
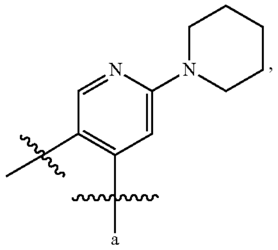
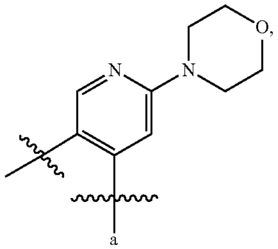
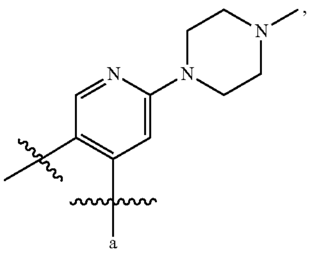
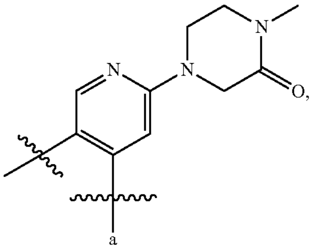

-continued
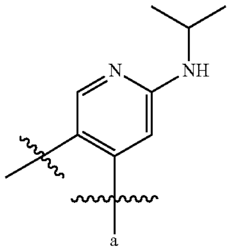
,
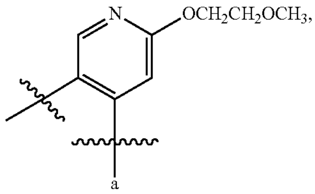
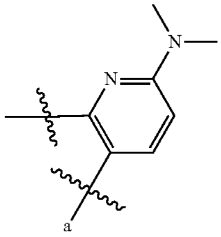
,
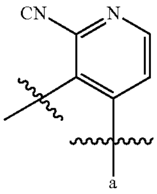
,
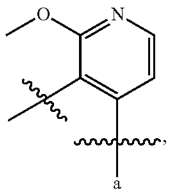
,
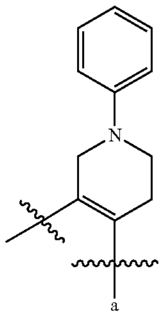
,
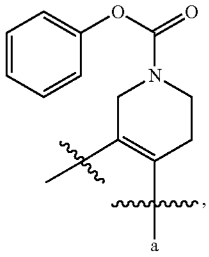
,
-continued
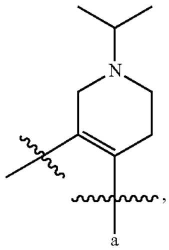
,
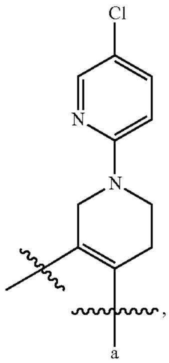
,
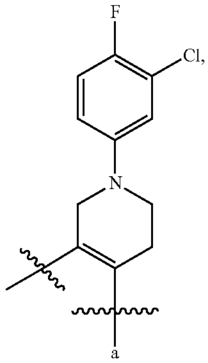
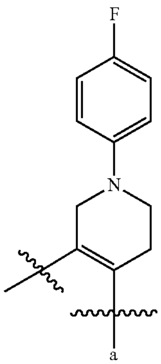
or
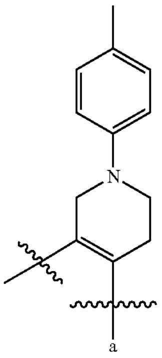
; or, -continued
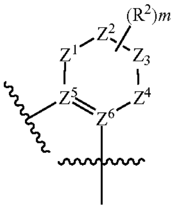
is
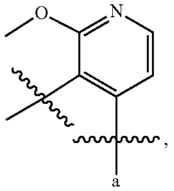
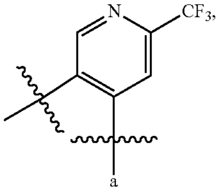
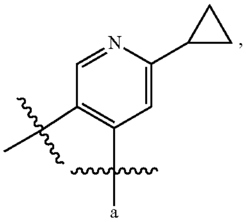
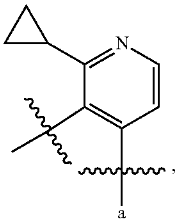
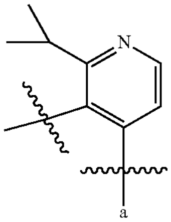
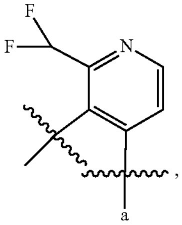
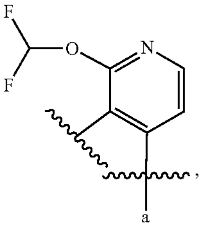
-continued
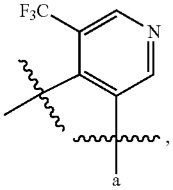
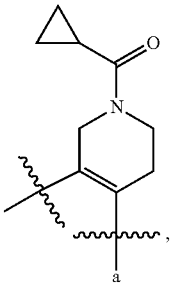
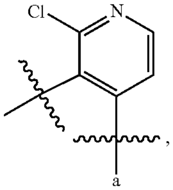
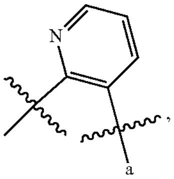
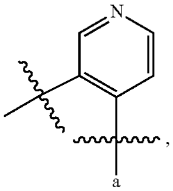
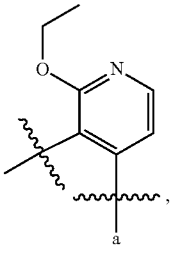
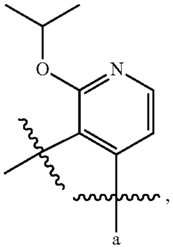

-continued
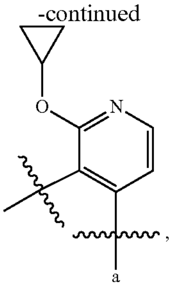
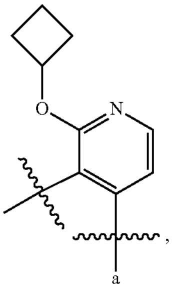
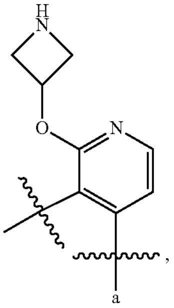
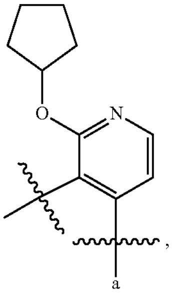
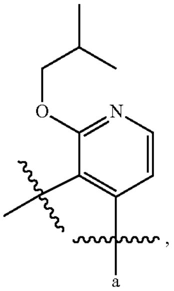
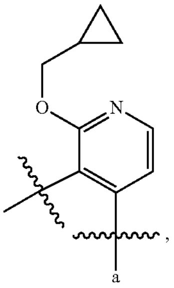
-continued
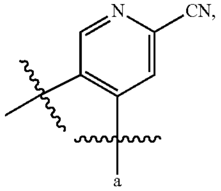
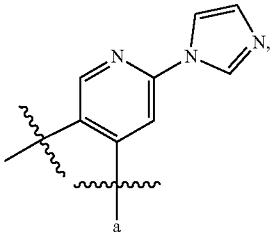
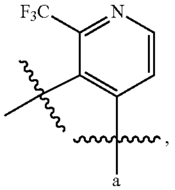
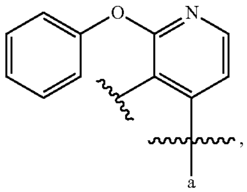
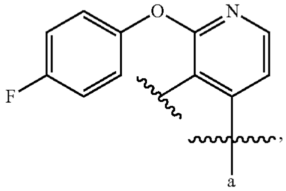
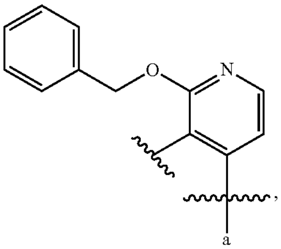
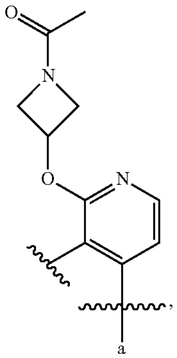

-continued
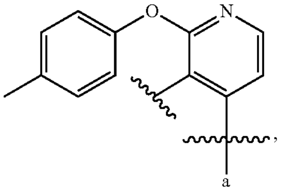,
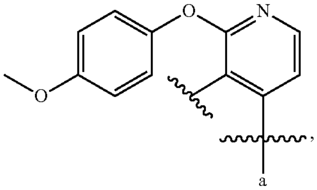,
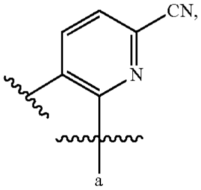,
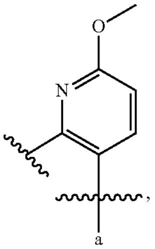,
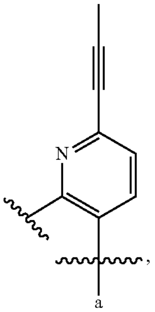,
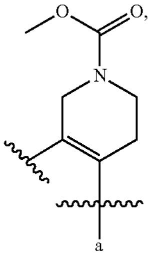,
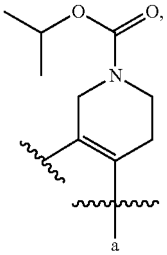,
-continued
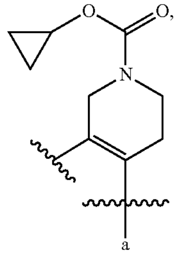,
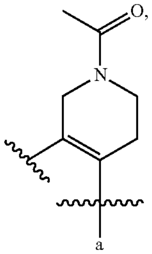,
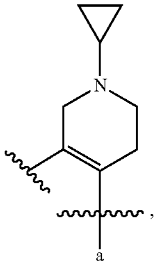,
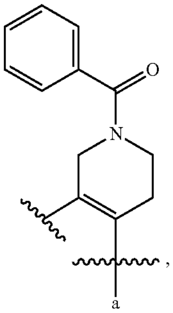,
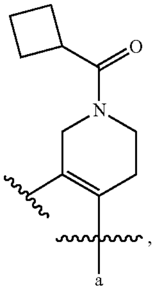,
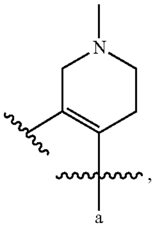, -continued

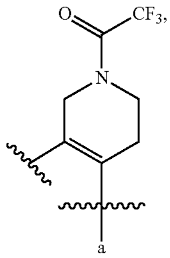

, or

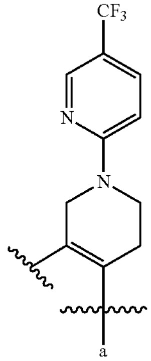

; or

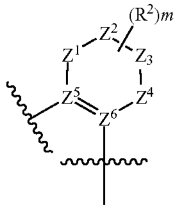

is

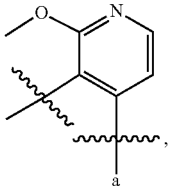

,

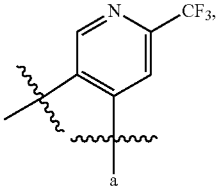

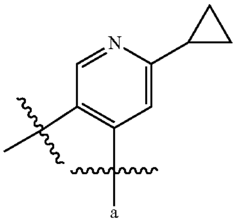

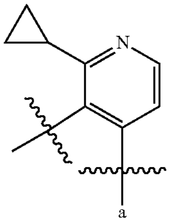

,

-continued

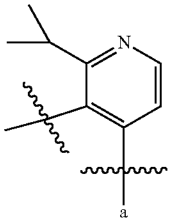

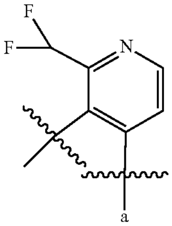

,

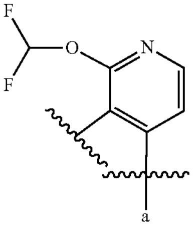

,

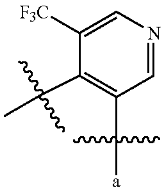

, or

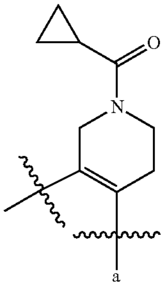

;

a end represents the position connected to $Z^{10}$.

6. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 1, wherein, the compound is any of the following schemes:

scheme 1:

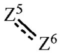

is a double bond;

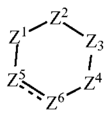

is benzene ring, 6-membered heteroaromatic ring having one or two heteroatoms N or 6-membered heterocycloalkene having one heteroatom N;

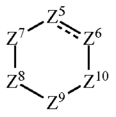

is benzene ring;

$R^1$ is

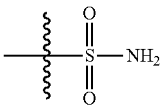 or 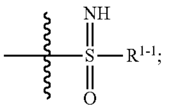

$R^{1-1}$ is $C_1$-$C_6$ alkyl, $C_3$-$C_6$ cycloalkyl, $C_1$-$C_6$ alkyl substituted by one or more $R^{1-1-1}$ or $C_3$-$C_6$ cycloalkyl substituted by one or more $R^{1-1-2}$;

$R^{1-1-1}$ and $R^{1-1-2}$ are independently halogen;

$R^3$ is

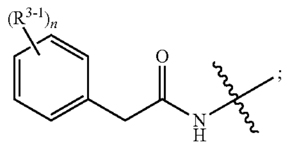

n is 1, 2 or 3;

$R^{3-1}$ is independently halogen, cyano or hydroxyl;

m is 0, 1;

$R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heterocycloalkyl with 1, 2 or 3 heteroatoms selected from one or more of N, O and S", "5- to 6-membered heteroaryl with 1, 2 or 3 heteroatoms selected from one or more of N, O and S", —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$;

$R^{2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently halogen, hydroxyl, $C_3$-$C_6$ cycloalkyl, or, $C_6$-$C_{10}$ aryl substituted by one or more $R^{2-6-1-1}$;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-7}$ is $C_1$-$C_6$ alkyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{2-10}$ is independently $C_1$-$C_6$ alkyl or oxo;

scheme 2:

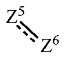

is a double bond;

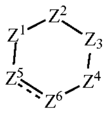

is benzene ring, 6-membered heteroaromatic ring having one or two heteroatoms N or 6-membered heterocycloalkene having one heteroatom N;

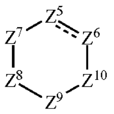

is benzene ring;

$R^1$ is

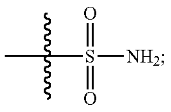 [SMILES: *S(N)(=O)=O]

$R^3$ is

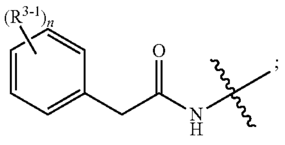

n is 1, 2 or 3;

$R^{3-1}$ is independently halogen, cyano or hydroxyl;

m is 0 or 1;

$R^2$ is oxo, halogen, cyano, amino, $C_1$-$C_{10}$ alkyl, $C_1$-$C_{10}$ alkyl substituted by one or more $R^{2-1}$ $C_3$-$C_6$ cycloalkyl, "5- to 6-membered heteroaryl with 1, 2 or 3 heteroatoms selected from one or more of N, O and S, or, —$OR^{2-6}$;

$R^{2-1}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently halogen, $C_3$-$C_6$ cycloalkyl, or, $C_6$-$C_{10}$ aryl substituted by one or more $R^{2-6-1-1}$; $R^{2-6-1-1}$ is independently halogen;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-10}$ is independently $C_1$-$C_6$ alkyl or oxo;

scheme 3:

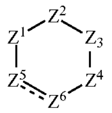

is benzene ring, or 6-membered heteroaromatic ring having one or two heteroatoms N;

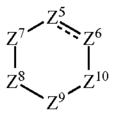

is benzene ring;

$R^1$ is

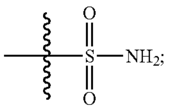 [SMILES: *S(N)(=O)=O]

$R^3$ is

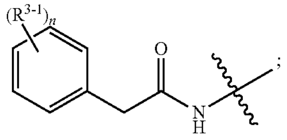

n is 1, 2 or 3;

$R^{3-1}$ is independently halogen, cyano or hydroxyl;

m is 0 or 1;

$R^2$ is oxo, halogen, cyano, $C_1$-$C_{10}$ alkyl or $C_1$-$C_{10}$ alkyl substituted by one or more $R^{2-1}$, $C_3$-$C_6$ cycloalkyl, "5- to 6-membered heteroaryl with 1, 2 or 3 heteroatoms selected from one or more of N, O and S", or, —$OR^{2-6}$;

$R^{2-1}$ is independently halogen;

$R^{2-6}$ is $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently halogen, $C_3$-$C_6$ cycloalkyl, or, $C_6$-$C_{10}$ aryl substituted by one or more $R^{2-6-1-1}$; $R^{2-6-1-1}$ is independently halogen;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

scheme 4:

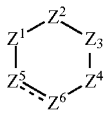

is benzene ring, or 6-membered heteroaromatic ring having one heteroatom N;

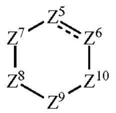

is benzene ring;

$R^1$ is

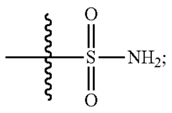 [SMILES: *S(N)(=O)=O]

$R^3$ is

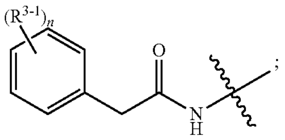

n is 1, 2 or 3;

$R^{3-1}$ is independently halogen, cyano or hydroxyl;

m is 0 or 1;

$R^2$ is chlorine, cyano, $C_1$-$C_{10}$ alkyl, $C_1$-$C_{10}$ alkyl substituted by one or more $R^{2-1}$, $C_3$-$C_6$ cycloalkyl, "5- to 6-membered heteroaryl with 1, 2 or 3 heteroatoms selected from one or more of N, O and S", or, —$OR^{2-6}$;

$R^{2-1}$ is independently halogen;

$R^{26}$ is $C_1$-$C_4$ alkyl, $C_1$-$C_2$ alkyl substituted by one or more $R^{2-6-1}$, $C_3$-$C_6$ cycloalkyl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$; and when $R^2$ is chlorine, $R^2$ is located on $Z^1$ or $Z^4$;

$R^{2-6-1}$ is independently halogen, $C_3$-$C_6$ cycloalkyl, or, $C_6$-$C_{10}$ aryl substituted by one or more $R^{2-6-1-1}$;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

scheme 5:

wherein,

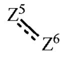

is a double bond;

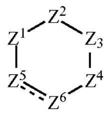

is benzene ring, 6-membered heteroaromatic ring having one or two heteroatoms N or 6-membered heterocycloalkene having one heteroatom N;

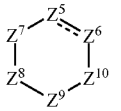

is benzene ring;

$R^1$ is

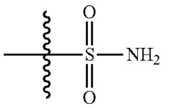 or 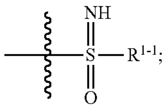

$R^{1-1}$ is $C_1$-$C_6$ alkyl;

$R^3$ is

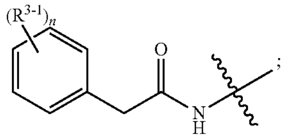

n is 1, 2 or 3;

$R^{3-1}$ is independently halogen, cyano, hydroxyl, or, $C_1$-$C_6$ alkoxy substituted by one or more $R^{3-1-2}$;

m is 0 or 1;

$R^2$ is oxo, halogen, cyano, amino, isocyano, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted by one or more $R^{2-26}$, $C_2$-$C_{10}$ alkynyl, $C_2$-$C_{10}$ alkynyl substituted by one or more $R^{2-27}$, $C_3$-$C_6$ cycloalkyl, "5- to 6-membered heterocycloalkyl with 1, 2 or 3 heteroatoms selected from one or more of N, O and S", "3- to 4-membered heterocycloalkyl with 1 or 2 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)-$R^{2-2}$, —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$;

$R^{2-1}$ is independently halogen, $C_3$-$C_6$ cycloalkyl or phenyl;

$R^{2-2}$ is $C_1$-$C_6$ alkyl, $C_3$-$C_6$ cycloalkyl, phenyl, or, $C_1$-$C_6$ alkyl substituted by one or more $R^{2-2-2}$; $R^{2-2-2}$ is independently halogen;

$R^{2-4}$ and $R^{2-5}$ are independently halogen, $C_1$-$C_6$ alkyl, $C_1$-$C_6$ alkyl substituted by one or more $R^{2-4-3}$; $R^{2-4-3}$ is halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently halogen, hydroxyl, $C_1$-$C_6$ alkoxy, $C_3$-$C_6$ cycloalkyl, or, $C_6$-$C_{10}$ aryl substituted by one or more $R^{2-6-1-1}$;

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-1-2}$ is independently $C_1$-$C_6$ alkyl;

$R^{2-7}$ is $C_1$-$C_6$ alkyl, $C_3$-$C_6$ cycloalkyl or phenyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{2-10}$ is independently $C_1$-$C_6$ alkyl or oxo;

$R^{2-26}$ and $R^{2-27}$ are independently halogen or $C_1$-$C_6$ alkyl;

scheme 6:

the compound represented by formula I is any of the following compound:

1

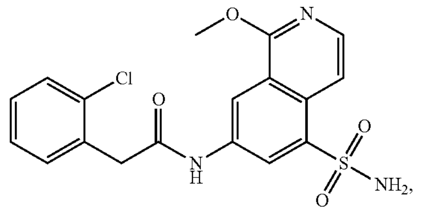

2

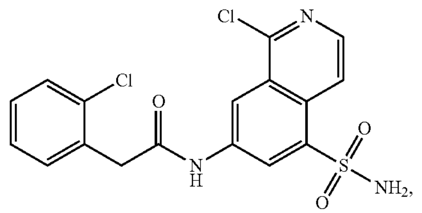

3

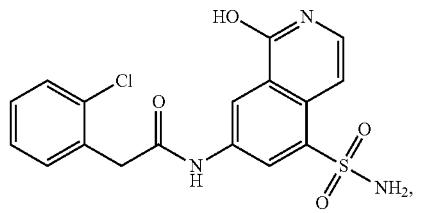

-continued
4
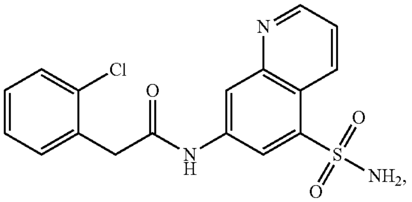
5
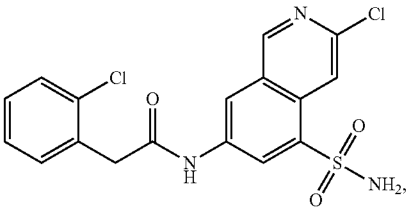
6
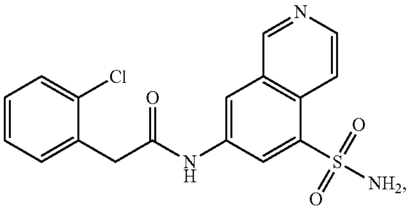
7
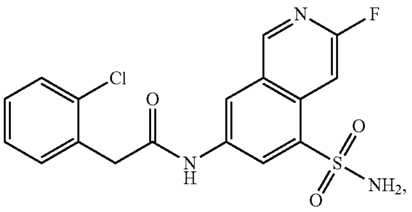
8
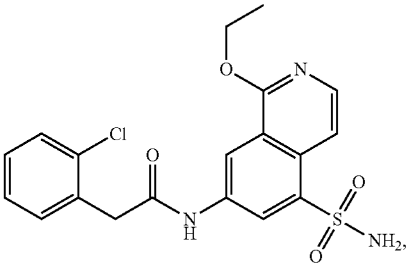
9
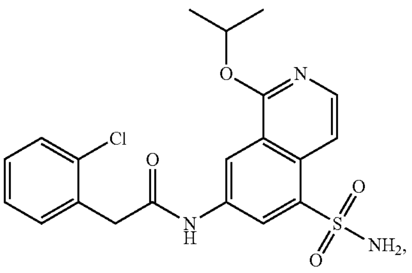
-continued
10
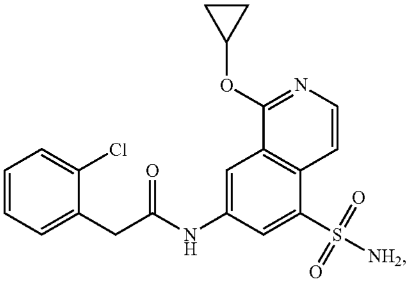
11
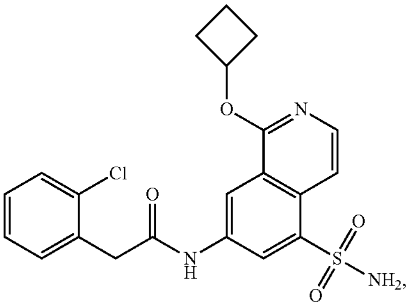
12
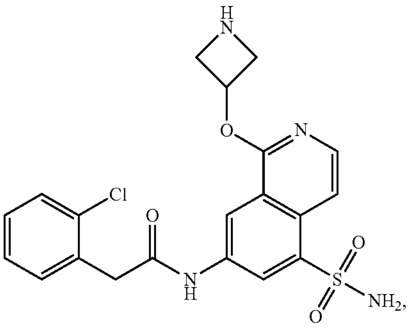
13
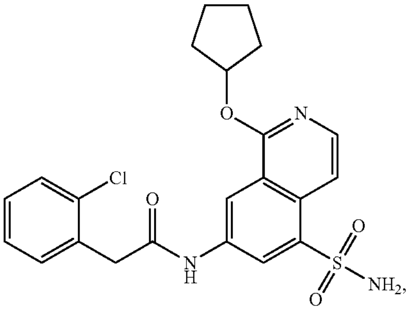
14
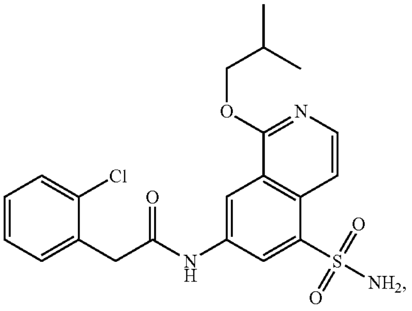

-continued
15
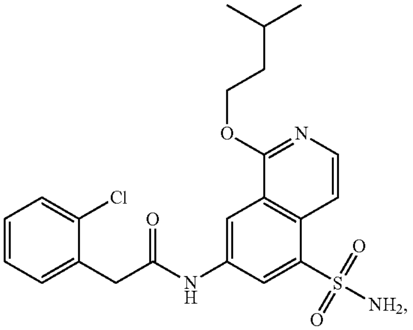
16
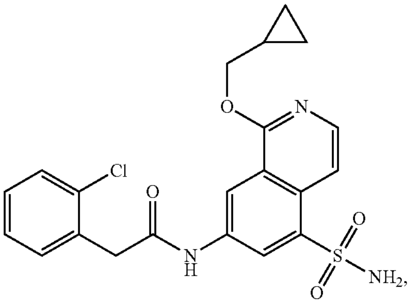
17
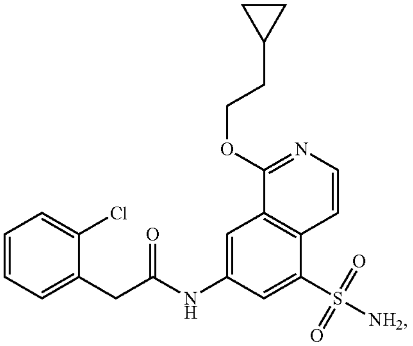
18
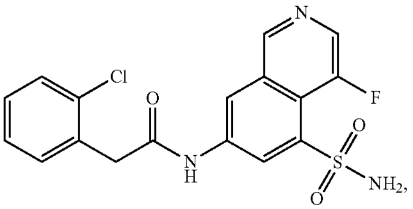
19
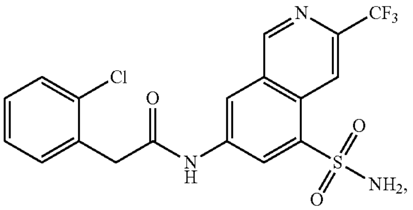
20
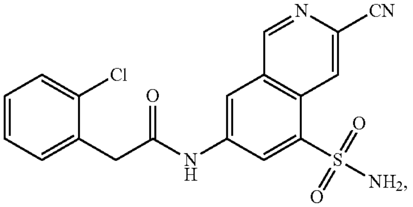
-continued
21
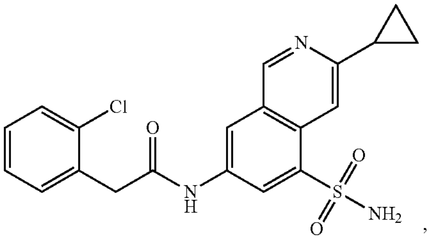
22
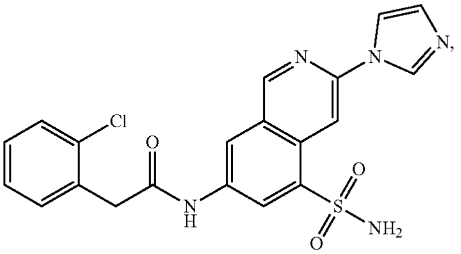
23
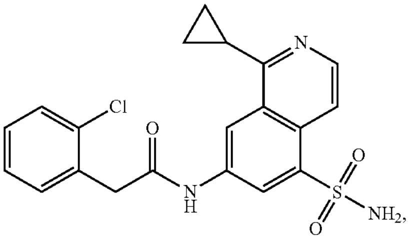
24
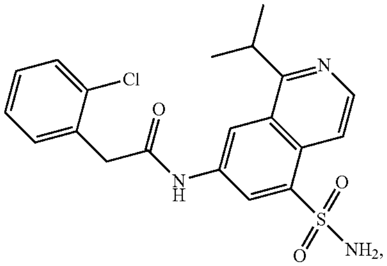
25
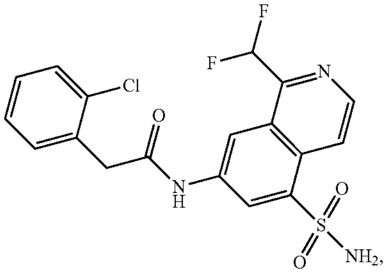
26
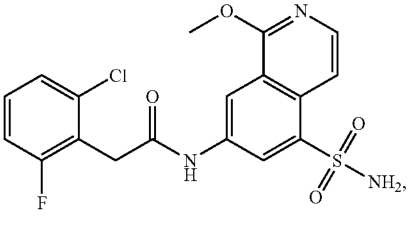

-continued
27
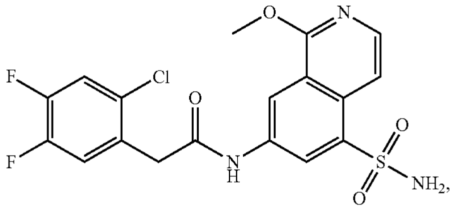
28
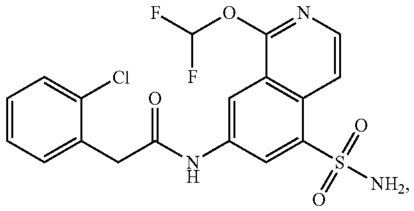
29
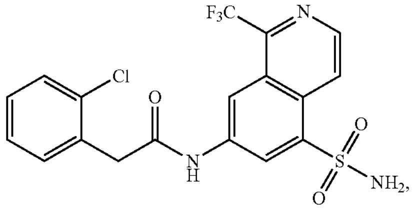
30
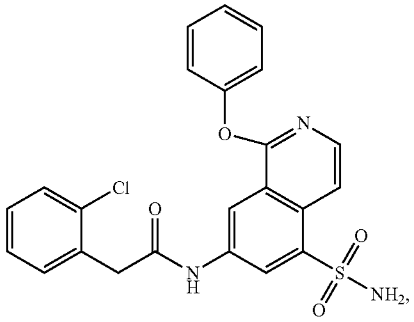
31
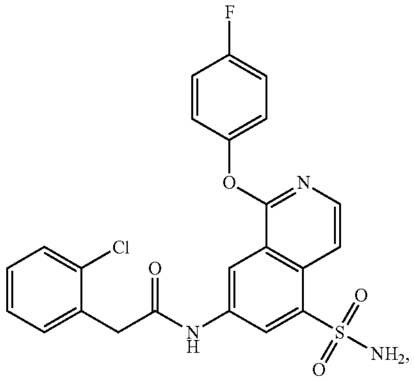
-continued
32
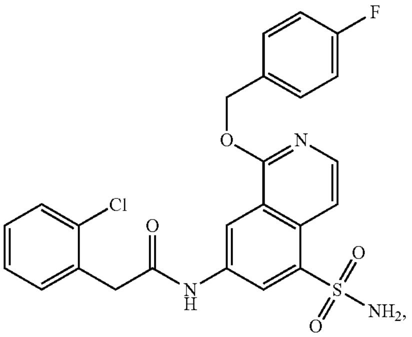
33
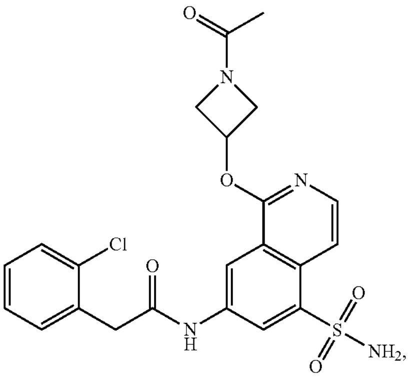
34
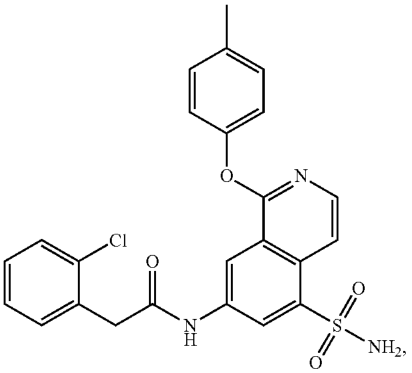
35
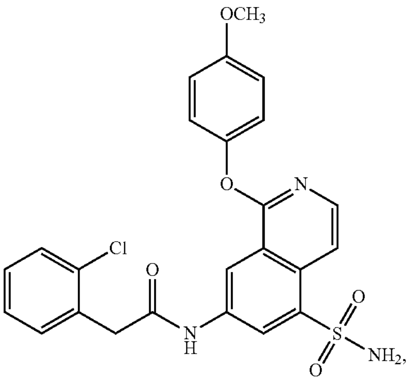

-continued
36
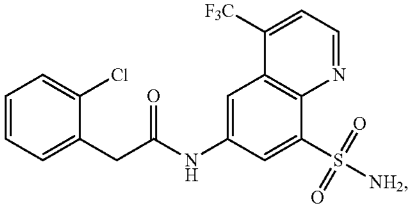
37
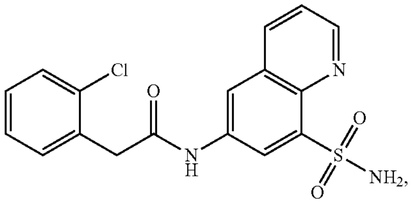
38
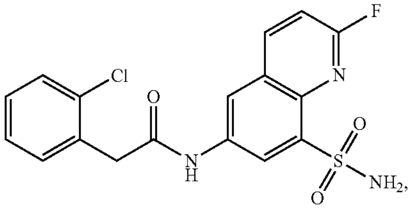
39
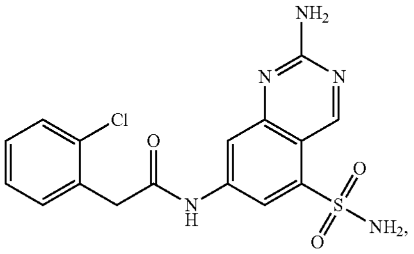
40
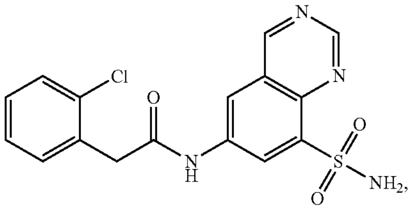
41
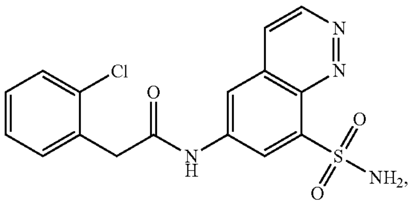
42
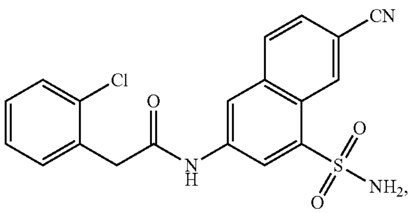
-continued
43
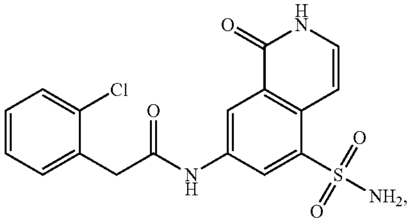
44
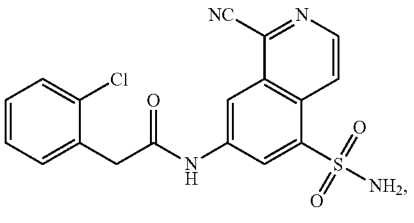
45
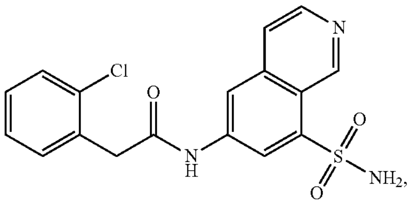
46
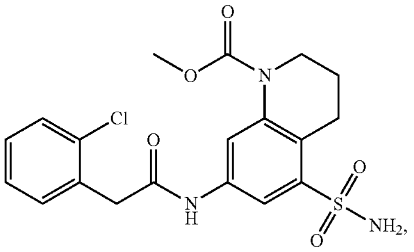
47
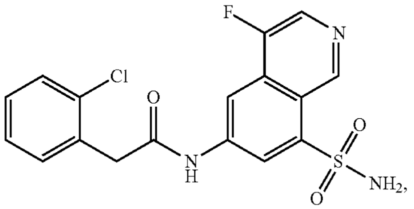
48
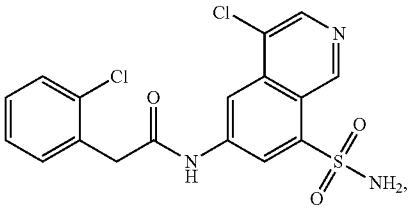

-continued
49
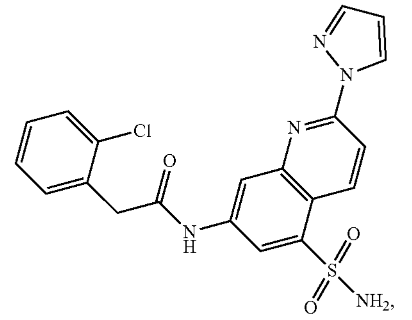
50
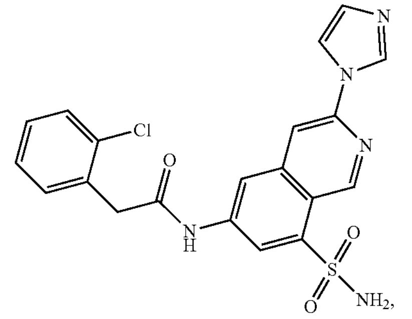
51
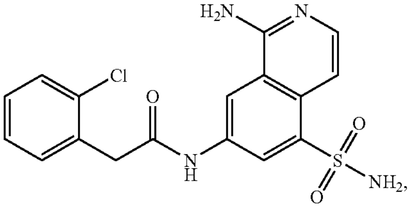
52
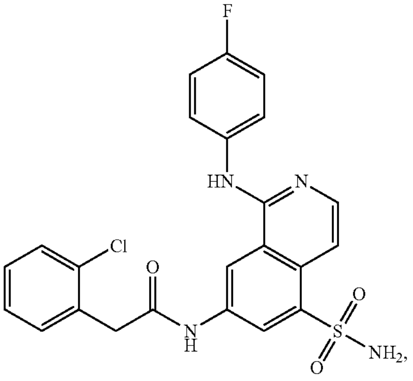
53
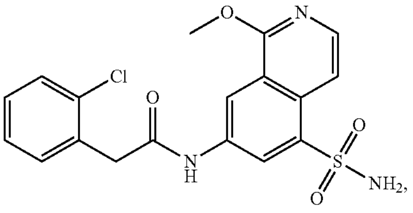
-continued
54
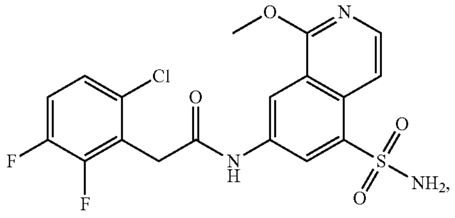
55
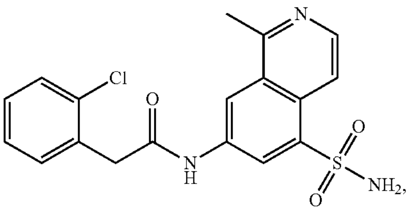
56
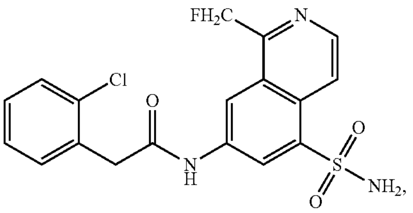
57
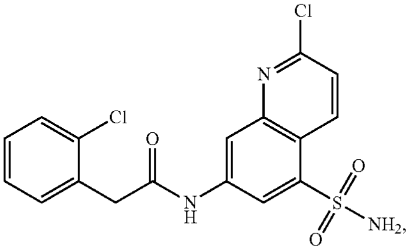
58
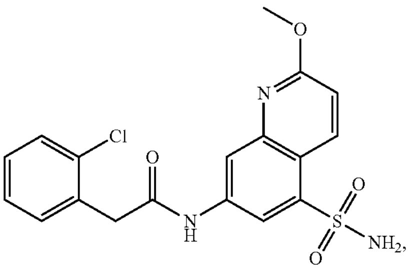
59
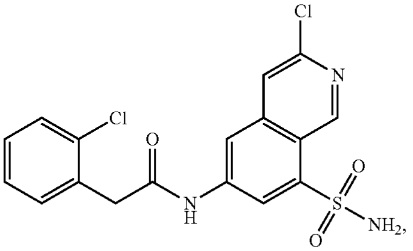

-continued
60
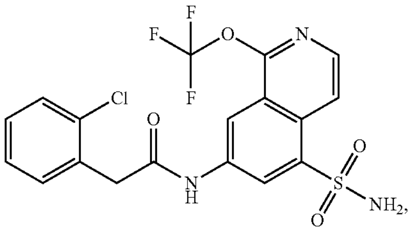
61
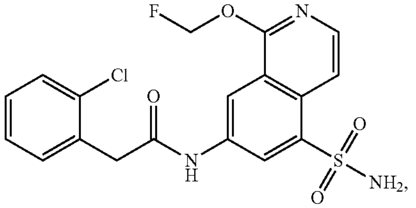
62
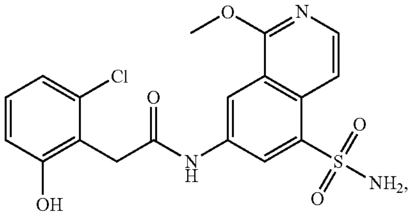
63
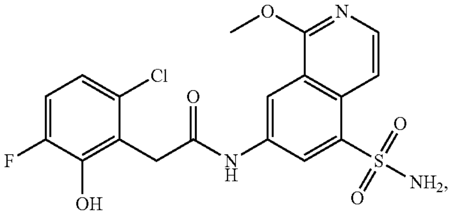
64
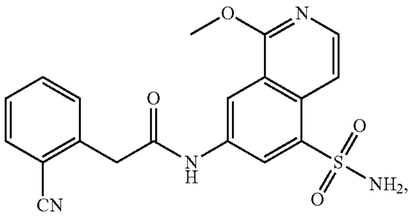
65
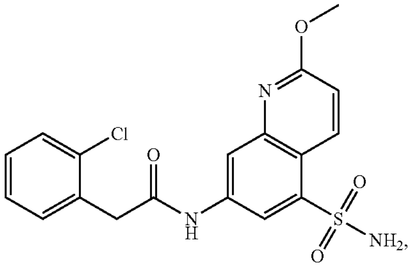
-continued
66
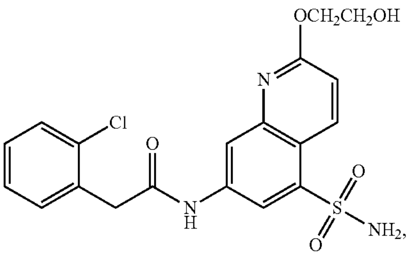
67
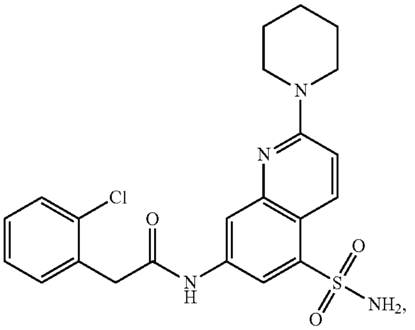
68
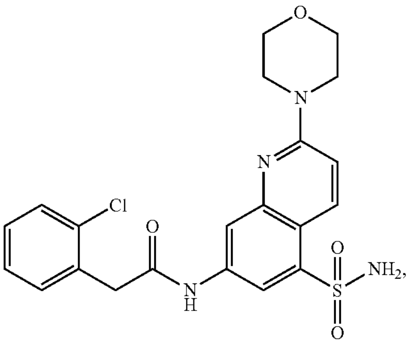
69
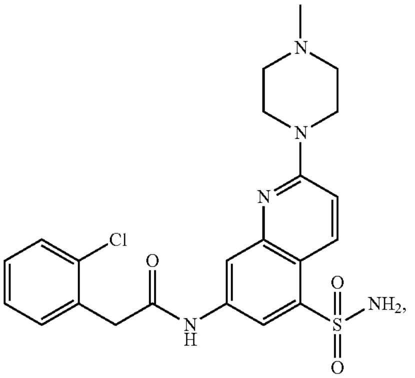

-continued
70
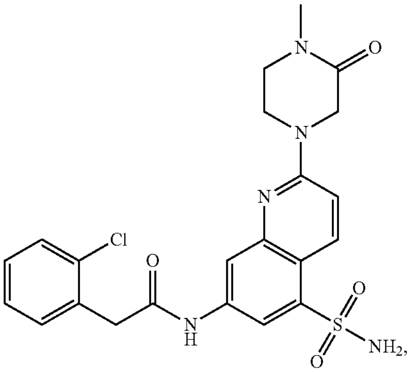
71
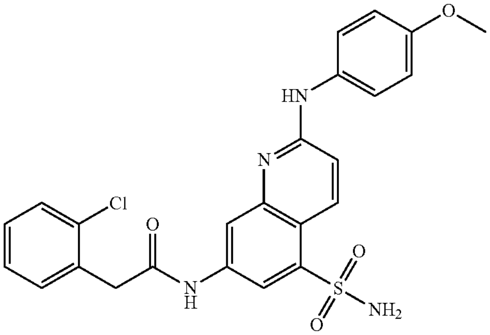
,
72
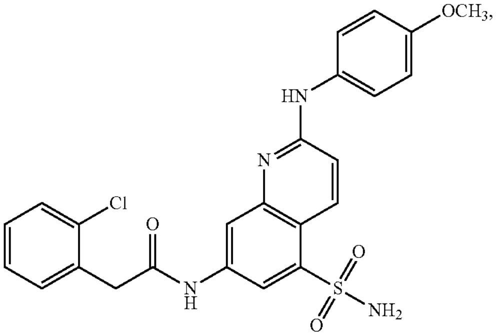
73
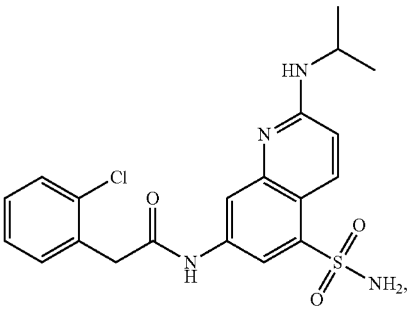
-continued
74
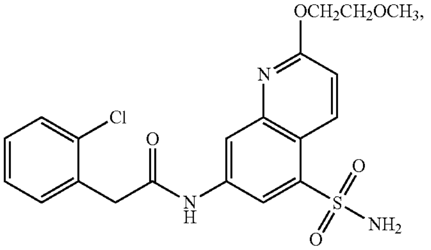
75
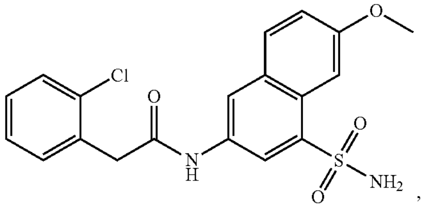
,
76
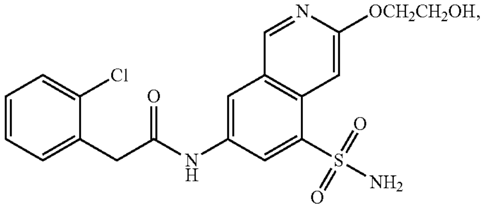
77
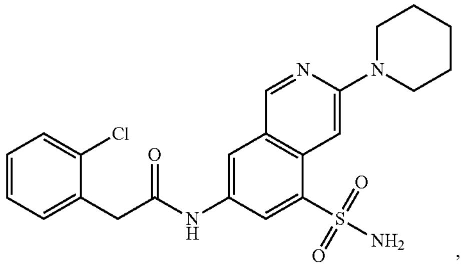
,
78
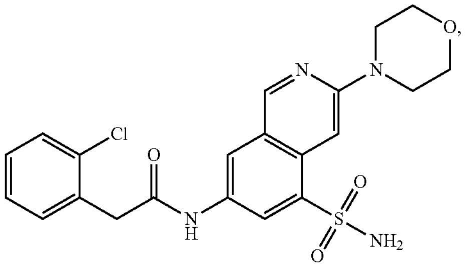
79
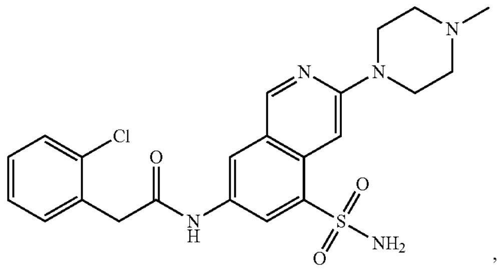
, -continued
80
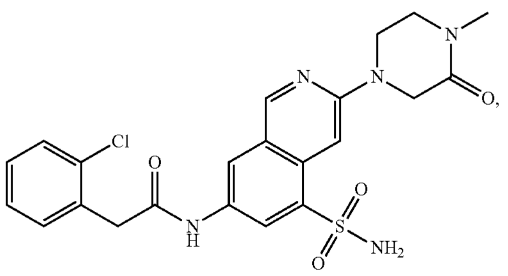
81
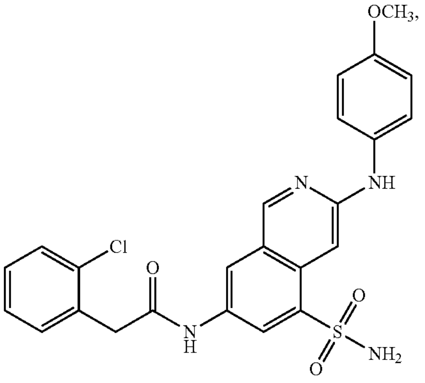
82
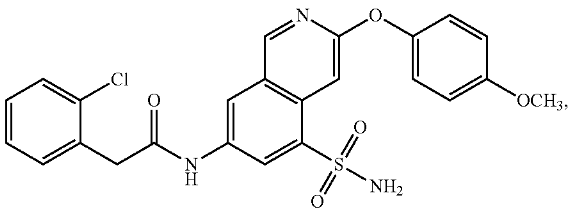
83
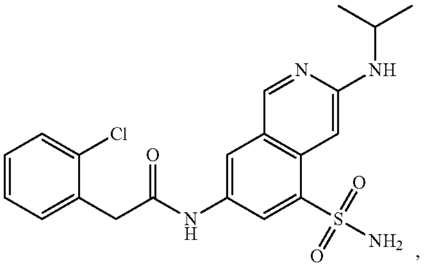
84
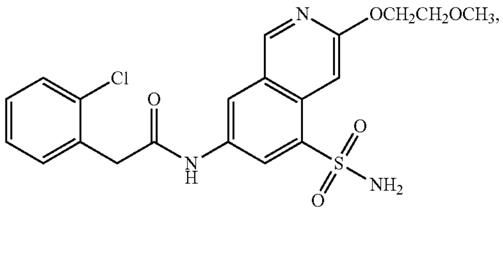
-continued
85
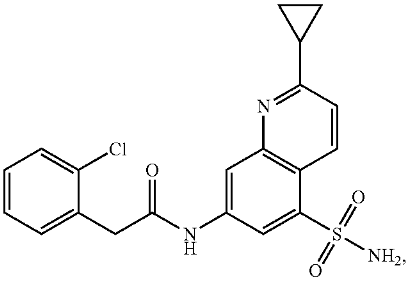
86
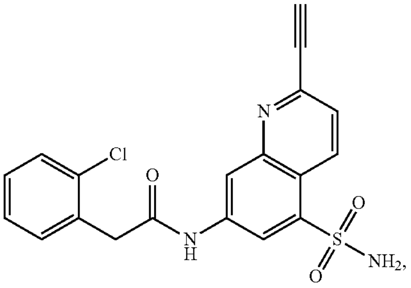
87
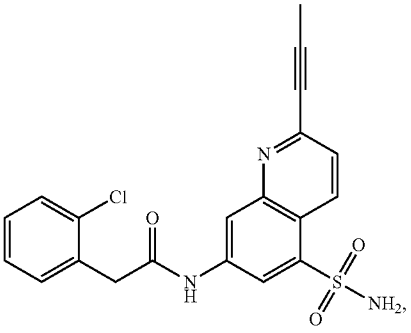
88
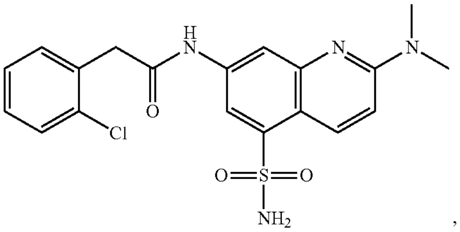
89
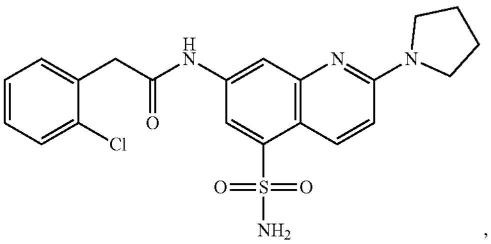
91
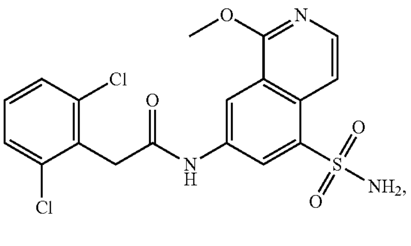

-continued
92
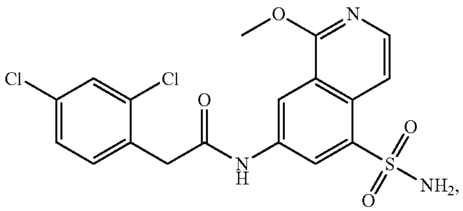
93
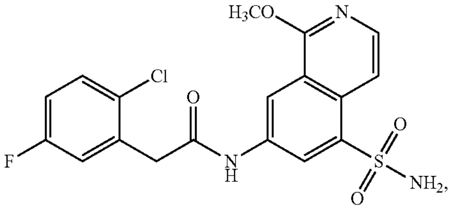
94
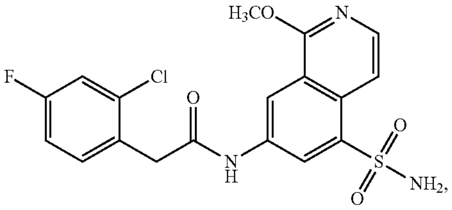
95
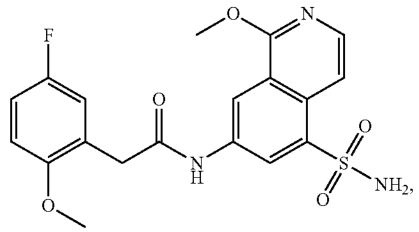
96
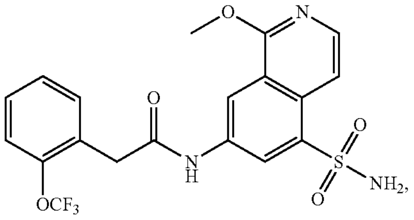
97
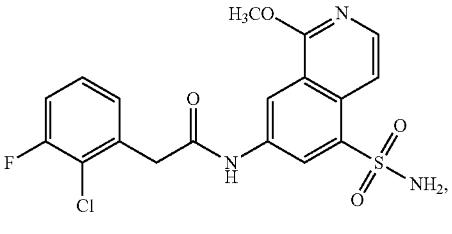
98
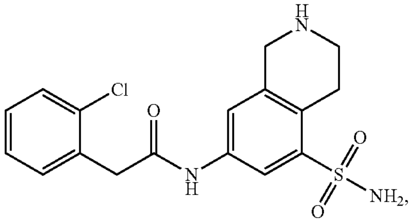
-continued
99
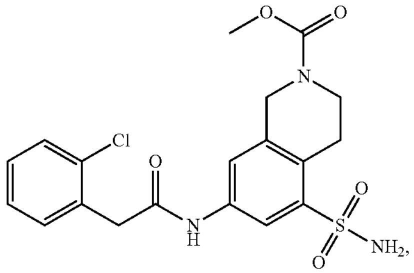
100
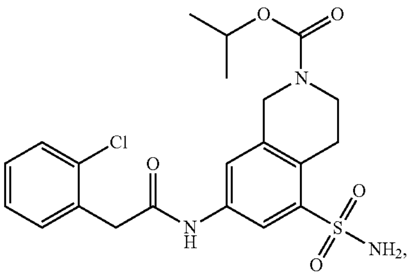
101
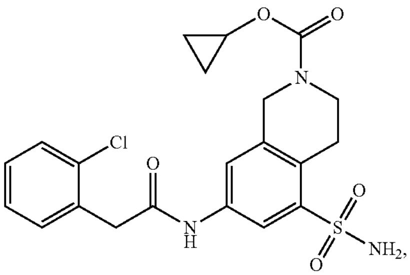
102
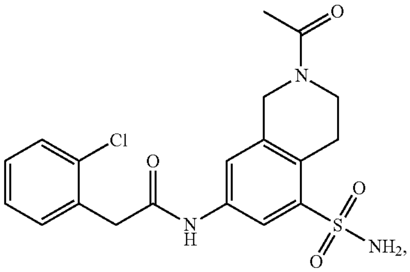
103
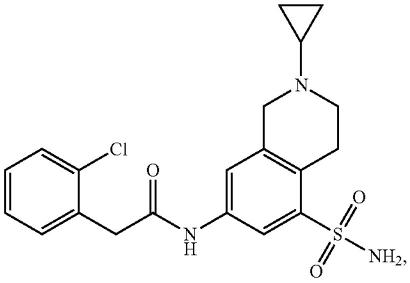

-continued
104
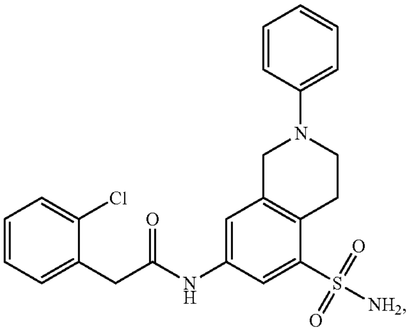
105
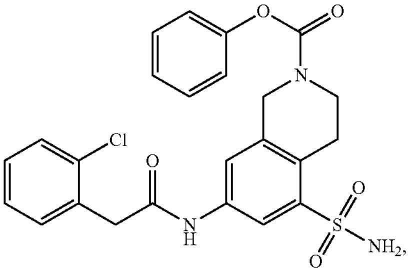
106
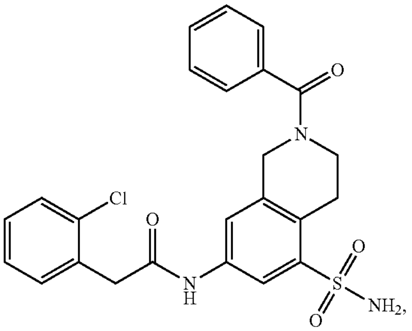
107
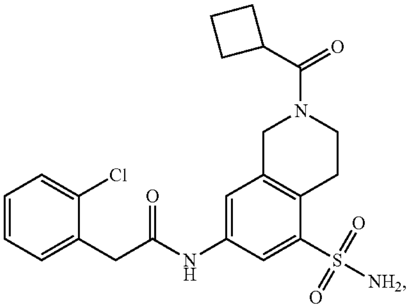
108
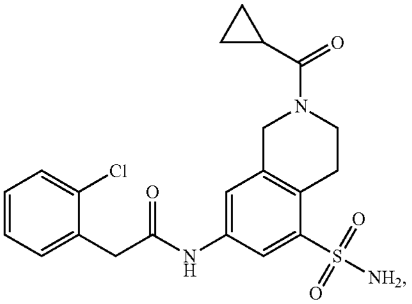
-continued
109
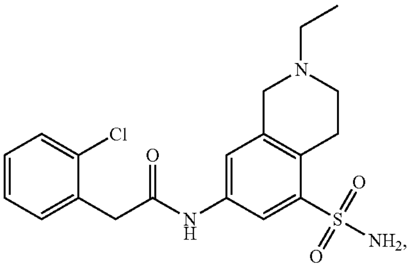
110
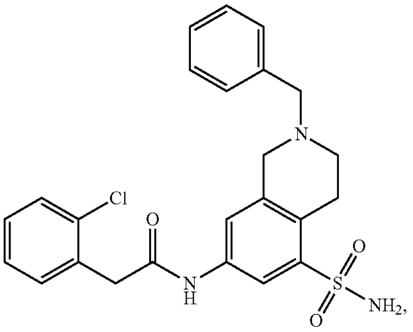
111
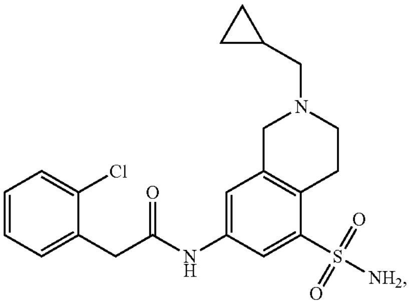
112
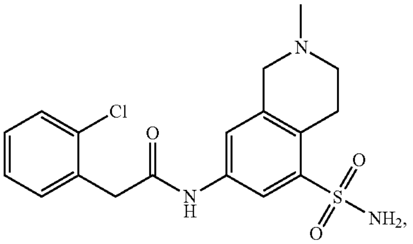
113
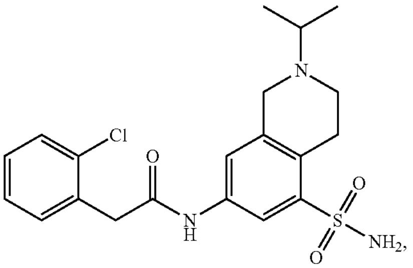

-continued
114
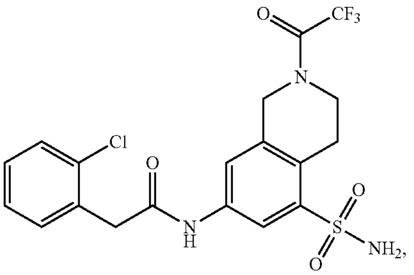
115
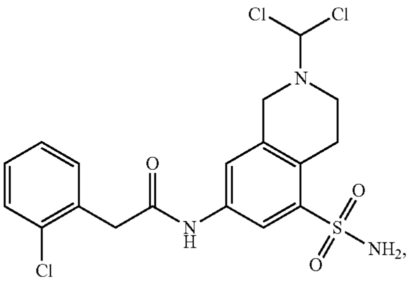
116
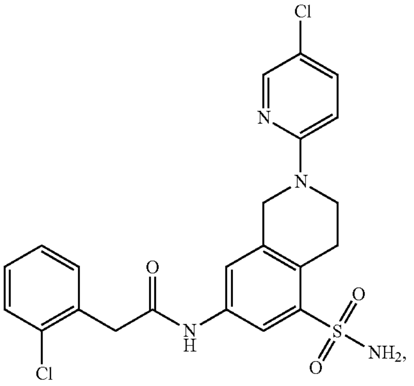
117
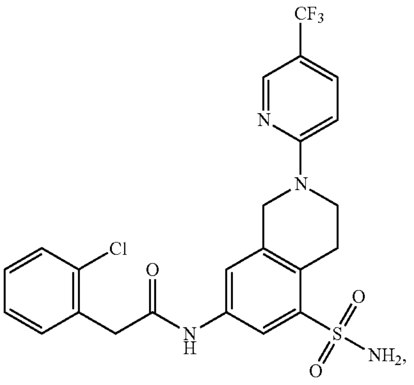
-continued
118
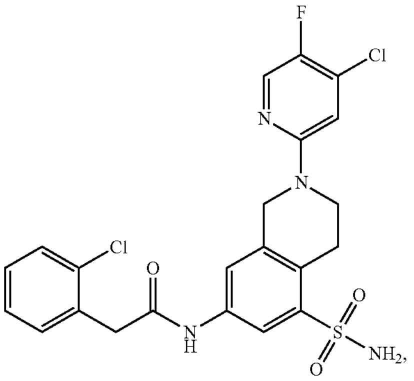
119
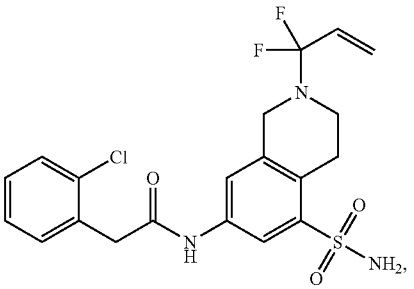
120
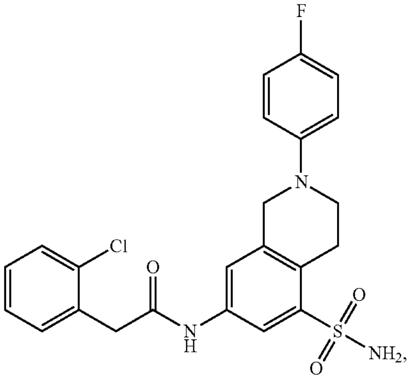
121
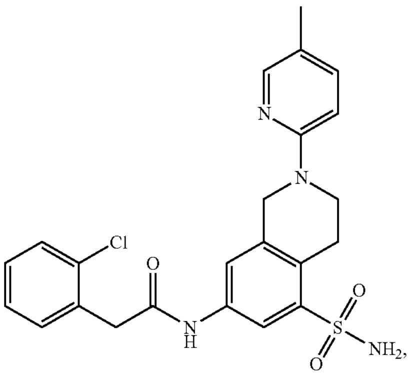

-continued

122

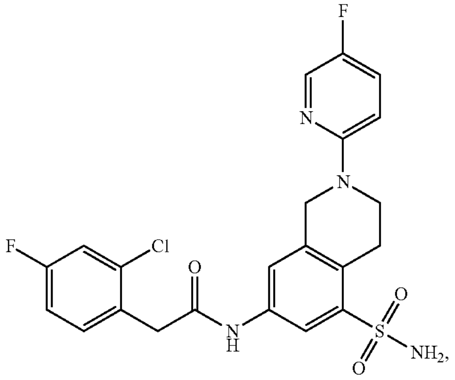

123

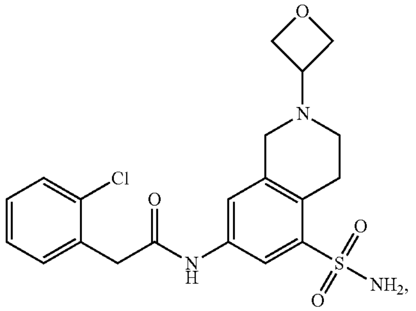

85-1

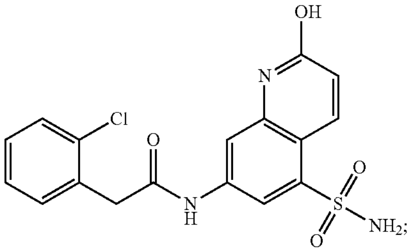

or, scheme 7:

the pharmaceutically acceptable salt of the compound represented by formula I is the following compound: trifluoroacetate of

71

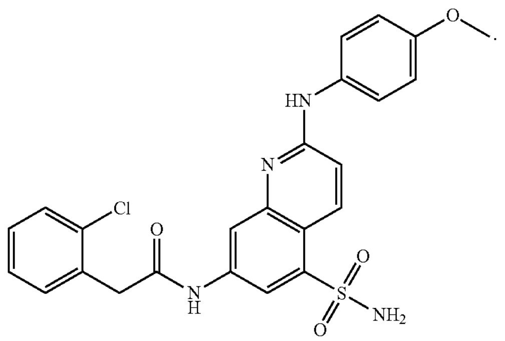

7. A preparation method of the compound represented by formula I as defined in claim 1, wherein, the method is any of the following schemes:

scheme 1: in solvent, under the action of a base, a compound represented by formula II is subjected to the following reaction to obtain the compound represented by formula I,

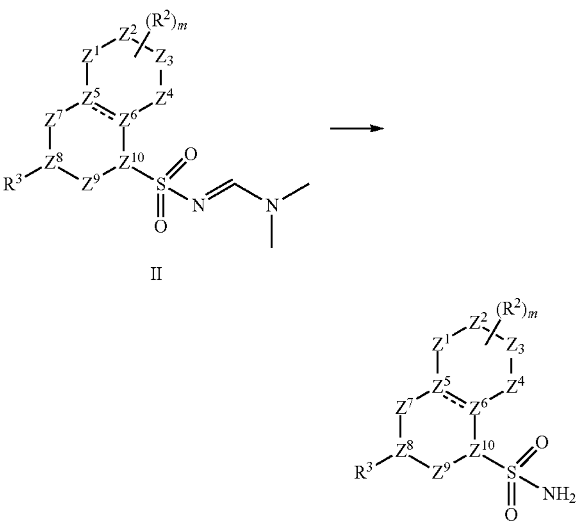

II

I wherein, the base can e sodium ethoxide, ammonia or water hydrazine;

scheme 2: in solvent, a compound represented by formula III and ammonia are subjected to the following reaction to obtain the compound represented by formula I,

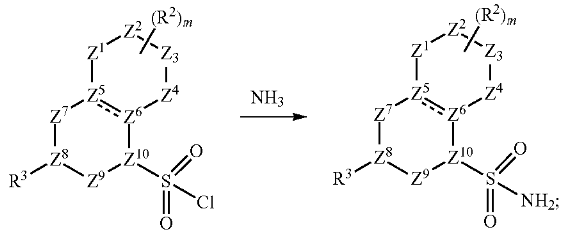

III

I or, scheme 3: in solvent, under the action of trifluoroacetic acid, a compound represented by formula IV is subjected to the following reaction to obtain the compound represented by formula I,

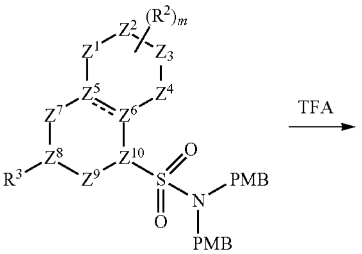

IV

-continued

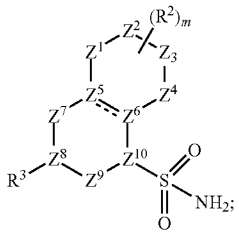

I

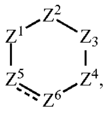, 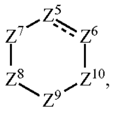, 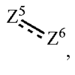,

8. A compound represented by formula II, III or IV,

II

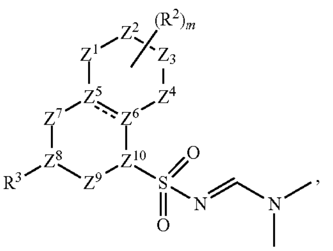

III

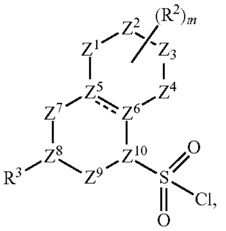 or

IV

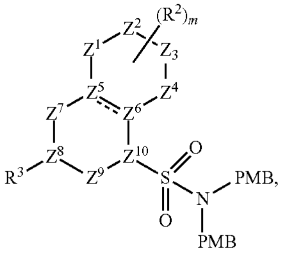 wherein,

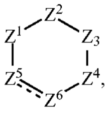, 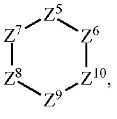, 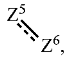, wherein,

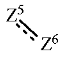

is a single bond or a double bond;

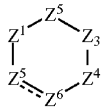

is benzene ring, 6-membered heteroaromatic ring having one or two heteroatoms N or 6-membered heterocycloalkene having one heteroatom N;

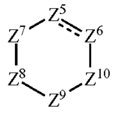

is benzene ring;

$R^3$ is

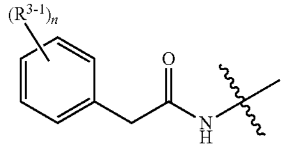 or 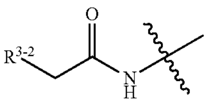 ;

n is 0, 1, 2 or 3;

$R^{3-1}$ is independently halogen, cyano, hydroxyl, $C_1$-$C_6$ alkyl, $C_1$-$C_6$ alkoxy, $C_3$-$C_6$ cycloalkyl, $C_1$-$C_6$ alkyl substituted by one or more $R^{3-1}$, $C_1$-$C_6$ alkoxy substituted by one or more $R^{3-1-2}$, or $C_1$-$C_6$ alkoxy substituted by $C_1$-$C_6$ alkoxy; $R^{3-1-1}$ and $R^{3-1-2}$ are independently halogen;

$R^{3-2}$ is $C_3$-$C_6$ cycloalkyl substituted by one or more $R^{3-2-1}$, "5- to 6-membered heterocycloalkyl with 1, 2 or 3 heteroatoms selected from one or more of N, O and S" substituted by one or more $R^{3-2-2}$, "7- to 8-membered heterocycloalkyl with 1, 2 or 3 heteroatoms selected from one or more of N, O and S" substituted by one or more $R^{3-2-2}$ or "5- to 6-membered heteroaryl with 1, 2 or 3 heteroatoms selected from one or more of N, O and S" substituted by one or more $R^{3-2-3}$;

$R^{3-2-1}$, $R^{3-2-2}$ and $R^{3-2-3}$ are independently halogen, hydroxyl, $C_1$-$C_6$ alkyl, $C_3$-$C_6$ cycloalkyl, $C_1$-$C_6$ alkoxy, or, $C_1$-$C_6$ alkoxy substituted by $C_1$-$C_6$ alkoxy;

m is 0, 1, 2, 3 or 4;

$R^2$ is oxo, halogen, cyano, isocyano, amino, $C_1$-$C_{10}$ alkyl, $C_1$-$C_{10}$ alkyl substituted by one or more $R^{2-1}$, $C_2$-$C_{10}$ alkenyl, $C_2$-$C_{10}$ alkenyl substituted one or more $R^{2-26}$, $C_2$-$C_{10}$ alkynyl, $C_2$-$C_{10}$ alkynyl substituted by one or more $R^{2-27}$, $C_3$-$C_6$ cycloalkyl, $C_3$-$C_6$ cycloalkyl substituted by one or more $R^{2-3}$, "5- to 6-membered heterocycloalkyl with 1, 2 or 3 heteroatoms selected from one or more of N, O and S", "3- to 4-membered heterocycloalkyl with 1 or 2 heteroatoms selected from one or more of N, O and S", phenyl, phenyl substituted by one or more $R^{2-4}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-5}$, —(C═O)—$R^{2-2}$, —$OR^{2-6}$, —C(═O)$OR^{2-7}$, —$NR^{2-8}R^{2-9}$, "5- to 6-membered heterocycloalkyl with 1, 2 or 3 heteroatoms selected from one or more of N, O and S" substituted by one or more $R^{2-10}$, "3- to 4-membered heterocycloalkyl with 1 or 2 heteroatoms selected from one or more of N, O and S" substituted by one or more $R^{2-10}$, —C(═O)NHR$^{2-11}$, —C(═O)NR$^{2-12}$R$^{2-13}$, —NR$^{2-14}$C(═O)R$^{2-1}$, —NR$^{2-16}$S(═O)$_2$R$^{2-17}$, —NR$^{2-18}$S(═O)R$^{2-19}$, —S(═O)$_2$NHR$^{2-20}$, —S(═O)NHR$^{2-21}$, —S(═O)$_2$NR$^{2-22}$R$^{2-23}$, —S(═O)$_2$R$^{2-24}$ or —S(═O)R$^{2-25}$;

$R^{2-1}$ is independently halogen, hydroxyl, $C_3$-$C_6$ cycloalkyl, $C_3$-$C_6$ cycloalkyl substituted by one or more $R^{2-1-8}$, "4- to 6-membered heterocycloalkyl with 1, 2 or 3 heteroatoms selected from one or more of N, O and S", "4- to 6-membered heterocycloalkyl with 1, 2 or 3 heteroatoms selected from one or more of N, O and S" substituted by one or more $R^{2-1-7}$, phenyl, phenyl substituted by one or more $R^{2-1-1}$, "5- to 6-membered heteroaryl with 1, 2 or 3 heteroatoms selected from one or more of N, O and S", "5- to 6-membered heteroaryl with 1, 2 or 3 heteroatoms selected from one or more of N, O and S" substituted by one or more $R^{2-1-6}$, —OR$^{2-1-2}$, —N(R$^{2-1-3}$)(R$^{2-1-4}$), or, —S(═O)$_2$R$^{2-1-5}$;

$R^{2-1}$, $R^{2-1-6}$, $R^{2-1-7}$ and $R^{2-1-8}$ are independently oxo, hydroxyl, amino, carboxyl, halogen, —CN, $C_1$-$C_6$ alkyl, $C_1$-$C_6$ alkyl substituted by one or more halogen, —OR$^{2-1-1}$, or, —N(R$^{2-1-1-2}$)(R$^{2-1-1-3}$); $R^{2-1-1}$, $R^{2-1-1-2}$ and $R^{2-1-1-3}$ are independently $C_1$-$C_6$ alkyl;

$R^{2-1-2}$ is independently $C_1$-$C_6$ alkyl or $C_3$-$C_6$ cycloalkyl;

$R^{2-1-3}$ and $R^{2-1-4}$ are independently hydrogen, $C_1$-$C_6$ alkyl or $C_3$-$C_6$ cycloalkyl;

$R^{2-1-5}$ is independently $C_1$-$C_6$ alkyl or $C_3$-$C_6$ cycloalkyl;

$R^{2-3}$ is independently $C_1$-$C_6$ alkyl;

$R^{2-4}$ and $R^{2-5}$ are independently halogen, hydroxyl, $C_1$-$C_6$ alkyl, $C_1$-$C_6$ alkyl substituted by one or more $R^{2-4-3}$, —N(R$^{2-4-1}$)(R$^{2-4-2}$) or $C_1$-$C_6$ alkoxy; $R^{2-4-1}$ and $R^{2-4-2}$ are independently hydrogen, $C_1$-$C_6$ alkyl or $C_3$-$C_6$ cycloalkyl; $R^{2-4-3}$ is halogen;

$R^{2-2}$ is $C_1$-$C_6$ alkyl, $C_3$-$C_6$ cycloalkyl, phenyl, $C_1$-$C_6$ alkyl substituted by one or more $R^{2-2-2}$, or, phenyl substituted by one or more $R^{2-2-1}$; $R^{2-2-1}$ is independently halogen; $R^{2-2-2}$ is independently halogen;

$R^{2-6}$ is hydrogen, $C_1$-$C_{10}$ alkyl, $C_1$-$C_{10}$ alkyl substituted by one or more $R^{2-6-1}$, $C_3$-$C_6$ cycloalkyl, $C_6$-$C_{10}$ aryl, $C_6$-$C_{10}$ aryl substituted by one or more $R^{2-6-2}$, "3- to 6-membered heterocycloalkyl with 1, 2 or 3 heteroatoms selected from one or more of N, O and S" or, "3- to 6-membered heterocycloalkyl with 1, 2 or 3 heteroatoms selected from one or more of N, O and S" substituted by one or more $R^{2-6-3}$;

$R^{2-6-1}$ is independently oxo, halogen, hydroxyl, amino, carboxyl, —CN, $C_1$-$C_6$ alkyl, $C_1$-$C_6$ alkyl substituted by one or more halogen, $C_1$-$C_6$ alkoxy, $C_3$-$C_6$ cycloalkyl, $C_6$-$C_{10}$ aryl, $C_6$-$C_{10}$ aryl substituted by one or more $R^{2-6-1-1}$, —OR$^{2-6-1-2}$ or —N(R$^{2-6-1-3}$)(R$^{2-6-1-4}$);

$R^{2-6-2}$ is independently halogen, $C_1$-$C_6$ alkyl or $C_1$-$C_6$ alkoxy;

$R^{2-6-3}$ is independently —C(═O)—$C_1$-$C_6$ alkyl;

$R^{2-6-1-1}$ is independently halogen;

$R^{2-6-1-2}$, $R^{2-6-1-3}$ and $R^{2-6-1-4}$ are independently $C_1$-$C_6$ alkyl;

$R^{2-7}$ is $C_1$-$C_6$ alkyl, $C_3$-$C_6$ cycloalkyl or phenyl;

$R^{2-8}$ and $R^{2-9}$ are independently hydrogen, $C_1$-$C_6$ alkyl, $C_6$-$C_{10}$ aryl, or $C_6$-$C_{10}$ aryl substituted by one or more $R^{2-8-1}$;

$R^{2-8-1}$ is halogen or $C_1$-$C_6$ alkoxy;

$R^{2-10}$ is independently $C_1$-$C_6$ alkyl or oxo;

$R^{2-26}$ and $R^{2-27}$ are independently halogen or $C_1$-$C_6$ alkyl;

$R^{2-11}$, $R^{2-12}$, $R^{2-13}$, $R^{2-14}$, $R^{2-1}$, $R^{2-16}$, $R^{2-17}$, $R^{2-18}$, $R^{2-19}$, $R^{2-20}$, $R^{2-21}$, $R^{2-22}$, $R^{2-23}$, $R^{2-24}$ and $R^{2-2}$ are independently $C_1$-$C_6$ alkyl, $C_1$-$C_6$ alkoxy, $C_3$-$C_6$ cycloalkyl, "5- to 6-membered heterocycloalkyl with 1, 2 or 3 heteroatoms selected from one or more of N, O and S", phenyl, phenyl substituted by one or more $R^{2-11-1}$, "5- to 6-membered heteroaryl with 1, 2 or 3 heteroatoms selected from one or more of N, O and S", or "5- to 6-membered heteroaryl with 1, 2 or 3 heteroatoms selected from one or more of N, O and S" substituted by one or more $R^{2-1-2}$;

$R^{2-11-1}$ and $R^{2-11-2}$ are independently halogen, cyano, hydroxyl, $C_1$-$C_6$ alkyl, $C_1$-$C_6$ alkoxy or $C_3$-$C_6$ cycloalkyl;

$R^2$ is located on

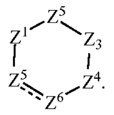

9. The compound represented by formula II, III or IV as claimed in claim 8, wherein, the compound represented by formula II is 1-8

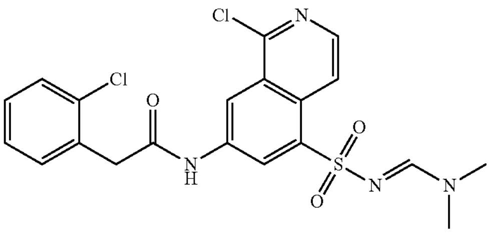

, 3-1

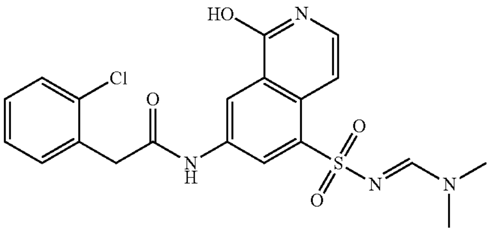

, 5-8

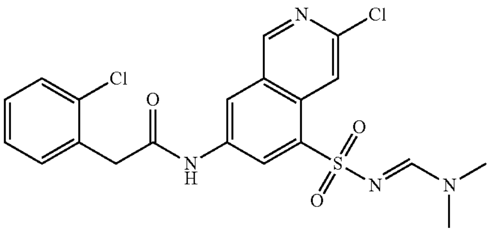

, 26-2

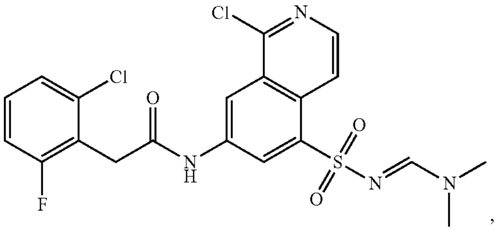

,

-continued
31-1
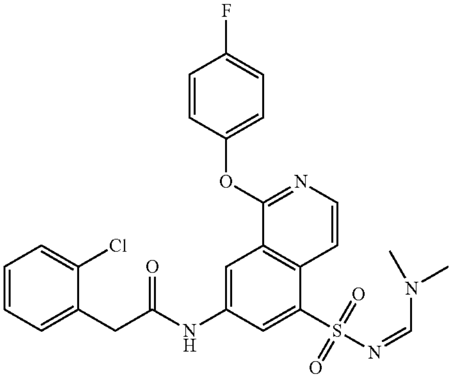
,
71-1
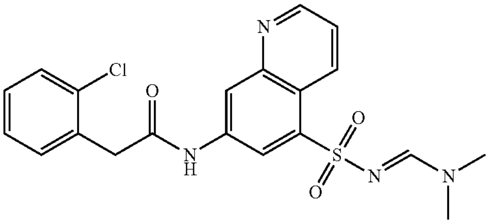
,
71-2
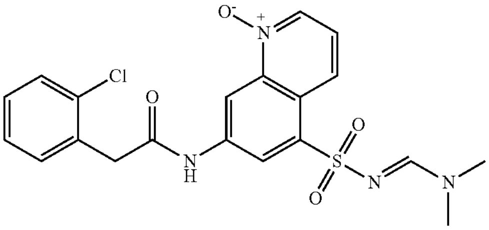
,
71-3
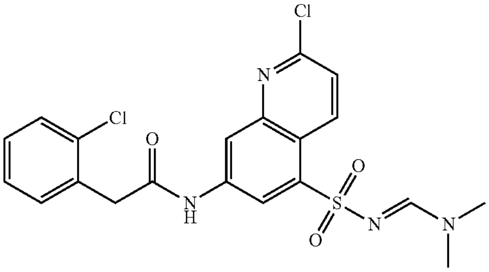
,
71-5
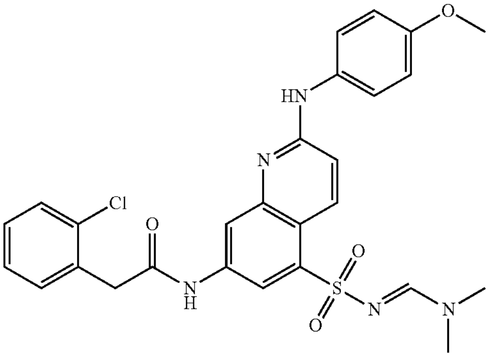
,
-continued
85-2
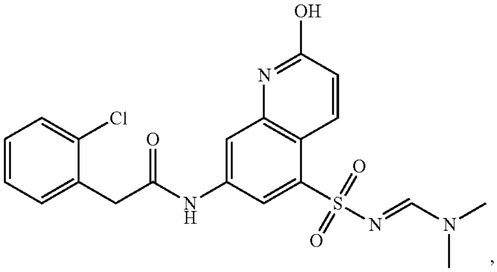
,
85-3
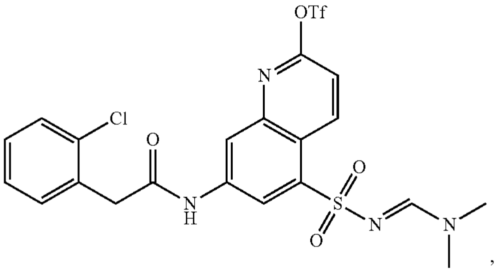
,
85-4
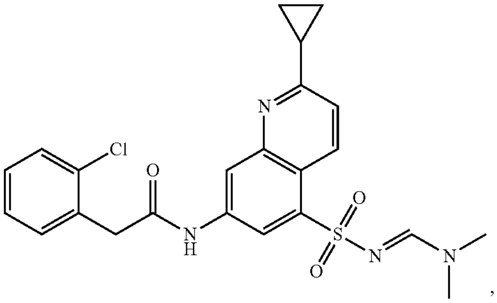
,
86-1
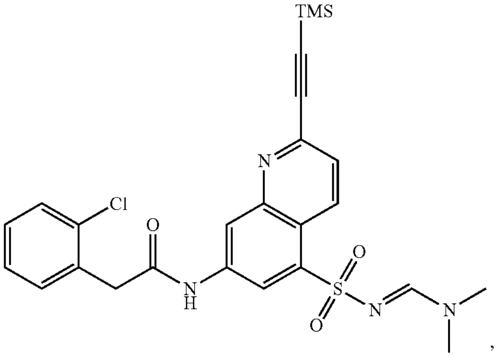
,
86-2
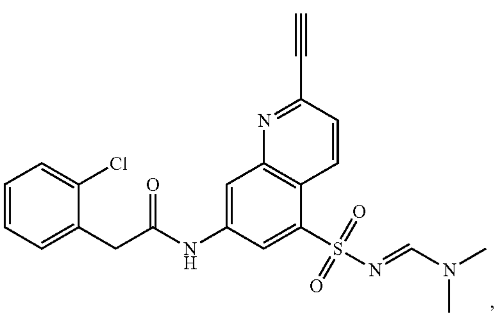
, -continued
87-2
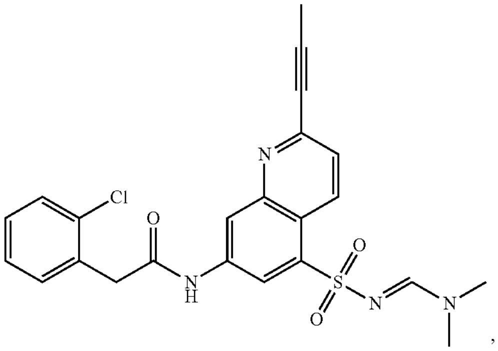
98-5
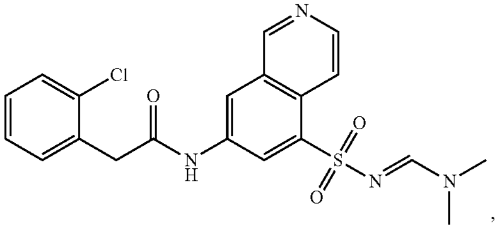
98-6
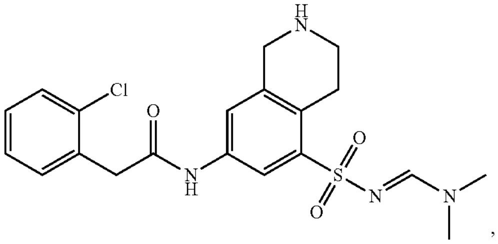
99-2
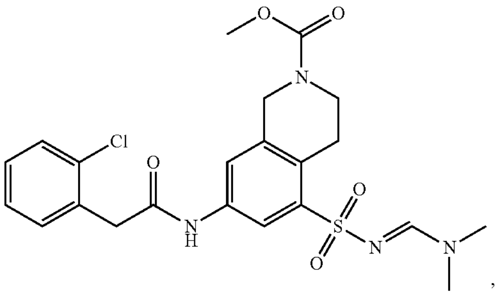
103-2
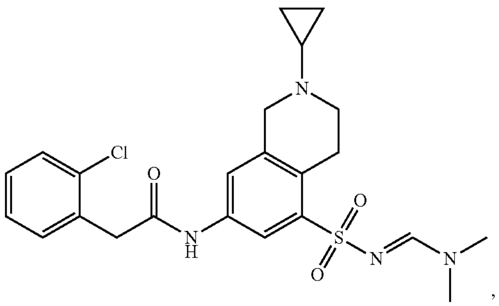
-continued
106-2
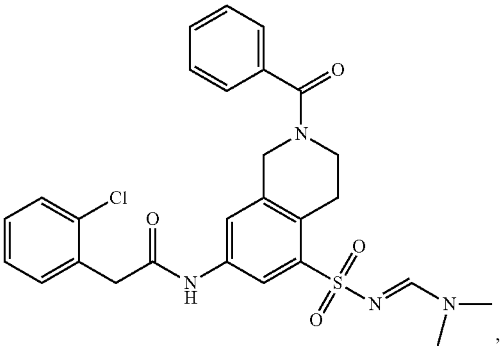
107-2
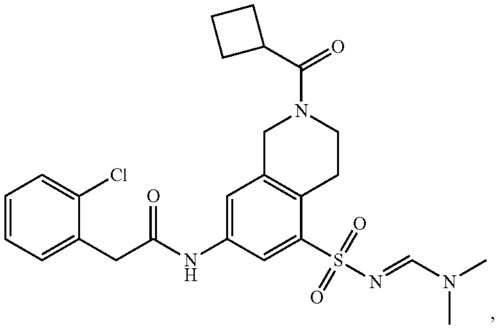
108-2
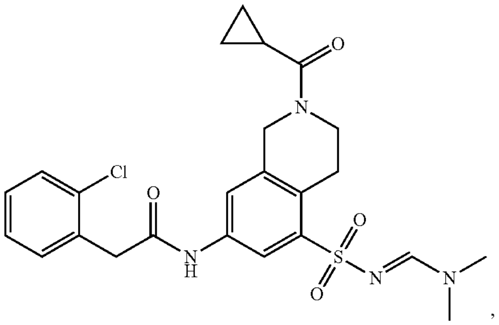
109-1
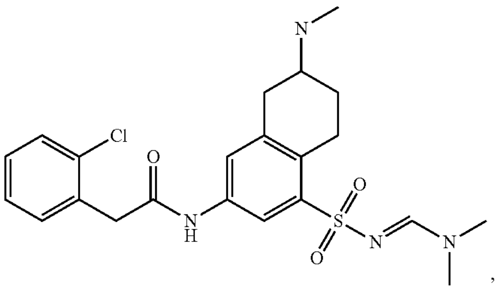

110-1
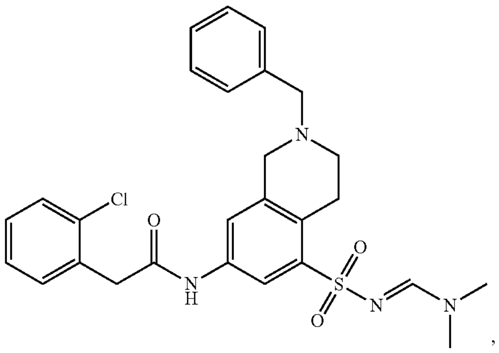
111-2
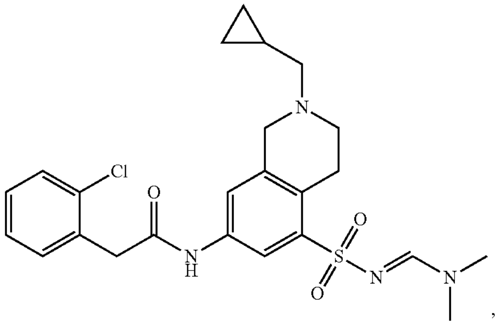
112-1
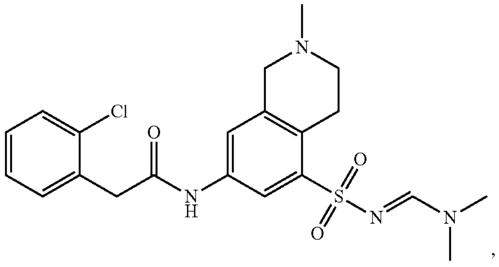
113-1
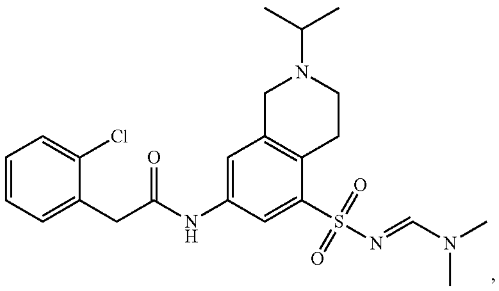
115-1
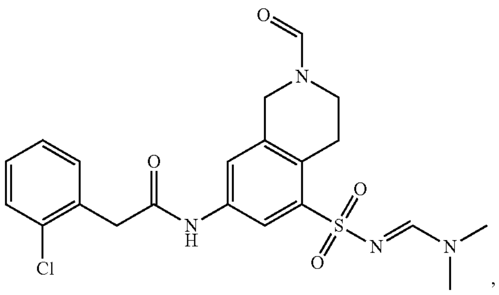
115-2
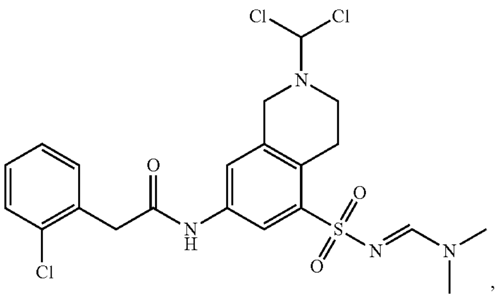
116-2
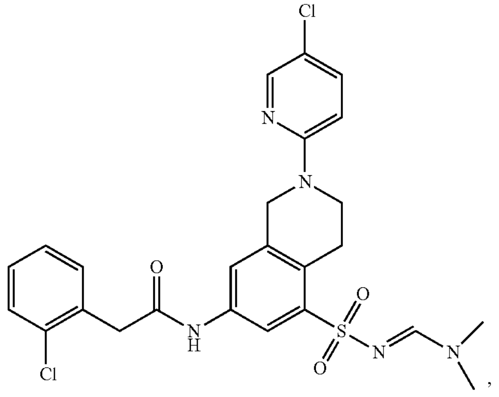
117-2
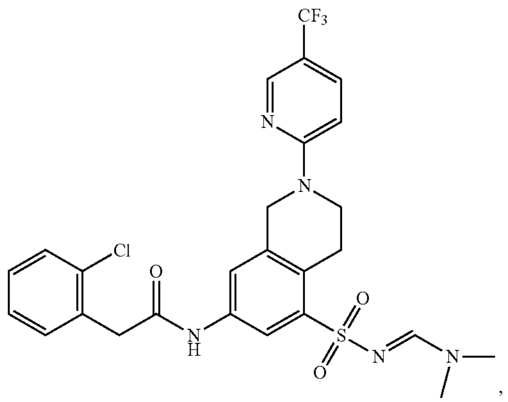
118-2
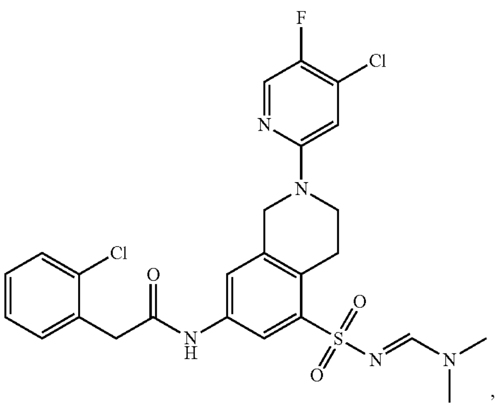

-continued
119-2
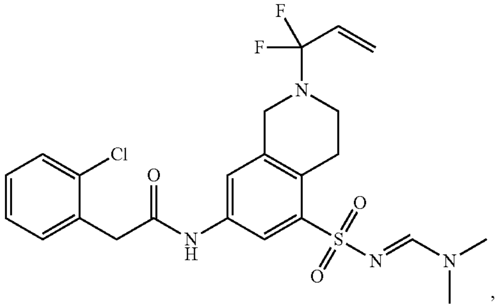
,
120-2
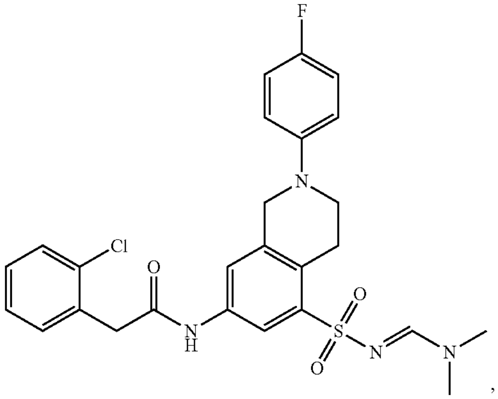
,
121-2
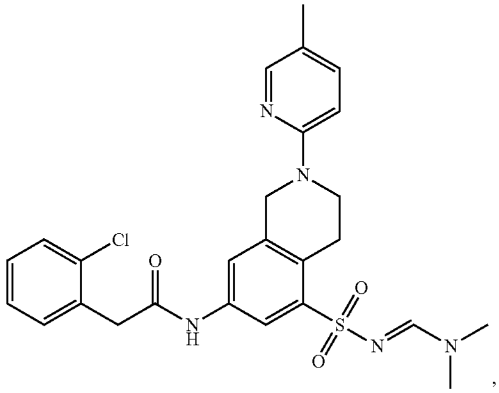
, or
123-2
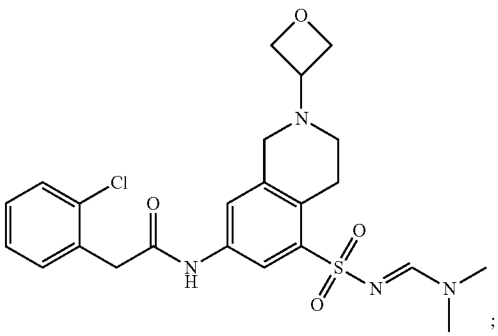
;
the compound represented by formula III is
4-9
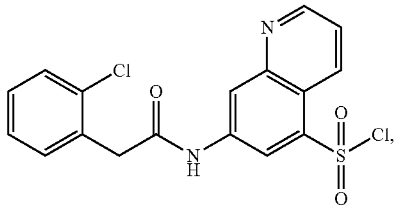
65-7
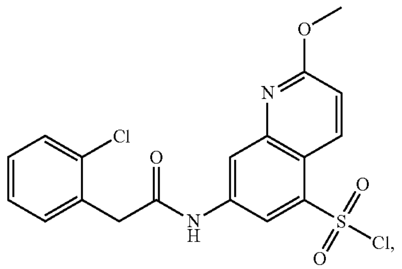
68-5
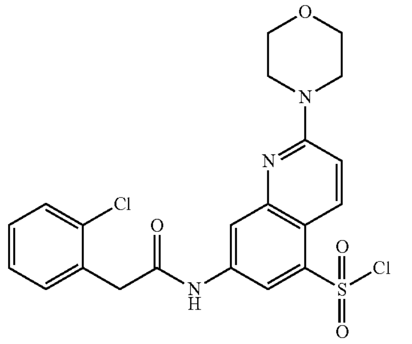
or
69-3
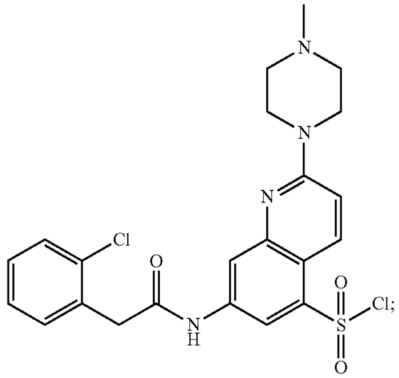
the compound represented by formula IV is
6-5
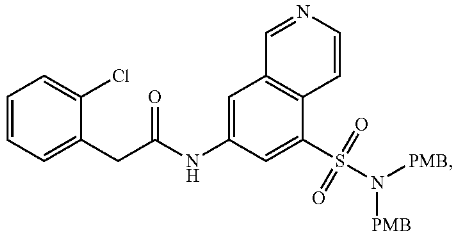

24-6
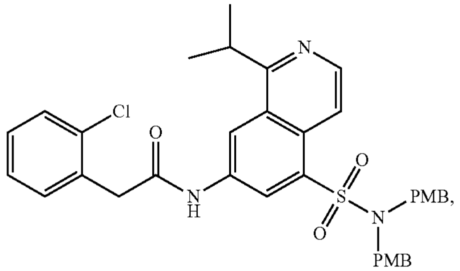
25-5
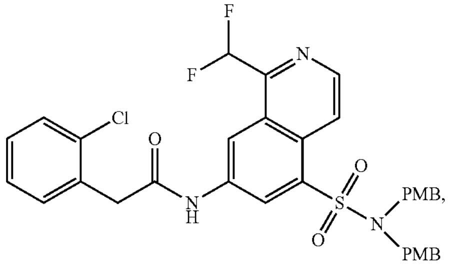
28-4
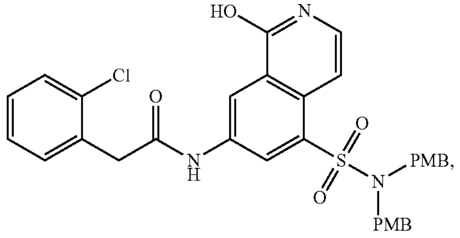
28-6
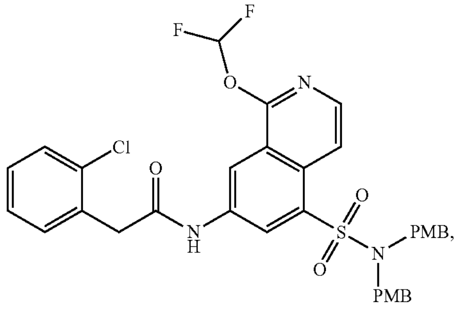
37-4
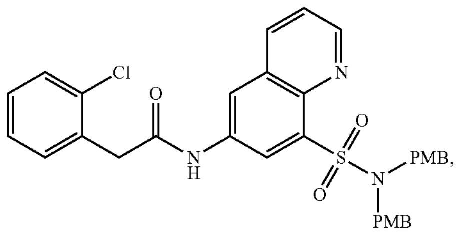
42-10
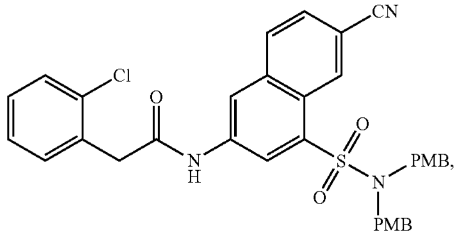
54-3
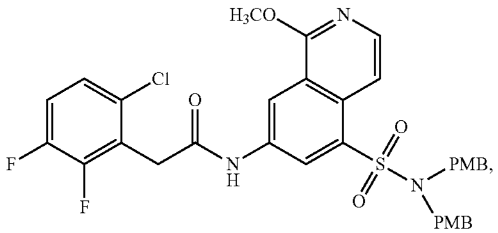
55-6
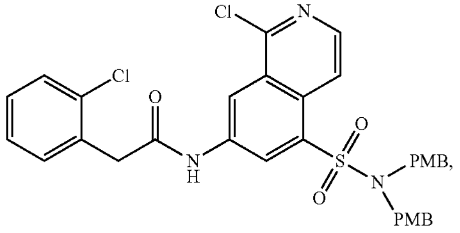
55-7
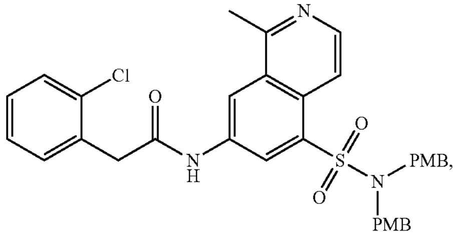
57-1
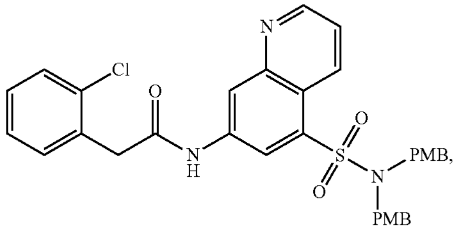
57-2
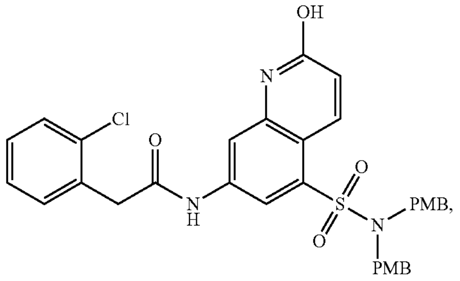
57-3
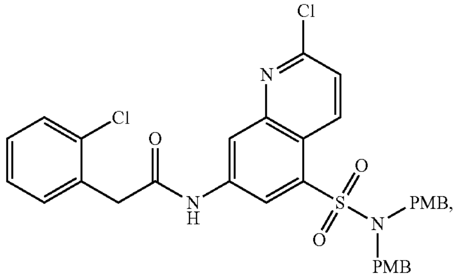

-continued
90-4
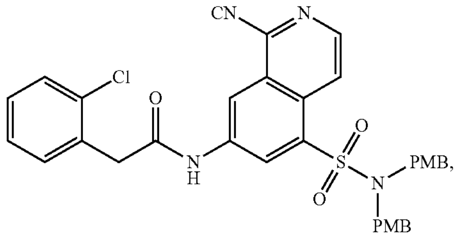
92-2
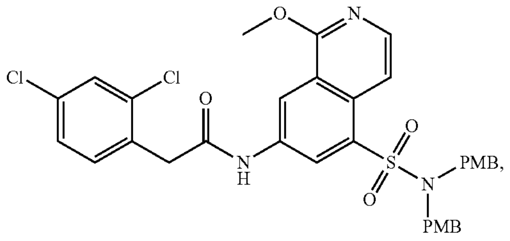
93-1
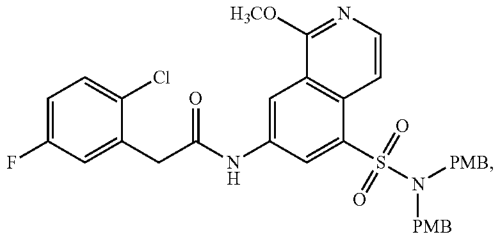
94-1
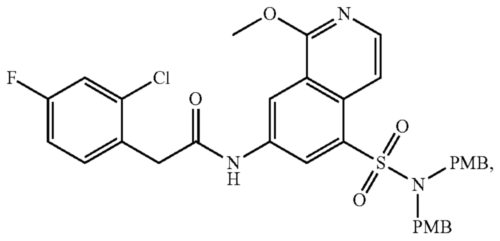
95-1
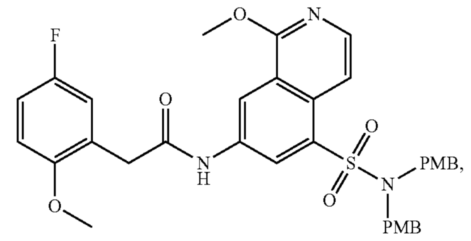
96-2
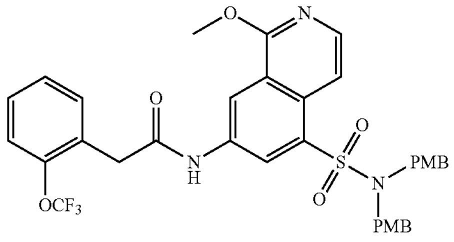
or
-continued
97-2
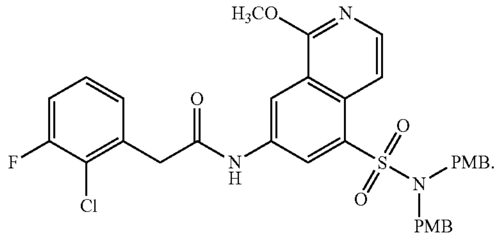
10. A compound represented by the following formula, and the compound is selected form,
1-3
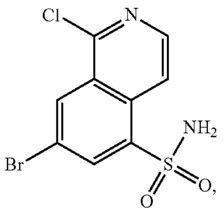
1-4
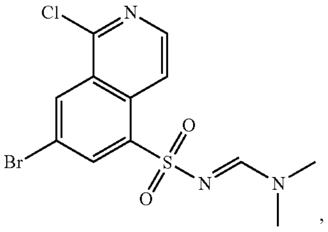
1-5
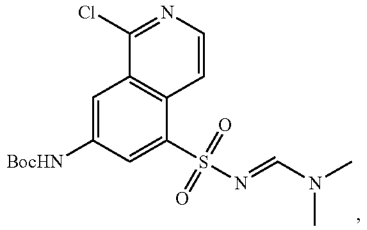
1-6
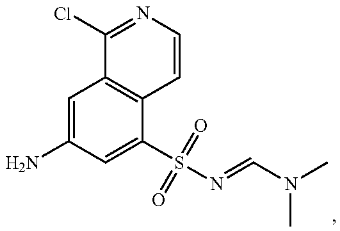
4-4
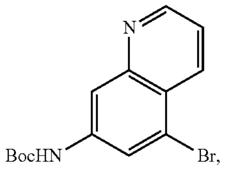

-continued
4-6
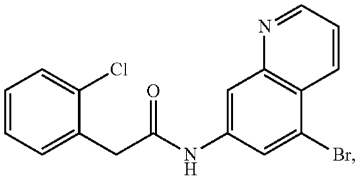
4-8
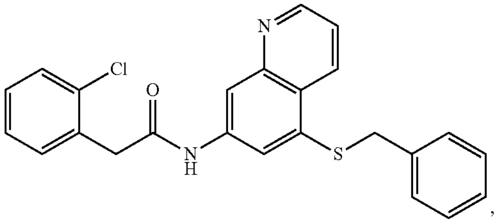
5-2
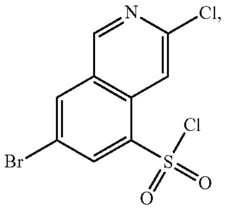
5-3
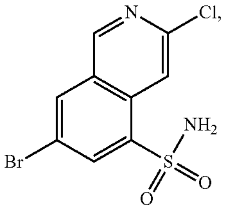
5-4
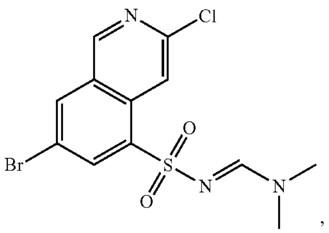
5-5
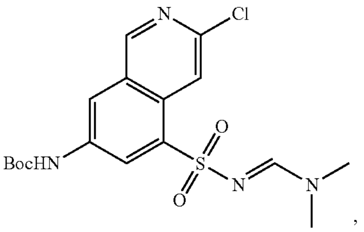
5-6
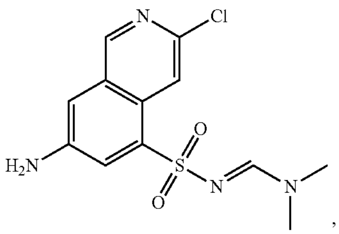
-continued
6-3
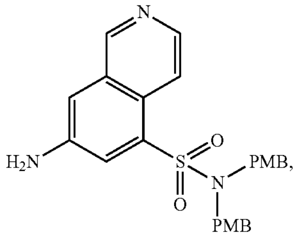
24-3
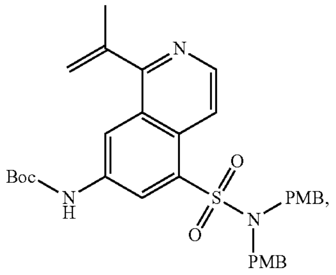
24-4
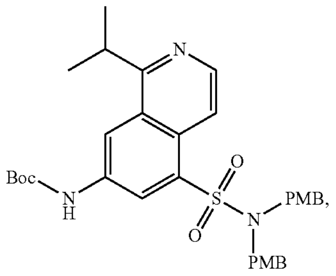
24-5
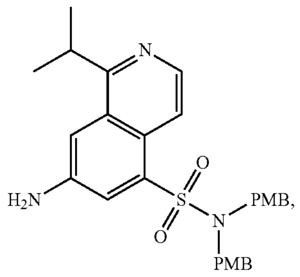
25-1
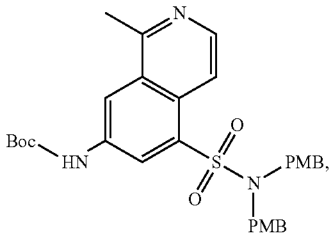
25-2
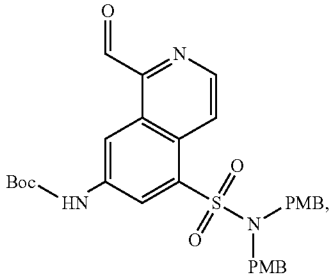

-continued
25-3
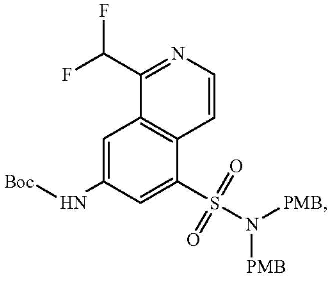
25-4
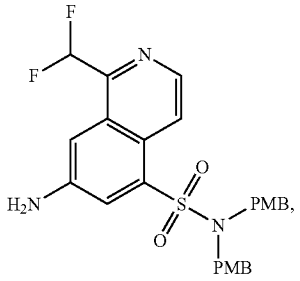
28-1
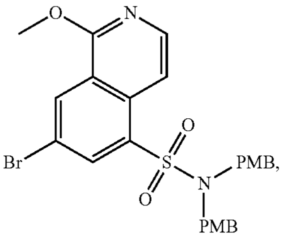
28-2
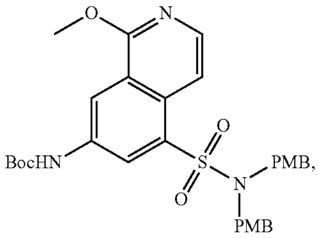
28-3
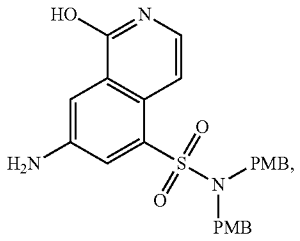
28-4
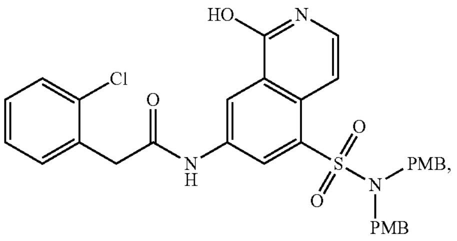
-continued
37-3
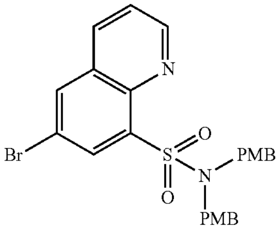
42-5
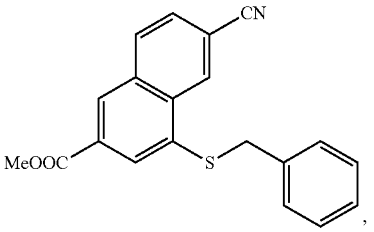
42-6
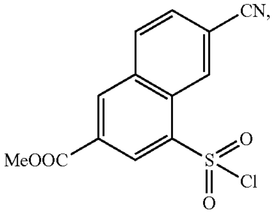
42-7
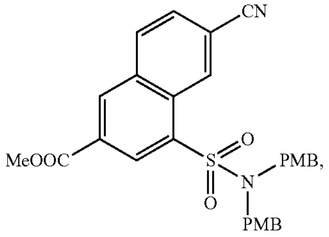
42-8
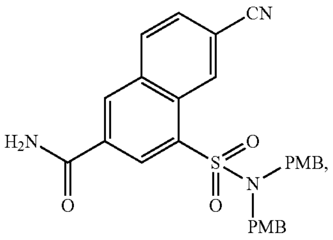
42-9
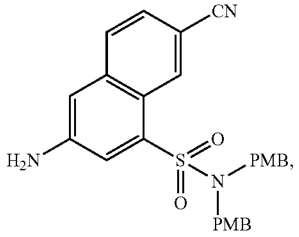

-continued
54-1
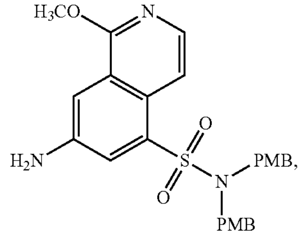
55-1
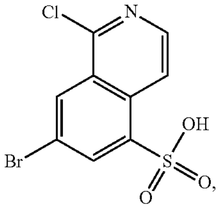
55-2
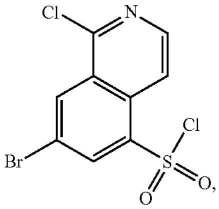
55-3
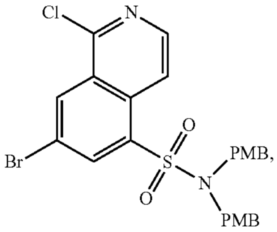
55-4
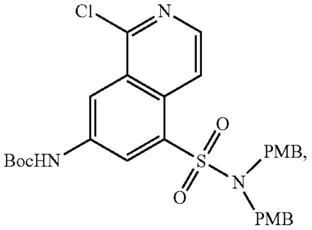
55-5
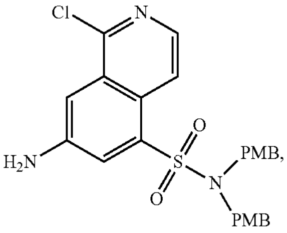
65-1
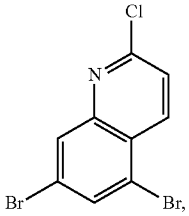
-continued
65-2
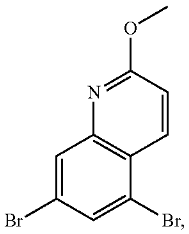
65-3
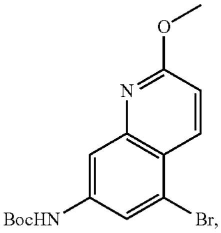
65-4
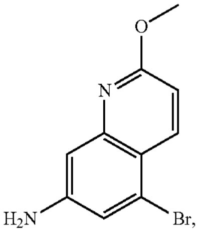
65-5
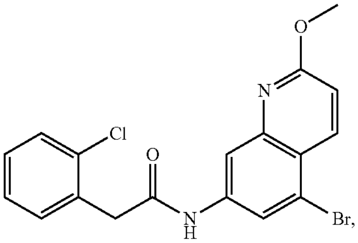
65-6
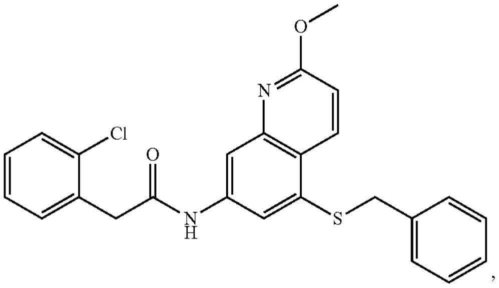
68-1
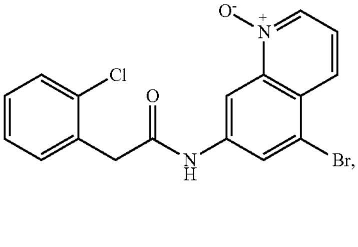

-continued
68-2
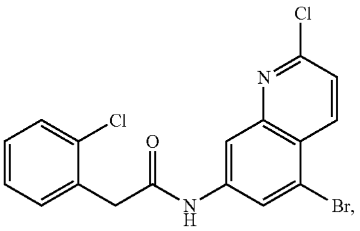
68-3
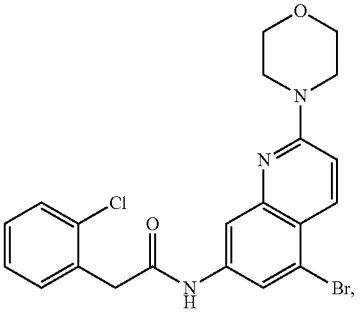
68-4
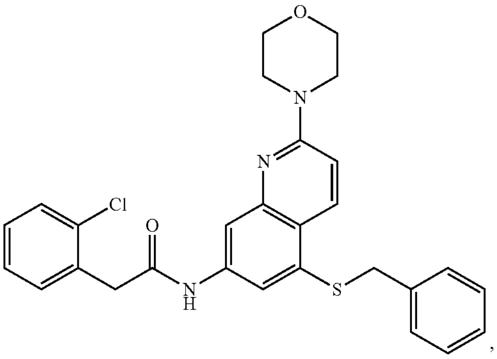
69-1
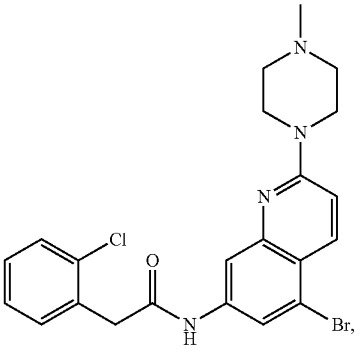
-continued
69-2
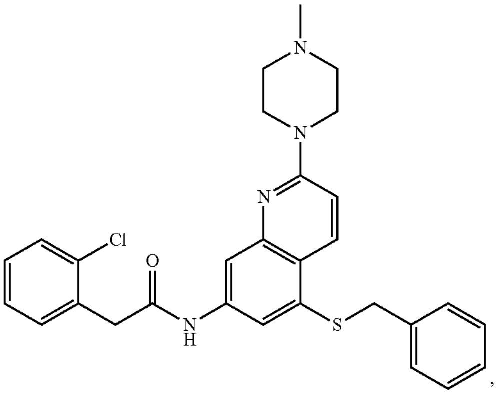
90-1
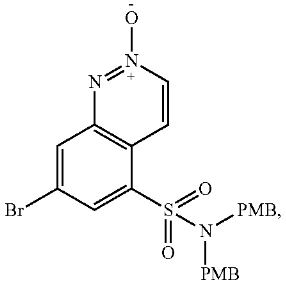
90-3
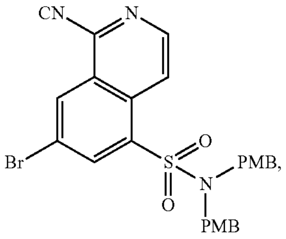
98-1
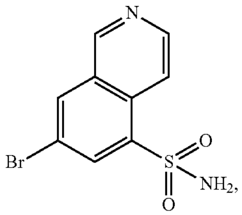
98-2
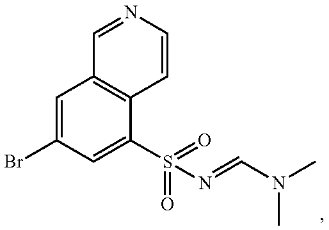

-continued 98-3

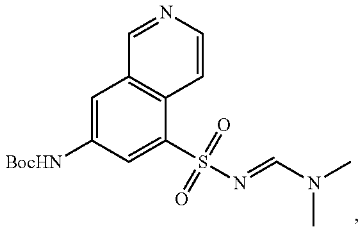

98-4

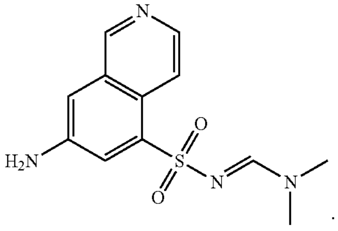

11. A pharmaceutical composition, comprising substance A and at least one of pharmaceutical excipients;

the substance A is the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as defined in claim 1.

12. A method for treating disease comprising administering a therapeutically effective amount of substance A to a patient;

the substance A is the fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as defined in claim 1;

the diseases is urinary tract disease, respiratory disease, pain, inflammation, arthritis, myocardial infarction, rheumatoid arthritis, atherosclerosis, inflammatory bowel disease, gastric bowel dysfunction, or endometriosis;

the urinary tract disease is urinary incontinence, or cystitis;

the respiratory diseases are breathing disorder comprising chronic obstructive pulmonary disease, asthma, or cough.

13. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 3, wherein, when $R^{1-1}$ is $C_1$-$C_6$ alkyl, the $C_1$-$C_6$ alkyl is methyl, ethyl, n-propyl, isopropyl, n-butyl, isobutyl, sec-butyl or tert-butyl;

or, when $R^{3-1}$ is independently halogen, the halogen is fluorine or chlorine;

or, when $R^2$ is halogen, the halogen is fluorine or chlorine;

or, when $R^2$ is $C_1$-$C_{10}$ alkyl, the $C_1$-$C_{10}$ alkyl is methyl, ethyl, n-propyl, isopropyl, n-butyl, isobutyl, sec-butyl or tert-butyl;

or, when $R^2$ is $C_1$-$C_{10}$ alkyl substituted by one or more $R^{2-1}$, the $C_1$-$C_{10}$ alkyl is methyl, ethyl, n-propyl, isopropyl, n-butyl, isobutyl, sec-butyl or tert-butyl;

or, when $R^2$ is $C_3$-$C_6$ cycloalkyl, the $C_3$-$C_6$ cycloalkyl is cyclopropyl or cyclobutyl;

or, when $R^2$ is "5- to 6-membered heterocycloalkyl with 1, 2 or 3 heteroatoms selected from one or more of N, O and S", in the 5- to 6-membered heterocycloalkyl, the heteroatom number is 1 or 2;

or, when $R^2$ is "5- to 6-membered heteroaryl with 1, 2 or 3 heteroatoms selected from one or more of N, O and S", in the 5- to 6-membered heteroaryl, the heteroatom number is 2;

or, when $R^2$ is "5- to 6-membered heterocycloalkyl with 1, 2 or 3 heteroatoms selected from one or more of N, O and S" substituted by one or more $R^{2-10}$, in the 5- to 6-membered heterocycloalkyl, the heteroatom number is 2;

or, when $R^{2-1}$ is independently halogen, the halogen is fluorine;

or, when $R^{2-6}$ is $C_1$-$C_{10}$ alkyl, the $C_1$-$C_{10}$ alkyl is methyl, ethyl, n-propyl, isopropyl, n-butyl, isobutyl, sec-butyl tert-butyl, n-pentyl, isopentyl or n-butyl;

or, when $R^{2-6}$ is $C_1$-$C_{10}$ alkyl substituted by one or more $R^{2-6-1}$, the $C_1$-$C_{10}$ alkyl is methyl, ethyl, n-propyl, isopropyl, n-butyl, isobutyl, sec-butyl or tert-butyl;

or, when $R^{2-6}$ is $C_3$-$C_6$ cycloalkyl, the $C_3$-$C_6$ cycloalkyl is cyclopropyl, cyclobutyl or cyclopentyl;

or, when $R^{2-6}$ is $C_6$-$C_{10}$ aryl substituted by one or more $R^{2-6-2}$, the $C_6$-$C_{10}$ aryl is phenyl;

or, when $R^{2-6}$ is "3- to 6-membered heterocycloalkyl with 1, 2 or 3 heteroatoms selected from one or more of N, O and S", the 3- to 6-membered heterocycloalkyl is 3- to 4-membered heterocycloalkyl; in the 3- to 4-membered heterocycloalkyl, the heteroatoms is N;

or, when $R^{2-6}$ is "3- to 6-membered heterocycloalkyl with 1, 2 or 3 heteroatoms selected from one or more of N, O and S" substituted by one or more $R^{2-6-3}$, the 3- to 6-membered heterocycloalkyl is 3- to 4-membered heterocycloalkyl; in the 3- to 4-membered heterocycloalkyl, the heteroatoms is N;

or, when $R^{2-6-1}$ is independently fluorine;

or, when $R^{2-6-1}$ is independently $C_1$-$C_6$ alkoxy, the $C_1$-$C_6$ alkoxy is methoxy, ethoxy, n-propoxy, isopropoxy, n-butoxy, isobutoxy, sec-butoxy or tert-butoxy;

or, when $R^{2-6-1}$ is independently $C_3$-$C_6$ cycloalkyl, the $C_3$-$C_6$ cycloalkyl is cyclopropyl;

or, when $R^{2-6-1}$ is independently $C_6$-$C_{10}$ aryl substituted by one or more $R^{2-6-1-1}$, the $C_6$-$C_{10}$ aryl is phenyl;

or, when $R^{2-6-2}$ is independently halogen, the halogen is fluorine;

or, when $R^{2-6-2}$ is independently $C_1$-$C_6$ alkyl, the $C_1$-$C_6$ alkyl is methyl, ethyl, n-propyl, isopropyl, n-butyl, isobutyl, sec-butyl or tert-butyl;

or, when $R^{2-6-2}$ is independently $C_1$-$C_6$ alkoxy, the $C_1$-$C_6$ alkoxy is methoxy, ethoxy, n-propoxy, isopropoxy, n-butoxy, isobutoxy, sec-butoxy or tert-butoxy;

or, when $R^{2-6-3}$ is independently —C(═O)—$C_1$-$C_4$ alkyl, in the —C(═O)—$C_1$-$C_4$ alkyl, the $C_1$-$C_4$ alkyl is methyl;

or, $R^{2-6-1-1}$ is independently fluorine;

or, $R^{2-7}$ is methyl, ethyl, n-propyl, isopropyl, n-butyl, isobutyl, sec-butyl or tert-butyl;

or, when $R^{2-8}$ and $R^{2-9}$ are independently $C_1$-$C_6$ alkyl, the $C_1$-$C_6$ alkyl is methyl, ethyl, n-propyl, isopropyl, n-butyl, isobutyl, sec-butyl or tert-butyl;

or, when $R^{2-8}$ and $R^{2-9}$ are independently $C_6$-$C_{10}$ aryl substituted by one or more $R^{2-8-1}$, in the $C_6$-$C_{10}$ aryl substituted by one or more $R^{2-8-1}$, the $C_6$-$C_{10}$ aryl is phenyl;

or, when $R^{2-8-1}$ is halogen, the halogen is fluorine;

or, when $R^{2-8-1}$ is $C_1$-$C_6$ alkoxy, the $C_1$-$C_6$ alkoxy is methoxy, ethoxy, n-propoxy, isopropoxy, n-butoxy, isobutoxy, sec-butoxy or tert-butoxy;

or, when $R^{2-10}$ is independently $C_1$-$C_6$ alkyl, the $C_1$-$C_6$ alkyl is methyl, ethyl, n-propyl, isopropyl, n-butyl, isobutyl, sec-butyl or tert-butyl;

or, when $R^{1-1}$ is $C_1$-$C_6$ alky substituted by one or more $R^{1-1-1}$, in the $C_1$-$C_6$ alky substituted by one or more $R^{1-1-1}$, the $C_1$-$C_6$ alkyl is methyl, ethyl, n-propyl, isopropyl, n-butyl, isobutyl, sec-butyl or tert-butyl;

or, when $R^{3-1}$ is independently $C_1$-$C_6$ alkoxy or $C_1$-$C_6$ alkoxy substituted by one or more $R^{3-1-2}$, in the $C_1$-$C_6$ alkoxy or $C_1$-$C_6$ alkoxy substituted by one or more $R^{3-1-2}$, the $C_1$-$C_6$ alkoxy is methoxy, ethoxy, n-propoxy, isopropoxy, n-butoxy, isobutoxy, sec-butoxy or tert-butoxy;

or, when $R^{3-1-1}$ and $R^{3-1-2}$ are independently halogen, the halogen is fluorine or chlorine;

or, when $R^2$ is $C_2$-$C_{10}$ alkenyl, $C_2$-$C_{10}$ alkenyl substituted by one or more $R^{2-26}$, in the $C_2$-$C_{10}$ alkenyl and $C_2$-$C_{10}$ alkenyl substituted by one or more $R^{2-26}$, the $C_2$-$C_{10}$ alkenyl is vinyl or allyl;

or, when $R^2$ is $C_2$-$C_{10}$ alkynyl or $C_2$-$C_{10}$ alkynyl substituted by one or more $R^{2-27}$, in the $C_2$-$C_{10}$ alkynyl and $C_2$-$C_{10}$ alkynyl substituted by one or more $R^{2-27}$, the $C_2$-$C_{10}$ alkynyl is ethynyl and propynyl;

or, when $R^{2-26}$ and $R^{2-27}$ are independently halogen, the halogen is fluorine or chlorine;

or, when $R^2$ is "3- to 4-membered heterocycloalkyl with 1 or 2 heteroatoms selected from one or more of N, O and S" or "3- to 4-membered heterocycloalkyl with 1 or 2 heteroatoms selected from one or more of N, O and S" substituted by one or more $R^{2-10}$, in the 3- to 4-membered heterocycloalkyl, the heteroatoms are selected from one or more of N and O and the heteroatom number is 1 or 2;

or, when $R^2$ is "5- to 6-membered heteroaryl with 1, 2 or 3 heteroatoms selected from one or more of N, O and S" substituted by one or more $R^{2-5}$, in the 5- to 6-membered heteroaryl, the heteroatoms are N, the heteroatom number is 1;

or, when $R^{2-1}$ is independently $C_3$-$C_6$ cycloalkyl, the $C_3$-$C_6$ cycloalkyl is cyclopropyl or cyclobutyl;

or, when $R^{2-2}$ is $C_1$-$C_6$ alkyl or $C_1$-$C_6$ alkyl substituted by one or more $R^{2-2-2}$, the $C_1$-$C_6$ alkyl is methyl;

or, when $R^{2-2}$ is $C_3$-$C_6$ cycloalkyl, the $C_3$-$C_6$ cycloalkyl is cyclopropyl or cyclobutyl;

or, when $R^{2-2-2}$ is independently halogen, the halogen is fluorine or chlorine;

or, when $R^{2-4}$ and $R^{2-5}$ are independently fluorine or chlorine;

or, when $R^{2-4}$ and $R^{2-5}$ are independently $C_1$-$C_6$ alkyl or $C_1$-$C_6$ alkyl substituted by one or more $R^{2-4-3}$, in the $C_1$-$C_6$ alkyl and $C_1$-$C_6$ alkyl substituted by one or more $R^{2-4-3}$, the $C_1$-$C_6$ alkyl is methyl;

or, when $R^{2-4-3}$ is halogen, the halogen is fluorine or chlorine;

or, when $R^{2-7}$ is $C_3$-$C_6$ cycloalkyl, the $C_3$-$C_6$ cycloalkyl is cyclopropyl.

14. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 13, wherein, in the 6-membered heterocycloalkene,

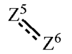

is a double bond;

or, when $R^{1-1}$ is $C_1$-$C_6$ alkyl, the $C_1$-$C_6$ alkyl is methyl;

or, when $R^2$ is $C_1$-$C_{10}$ alkyl, the $C_1$-$C_{10}$ alkyl is methyl or isopropyl;

or, when $R^2$ is $C_1$-$C_{10}$ alkyl substituted by one or more $R^{2-1}$, the $C_1$-$C_{10}$ alkyl is methyl;

or, when $R^2$ is "5- to 6-membered heterocycloalkyl with 1, 2 or 3 heteroatoms selected from one or more of N, O and S", in the 5- to 6-membered heterocycloalkyl, the 5- to 6-membered heterocycloalkyl is

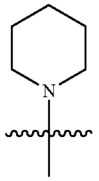

or

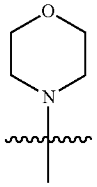

;

or, when $R^2$ is "5- to 6-membered heteroaryl with 1, 2 or 3 heteroatoms selected from one or more of N, O and S", in the 5- to 6-membered heteroaryl, the 5- to 6-membered heteroaryl is

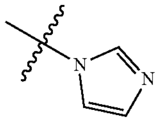

or

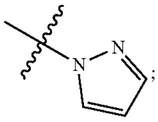

;

or, when $R^2$ is "5- to 6-membered heterocycloalkyl with 1, 2 or 3 heteroatoms selected from one or more of N, O and S" substituted by one or more $R^{2-10}$, in the 5- to 6-membered heterocycloalkyl, the 5- to 6-membered heterocycloalkyl is

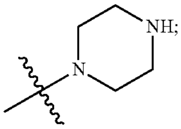 [SMILES: *N1CCNCC1]

;

or, when $R^{2-6}$ is $C_1$-$C_{10}$ alkyl, the $C_1$-$C_{10}$ alkyl is methyl, ethyl, isobutyl or isopentyl;

or, when $R^{2-6}$ is $C_1$-$C_{10}$ alkyl substituted by one or more $R^{2-6-1}$, the $C_1$-$C_{10}$ alkyl is methyl or ethyl;

or, when $R^{2-6}$ is "3- to 6-membered heterocycloalkyl with 1, 2 or 3 heteroatoms selected from one or more of N, O and S", the 3- to 6-membered heterocycloalkyl is 3- to 4-membered heterocycloalkyl; in the 3- to 4-membered heterocycloalkyl, the heteroatoms is N, the heteroatom number is 1;

or, when $R^{2-6}$ is "3- to 6-membered heterocycloalkyl with 1, 2 or 3 heteroatoms selected from one or more of N, O and S" substituted by one or more $R^{2-6-3}$, the 3- to 6-membered heterocycloalkyl is 3- to 4-membered heterocycloalkyl; in the 3- to 4-membered heterocycloalkyl, the heteroatoms is N, the heteroatom number is 1;

or, when $R^{2-6-1}$ is independently $C_1$-$C_6$ alkoxy, the $C_1$-$C_6$ alkoxy is methoxy;

or, when $R^{2-6-2}$ is independently $C_1$-$C_6$ alkyl, the $C_1$-$C_6$ alkyl is methyl;

or, when $R^{2-6-2}$ is independently $C_1$-$C_6$ alkoxy, the $C_1$-$C_6$ alkoxy is methoxy;

or, $R^{2-7}$ is methyl;

or, when $R^{2-8}$ and $R^{2-9}$ are independently $C_1$-$C_6$ alkyl, the $C_1$-$C_6$ alkyl is isopropyl;

or, when $R^{2-8-1}$ is $C_1$-$C_6$ alkoxy, the $C_1$-$C_6$ alkoxy is methoxy;

or, when $R^{2-10}$ is independently $C_1$-$C_6$ alkyl, the $C_1$-$C_6$ alkyl is methyl;

or, when $R^{3-1}$ is independently $C_1$-$C_6$ alkoxy or $C_1$-$C_6$ alkoxy substituted by one or more $R^{3-1-2}$, in the $C_1$-$C_6$ alkoxy or $C_1$-$C_6$ alkoxy substituted by one or more $R^{3-1-2}$, the $C_1$-$C_6$ alkoxy is methoxy;

or, when $R^2$ is "3- to 4-membered heterocycloalkyl with 1 or 2 heteroatoms selected from one or more of N, O and S" or "3- to 4-membered heterocycloalkyl with 1 or 2 heteroatoms selected from one or more of N, O and S" substituted by one or more $R^{2-10}$, in the 3- to 4-membered heterocycloalkyl, the 3- to 4-membered heterocycloalkyl is

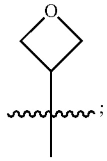 [SMILES: *C1COC1]

or, when $R^2$ is "5- to 6-membered heteroaryl with 1, 2 or 3 heteroatoms selected from one or more of N, O and S" substituted by one or more $R^{2-5}$, in the 5- to 6-membered heteroaryl, the 5- to 6-membered heteroaryl is

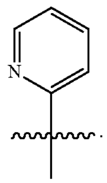

15. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 14, wherein, when $R^2$ is "5- to 6-membered heteroaryl with 1, 2 or 3 heteroatoms selected from one or more of N, O and S", in the 5- to 6-membered heteroaryl, the 5- to 6-membered heteroaryl is

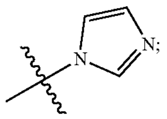 [SMILES: *n1ccnc1]

or, when $R^{2-6}$ is "3- to 6-membered heterocycloalkyl with 1, 2 or 3 heteroatoms selected from one or more of N, O and S", the 3- to 6-membered heterocycloalkyl is 3- to 4-membered heterocycloalkyl; in the 3- to 4-membered heterocycloalkyl, the 3- to 4-membered heterocycloalkyl is

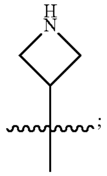 [SMILES: *C1CNC1]

or, when $R^{2-6}$ is "3- to 6-membered heterocycloalkyl with 1, 2 or 3 heteroatoms selected from one or more of N, O and S" substituted by one or more $R^{2-6-3}$, the 3- to 6-membered heterocycloalkyl is 3- to 4-membered heterocycloalkyl; in the 3- to 4-membered heterocycloalkyl, the 3- to 4-membered heterocycloalkyl is

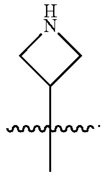 [SMILES: *C1CNC1]

16. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 4, wherein, $R^{3-1}$ is independently halogen, cyano or hydroxyl;

or, $R^2$ is oxo, halogen, cyano, amino, $C_1$-$C_{10}$ alkyl, $C_1$-$C_{10}$ alkyl substituted by one or more $R^{2-1}$, $C_3$-$C_6$ cycloalkyl, "5- to 6-membered heterocycloalkyl with 1, 2 or 3 heteroatoms selected from one or more of N, O and S", "5- to 6-membered heteroaryl with 1, 2 or 3 heteroatoms selected from one or more of N, O and S", —$OR^{2-6}$, —C(═O)$OR^{2-7}$, —$NR^{2-8}R^{2-9}$, or, "5- to 6-membered heterocycloalkyl with 1, 2 or 3 heteroatoms selected from one or more of N, O and S" substituted by one or more $R^{2-10}$;

or, $R^{2-6-1}$ is independently halogen, $C_3$-$C_6$ cycloalkyl or $C_6$-$C_{10}$ aryl substituted by one or more $R^{2-6-1-1}$;

or, $R^{2-1}$ is independently halogen.

17. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 5, wherein, when $R^3$ is
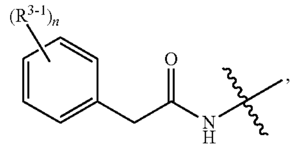
,
the $R^3$ is
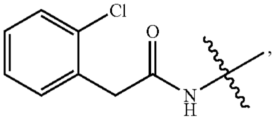
,
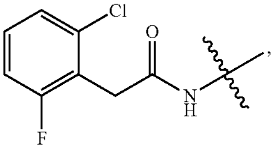
,
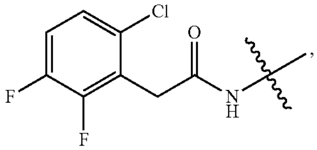
,
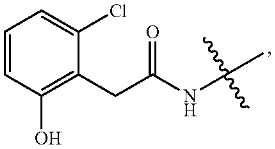
,
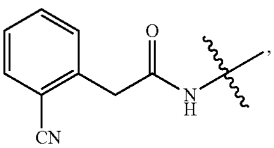
,
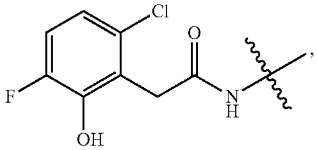
,
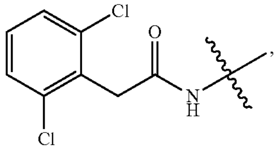
,
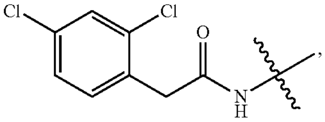
,
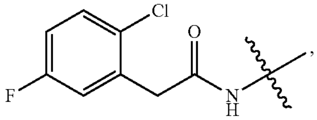
,
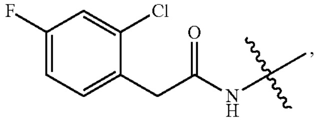
,
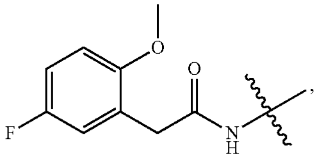
,
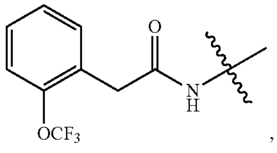
,
-continued
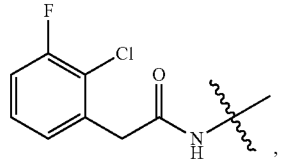
, or
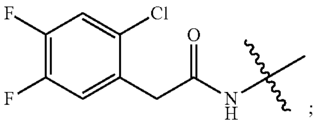
;
or, when $R^3$ is
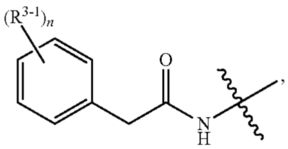
,
the $R^3$ is
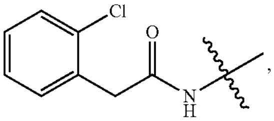
,
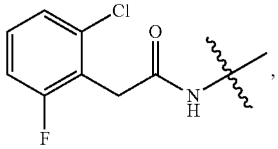
,
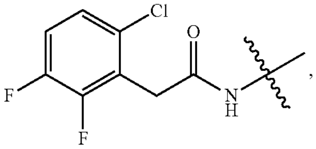
,
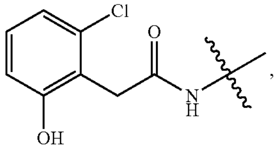
,
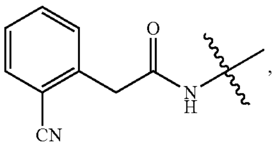
,
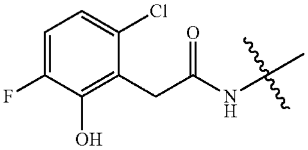
or
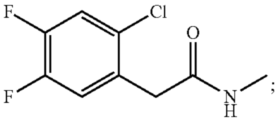
;
or, when $R^3$ is
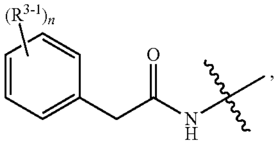
, the $R^3$ is
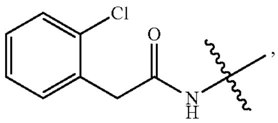
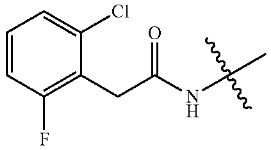
or
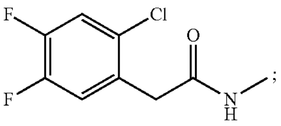
; or,
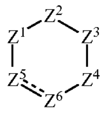
is
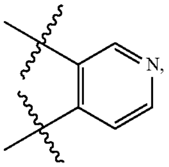
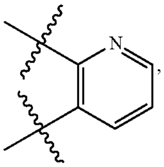
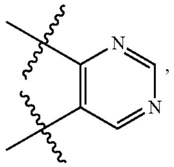
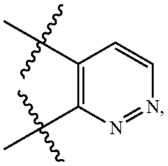
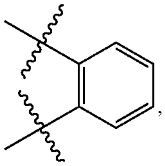
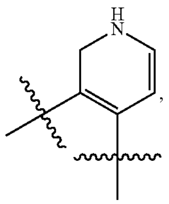
or
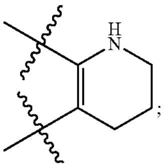
; or,
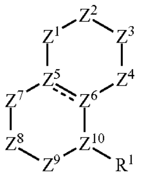
is
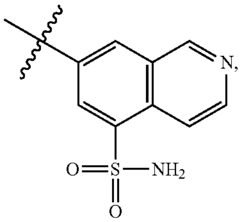
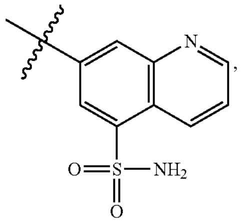
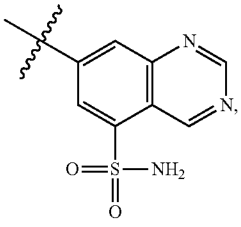
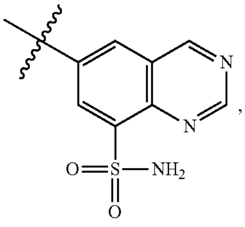
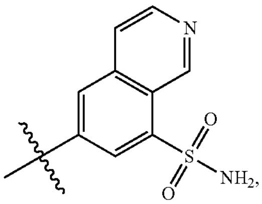
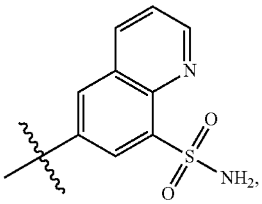
-continued
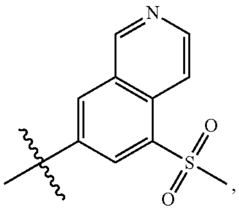
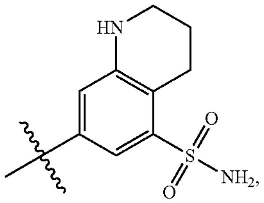
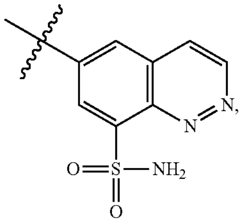
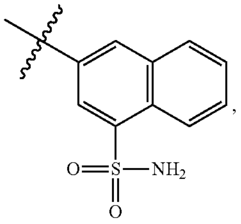
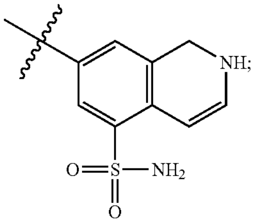
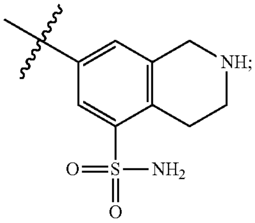
; or,
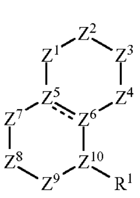
is
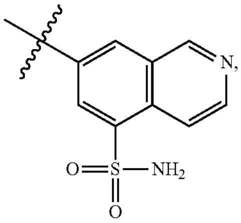
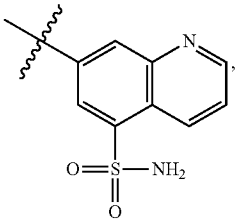
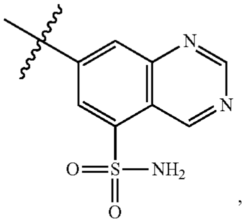
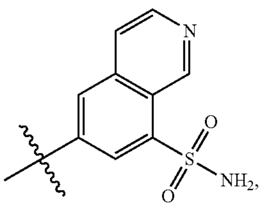
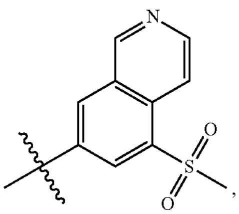
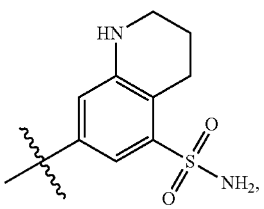

-continued

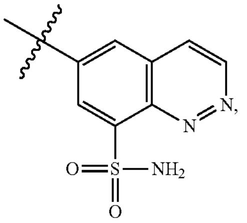

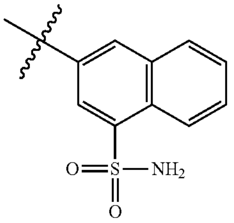

or

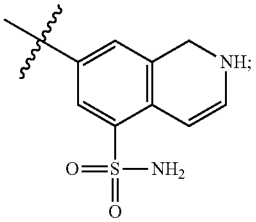

or,

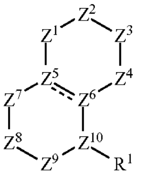

is

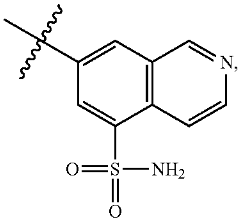

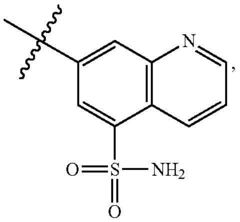

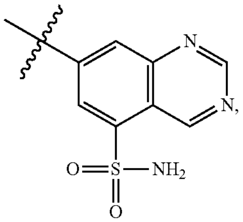

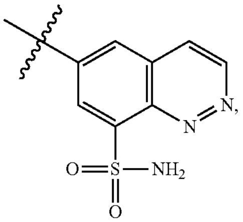

-continued

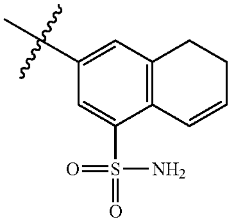

or

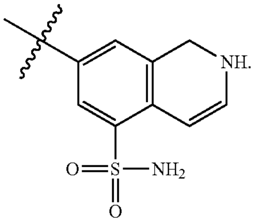

18. The method as claimed in claim 12, wherein, the pain is inflammatory pain, surgical pain, visceral pain, toothache, premenstrual pain, central pain, pain caused by burns, migraine, cluster headache or chronic pain;

or, the animal is human;

or, the bronchospasm or cough is chronic cough.

19. The fused ring compound represented by formula I, the pharmaceutically acceptable salt thereof, the stereoisomer thereof, the tautomer thereof, the isotopic compound thereof, the crystal form thereof, the nitrogen oxide thereof, the solvate thereof or the solvate of the pharmaceutically acceptable salt thereof as claimed in claim 1, wherein,

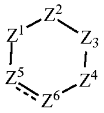

is 6-membered heterocycloalkene having one heteroatom N.

* * * * *